US012595417B2

(12) United States Patent
Wang et al.

(10) Patent No.: US 12,595,417 B2
(45) Date of Patent: *Apr. 7, 2026

(54) LIQUID-CRYSTAL MEDIUM

(71) Applicant: MERCK PATENT GmbH, Darmstadt (DE)

(72) Inventors: Jing Wang, Pudong New Area Shanghai (CN); Sven Christian Laut, Darmstadt (DE); Hee-Kyu Lee, Pudong New Area Shanghai (CN); Aaron Lackner, Darmstadt (DE); Dmitry Ushakov, Darmstadt (DE); Rocco Fortte, Darmstadt (DE); Philipp Wucher, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/978,065

(22) Filed: Dec. 12, 2024

(65) Prior Publication Data

US 2025/0215323 A1 Jul. 3, 2025

(30) Foreign Application Priority Data

Dec. 26, 2023 (WO) ................ PCT/CN2023/141800

(51) Int. Cl.

*C09K 19/34* (2006.01)
*C07C 13/28* (2006.01)
*C07C 25/18* (2006.01)
*C09K 19/54* (2006.01)

(52) U.S. Cl.

CPC .......... *C09K 19/3491* (2013.01); *C07C 13/28* (2013.01); *C07C 25/18* (2013.01); *C09K 19/542* (2013.01); *C07C 2601/14* (2017.05); *C07C 2601/16* (2017.05)

(58) Field of Classification Search

CPC ..................................................... C09K 19/54
See application file for complete search history.

(56) References Cited

U.S. PATENT DOCUMENTS

| | | | |
|---|---|---|---|
| 6,861,107 B2 | 3/2005 | Klasen-Memmer et al. | |
| 7,169,449 B2 | 1/2007 | Nakanishi et al. | |
| 2004/0191428 A1 | 9/2004 | Tsuda et al. | |
| 2006/0066793 A1 | 3/2006 | Ohmuro et al. | |
| 2006/0103804 A1 | 5/2006 | Hirosawa | |
| 2018/0179444 A1* | 6/2018 | Park | G02F 1/134309 |

FOREIGN PATENT DOCUMENTS

| | | |
|---|---|---|
| EP | 1170626 A2 | 1/2002 |
| EP | 1897928 A1 | 3/2008 |

OTHER PUBLICATIONS

Jung et al., "Analysis of Optimal Phase Retardation of a Fringe Field-Driven Homogeneously Aligned Nematic Liquid Crystal Cell", Japanese Journal of Applied Physics, vol. 43, No. 3, Mar. 2004, pp. 1028-1031. (5 pages).

Lee et al., "Electro-optic characteristics and switching principle of a nematic liquid crystal cell controlled by fringe-field switching" Applied Physics Letters, vol. 73, No. 20, Nov. 1998, pp. 2882-2883. (4 pages).

Tschierske et al., "Definitions of basic terms related to low molecular weight and polymer liquid crystals", Applied Chemistry, (Nov. 19, 2004), vol. 116, Issue 45, pp. 6340-6368. (with English translation 115 pages total).

Yun et al., "Achieving high light efficiency and fast response time in fringe field switching mode using a liquid crystal with negative dielectric anisotropy" Liquid Crystals, vol. 39, No. 9, 2012, pp. 1141-1148. (10 pages).

* cited by examiner

*Primary Examiner* — Chanceity N Robinson

(74) *Attorney, Agent, or Firm* — Buchanan Ingersoll & Rooney PC

(57) ABSTRACT

A liquid-crystal (LC) material comprising one or more compounds of the formula I

I

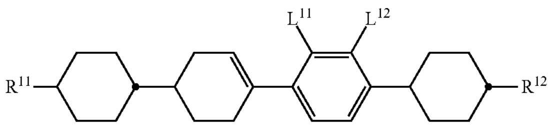

having negative dielectric anisotropy, wherein i) $R^{11}$ and $R^{12}$ identically or differently, denote H, straight chain alkyl or alkoxy having 1 to 15 C atoms, straight chain alkenyl or alkenyloxy having 2 to 15 C atoms or branched alkyl, alkoxy, alkenyl, alkenyloxy each having 3 to 15 C atoms and ii) one of $L^{11}$ and $L^{12}$ denotes H, and the other one of $L^{11}$ and $L^{12}$ denotes H, F, Cl, $CF_3$ or $CHF_2$. Also, the use of such liquid-crystal material for optical, electro-optical and electronic purposes, such as for example in LC displays, in particular energy saving displays based on the ECB, IPS or FFS effect.

15 Claims, No Drawings

LIQUID-CRYSTAL MEDIUM

CROSS-REFERENCE TO RELATED APPLICATIONS

This application filed under 35 U.S.C. § 111(a) claims priority benefit under 35 U.S.C. §§ 119(a) and 365(a) of and to PCT International Application No. PCT/CN2023/141800, filed Dec. 26, 2023, the entire contents of which are incorporated herein by reference in their entirety and for all purposes.

BACKGROUND OF THE INVENTION

The present invention relates to liquid-crystal (LC) media having negative dielectric anisotropy and to the use thereof for optical, electro-optical and electronic purposes, in particular in LC displays.

One of the liquid-crystal display (LCD) modes used at present is the TN ("twisted nematic") mode. However, TN LCDs have the disadvantage of a strong viewing-angle dependence of the contrast.

In addition, so-called VA ("vertically aligned") displays are known which have a broader viewing angle. The LC cell of a VA display contains a layer of an LC medium between two transparent electrodes, where the LC medium usually has a negative dielectric anisotropy. In the switched-off state, the molecules of the LC layer are aligned perpendicular to the electrode surfaces (homeotropically) or have a tilted homeotropic alignment. On application of an electrical voltage to the two electrodes, a realignment of the LC molecules parallel to the electrode surfaces takes place.

Also known are so-called IPS ("in-plane switching") displays, which contain an LC layer between two substrates, where the two electrodes are arranged on only one of the two substrates and preferably have intermeshed, comb-shaped structures. On application of a voltage to the electrodes, an electric field which has a significant component parallel to the LC layer is thereby generated between them. This causes realignment of the LC molecules in the layer plane.

Furthermore, so-called FFS ("fringe-field switching") displays have been reported (see, inter alia, S. H. Jung et al., Jpn. J. Appl. Phys., Volume 43, No. 3, 2004, 1028), which contain two electrodes on the same substrate, one of which is structured in a comb-shaped manner and the other is unstructured. A strong, so-called "fringe field" is thereby generated, i.e., a strong electric field close to the edge of the electrodes, and, throughout the cell, an electric field which has both a strong vertical component and also a strong horizontal component. FFS displays have a low viewing-angle dependence of the contrast. FFS displays usually contain an LC medium with positive dielectric anisotropy, and an alignment layer, usually of polyimide, which provides planar alignment to the molecules of the LC medium.

FFS displays can be operated as active-matrix or passive-matrix displays. In the case of active-matrix displays, individual pixels are usually addressed by integrated, non-linear active elements, such as, for example, transistors (for example thin-film transistors ("TFTs")), while in the case of passive-matrix displays, individual pixels are usually addressed by the multiplex method, as known from the prior art.

Furthermore, FFS displays have been disclosed (see S. H. Lee et al., Appl. Phys. Lett. 73(20), 1998, 2882-2883 and S. H. Lee et al., Liquid Crystals 39(9), 2012, 1141-1148), which have similar electrode design and layer thickness as FFS displays but comprise a layer of an LC medium with negative dielectric anisotropy instead of an LC medium with positive dielectric anisotropy. The LC medium with negative dielectric anisotropy shows a more favorable director orientation that has less tilt and more twist orientation compared to the LC medium with positive dielectric anisotropy, as a result of which these displays have a higher transmission. The displays further comprise an alignment layer, preferably of polyimide provided on at least one of the substrates that is in contact with the LC medium and induces planar alignment of the LC molecules of the LC medium. These displays are also known as "Ultra Brightness FFS (UB-FFS)" mode displays. These displays require an LC medium with high reliability.

In VA displays of the more recent type, uniform alignment of the LC molecules is restricted to a plurality of relatively small domains within the LC cell. Disclinations may exist between these domains, also known as tilt domains. VA displays having tilt domains have, compared with conventional VA displays, a greater viewing-angle independence of the contrast and the grey shades. In addition, displays of this type are simpler to produce since additional treatment of the electrode surface for uniform alignment of the molecules in the switched-on state, such as, for example, by rubbing, is no longer necessary. Instead, the preferential direction of the tilt or pretilt angle is controlled by a special design of the electrodes.

In so-called MVA ("multidomain vertical alignment") displays, this is usually achieved by the electrodes having protrusions which cause a local pretilt. As a consequence, the LC molecules are aligned parallel to the electrode surfaces in different directions in different, defined regions of the cell on application of a voltage. "Controlled" switching is thereby achieved, and the formation of interfering disclination lines is prevented. Although this arrangement improves the viewing angle of the display, it results, however, in a reduction in its transparency to light. A further development of MVA uses protrusions on only one electrode side, while the opposite electrode has slits, which improves the transparency to light. The slitted electrodes generate an inhomogeneous electric field in the LC cell on application of a voltage, meaning that controlled switching is still achieved. For further improvement of the transparency to light, the separations between the slits and protrusions can be increased, but this in turn results in a lengthening of the response times. In so-called PVA ("patterned VA") displays, protrusions are rendered completely superfluous in that both electrodes are structured by means of slits on the opposite sides, which results in increased contrast and improved transparency to light but is technologically difficult and makes the display more sensitive to mechanical influences ("tapping", etc.). For many applications, such as, for example, monitors and especially TV screens, however, a shortening of the response times and an improvement in the contrast and luminance (transmission) of the display are demanded.

A further development are displays of the so-called PS ("polymer sustained") or PSA ("polymer sustained alignment") type, for which the term "polymer stabilised" is also occasionally used. In these, a small amount (for example 0.3% by weight, typically <1% by weight) of one or more polymerisable, compound(s), preferably polymerisable monomeric compound(s), is added to the LC medium and, after filling the LC medium into the display, is polymerised, or crosslinked in situ, usually by UV photopolymerisation, optionally while a voltage is applied to the electrodes of the display. The polymerisation is carried out at a temperature where the LC medium exhibits a liquid crystal phase, usually at room temperature. The addition of polymerisable mesogenic or liquid-crystalline compounds, also known as reactive mesogens or "RMs", to the LC mixture has proven particularly suitable.

In the meantime, the PS(A) principle is being used in various conventional LC display modes. Thus, for example, PS-VA, PS-OCB, PS-IPS, PS-FFS, PS-UB-FFS and PS-TN displays are known. The polymerisation of the RMs preferably takes place with an applied voltage in the case of PS-VA and PS-OCB displays, and with or without, preferably without, an applied voltage in the case of PS-IPS displays. As can be demonstrated in test cells, the PS(A) method results in a pretilt in the cell. In the case of PS-VA displays, the pretilt has a positive effect on response times. For PS-VA displays, a standard MVA or PVA pixel and electrode layout can be used. In addition, however, it is also possible, for example, to manage with only one structured electrode side and no protrusions, which significantly simplifies production and at the same time results in very good contrast and in very good transparency to light.

PS-VA displays are described, for example, in EP 1 170 626 A2, U.S. Pat. Nos. 6,861,107, 7,169,449, US 2004/0191428 A1, US 2006/0066793 A1, and US 2006/0103804 A1.

In particular for monitor and especially TV applications, optimisation of the response times, but also of the contrast and luminance (thus also transmission) of the LC display continues to be demanded. The PSA method can provide significant advantages here. In particular in the case of PS-VA, PS-IPS and PS-FFS displays, a shortening of the response times, which correlate with a measurable pretilt in test cells, can be achieved without significant adverse effects on other parameters.

Another problem observed in prior art is that the use of conventional LC media in LC displays, including but not limited to displays of the PSA type, often leads to the occurrence of mura in the display, especially when the LC medium is filled in the display cell manufactured using the one drop filling (ODF) method. This phenomenon is also known as "ODF mura". It is therefore desirable to provide LC media which lead to reduced ODF mura.

Another problem observed in prior art is that LC media for use in PSA displays, including but not limited to displays of the PSA type, do often exhibit high viscosities and, as a consequence, high switching times. In order to reduce the viscosity and switching time of the LC medium, it has been suggested in prior art to add LC compounds with an alkenyl group. However, it was observed that LC media containing alkenyl compounds often show a decrease of the reliability and stability, and a decrease of the VHR especially after exposure to UV radiation. Especially for use in PSA displays this is a considerable disadvantage because the photopolymerisation of the RMs in the PSA display is usually carried out by exposure to UV radiation, which may cause a VHR drop in the LC medium.

In addition there is a great demand for PSA displays, and LC media and polymerisable compounds for use in such PSA displays, which enable a high specific resistance at the same time as a large working-temperature range, short response times, even at low temperatures, and a low threshold voltage, a low pretilt angle, a multiplicity of grey shades, high contrast and a broad viewing angle, have high reliability and high values for the VHR after UV exposure, and, in case of the polymerisable compounds, have low melting points and a high solubility in the LC host mixtures. In PSA displays for mobile applications, it is especially desired to have available LC media that show low threshold voltage and high birefringence.

One display trend is to achieve the fastest possible response time to have the best motion picture quality. In this respect, media with negative dielectric anisotropy have an intrinsic disadvantage compared to LC media with positive dielectric anisotropy. On the other hand, mixtures with negative dielectric anisotropy enable a higher transmittance in standard FFS cell layouts and therefore its use has a positive impact on the power consumption and the environment. There is a need in the art to achieve both, fast response time and higher transmittance. Especially for use in mobile devices there is great demand for displays with high transmission, which enable the use of less intensive backlight, which, therefore, leads to longer battery lifetime, hence, more sustainable products. Alternatively, displays with higher brightness can be achieved having improved contrast especially under ambient light. Also, the popularity of 8K and gaming monitors leads to an increased need for LC display panels having higher refresh rates and thus for LC media having faster response times.

Another important display trend is to achieve a high contrast ratio. Contrast ratio is described by the ratio between the bright and the dark state of the display. In LCD especially in IPS/FFS technology the dark state is strongly impacted by the scattering parameter and has therefore a significant impact on the contrast ratio. To improve the contrast ratio and to reduce the scattering parameter LC mixtures with high elastic constants are necessary. Here, current LC singles and LC mixtures are limited in achieving extremely high elastic constants. Therefore, new materials need to be found to increase the contrast ratio of future displays even further.

SUMMARY OF THE INVENTION

There is thus still a great demand for VA, FFS or PSA displays, and LC media optionally comprising polymerisable compounds for use in VA, FFS or PSA displays, which do not show the drawbacks as described above, or only do so to a small extent, and have improved properties.

The invention is based on the object of providing novel suitable LC media, which do not have the disadvantages indicated above or do so to a reduced extent.

Surprisingly, it has now been found that liquid crystalline media with a suitably high negative Δε, a suitable phase range and Δn and high LTS can be realized which do not exhibit the drawbacks of the materials of the prior art or at least do exhibit them to a significantly lesser degree by using liquid crystalline media comprising a compound of formula I.

The invention relates to a liquid crystal medium comprising the compound of the formula I

I

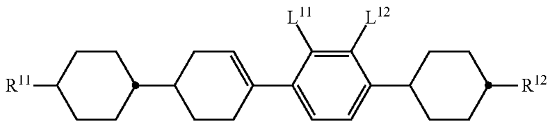

in which $R^{11}$ and $R^{12}$ identically or differently, denote H, straight chain alkyl or alkoxy having 1 to 15 C atoms, straight chain alkenyl or alkenyloxy having 2 to 15 C atoms or branched alkyl, alkoxy, alkenyl, alkenyloxy each having 3 to 15 C atoms, where one or more $CH_2$ groups in these radicals may each be replaced, independently of one another, by

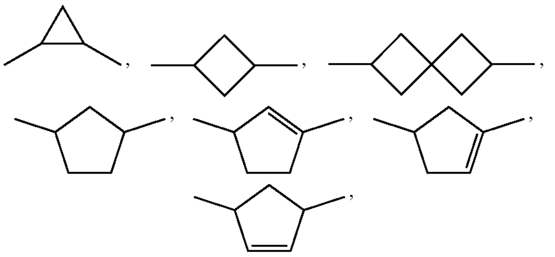

—CH═CH—, —C≡C—, $—CF_2O—$, $—OCF_2—$, —O—, —CO—O— or —O—CO— in such a way that O atoms are not linked directly to one another, and in which one or more H atoms may be replaced by halogen, one of $L^{11}$ and $L^{12}$ denotes H, and the other one of $L^{11}$ and $L^{12}$ denotes H, F, Cl, $CF_3$ or $CHF_2$, preferably H or F, very preferably H;

where the medium preferably comprises one or more compounds selected from the group of compounds of the formulae IIA, IIB, IIC and IID

IIA

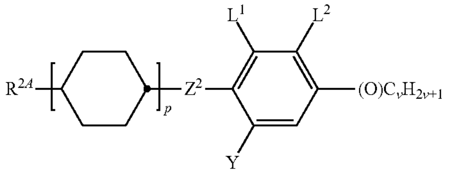

IIB

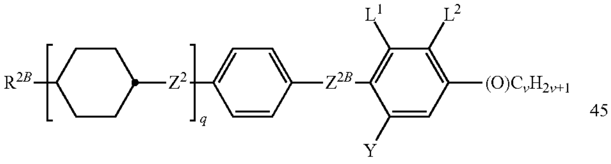

IIC

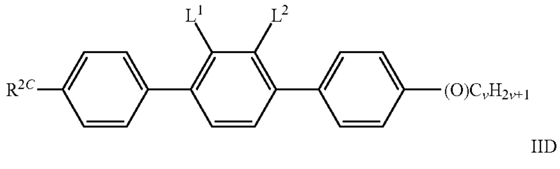

IID

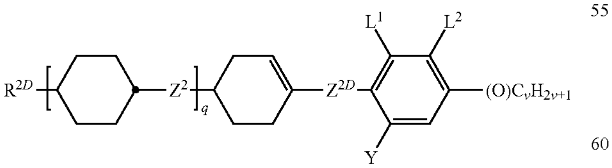

in which $R^{2A}$, $R^{2B}$, $R^{2C}$ and $R^{2D}$ identically or differently, denote H, straight chain alkyl or alkoxy having 1 to 15 C atoms, straight chain alkenyl or alkenyloxy having 2 to 15 C atoms or branched alkyl, alkoxy, alkenyl, alkenyloxy each having 3 to 15 C atoms, where one or more $CH_2$ groups in these radicals may each be replaced, independently of one another, by

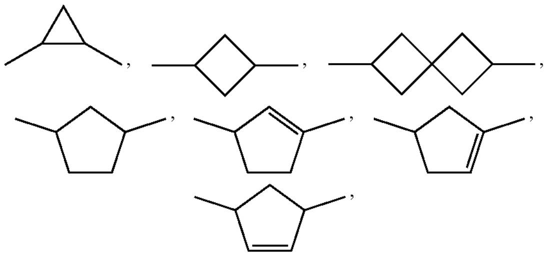

—CH═CH—, —C≡C—, $—CF_2O—$, $—OCF_2—$, —O—, —CO—O— or —O—CO— in such a way that O atoms are not linked directly to one another, and in which one or more H atoms may be replaced by halogen, $L^1$ and $L^2$, each, independently of one another, denote F, Cl, $CF_3$ or $CHF_2$, Y denotes H, F, Cl, $CF_3$, $CHF_2$ or $CH_3$, preferably H or $CH_3$, more preferably H, $Z^2$, $Z^{2B}$ and $Z^{2D}$ each, independently of one another, denote a single bond, $—CH_2CH_2—$, —CH═CH—, $—CF_2O—$, $—OCF_2—$, $—CH_2O—$, $—OCH_2—$, —COO—, —OCO—, $—C_2F_4—$, —CF═CF— or $—CH═CHCH_2O—$, (O) denotes O or a single bond, p denotes 0, 1 or 2, q denotes 0 or 1, and v denotes an integer from 1 to 6.

The invention furthermore relates to an LC display comprising an LC medium according to the invention, in particular a VA, IPS, FFS or UB-FFS or PSA display, particularly preferably an FFS, UB-FFS, VA or a PS-VA display.

The invention furthermore relates to the use of the LC media according to the invention in PSA displays, in particular to the use in PSA displays containing an LC medium, to produce a tilt angle in the LC medium by in-situ polymerisation of polymerisable reactive mesogens (RM) in the PSA display, preferably in an electric or magnetic field.

The invention furthermore relates to a process for preparing an LC medium as described above and below, comprising the steps of mixing one or more compounds of the formula I with one or more compounds of the formulae IIA, IIB, IIC and/or IID, and optionally with one or more chiral dopants, and optionally with one or more polymerisable compounds and optionally with further LC compounds and/or additives.

The invention furthermore relates to the use of LC media according to the invention in polymer stabilised SA-VA displays, and to a polymer stabilised SA-VA display comprising the LC medium according to the invention.

The invention furthermore relates to a process for manufacturing an LC display as described above and below, comprising the steps of filling, or otherwise providing an LC medium, which optionally comprises one or more polymerisable compounds as described above and below, between the substrates of the display, and optionally polymerising the polymerisable compounds.

The LC media according to the invention show the following advantageous properties, in particular when used in FFS displays:

excellent low-temperature stability (LTS)
improved contrast ratio of the display,
high transmission of the display,
a high clearing temperature,
a high voltage-holding-ratio,
low rotational viscosity
fast switching,
fast response time that enables LCDs with low power consumption to enlarge the battery lifetime for mobile devices,
sufficient stability against heat and/or UV in particular when used outdoors,
high elastic constants.

According to another aspect of the present invention there is provided a compound of the formula I defined above, in which one of the radicals $L^{11}$ and $L^{12}$ denotes H, and the other one of the radicals $L^{11}$ and $L^{12}$ denotes F, Cl, $CF_3$ or $CHF_2$.

According to another aspect of the present invention there is provided a compound of the formula (3) defined below in scheme 1.

The compounds of the general formula I are prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and are suitable for said reactions. Use can be made here of variants which are known per se but are not mentioned here in greater detail.

If desired, the starting materials can also be formed in situ by not isolating them from the reaction mixture, but instead by immediately reacting them further into the compounds of the general formula I.

DETAILED DESCRIPTION OF THE INVENTION

The compounds of the formula I can be synthesized in analogy to the synthesis of the structurally related chloro-fluoro derivatives shown in EP 1 897 928 A1.

A preferred synthetic pathway towards compounds of formula I is shown in scheme 1.

Scheme 1

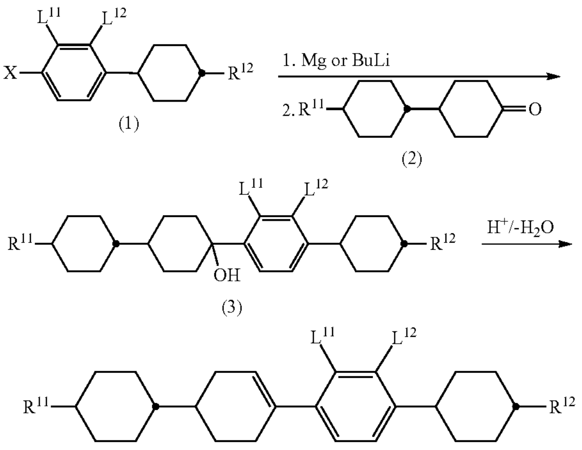

(1)
(2)
(3)

in which X denotes Br or I and the other occurring groups have the meanings given above.

The compounds of the formula I are preferably selected from the compounds of the formulae I-1 to I-3

I-1

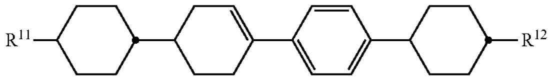

I-2

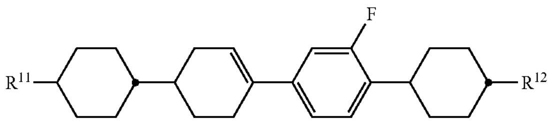

I-3

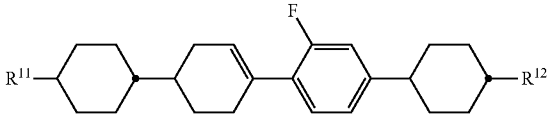

in which $R^{11}$ and $R^{12}$ have the meanings defined above for formula I and preferably denote straight chain alkyl having 1 to 7 C atoms, or straight chain alkenyl having 2 to 15 C atoms where one or more $CH_2$ groups in these radicals may each be replaced, independently of one another, by

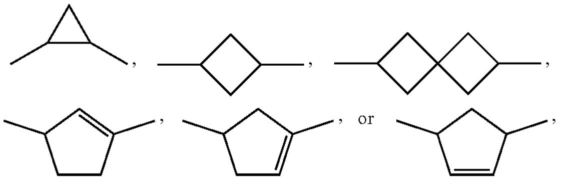

More preferably the medium according to the invention comprises one or more compounds of the formula I-1, very preferably selected from the compounds of the formulae I-1-1 to I-1-32

I-1-1

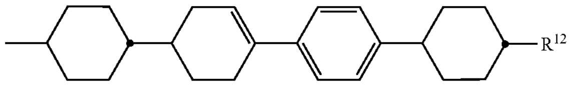

I-1-2

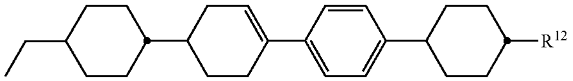

I-1-3

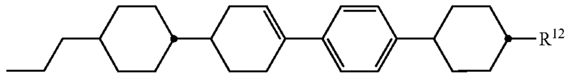

I-1-4

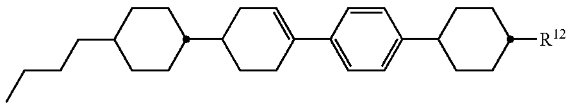

I-1-5

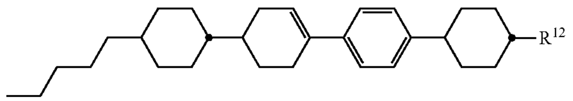

-continued
I-1-6
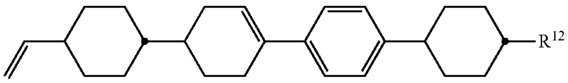
I-1-7
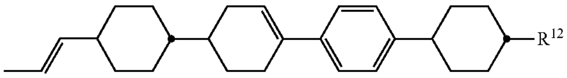
I-1-8
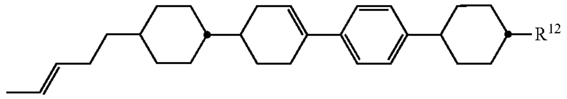
I-1-9
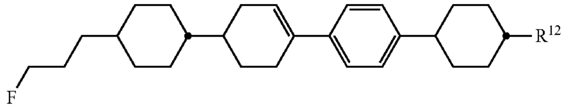
I-1-10
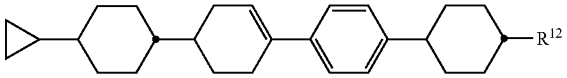
I-1-11
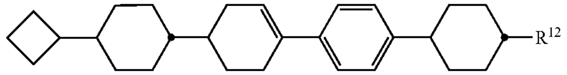
I-1-12
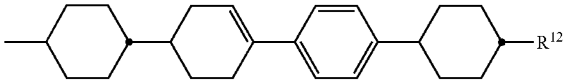
I-1-13
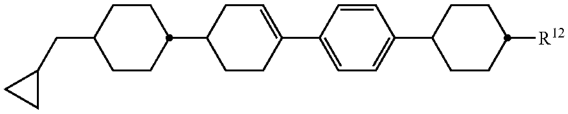
I-1-14
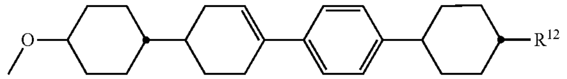
I-1-15
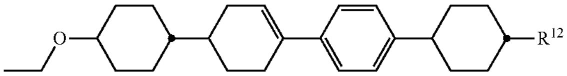
I-1-16
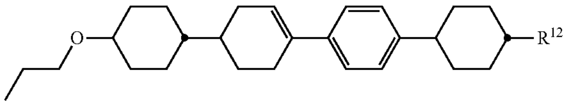
I-1-17
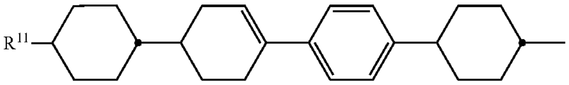
I-1-18
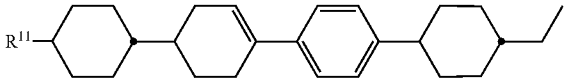
-continued
I-1-19
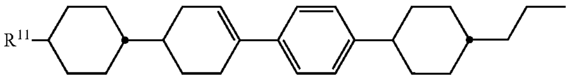
I-1-20
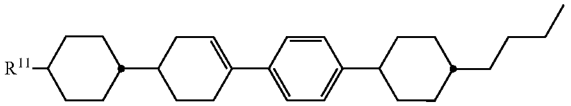
I-1-21
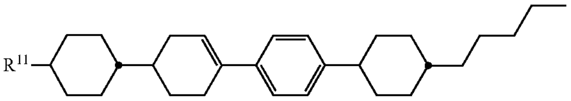
I-1-22
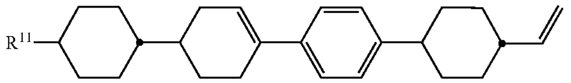
I-1-23
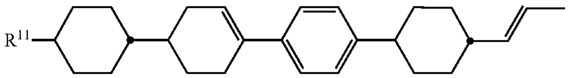
I-1-24
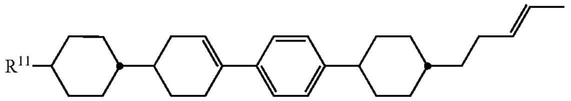
I-1-25
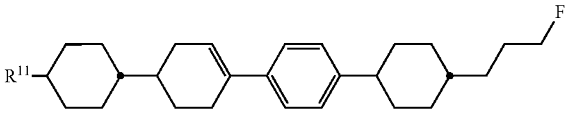
I-1-26
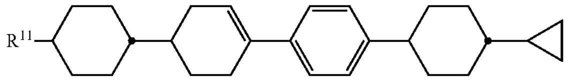
I-1-27
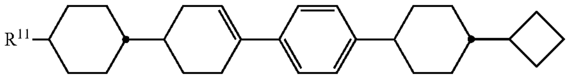
I-1-28
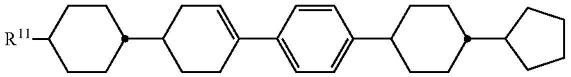
I-1-29
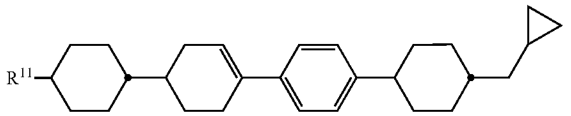
I-1-30
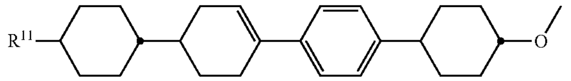
I-1-31
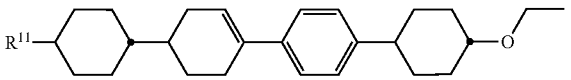

-continued
I-1-32
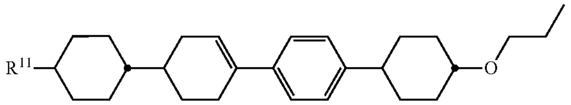
in which $R^{11}$ and $R^{12}$ denote straight chain alkyl having 1 to 7 C atoms or straight chain alkenyl having 2 to 7 C atoms.
The compounds of the formula I-2 are preferably selected from the compounds of the formulae I-2-1 to I-2-32:
I-2-1
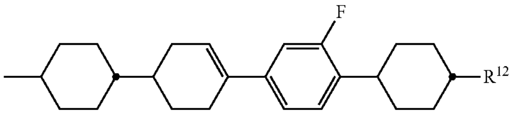
I-2-2
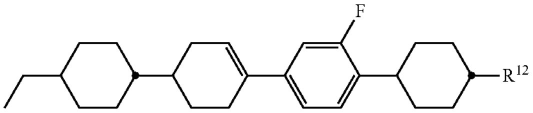
I-2-3
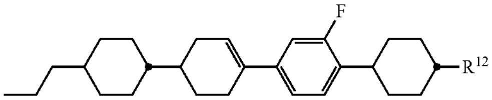
I-2-4
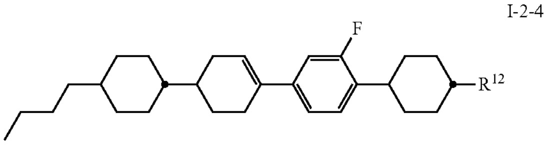
I-2-5
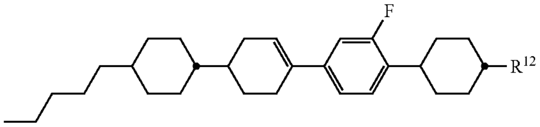
I-2-6
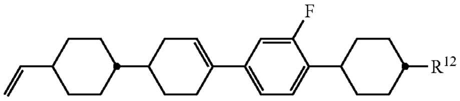
I-2-7
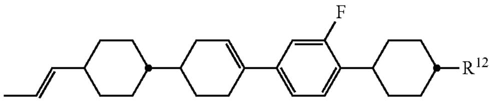
I-2-8
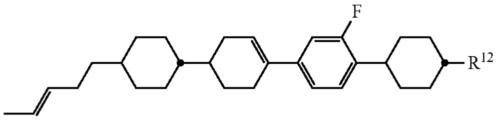
I-2-9
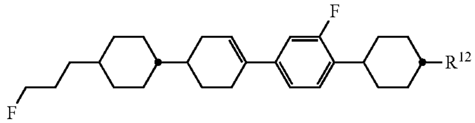
-continued
I-2-10
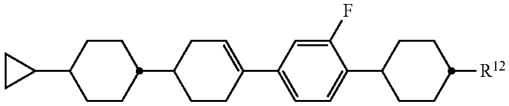
I-2-11
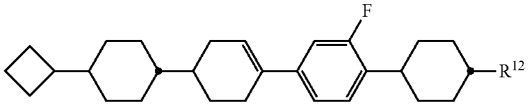
I-2-12
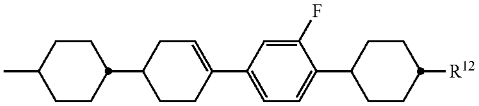
I-2-13
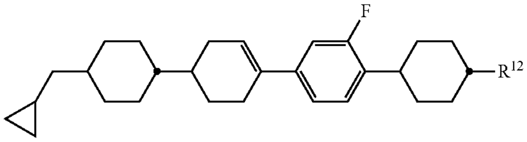
I-2-14
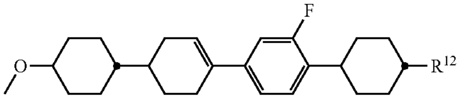
I-2-15
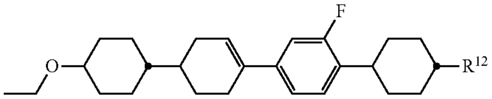
I-2-16
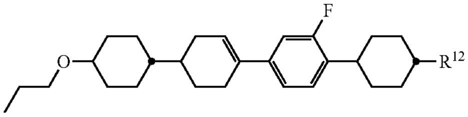
I-2-17
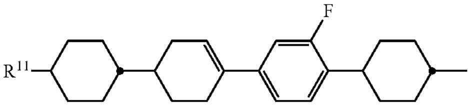
I-2-18
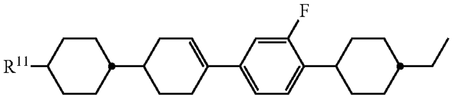
I-2-19
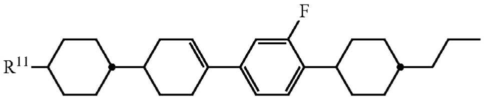
I-2-20
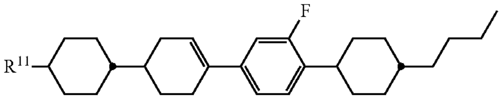
I-2-21
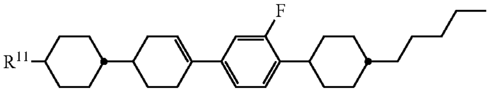
I-2-22
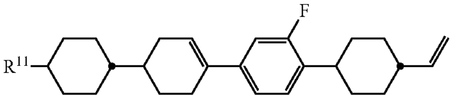

-continued
I-2-23
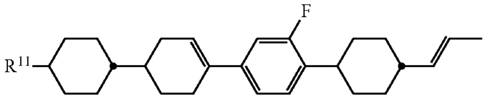
I-2-24
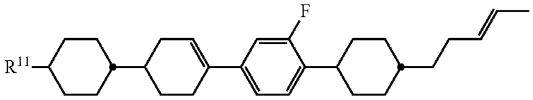
I-2-25
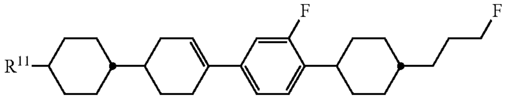
I-2-26
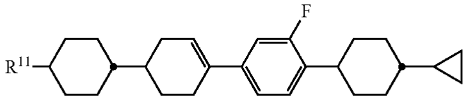
I-2-27
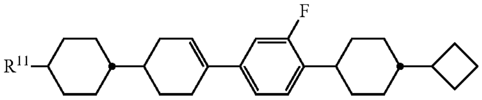
I-2-28
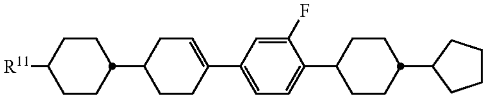
I-2-29
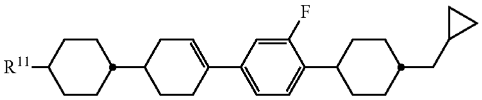
I-2-30
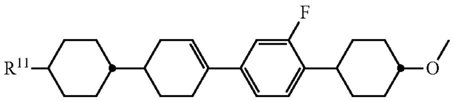
I-2-31
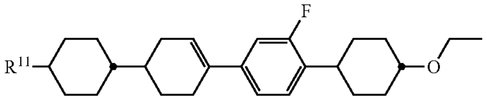
I-2-32
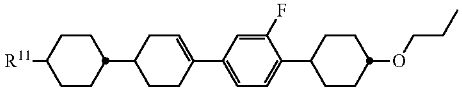
The compounds of the formula I-3 are preferably selected from the compounds of the formulae I-3-1 to I-3-32:
I-3-1
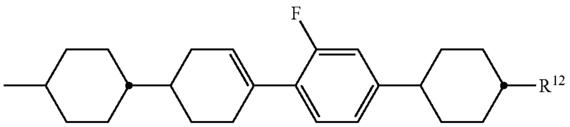
I-3-2
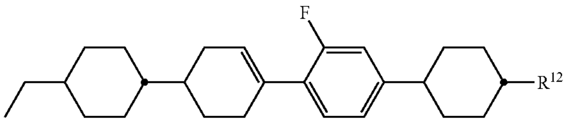
-continued
I-3-3
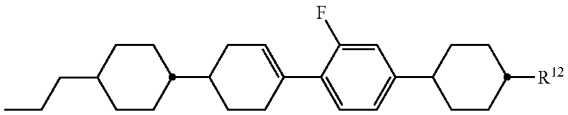
I-3-4
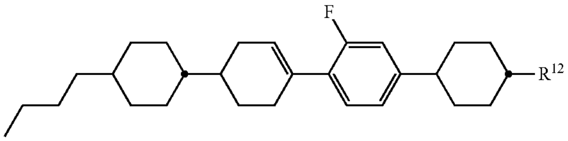
I-3-5
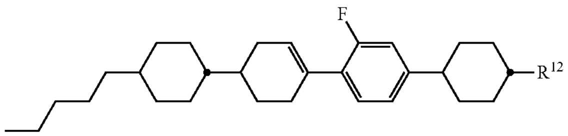
I-3-6
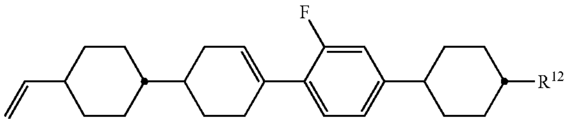
I-3-7
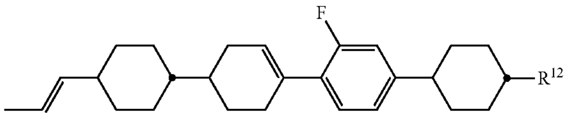
I-3-8
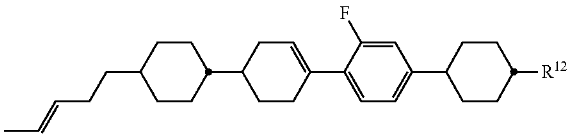
I-3-9
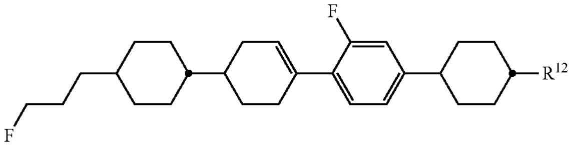
I-3-10
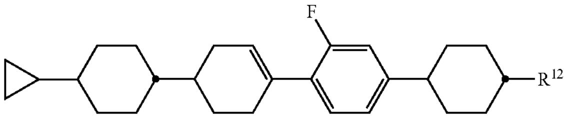
I-3-11
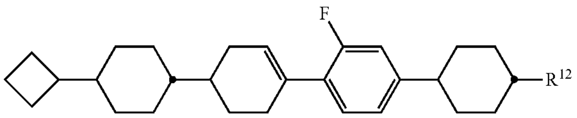
I-3-12
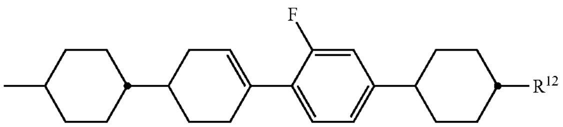

-continued
I-3-13
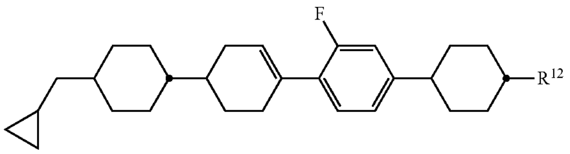
I-3-14
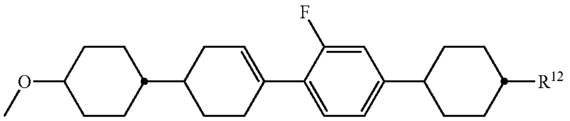
I-3-15
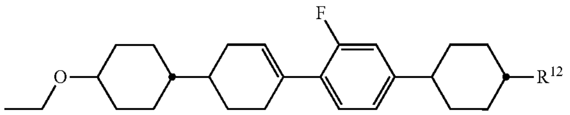
I-3-16
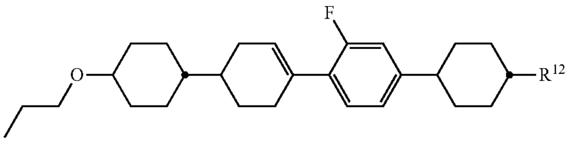
I-3-17
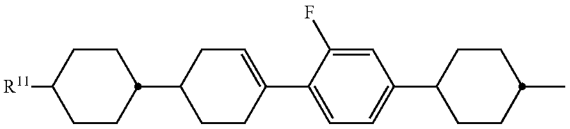
I-3-18
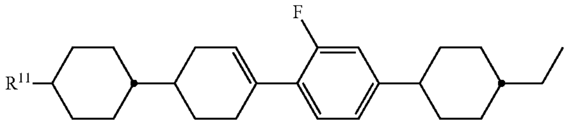
I-3-19
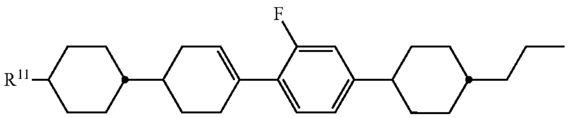
I-3-20
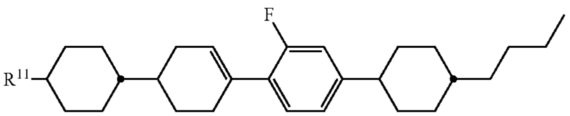
I-3-21
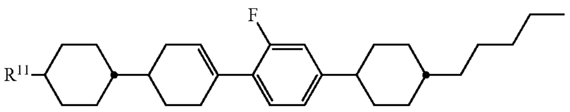
I-3-22
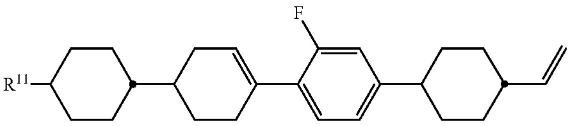
-continued
I-3-23
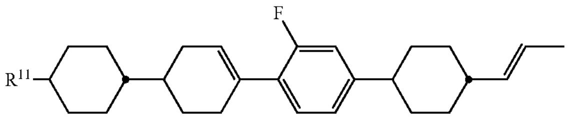
I-3-24
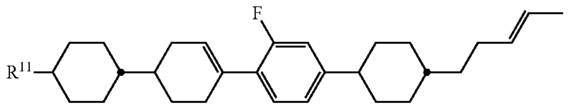
I-3-25
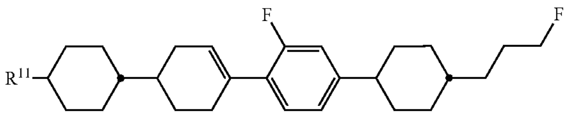
I-3-26
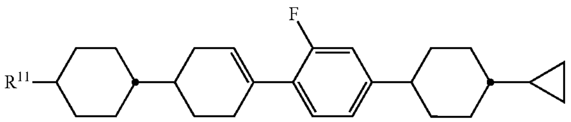
I-3-27
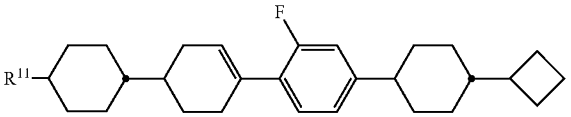
I-3-28
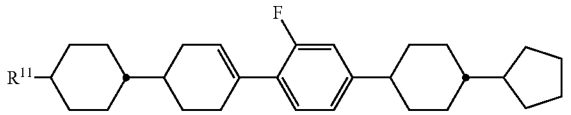
I-3-29
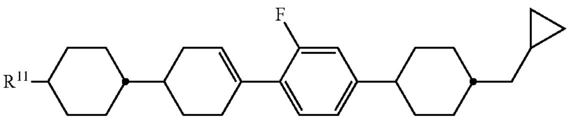
I-3-30
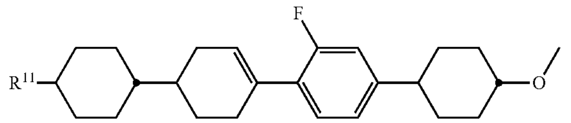
I-3-31
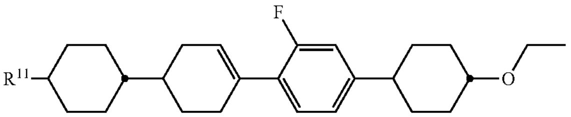
I-3-32
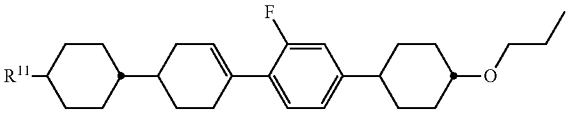
Preferred compounds of the formulae IIA, IIB, IIC and IID are indicated below:

-continued
IIA-1
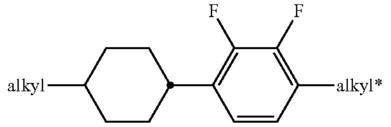
IIA-2
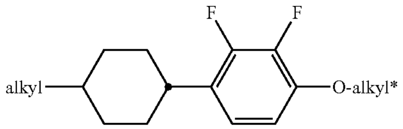
IIA-3
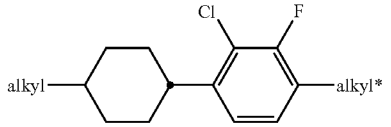
IIA-4
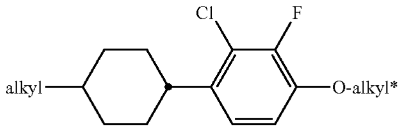
IIA-5
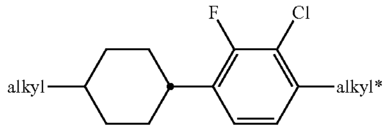
IIA-6
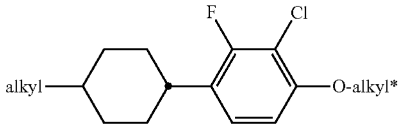
IIA-7
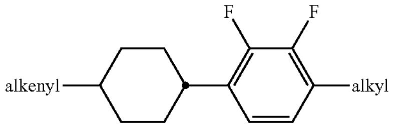
IIA-8
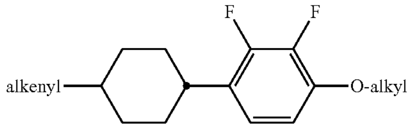
IIA-9
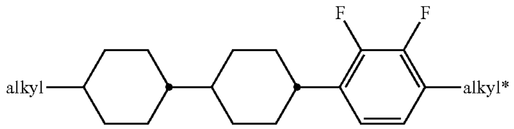
IIA-10
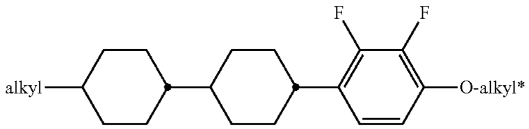
IIA-11
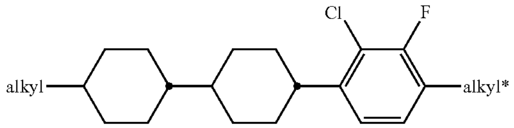
IIA-12
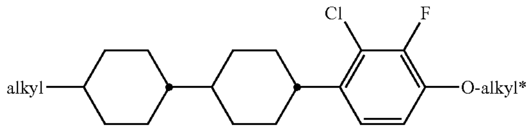
IIA-13
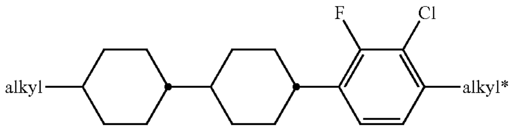
IIA-14
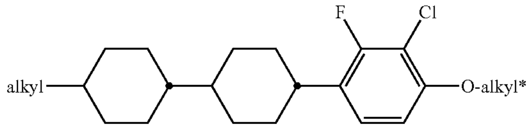
IIA-15
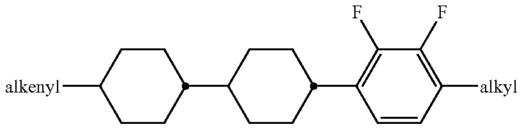
IIA-16
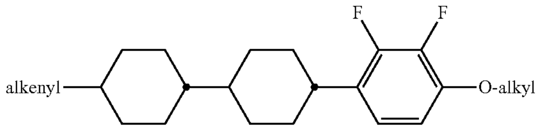
IIA-17
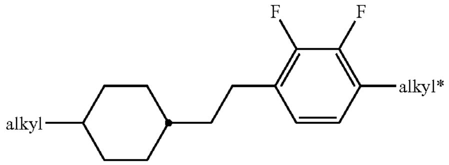
IIA-18
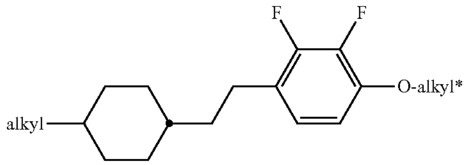
IIA-19
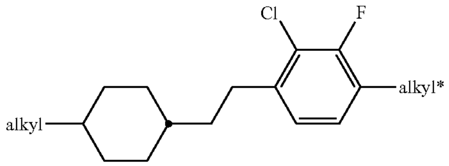
IIA-20
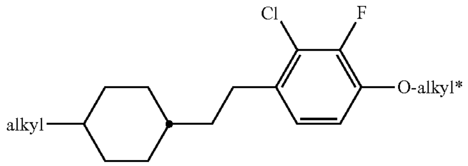

-continued
IIA-21
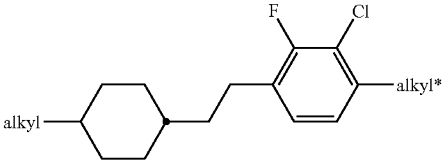
IIA-22
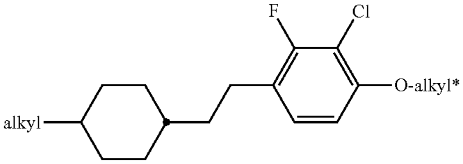
IIA-23
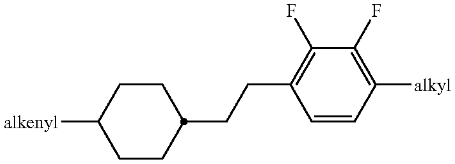
IIA-24
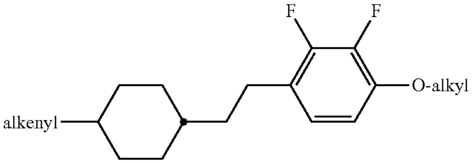
IIA-25
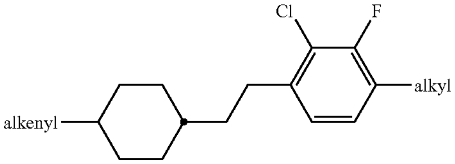
IIA-26
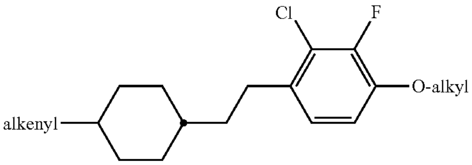
IIA-27
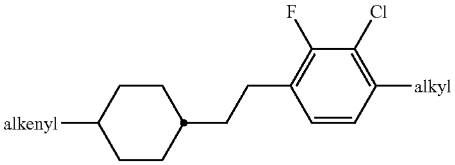
IIA-28
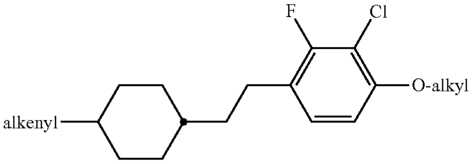
IIA-29
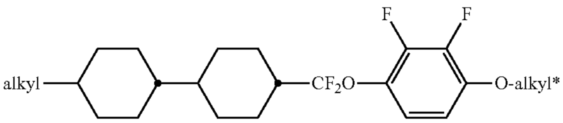
-continued
IIA-30
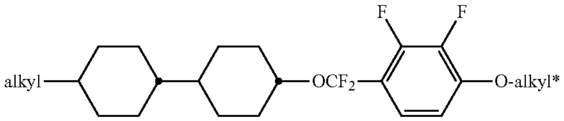
IIA-31
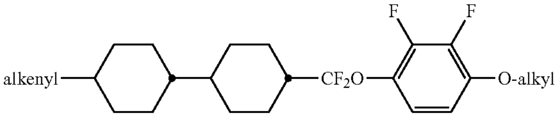
IIA-32
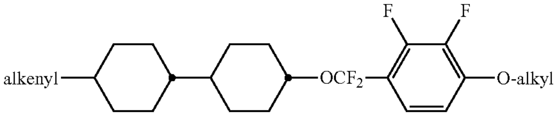
IIA-33
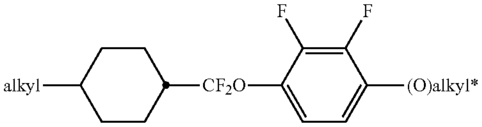
IIA-34
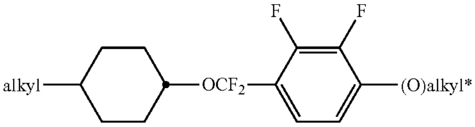
IIA-35
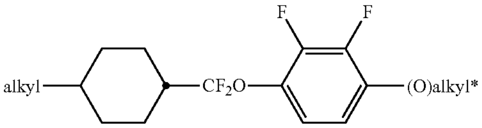
IIA-36
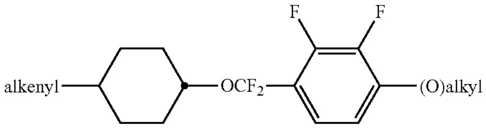
IIA-37
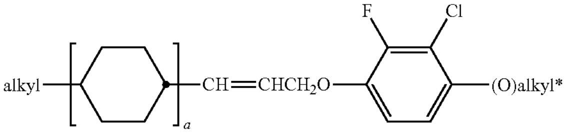
IIA-38
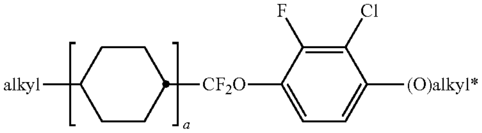
IIA-39
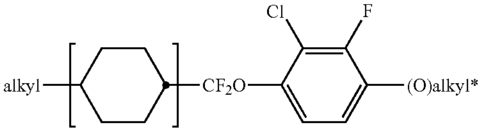
IIA-40
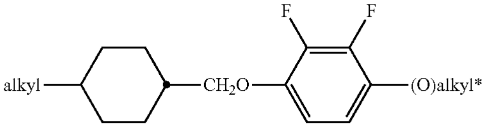

-continued
IIA-41
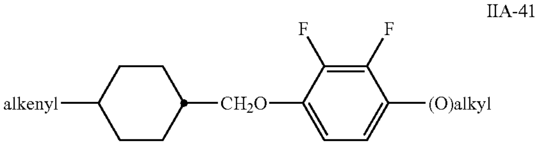
IIA-42
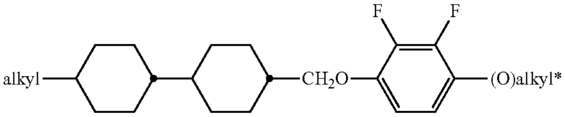
IIA-43
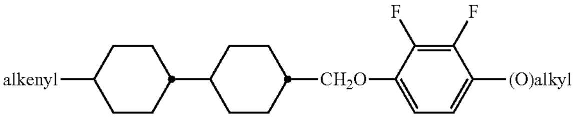
IIA-44
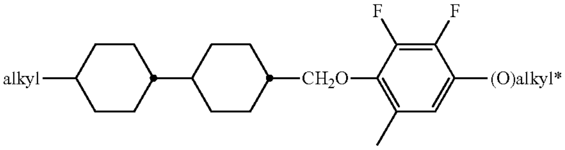
IIA-45
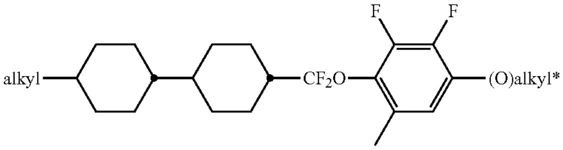
IIA-46
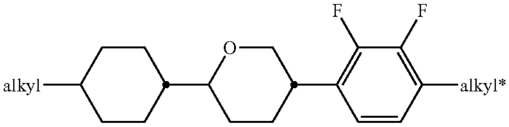
IIA-47
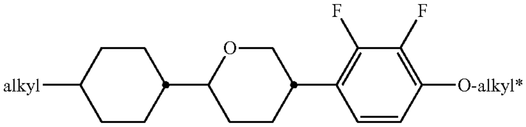
IIA-48
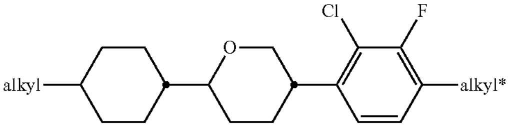
IIA-49
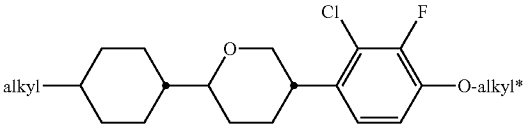
-continued
IIA-50
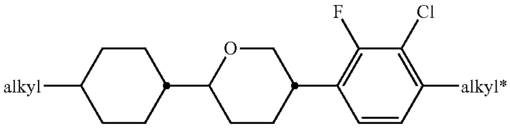
IIA-51
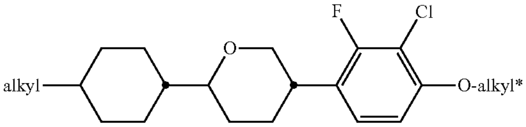
IIA-52
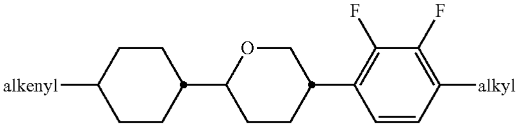
IIA-53
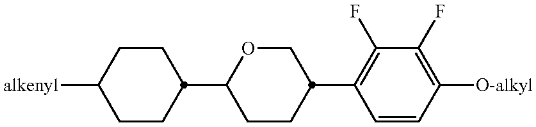
IIB-1
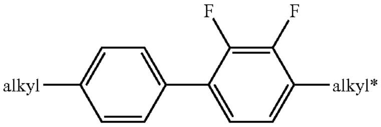
IIB-2
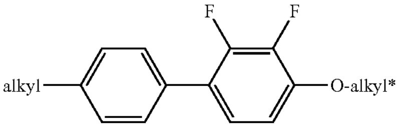
IIB-3
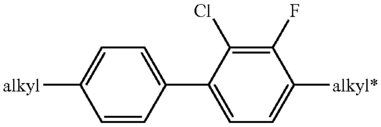
IIB-4
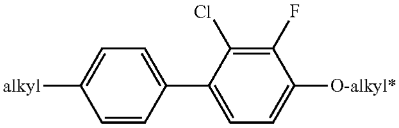
IIB-5
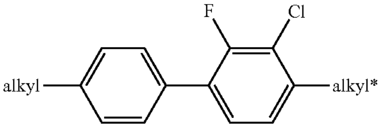
IIB-6
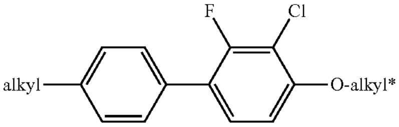
IIB-7
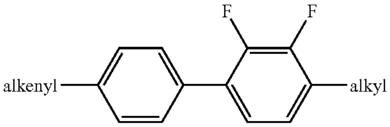

-continued
IIB-8
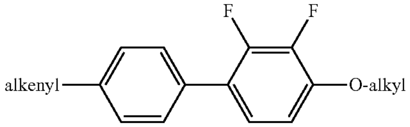
IIB-9
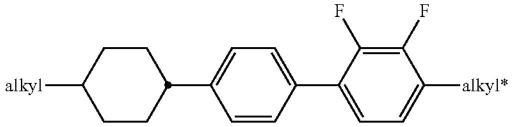
IIB-10
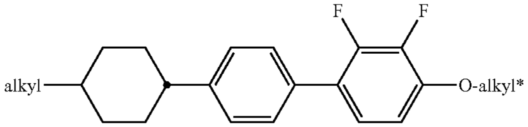
IIB-11
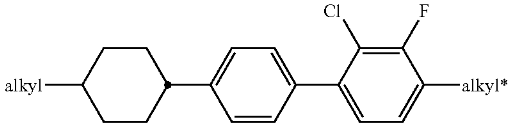
IIB-12
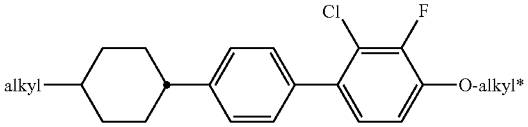
IIB-13
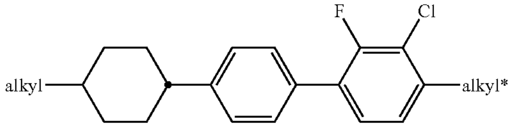
IIB-14
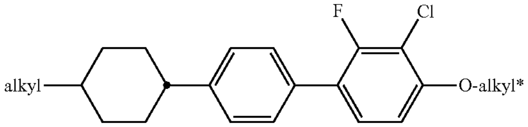
IIB-15
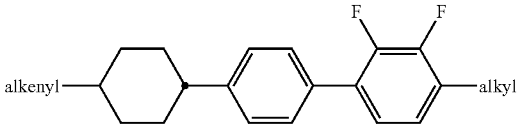
IIB-16
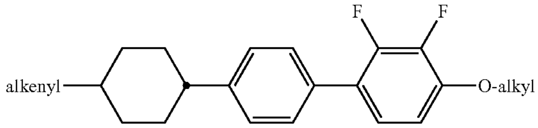
IIB-17
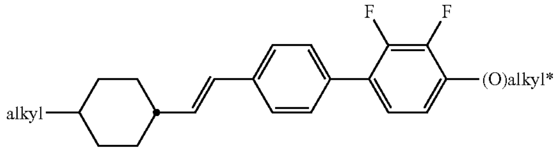
-continued
IIB-18
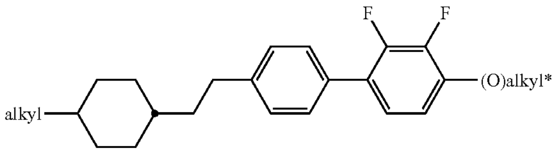
IIB-19
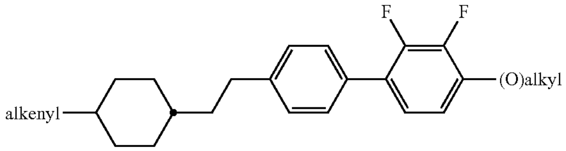
IIB-20
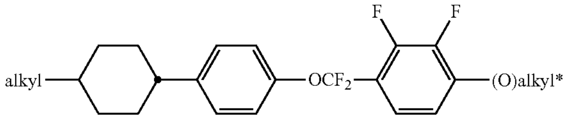
IIB-21
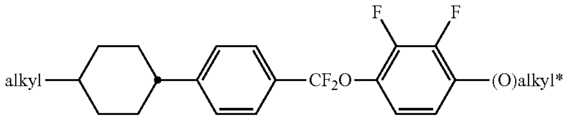
IIB-22
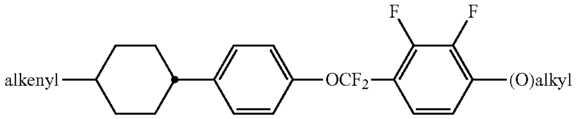
IIB-23
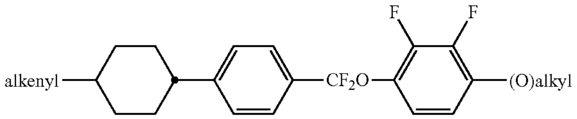
IIB-24
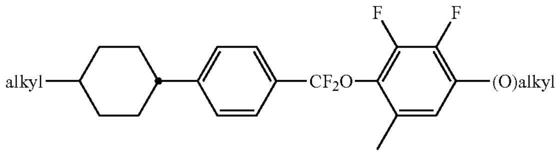
IIB-25
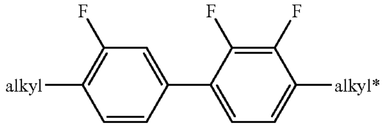
IIB-26
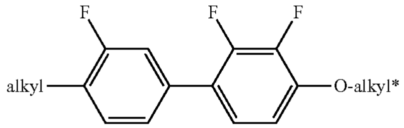
IIB-27
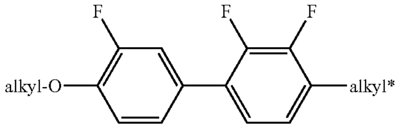

-continued

IIB-28

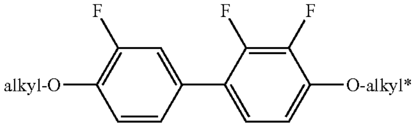

IIC-1

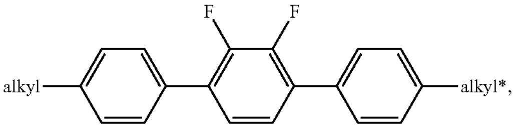

IID-1

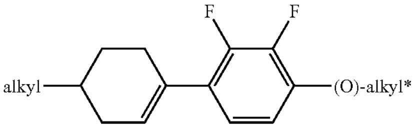

IID-2

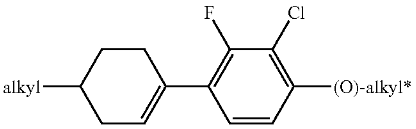

IID-3

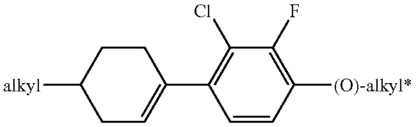

IID-4

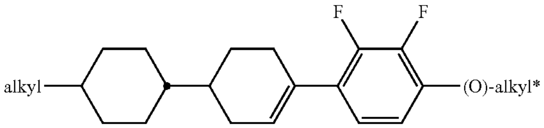

IID-5

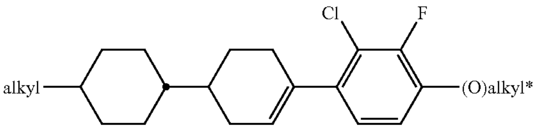

IID-6

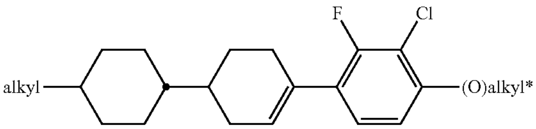

IID-7

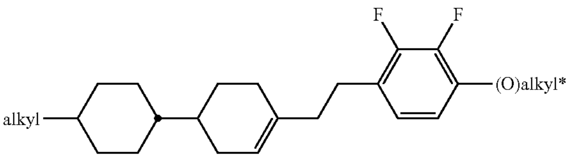

IID-8

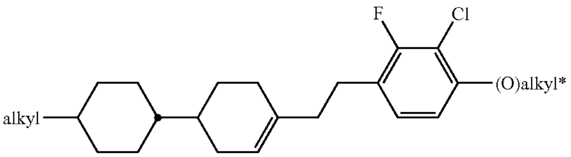

-continued

IID-9

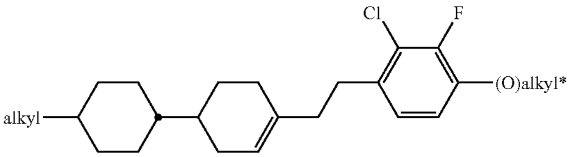

IID-10

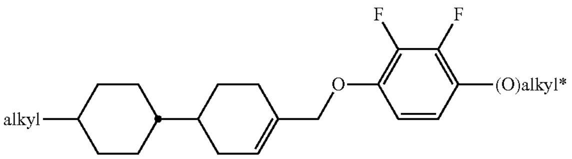

IID-11

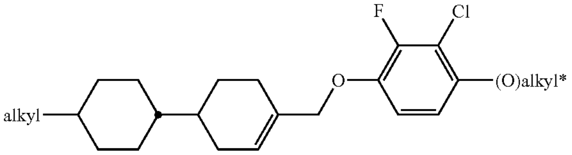

IID-12

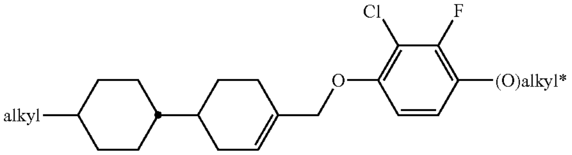

IID-13

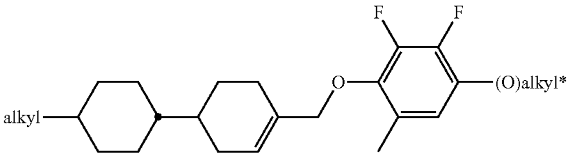

in which the parameter a denotes 1 or 2, alkyl and alkyl* each, independently of one another, denote a straight-chain alkyl radical having 1-6 C atoms, and alkenyl and alkenyl* each, independently of one another, denote a straight-chain alkenyl radical having 2-6 C atoms, and (O) denotes an oxygen atom or a single bond. Alkenyl and alkenyl* preferably denotes $CH_2$═CH—, $CH_2$═$CHCH_2CH_2$—, $CH_3$—CH═CH—, $CH_3$—$CH_2$—CH═CH—, $CH_3$—$(CH_2)_2$—CH═CH—, $CH_3$—$(CH_2)_3$—CH═CH— or $CH_3$—CH═CH—$(CH_2)_2$—.

Very preferred compounds of the formula IID are selected from the following sub-formulae:

IID-10-1

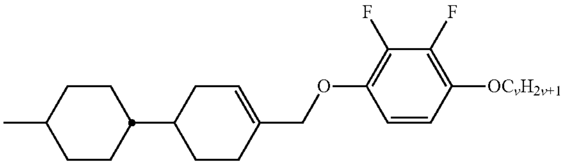

-continued
IID-10-2
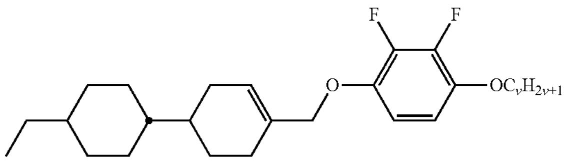
IID-10-3
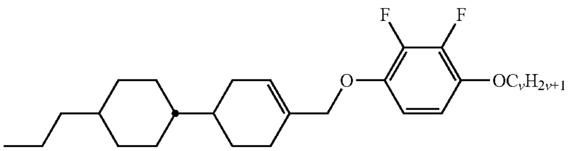
IID-10-4
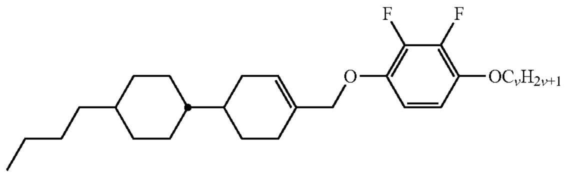
IID-10-5
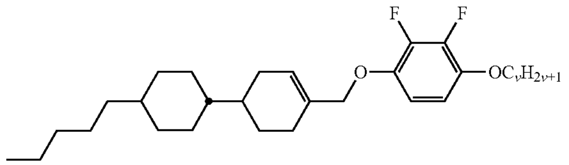
IID-10-6
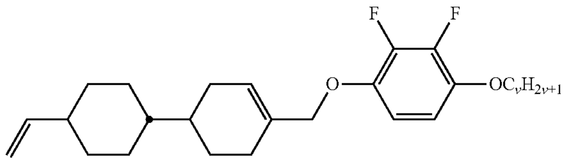
IID-10-7
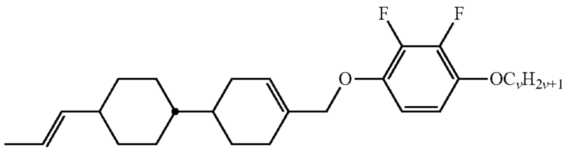
IID-10-8
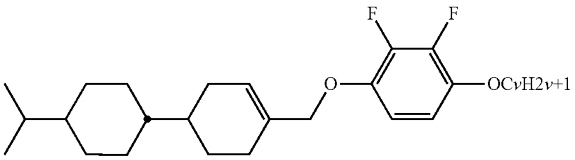
IID-10-9
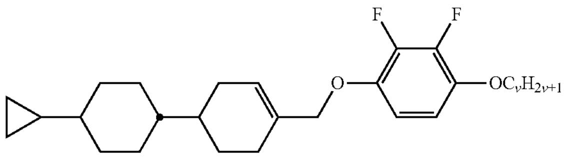
-continued
IID-10-10
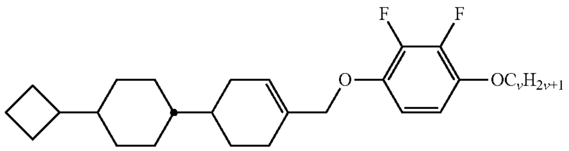
IID-10-11
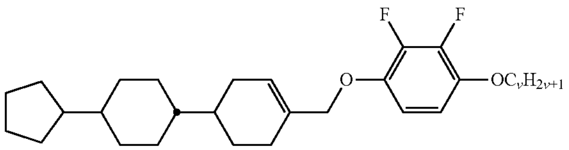
IID-10-12
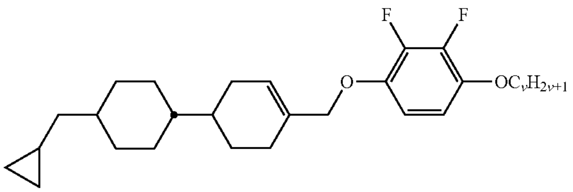
IID-10-13
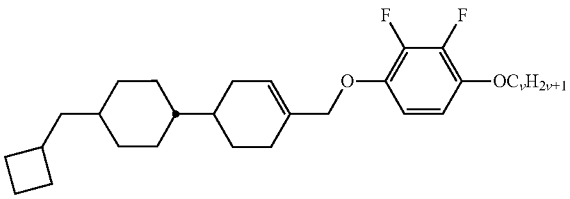
IID-10-14
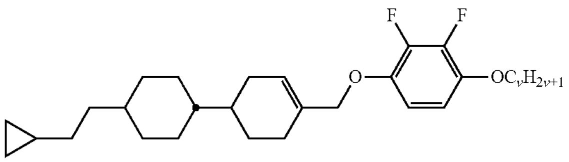
IID-10-15
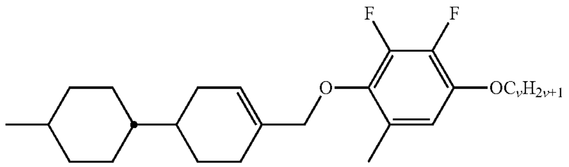
IID-10-16
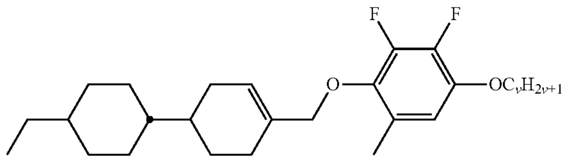
IID-10-17
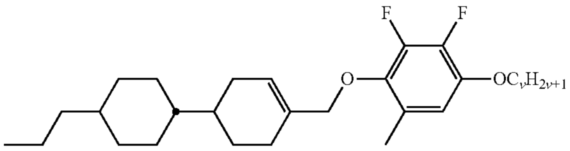

-continued
IID-10-18
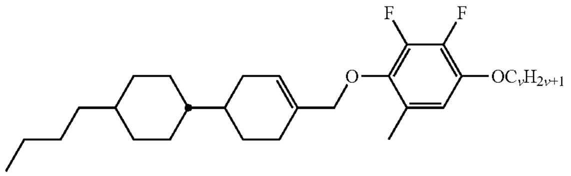
IID-10-19
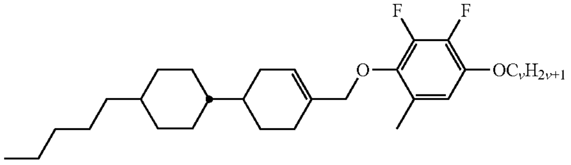
IID-10-20
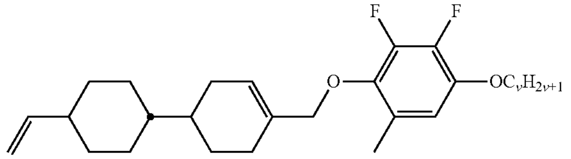
IID-10-21
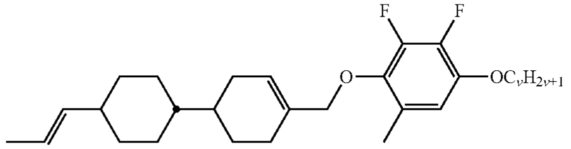
IID-10-22
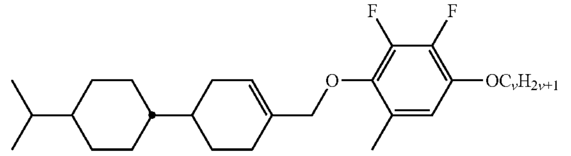
IID-10-23
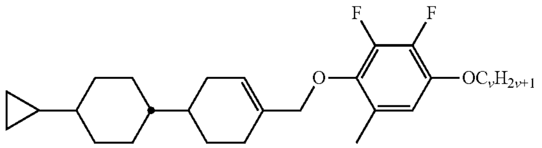
IID-10-24
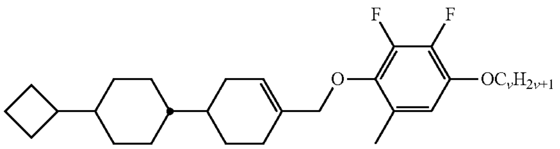
IID-10-25
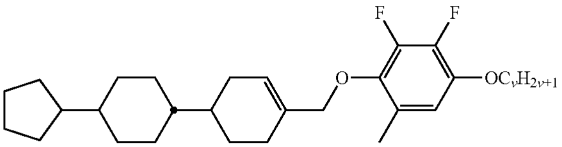
-continued
IID-10-26
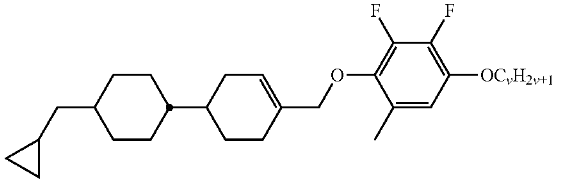
IID-10-27
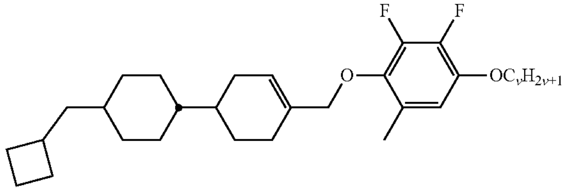
IID-10-28
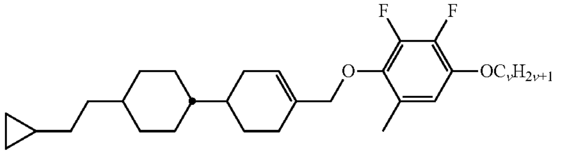
IID-10-29
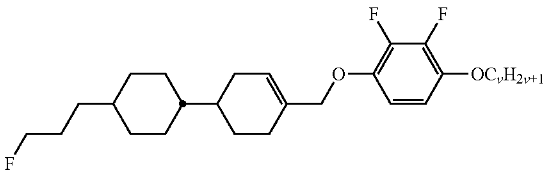
IID-10-30
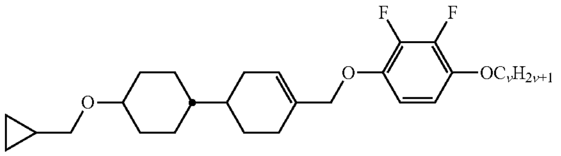
In a preferred embodiment, the medium comprises one or more compounds of formula
IID-10a
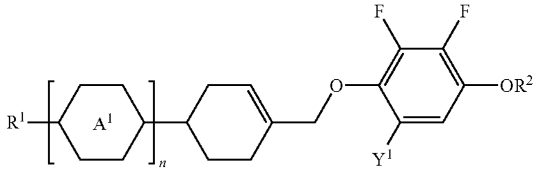
in which the occurring groups and parameters have the meanings given above under formula IID, and
$R^2$ denotes
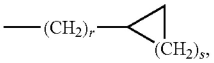
in which r is 0, 1, 2, 3, 4, 5 or 6 and s is 1, 2 or 3.
Preferred compounds of formula IID-10a are the compounds IID-10a-1 to IID-10a-14.

IID-10a-1

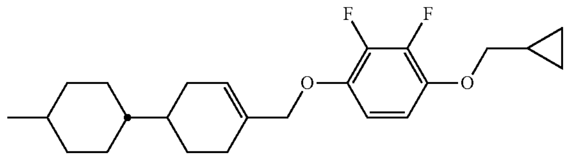

IID-10a-2

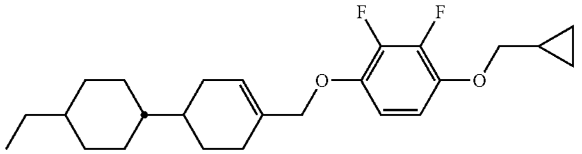

IID-10a-3

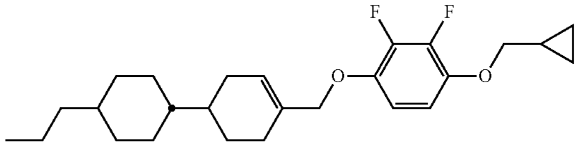

IID-10a-4

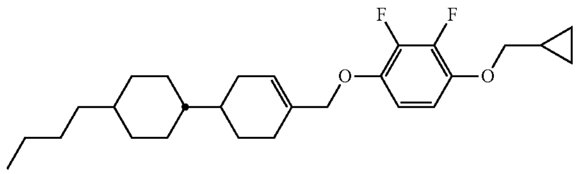

IID-10a-5

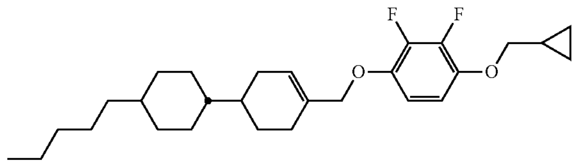

IID-10a-6

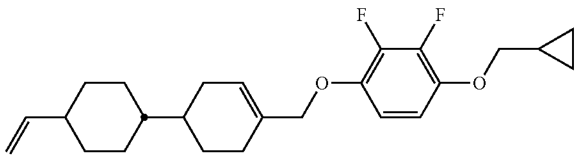

IID-10a-7

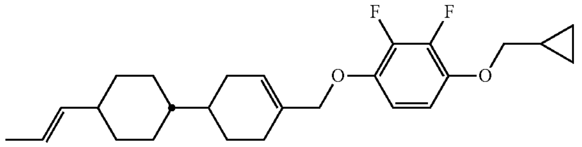

IID-10a-8

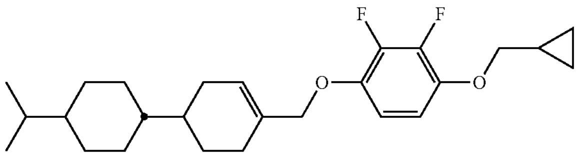

-continued

IID-10a-9

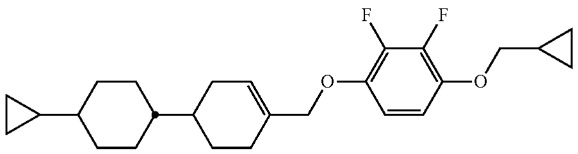

IID-10a-10

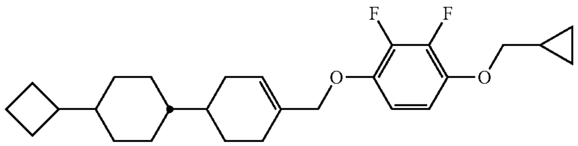

IID-10a-11

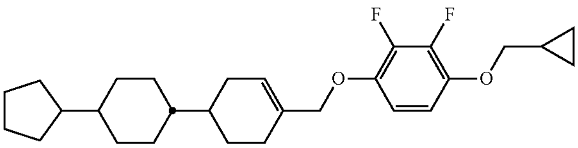

IID-10a-12

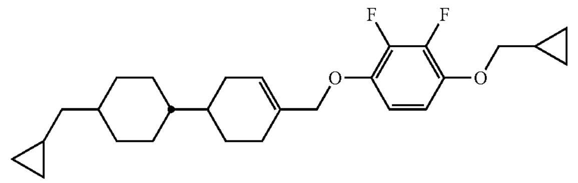

IID-10a-13

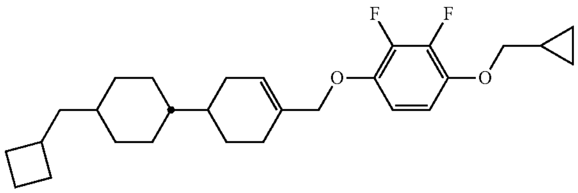

IID-10a-14

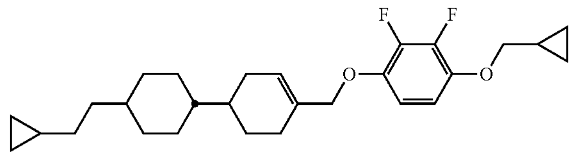

Particularly preferred mixtures according to the invention comprise one or more compounds of the formulae IIA-2, IIA-8, IIA-10, IIA-16, IIA-18, IIA-40, IIA-41, IIA-42, IIA-43, IIB-2, IIB-10, IIB-16, IIC-1, IID-4, and IID-10.

Preferred media according to the invention comprise at least one compound of the formula IIC-1,

IIC-1

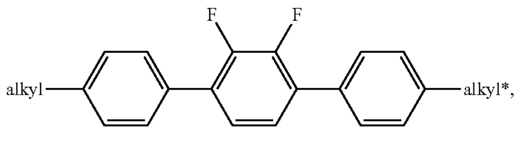

in which alkyl and alkyl* have the meanings indicated above.

In particular, the medium comprises one or more compounds of the formula IIA-2 selected from the following sub-formulae:

IIA-2-1

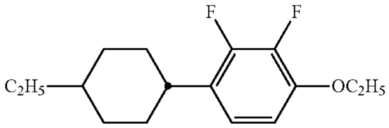

IIA-2-2

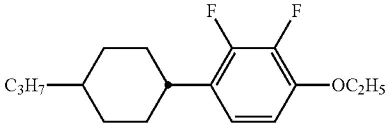

IIA-2-3

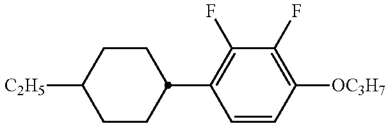

IIA-2-4

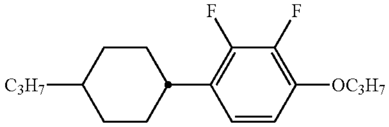

IIA-2-5

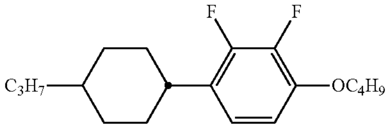

Alternatively, preferably in addition to the compounds of the formulae IIA-2-1 to IIA-2-5, the medium comprises one or more compounds of the formulae IIA-2a-1 to IIA-2a-5:

IIA-2a-1

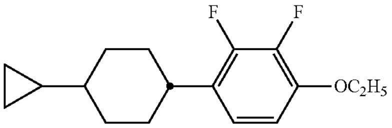

IIA-2a-2

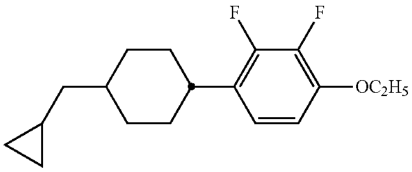

IIA-2a-3

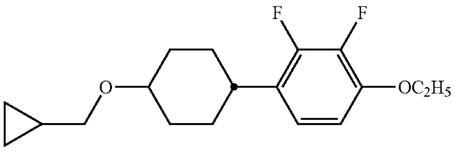

-continued

IIA-2a-4

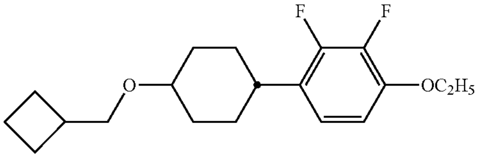

IIA-2a-5

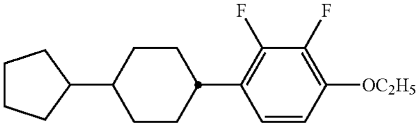

In particular, the medium comprises one or more compounds of the formula IIA-10 selected from the following sub-formulae:

IIA-10-1

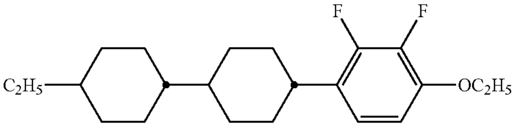

IIA-10-2

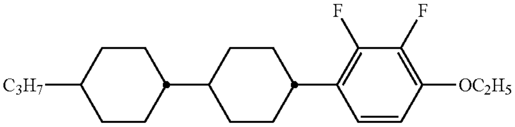

IIA-10-3

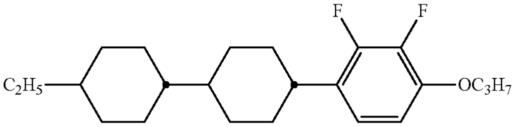

IIA-10-4

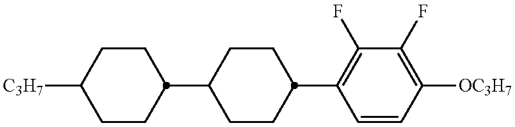

IIA-10-5

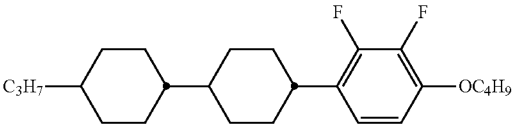

Alternatively, preferably in addition to the compounds of the formulae IIA-10-1 to IIA-10-5, the medium comprises one or more compounds of the formulae IIA-10a-1 to IIA-10a-5:

IIA-10a-1

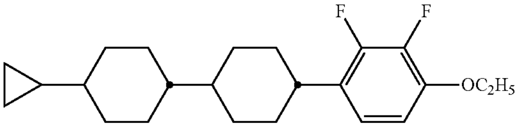

-continued

IIA-10a-2

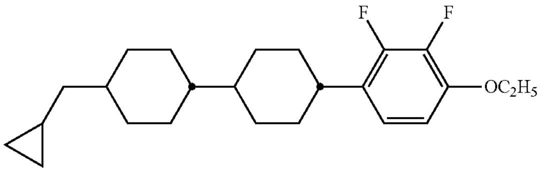

IIA-10a-3

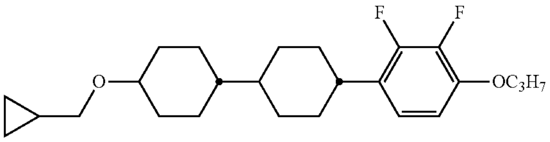

IIA-10a-4

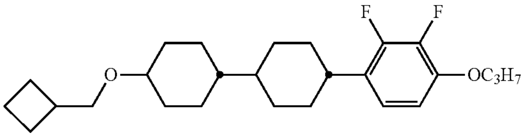

IIA-10a-5

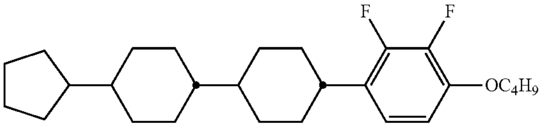

In particular, the medium comprises one or more compounds of the formula IIB-10 selected from the following sub-formulae:

IIB-10-1

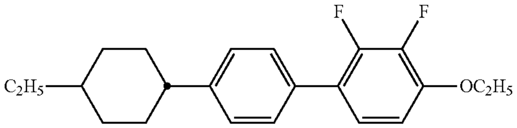

IIB-10-2

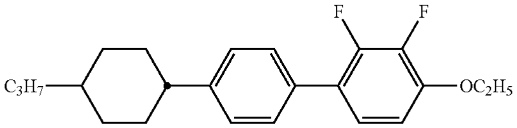

IIB-10-3

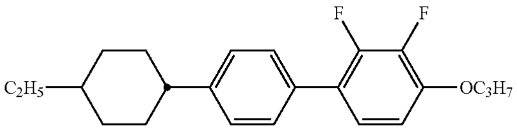

IIB-10-4

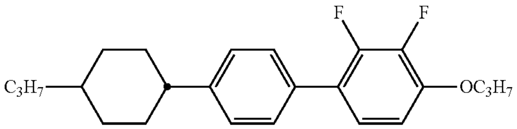

-continued

IIB-10-5

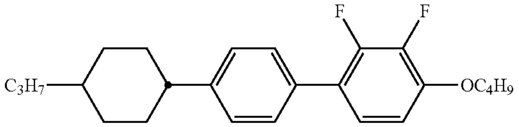

Alternatively, preferably in addition to the compounds of the formulae IIB-10-1 to IIB-10-5, the medium comprises one or more compounds of the formulae IIB-10a-1 to IIB-10a-5:

IIA-10a-1

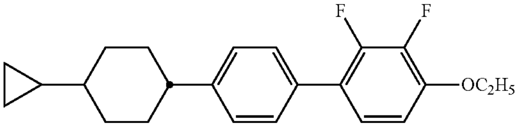

IIA-10a-2

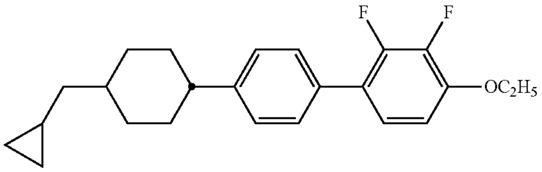

IIA-10a-3

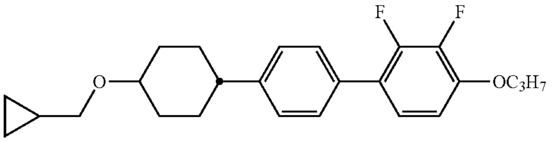

IIA-10a-4

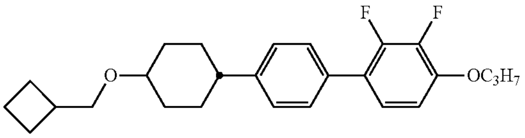

IIA-10a-5

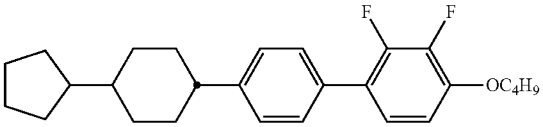

Alternatively, preferably in addition to the compounds of the formulae IIC-1, the medium comprises one or more compounds of the formulae IIC-1a-1 and IIC-1a-2

IIC-1a-1

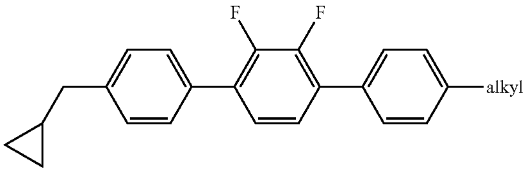

-continued

IIC-1a-2

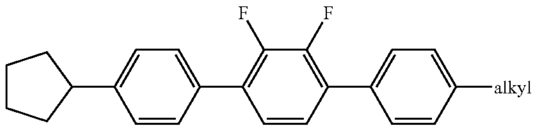

in which alkyl denotes straight chain alkyl having 1 to 7 C atoms, preferably 2 to 5 C atoms, very preferably denotes ethyl.

The medium according to the invention preferably comprises one or more compounds of formula III

III

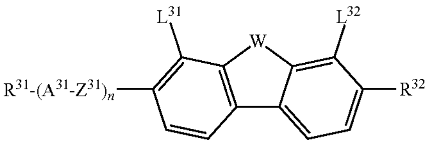

in which $R^{31}$ and $R^{32}$ each, independently of one another, denote H, an alkyl or alkoxy radical having 1 to 15 C atoms, where one or more $CH_2$ groups in these radicals may each be replaced, independently of one another, by

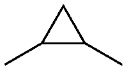, 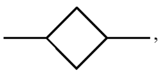, 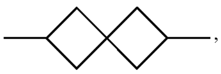,

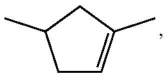, 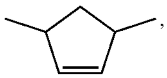, 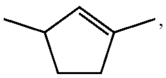,

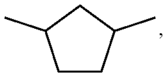,

—CH═CH—, —C≡C—, —$CF_2$O—, —O$CF_2$—, —O—, —CO—O— or —O—CO— in such a way that O atoms are not linked directly to one another, and in which one or more H atoms may be replaced by halogen, $A^{31}$ on each occurrence, independently of one another, denotes a) 1,4-cyclohexenylene or 1,4-cyclohexylene radical, in which one or two non-adjacent $CH_2$ groups may be replaced by —O— or —S—, b) a 1,4-phenylene radical, in which one or two CH groups may be replaced by N, or c) a radical from the group spiro[3.3]heptane-2,6-diyl, 1,4-bicyclo[2.2.2]octylene, naphthalene-2,6-diyl, decahydronaphthalene-2,6-diyl, 1,2,3,4-tetrahydronaphthalene-2,6-diyl, phenanthrene-2,7-diyl and fluorene-2,7-diyl, where the radicals a), b) and c) may be mono- or polysubstituted by halogen atoms, n denotes 0, 1 or 2, preferably 0 or 1, $Z^{31}$ on each occurrence independently of one another denotes —CO—O—, —O—CO—, —$CF_2$O—, —O$CF_2$—, —$CH_2$O—, —O$CH_2$—, —$CH_2$—, —$CH_2CH_2$—, —$(CH_2)_4$—, —CH═CH—$CH_2$O—, —$C_2F_4$—, —$CH_2CF_2$—, —$CF_2CH_2$—, —CF═CF—, —CH═CF—, —CF═CH—, —CH═CH—, —C≡C— or a single bond, and $L^{31}$ and $L^{32}$ each, independently of one another, denote F, Cl, $CF_3$ or $CHF_2$, preferably H or F, most preferably F, and W denotes O or S.

The compounds of formula III are preferably selected from the compounds of the formula III-1 and/or III-2

III-1

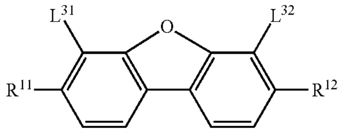

III-2

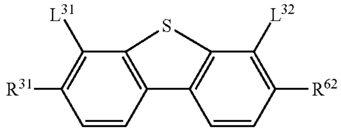

in which the occurring groups have the same meanings as given under formula III above and preferably $R^{31}$ and $R^{32}$ each, independently of one another, an alkyl, alkenyl or alkoxy radical having up to 15 C atoms, more preferably one or both of them denote an alkoxy radical and $L^{31}$ and $L^{32}$ each preferably denote F.

Preferably, the compounds of the formula III-1 are selected from the group of compounds of the formulae III-1-1 to III-1-11, preferably of formula III-1-6,

III-1-1

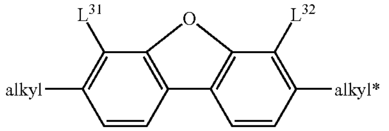

III-1-2

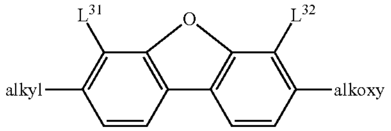

III-1-3

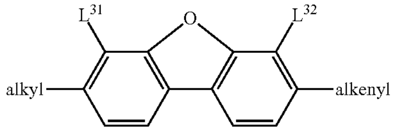

III-1-4

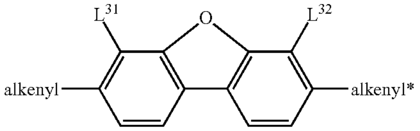

III-1-5

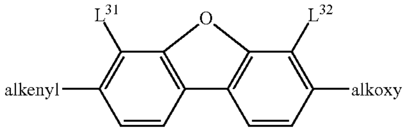

-continued

III-1-6

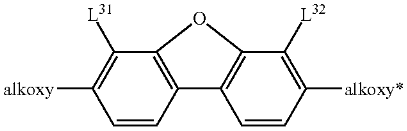

III-1-7

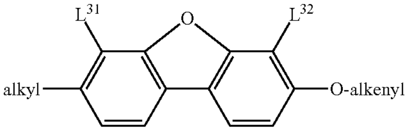

III-1-8

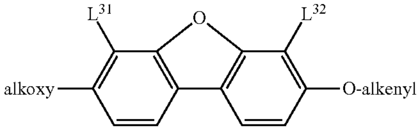

III-1-9

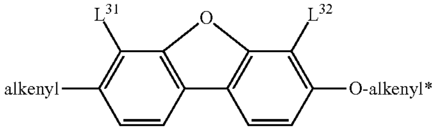

III-1-10

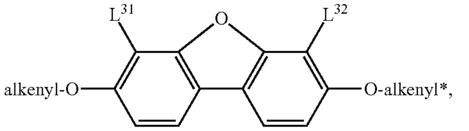

in which alkyl and alkyl* each, independently of one another, denote a straight-chain alkyl radical having 1-6 C atoms, alkenyl, and alkenyl* each, independently of one another, denote a straight-chain alkenyl radical having 2-6 C atoms, alkoxy and alkoxy* each, independently of one another, denote a straight-chain alkoxy radical having 1-6 C atoms, and $L^{31}$ and $L^{32}$ each, independently of one another, denote F or Cl, preferably both F.

Preferably, the compounds of the formula III-2 are selected from the group of compounds of the formulae III-2-1 to III-2-10, preferably of formula III-2-6,

III-2-1

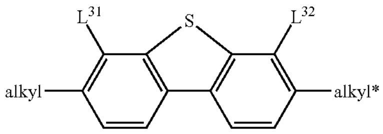

III-2-2

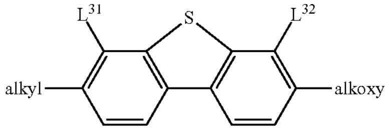

III-2-3

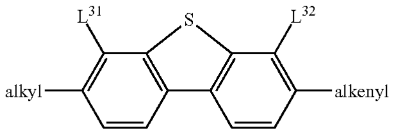

-continued

III-2-4

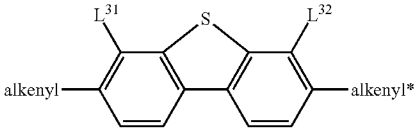

III-2-5

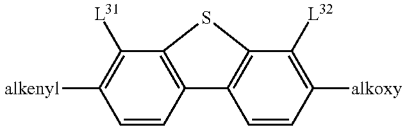

III-2-6

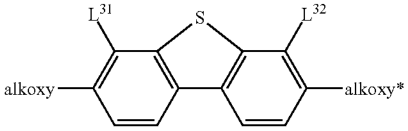

III-2-7

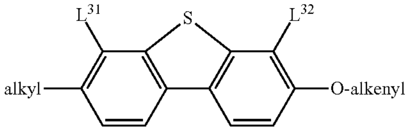

III-2-8

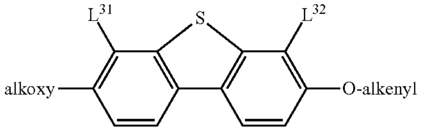

III-2-9

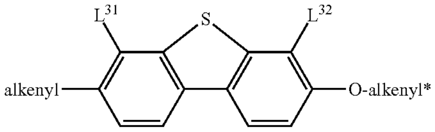

III-2-10

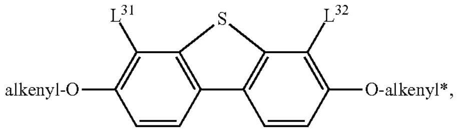

in which alkyl and alkyl* each, independently of one another, denote a straight-chain alkyl radical having 1-6 C atoms, alkenyl, and alkenyl* each, independently of one another, denote a straight-chain alkenyl radical having 2-6 C atoms, alkoxy and alkoxy* each, independently of one another, denote a straight-chain alkoxy radical having 1-6 C atoms, and $L^{31}$ and $L^{32}$ each, independently of one another, denote F or Cl, preferably both F.

Optionally the medium comprises one or more compounds of the formula IIIA-1 and/or IIIA-2

IIIA-1

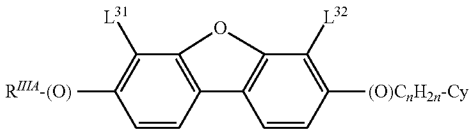

-continued

IIIA-2

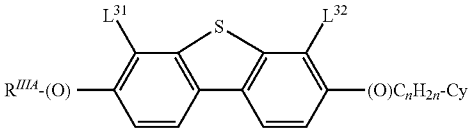

in which $L^{31}$ and $L^{32}$ have the same meanings as given under formula III, (O) denotes O or a single bond, $R^{IIIA}$ denotes alkyl or alkenyl having up to 7 C atoms or a group Cy-$C_mH_{2m+1}$—, m and n are, identically or differently, 0, 1, 2, 3, 4, 5 or 6, preferably 1, 2 or 3, very preferably 1, Cy denotes a cycloaliphatic group having 3, 4 or 5 ring atoms, which is optionally substituted with alkyl or alkenyl each having up to 3 C atoms, or with halogen or CN, and preferably denotes cyclopropyl, cyclobutyl, cyclopentyl, cyclopent-1-enyl, cyclopent-2-enyl and cyclopent-3-enyl.

The compounds of formula IIIA-1 and/or IIIA-2 are contained in the medium either alternatively or in addition to the compounds of formula III, preferably additionally.

Very preferred compounds of the formulae IIIA-1 and IIIA-2 are the following:

IIIA-1-1

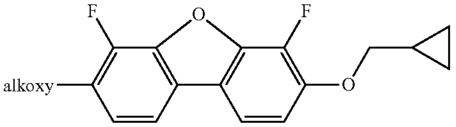

IIIA-1-2

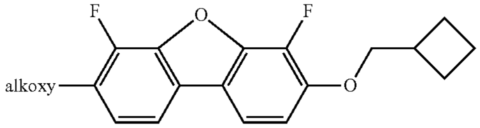

IIIA-1-3

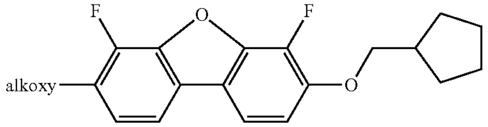

IIIA-1-4

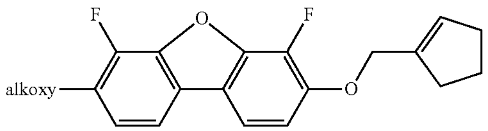

IIIA-1-5

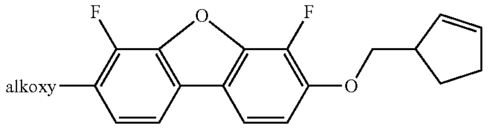

IIIA-1-6

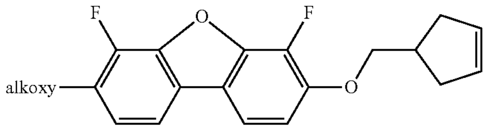

-continued

IIIA-2-1

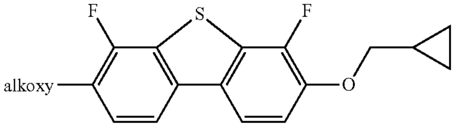

IIIA-2-2

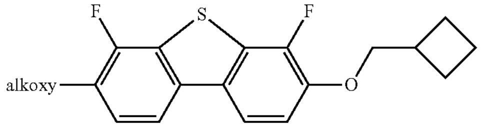

IIIA-2-3

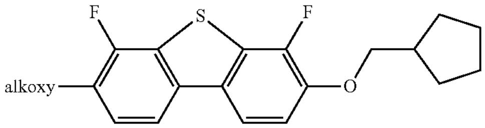

IIIA-2-4

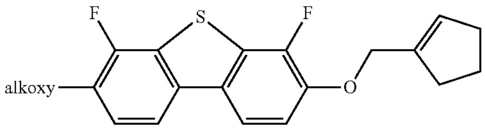

IIIA-2-5

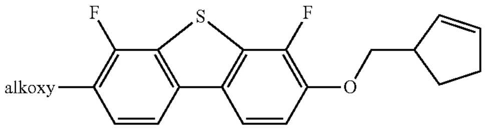

IIIA-2-6

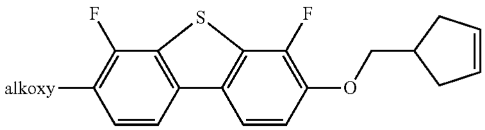

in which alkoxy denotes a straight-chain alkoxy radical having 1-6 C atoms or alternatively —$(CH_2)_nF$ in which n is 2,3,4, or 5, preferably $C_2H_4F$.

In a preferred embodiment of the present invention, the medium comprises one or more compounds of formula III-3

III-3

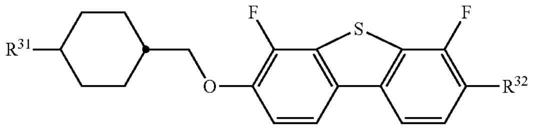

in which $R^{31}$, $R^{32}$ identically or differently, denote H, an alkyl or alkoxy radical having 1 to 15 C atoms, in which one or more $CH_2$ groups in these radicals are optionally replaced, independently of one another, by —C≡C—, —$CF_2O$—, —$OCF_2$—, —CH═CH—,

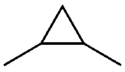, 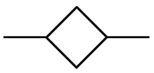, 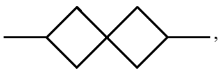,

-continued

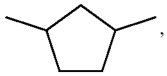,

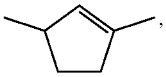,

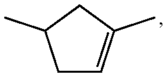,

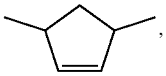,

—O—, —CO—O— or —O—CO— in such a way that O atoms are not linked directly to one another, and in which, in addition, one or more H atoms may be replaced by halogen.

The compounds of formula III-3 are preferably selected from the group of compounds of the formulae III-3-1 to III-3-10:

III-3-1

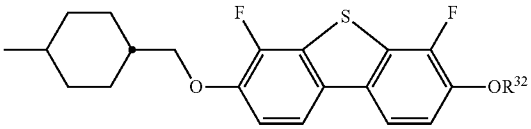

III-3-2

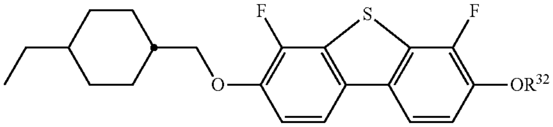

III-3-3

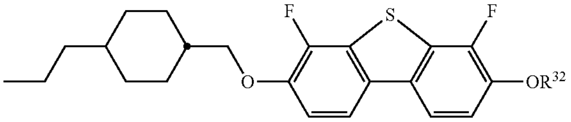

III-3-4

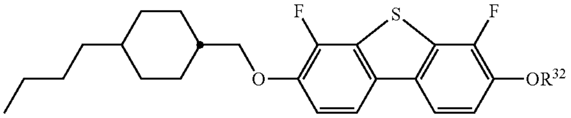

III-3-5

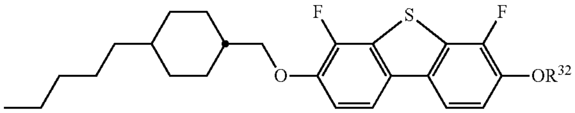

III-3-6

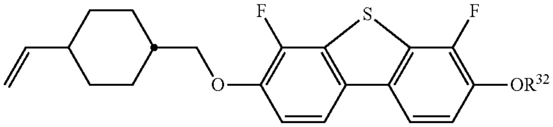

III-3-7

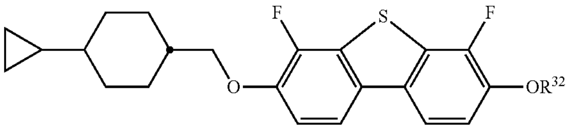

-continued

III-3-8

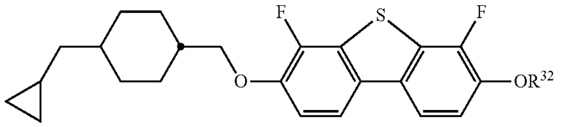

III-3-9

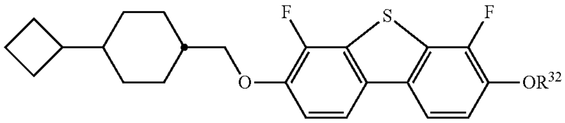

III-3-10

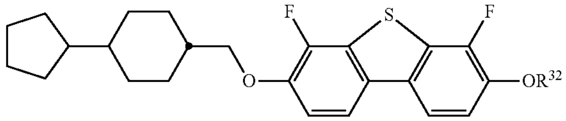

in which R denotes alkyl having 1 to 7 C-atoms, preferably ethyl, n-propyl or n-butyl, or alternatively cyclopropylmethyl, cyclobutylmethyl or cyclopentylmethyl or alternatively —$(CH_2)_n$F in which n is 2,3,4, or 5, preferably $C_2H_4F$.

In a preferred embodiment of the present invention, the medium comprises one or more compounds of the formulae III-4 to III-6, preferably of formula III-5,

III-4

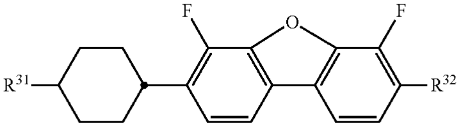

III-5

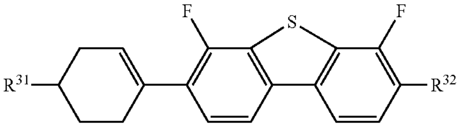

III-6

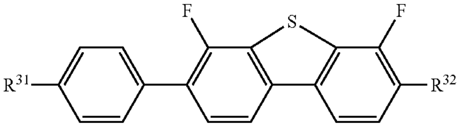

in which the parameters have the meanings given above, $R^{31}$ preferably denotes straight-chain alkyl and $R^{32}$ preferably denotes alkoxy, each having 1 to 7 C atoms.

In a preferred embodiment the medium comprises one or more compounds of the formula III selected from the group of compounds of formulae III-7 to III-9, preferably of formula III-8,

III-7

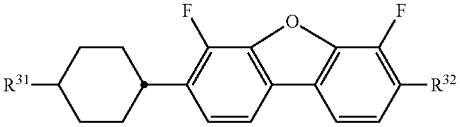

-continued

III-8

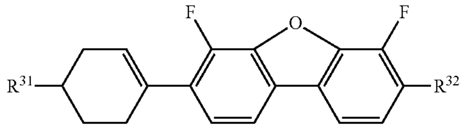

III-9

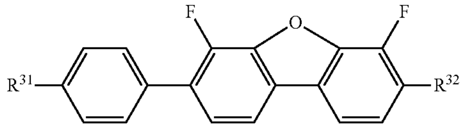

in which the parameters have the meanings given above, R preferably denotes straight-chain alkyl and $R^{32}$ preferably denotes alkoxy each having 1 to 7 C atoms.

In a preferred embodiment, the medium comprises one or more compounds of the formula IV,

IV

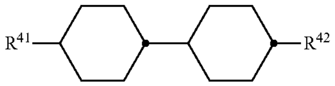

in which $R^{41}$ denotes an alkyl radical having 1 to 7 C atoms or an alkenyl radical having 2 to 7 C atoms, preferably an n-alkyl radical, particularly preferably having 2, 3, 4 or 5 C atoms, and $R^{42}$ denotes an alkyl radical having 1 to 7 C atoms or an alkoxy radical having 1 to 6 C atoms, both preferably having 2 to 5 C atoms, an alkenyl radical having 2 to 7 C atoms, preferably having 2, 3 or 4 C atoms, more preferably a vinyl radical or a 1-propenyl radical and in particular a vinyl radical.

The compounds of the formula IV are preferably selected from the group of the compounds of the formulae IV-1 to IV-4,

IV-1

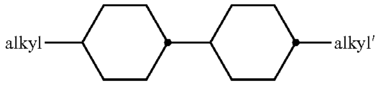

IV-2

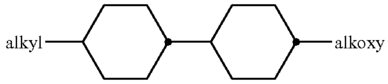

IV-3

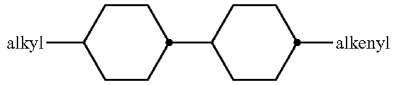

IV-4

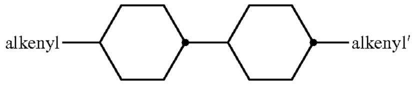

in which alkyl and alkyl', independently of one another, denote alkyl having 1 to 7 C atoms, preferably having 1 to 5 C atoms, alkenyl denotes an alkenyl radical having 2 to 5 C atoms, preferably having 2 to 4 C atoms, particularly preferably 2 C atoms, alkenyl' denotes an alkenyl radical having 2 to 5 C atoms, preferably having 2 to 4 C atoms, particularly preferably having 2 to 3 C atoms, and alkoxy denotes alkoxy having 1 to 5 C atoms, preferably having 2 to 4 C atoms.

The compounds of the formula IV-1 are preferably selected from the group of compounds of the formulae IV-1-1 to IV-1-6

IV-1-1

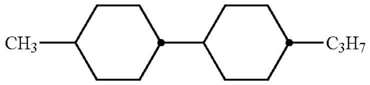

IV-1-2

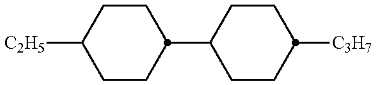

IV-1-3

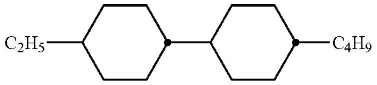

IV-1-4

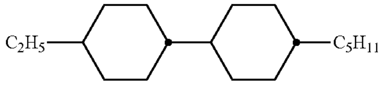

IV-1-5

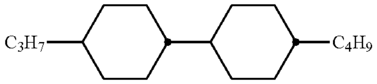

IV-1-6

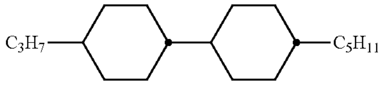

The compounds of the formula IV-2 are preferably selected from the compounds of the formulae IV-2-1 and IV-2-2

IV-2-1

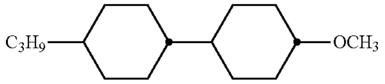

IV-2-2

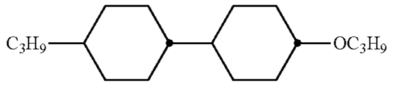

The compounds of the formula IV-3 are preferably selected from the group of the compounds of the formulae IV-3-1, IV-3-2 and IV-3-3:

IV-3-1

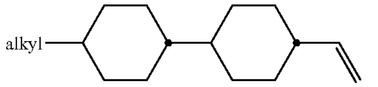

IV-3-2

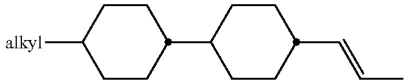

-continued

IV-3-3

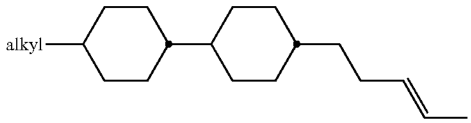

in which alkyl has the meanings defined above and where the compound of the formula I is excluded from formula IV-3-2.

The compounds of the formula IV-3-1, IV-3-2 and IV-3-3 are preferably selected from the following compounds:

IV-3-1a

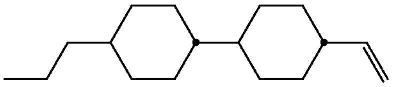

IV-3-1b

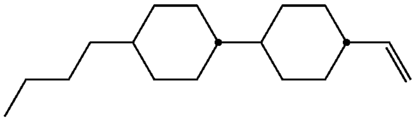

IV-3-1c

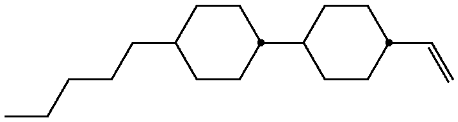

IV-3-2a

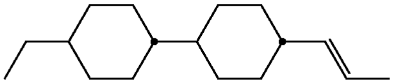

IV-3-2b

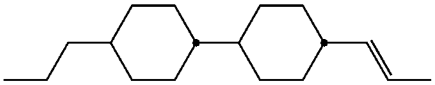

IV-3-2c

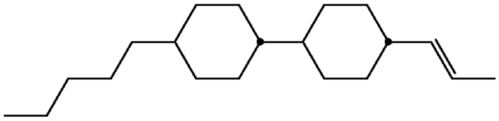

IV-3-3a

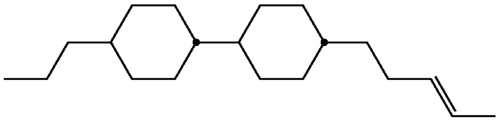

Very preferably, the medium according to the invention comprises a compound of formula IV-4 in particular selected from the compounds of the formulae IV-4-1 to IV-4-3

IV-4-1

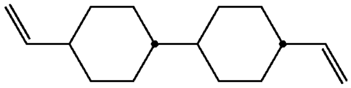

IV-4-2

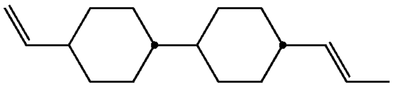

-continued

IV-4-3

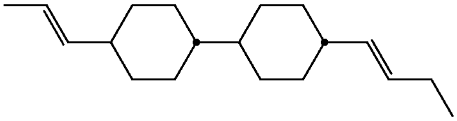

The liquid-crystalline medium preferably additionally comprises one or more compounds of the formula IVa, IVa

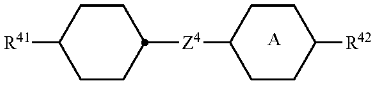

in which $R^{41}$ and $R^{42}$ each, independently of one another, denote a straight-chain alkyl, alkoxy, alkenyl, alkoxyalkyl or alkoxy radical having up to 12 C atoms, and

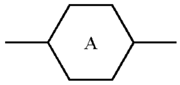 denotes 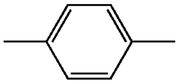,

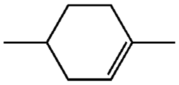, 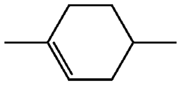,

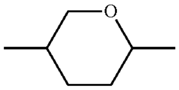 or 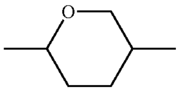, $Z^4$ denotes a single bond, —$CH_2CH_2$—, —CH=CH—, —$CF_2O$—, —$OCF_2$—, —$CH_2O$—, —$OCH_2$—, —COO—, —OCO—, —$C_2F_4$—, —$C_4He$—, —CF=CF—.

Preferred compounds of the formula IVa are indicated below:

IVa-1

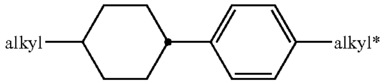

IVa-2

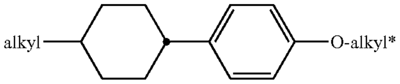

IVa-3

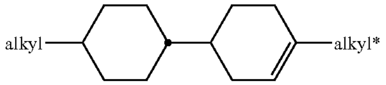

IVa-4

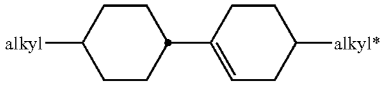

in which alkyl and alkyl* each, independently of one another, denote a straight-chain alkyl radical having 1 to 6 C atoms.

The medium according to the invention preferably comprises at least one compound of the formula IVa-1 and/or formula IVa-2.

The proportion of compounds of the formula IVa in the mixture as a whole is preferably less than 5% by weight, very preferably less than 2% by weight.

Preferably, the medium comprises one or more compounds of formula IVb-1 to IVb-4, more preferably of the compounds of the formulae IVb-1 to IVb-3

IVb-1

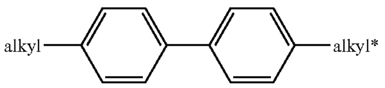

IVb-2

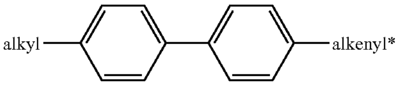

IVb-3

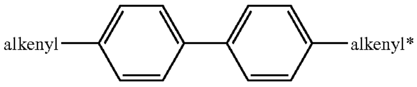

IVb-4

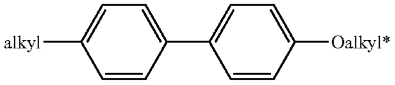

in which alkyl and alkyl* each, independently of one another, denote a straight-chain alkyl radical having 1 to 6 C atoms, and alkenyl and alkenyl* each, independently of one another, denote a straight-chain alkenyl radical having 2 to 6 C atoms.

Of the compounds of the formulae IVb-1 to IVb-3, the compounds of the formula IVb-2 are particularly preferred.

Particularly preferred biphenyls are

IVb-1-1

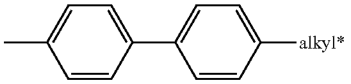

IVb-2-1

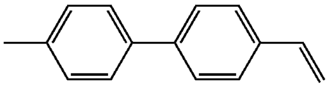

IVb-2-2

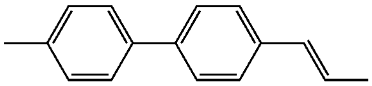

IVb-2-3

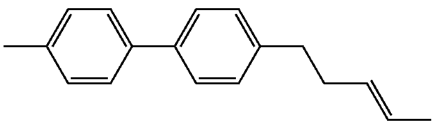

IVb-2-4

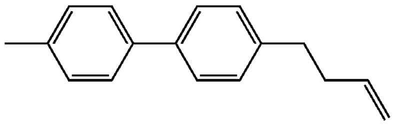

in which alkyl* denotes an alkyl radical having 1 to 6 C atoms and preferably denotes n-propyl. The medium according to the invention particularly preferably comprises one or more compounds of the formulae IVb-1-1 and/or IVb-2-3.

In a preferred embodiment, the medium according to the invention comprises one or more compounds of formula V

V

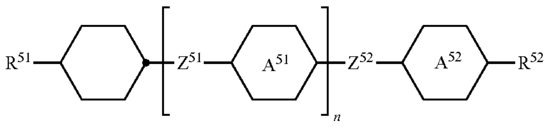

in which $R^{51}$, $R^{52}$ denote alkyl having 1 to 7 C atoms, alkoxy having 1 to 7 C atoms, or alkoxyalkyl, alkenyl or alkenyloxy having 2 to 7 C atoms,

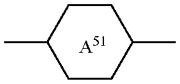 and 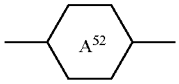 , identically or differently, denote

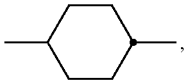 , 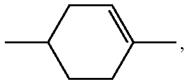 , 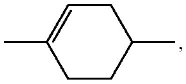 ,

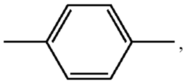 , 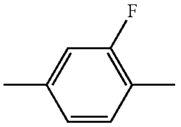 or

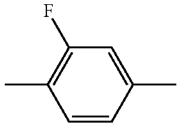 , $Z^{51}$, $Z^{52}$ each, independently of one another, denote —$CH_2$—$CH_2$—, —$CH_2$—O—, —CH═CH—, —C≡C—, —COO— or a single bond, and n is 1 or 2, where the compounds of the formula CL are excluded.

The compounds of formula V are preferably selected from the compounds of the formulae V-1, V-2 and V-3:

V-1

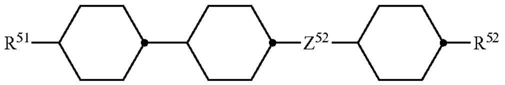

V-2

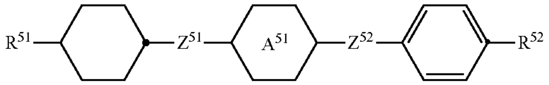

V-3

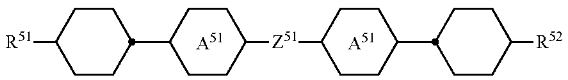

in which the groups occurring have the meanings given above for formula V.

The compounds of formula V-1 are preferably selected from the compounds of the formulae V-1-1 to V-1-8;

the compounds of formula V-2 are preferably selected from the compounds of the formulae V-2-1 to V-2-4; and the compounds of formula V-3 are preferably selected from the compounds of the formulae V-3-1 to V-3-4:

V-1-1

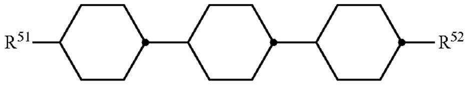

V-1-2

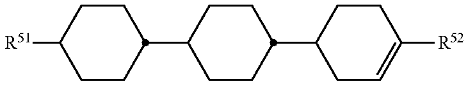

V-1-3

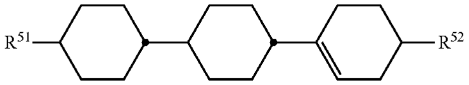

V-1-4

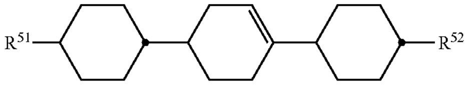

V-1-5

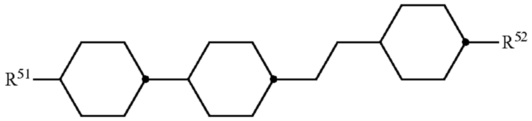

V-1-6

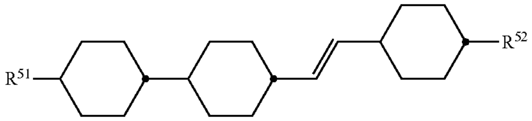

V-1-7

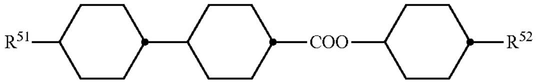

V-1-8

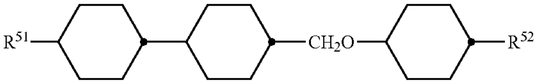

V-2-1

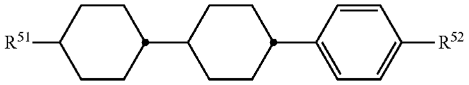

V-2-2

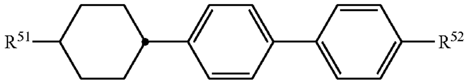

V-2-3

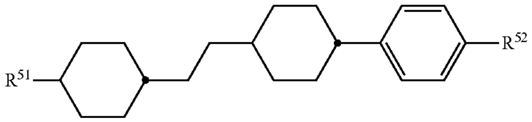

V-2-4

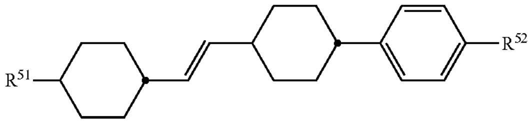

V-3-1

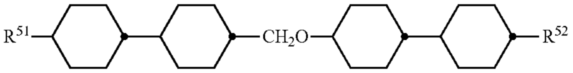

-continued

V-3-2

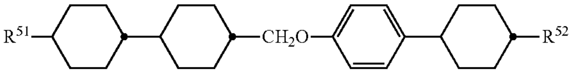

V-3-3

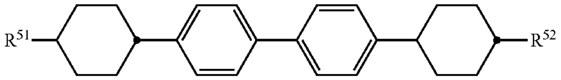

V-3-4

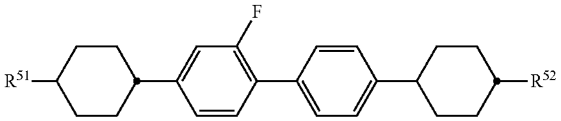

in which $R^{51}$ and $R^{52}$ have the meanings indicated for formula V above.

$R^{51}$ and $R^{52}$ preferably each, independently of one another, denote straight-chain alkyl having 1 to 7 C atoms or alkenyl having 2 to 7 C atoms.

Very preferred compounds of the formula V-2-1 are selected from the compounds of the formulae V-2-1a to V-2-1 g V-2-1a

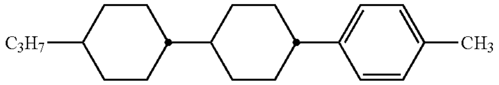

V-2-1b

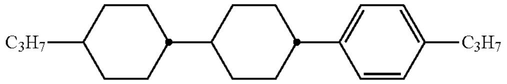

V-2-1c

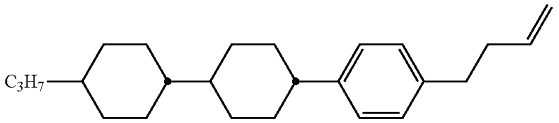

V-2-1d

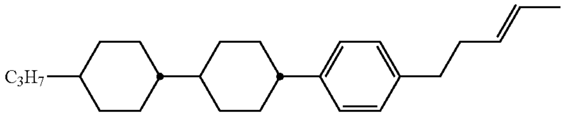

V-2-1e

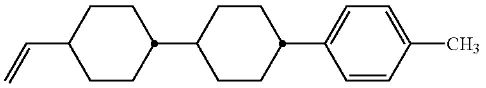

V-2-1f

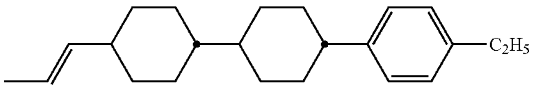

V-2-1g

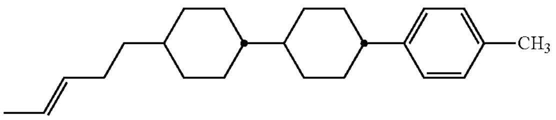

Very preferred compounds of the formula V-2-2 are selected from the compounds of the formulae V-2-2a to V-2-2i V-2-2a

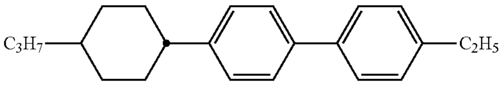

V-2-2b

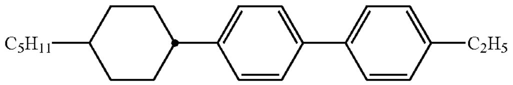

V-2-2c

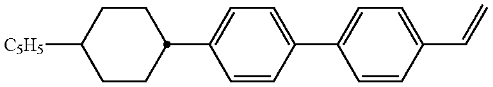

V-2-2d

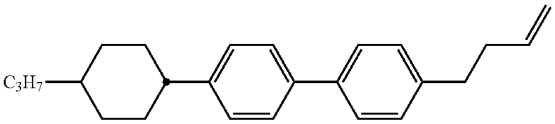

V-2-2e

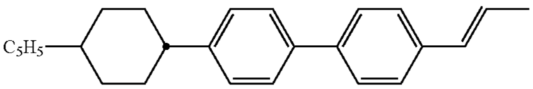

V-2-2f

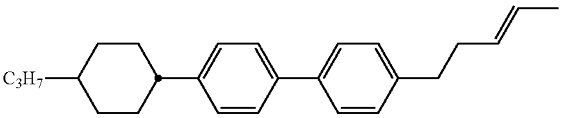

V-2-2g

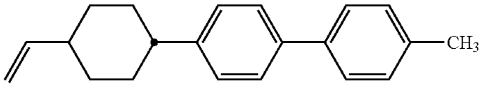

V-2-2h

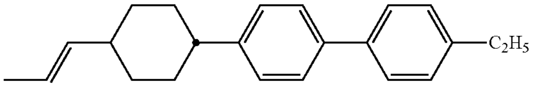

V-2-2i

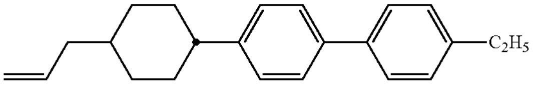

Preferably, the medium according to the invention comprises one or more compounds of the formula CL

CL

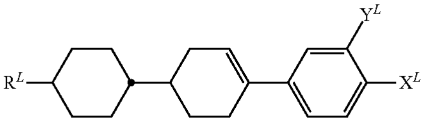

in which $R^L$ denotes H, a straight chain or branched alkyl or alkoxy radical having 1 to 15 C atoms, or a straight chain or branched alkenyl radical having 2 to 15 C atoms, where one or more $CH_2$ groups in these radicals may each be replaced, independently of one another, by

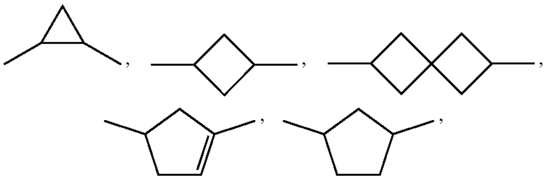

—C≡—, —$CF_2$O—, —O$CF_2$—, —CH═CH—, —O—, —CO—O— or —O—CO— in such a way that O atoms are not linked directly to one another, and in which, in addition, one or more H atoms may be replaced by halogen, $X^L$ denotes F, Cl, CN, $CHF_2$, $CF_3$, $OCF_3$, or, identically or differently, has one of the meanings of $R^L$, $Y^L$ denotes H, F, Cl or $CH_3$.

The compounds of formula CL are preferably selected form the group of compounds of the formulae CL-1, CL-2 and CL-3:

CL-1

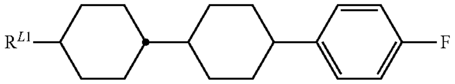

CL-2

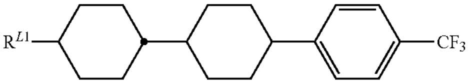

CL-3

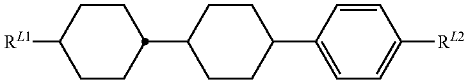

in which $R^{L1}$ and $R^{L2}$, identically or differently, have the meanings given above for formula I and, preferably denote alkyl or alkenyl having 1 to 7 C atoms or 2 to 7 C atoms, respectively, in which a $CH_2$ group may be replaced by cyclopropane-1,2-diyl, and $R^{L2}$ alternatively denotes alkoxy having 1 to 5 C atoms.

Very preferred compounds of the formula CL are selected from the compounds of the formulae CL-3-1 to CL-3-12:

CL-3-1

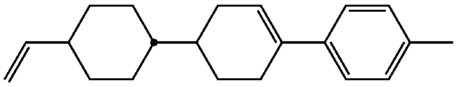

CL-3-2

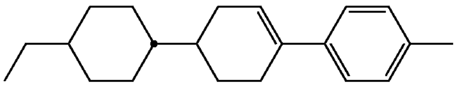

CL-3-3

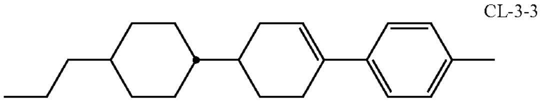

CL-3-4

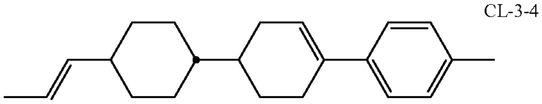

-continued

CL-3-5

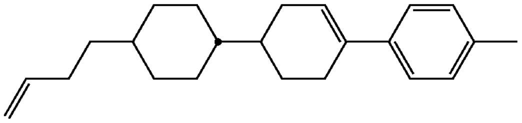

CL-3-6

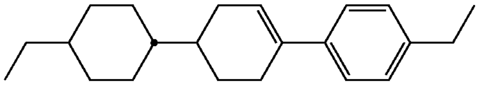

CL-3-7

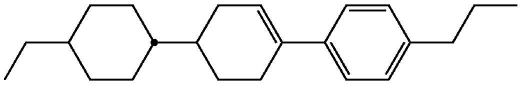

CL-3-8

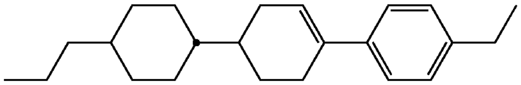

CL-3-9

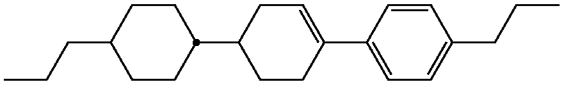

CL-3-10

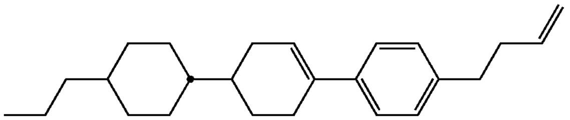

CL-3-11

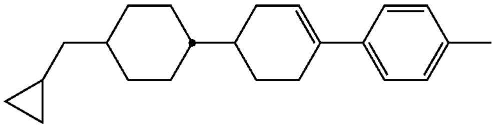

CL-3-12

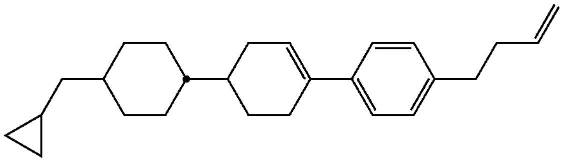

In a particularly preferred embodiment, the medium according to the invention comprises the compound CL-3-1 or CLP-3-3.

In a preferred embodiment of the present invention the medium additionally comprises one or more compounds of the formula VI,

VI

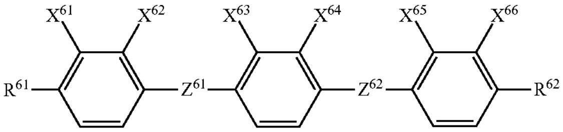

in which $R^{61}$ and $R^{62}$ denote H, F, straight chain alkyl or alkoxy having 1 to 15 C atoms, straight chain alkenyl or alkenyloxy having 2 to 15 C atoms or branched alkyl, alkoxy, alkenyl, alkenyloxy each having 3 to 15 C atoms, where one or more $CH_2$ groups in these radicals may each be replaced, independently of one another, by

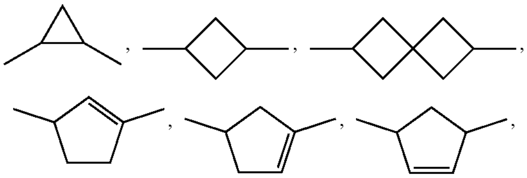

—C≡C—, —$CF_2O$—, —$OCF_2$—, —CH═CH—, —O—, —CO—O— or —O—CO— in such a way that O atoms are not linked directly to one another, and in which one or more H atoms may be replaced by halogen, $X^{61}$, $X^{62}$, $X^{63}$, $X^{64}$, $X^{65}$, and $X^{66}$, identically or differently, denote H or F, preferably at least one of $X^{61}$, $X^{62}$, $X^{63}$, $X^{64}$, $X^{65}$, and $X^{66}$ denotes F, more preferably at least two of $X^{61}$, $X^{62}$, $X^{63}$, $X^{64}$, $X^{65}$, and $X^{66}$ denote F;

$Z^{61}$ and $Z^{62}$, identically or differently, denote $CH_2CH_2$ or a single bond.

The compounds of the formula VI are preferably selected from the formulae VI-1 and VI-2:

VI-1

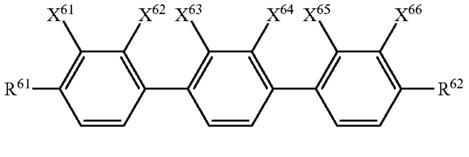

VI-2

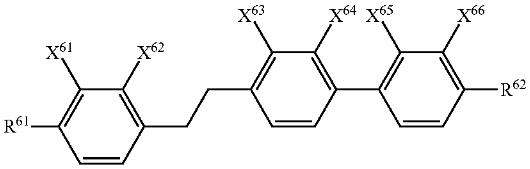

in which the occurring groups have the meanings given for formula VI.

The compounds of the formula VI-1 are preferably selected from the formulae VI-1-1 to VI-1-21, very preferably of the formula VI-1-4:

VI-1-2

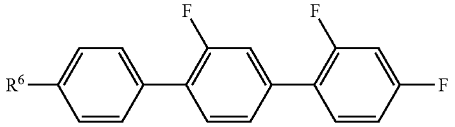

VI-1-2

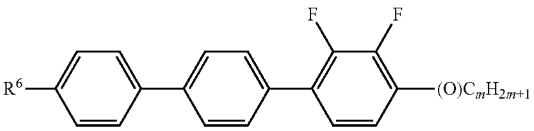

-continued
VI-1-3
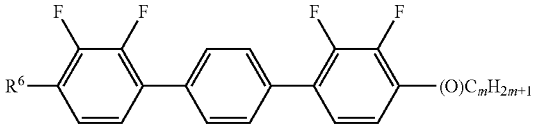
VI-1-4
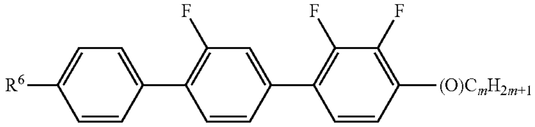
VI-1-5
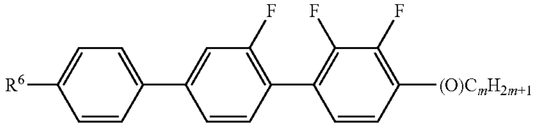
VI-1-6
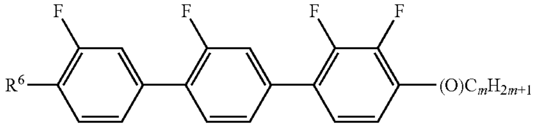
VI-1-7
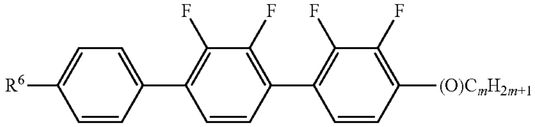
VI-1-8
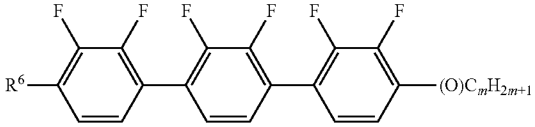
VI-1-9
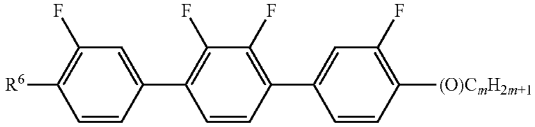
VI-1-10
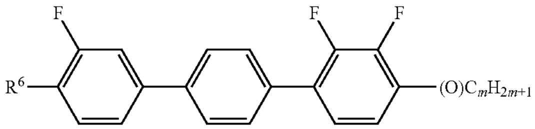
VI-1-11
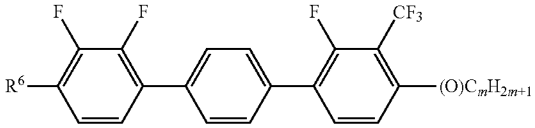
VI-1-12
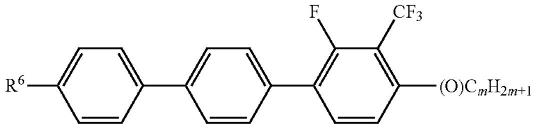
-continued
VI-1-13
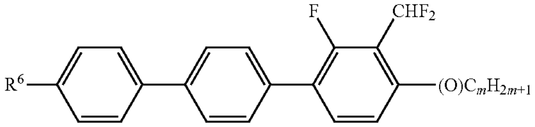
VI-1-14
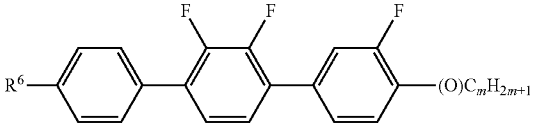
VI-1-15
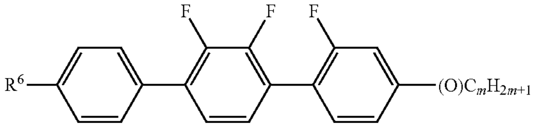
VI-1-16
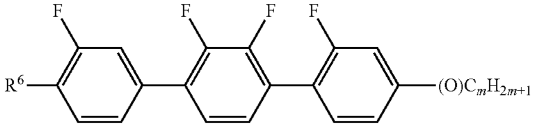
VI-1-17
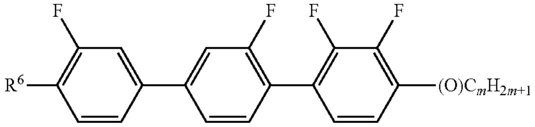
VI-1-18
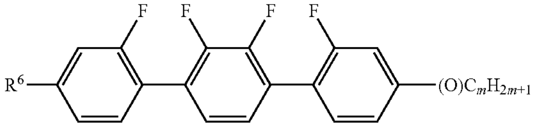
VI-1-19
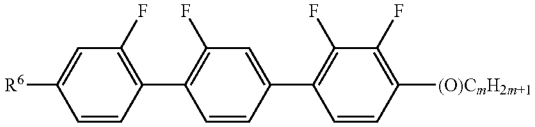
VI-1-20
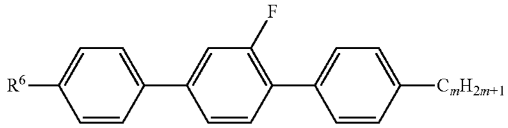
VI-1-21
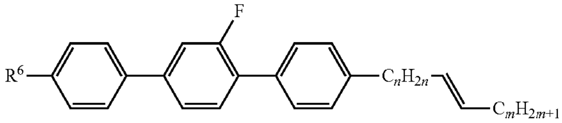
in which $R^6$ denotes a straight-chain alkyl or alkoxy radical having 1 to 6 C atoms, (O) denotes —O— or a single bond, and m is 0, 1, 2, 3, 4, 5 or 6 and n is 0, 1, 2, 3 or 4.
R preferably denotes methyl, ethyl, propyl, butyl, pentyl, hexyl, methoxy, ethoxy, propoxy, butoxy, pentoxy.

In the compounds of the formula VI-1-4, (O) preferably denotes —O—.
The compounds of the formula VI-2 are preferably selected from the formulae VI-2-1 to VI-2-15, very preferably of the formula VI-2-1:
VI-2-1
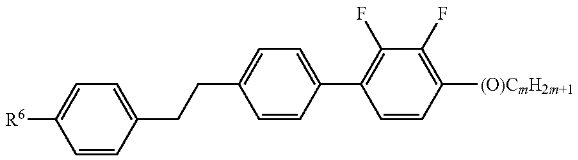
VI-2-2
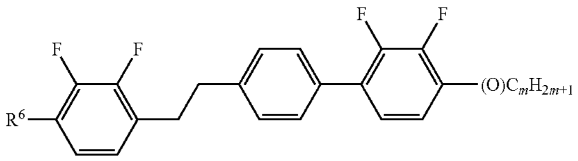
VI-2-3
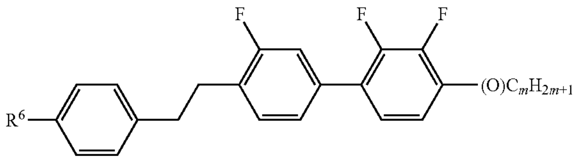
VI-2-4
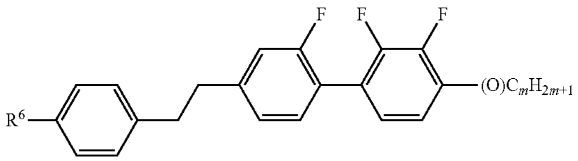
VI-2-5
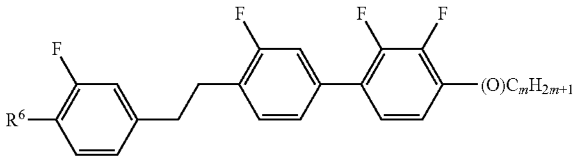
VI-2-6
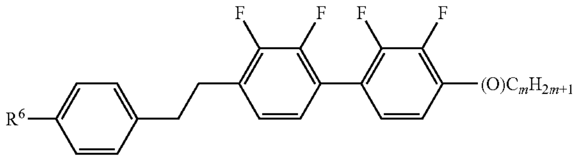
VI-2-7
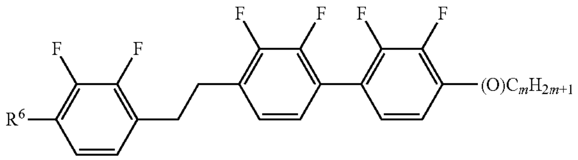
-continued
VI-2-8
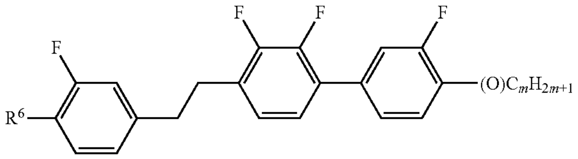
VI-2-9
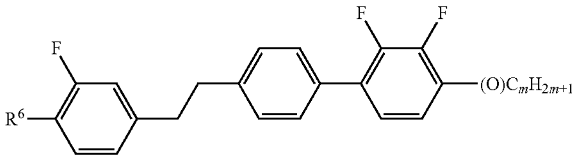
VI-2-10
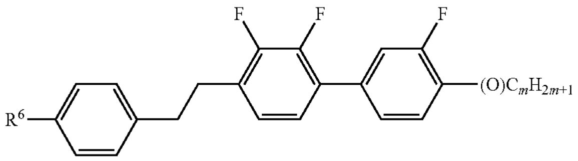
VI-2-11
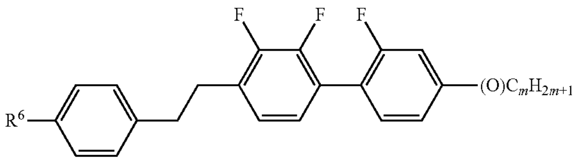
VI-2-12
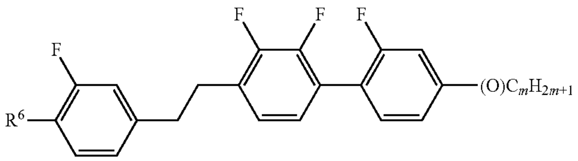
VI-2-13
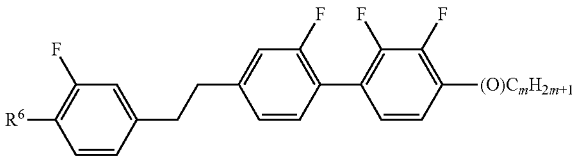
VI-2-14
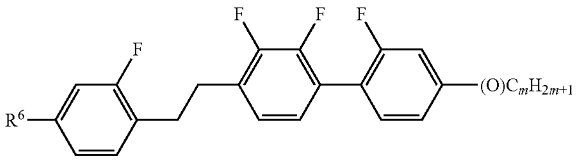
VI-2-15
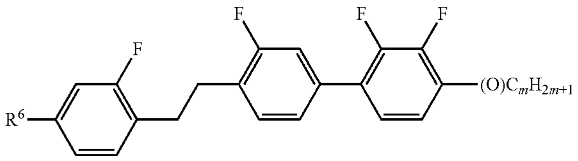
in which $R^6$ denotes a straight-chain alkyl or alkoxy radical having 1 to 6 C atoms, (O) denotes —O— or a single bond, and m is 0, 1, 2, 3, 4, 5 or 6 and n is 0, 1, 2, 3 or 4.

R preferably denotes methyl, ethyl, propyl, butyl, pentyl, hexyl, methoxy, ethoxy, propoxy, butoxy, pentoxy.

In a preferred embodiment of the present invention the medium additionally comprises one or more compounds of the formulae VII-1 to VII-9

VII-1

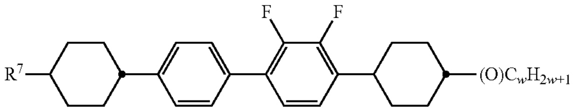

VII-2

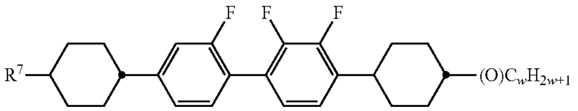

VII-3

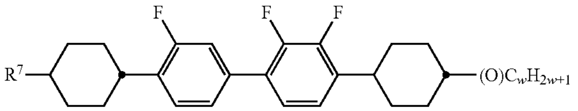

VII-4

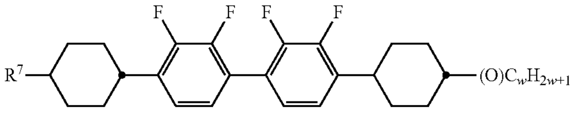

VII-5

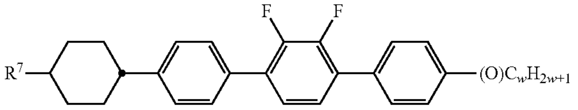

VII-6

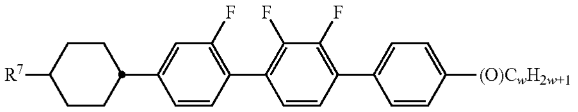

VII-7

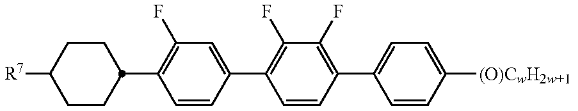

VII-8

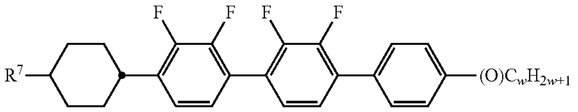

VII-9

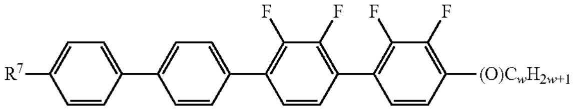

in which $R^7$ denotes a straight-chain alkyl or alkoxy radical having 1 to 6 C atoms, or a straight chain alkenyl radical having 2 to 6 C atoms, and w is an integer from 1 to 6.

Preferably, the medium according to the invention comprises one or more compounds of the formula VIII:

VIII

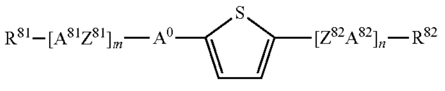

in which $R^{81}$ and $R^{82}$, identically or differently, denote H, halogen, CN, SCN, straight chain alkyl or alkoxy having 1 to 15 C atoms, straight chain alkenyl or alkenyloxy having 2 to 15 C atoms or branched alkyl, alkoxy, alkenyl or alkenyloxy having 3 to 15 C atoms, where one or more $CH_2$ groups in these radicals may each be replaced, independently of one another, by

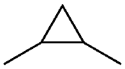, 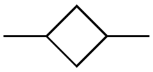, 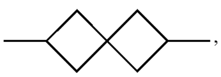, 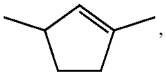, 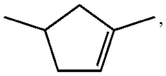, 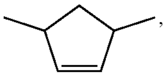, 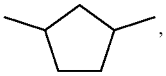, -C≡C—, —$CF_2O$—, —$OCF_2$—, —CH═CH—, by —O—, —CO—O— or —O—CO— in such a way that 0 atoms are not linked directly to one another, and in which one or more H atoms may be replaced by halogen, $A^0$, $A^{81}$, and $A^{82}$, each, independently of one another, denote phenylene-1,4-diyl, in which one or two CH groups may be replaced by N and one or more H atoms may be replaced by halogen, CN, $CH_3$, $CHF_2$, $CH_2F$, $CF_3$, $OCH_3$, $OCHF_2$ or $OCF_3$, cyclohexane-1,4-diyl, in which one or two non-adjacent $CH_2$ groups may be replaced, independently of one another, by 0 and/or S and one or more H atoms may be replaced by F, cyclohexene-1,4-diyl, bicyclo[1.1.1]pentane-1,3-diyl, bicyclo[2.2.2]octane-1,4-diyl, spiro[3.3]heptane-2,6-diyl, tetrahydropyran-2,5-diyl or 1,3-dioxane-2,5-diyl;

$Z^{81}$ and $Z^{82}$, each, independently of one another, denote —$CF_2O$—, —$OCF_2$—, —$CH_2O$—, —$OCH_2$—, —CO—O—, —O—CO—, —$C_2H_4$—, —$C_2F_4$, —$CF_2CH_2$—, —$CH_2CF_2$—, —CFHCFH—, —$CFHCH_2$—, —$CH_2CFH$—, —$CF_2CFH$—, —$CFHCF_2$—, —CH═CH—, —CF═CH—, —CH═CF—, —CF═CF—, —C≡C— or a single bond;

n denotes 0, 1, 2 or 3, preferably 0, 1 or 2, very preferably 0 or 1, particularly preferably 0; and m denotes 0, 1, 2 or 3, preferably 0, 1 or 2, very preferably 1 or 2, in particular 1.

$A^{81}$ and $A^{82}$ in formula I preferably denote phenylene-1,4-diyl, which may also be mono- or polysubstituted by F, furthermore cyclohexane-1,4-diyl, cyclohexenylene-1,4-diyl, tetrahydropyran-2,5-diyl or 1,3-dioxane-2,5-diyl, very preferably phenylene-1,4-diyl which may also be mono- or polysubstituted by F, or cyclohexane-1,4-diyl.

$Z^{81}$ and $Z^{82}$ in formula VIII preferably denote —$CF_2O$—, —$OCF_2$— or a single bond, very preferably a single bond.

$A^{81}$ and $A^{82}$ in formula VIII particularly preferably denote,

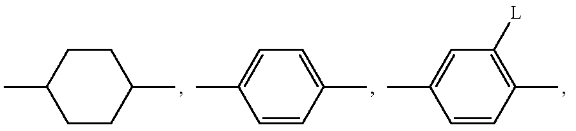

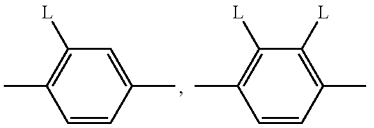

or

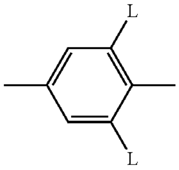

in which L denotes halogen, $CF_3$ or CN, preferably F.

Preference is furthermore given to compounds of the formula VIII in which $R^{81}$ and $R^{82}$ each, independently of one another, denote H, F, or alkyl, alkoxy, alkenyl or alkynyl having 1 to 8, preferably 1 to 5, C atoms, each of which is optionally substituted by halogen, in particular by F.

$R^{81}$ and $R^{82}$ preferably denote H, optionally fluorinated alkyl or alkoxy having 1 to 7 C atoms, optionally fluorinated alkenyl or alkynyl having 2 to 7 C atoms, optionally fluorinated cycloalkyl having 3 to 12 C atoms.

Preferably, at least one of $R^{81}$ and $R^{82}$ is not H, particularly preferably both of $R^{81}$ and $R^{82}$ are not H. $R^{81}$ is very particularly preferably alkyl. $R^{82}$ is furthermore preferably H, alkyl or fluorine. Very particularly preferably, $R^{81}$ is alkyl and $R^{82}$ is H or alkyl. $R^{81}$, $R^{82}$ each, independently of one another, very particularly preferably denote unbranched alkyl having 1 to 5 C atoms. If $R^{81}$ and $R^{82}$ denote substituted alkyl, alkoxy, alkenyl or alkynyl, the total number of C atoms in the two groups $R^{81}$ and $R^{82}$ is preferably less than 10.

Preferred compounds of the formula VIII are selected from the compounds of the formula VIIIa

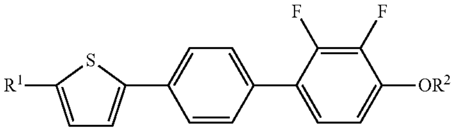

in which $R^1$ and $R^2$, identically or differently, denote straight chain alkyl having 1 to 15 C atoms, straight chain alkenyl having 2 to 15 C atoms or branched alkyl, or alkenyl having 3 to 15 C atoms, where one or more $CH_2$ groups in these radicals may each be replaced, independently of one another, by

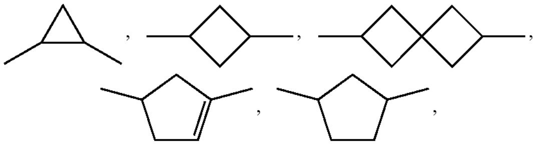

and in which one or more H atoms may be replaced by fluorine, preferably both of $R^1$ and $R^2$ denote straight chain alkyl having 1 to 6 C atoms.

Very preferred compounds of the formula VIIIa are selected from the compounds of the formulae VIIIa-1 to VIIIa-35:

VIIIa-1

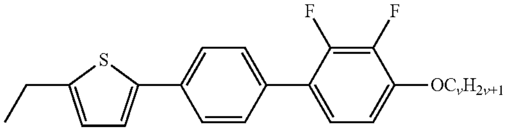

VIIIa-2

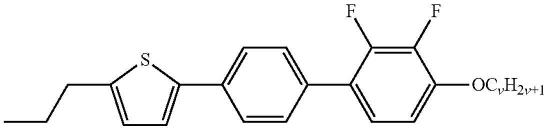

VIIIa-3

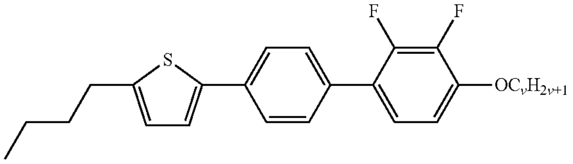

VIIIa-4

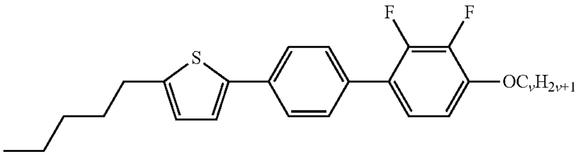

VIIIa-5

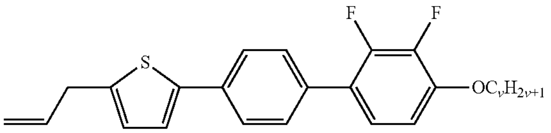

VIIIa-6

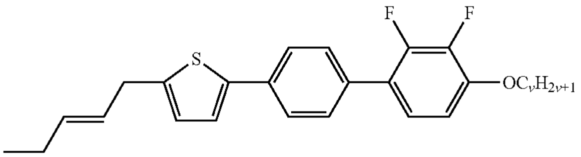

VIIIa-7

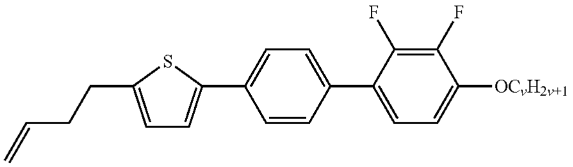

VIIIa-8

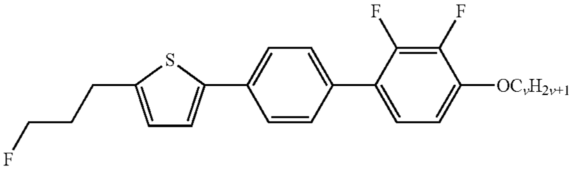

-continued
VIIIa-9
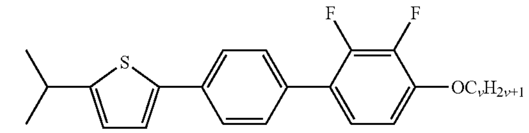
VIIIa-10
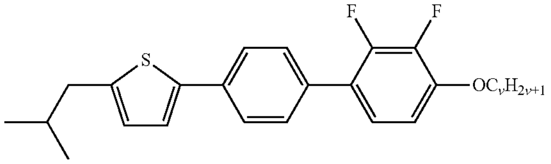
VIIIa-11
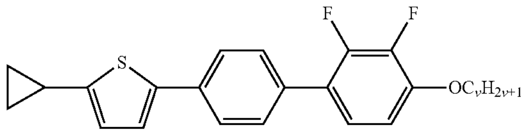
VIIIa-12
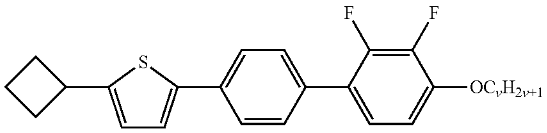
VIIIa-13
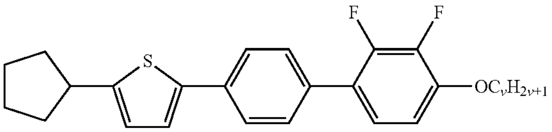
VIIIa-14
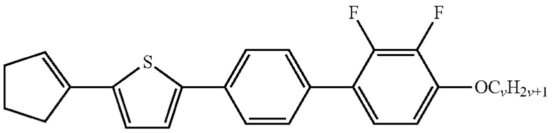
VIIIa-15
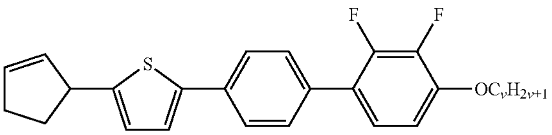
VIIIa-16
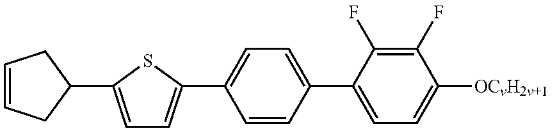
VIIIa-17
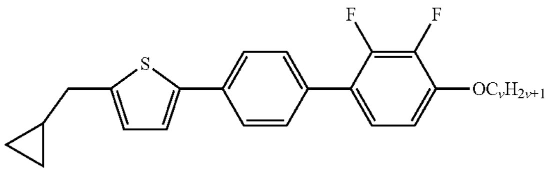
-continued
VIIIa-18
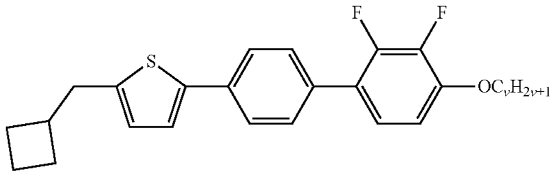
VIIIa-19
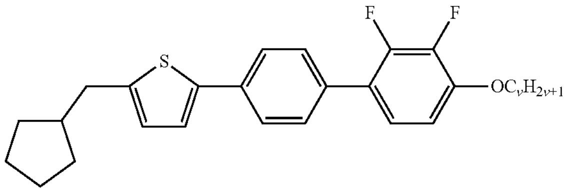
VIIIa-20
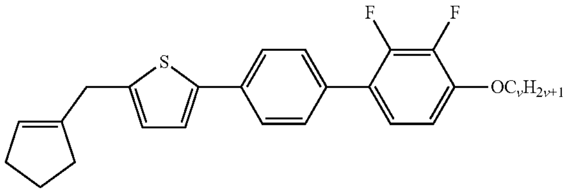
VIIIa-21
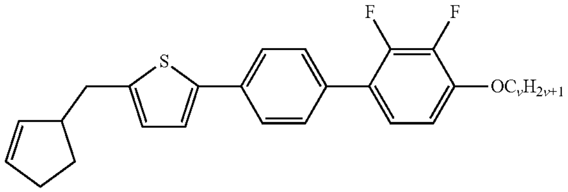
VIIIa-22
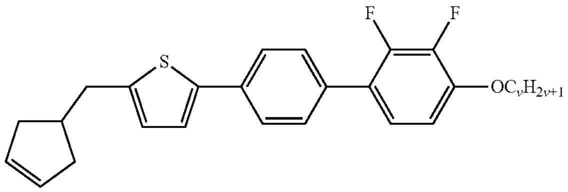
VIIIa-23
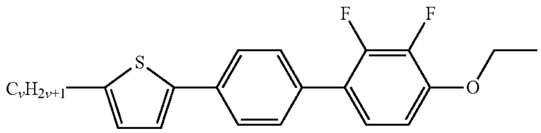
VIIIa-24
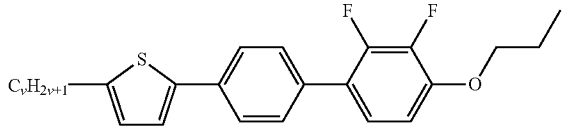
VIIIa-25
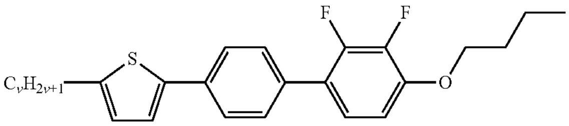

-continued

VIIIa-26

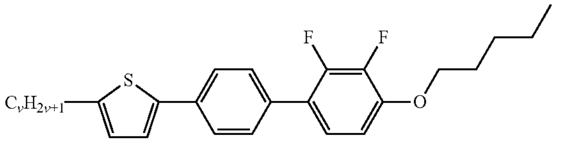

VIIIa-27

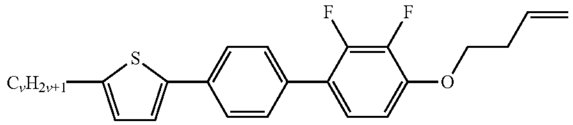

VIIIa-28

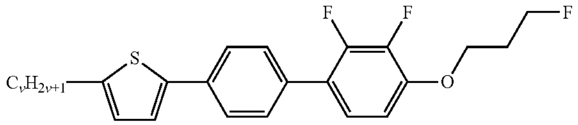

VIIIa-29

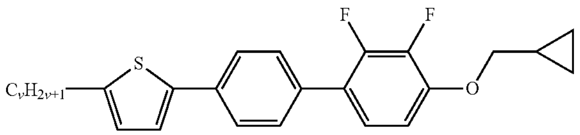

VIIIa-30

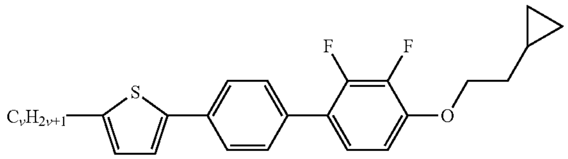

VIIIa-31

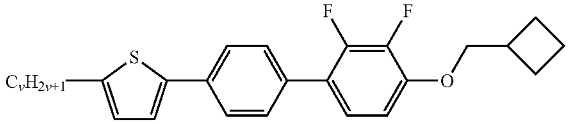

VIIIa-32

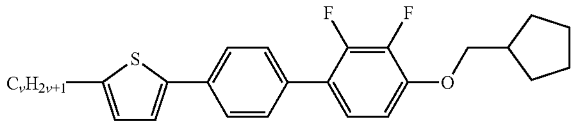

VIIIa-33

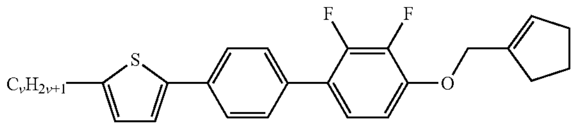

VIIIa-34

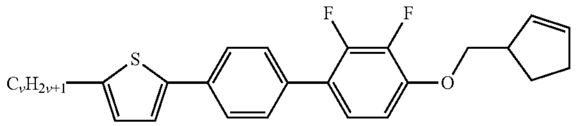

-continued

VIIIa-35

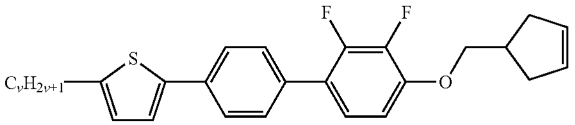

in which v is an integer from 1 to 6.

Further preferred compounds of the formula VIII are selected from the following sub-formulae:

VIII-1

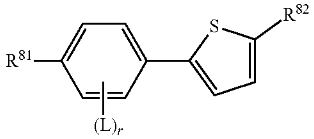

VIII-2

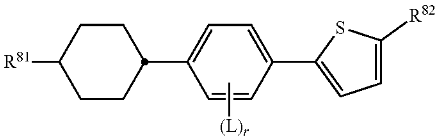

VIII-3

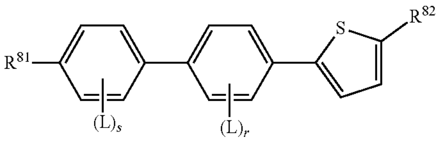

VIII-4

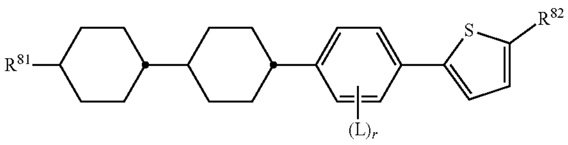

VIII-5

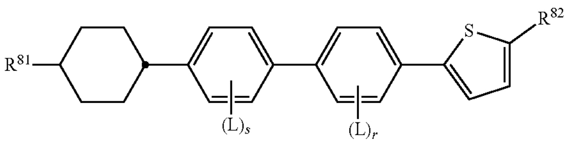

VIII-6

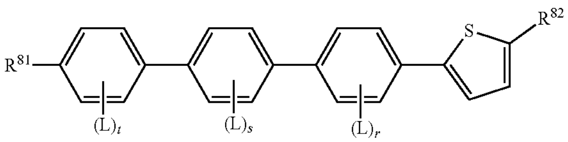

in which $R^{81}$, $R^{82}$ and L have the meanings indicated above, L preferably denotes F, and r, s and t independently are 0, 1, 2, 3, or 4. r preferably is 1 or 2, very preferably 2 and s and t independently are preferably 0 or 1, very preferably 0. $R^{81}$ and $R^{82}$ in particular independently denote n-alkyl having 1 to 5 C atoms.

In a first very preferred embodiment, the compounds of the formulae VIII-1 to VIII-6 are selected from the compounds of the formula VIII-1a to VIII-6a, in particular of the formula VIII-3a:

VIII-1a

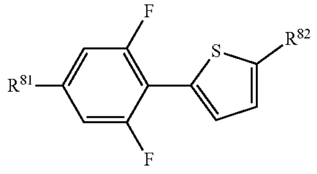

VIII-2a

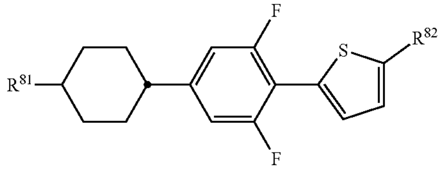

VIII-3a

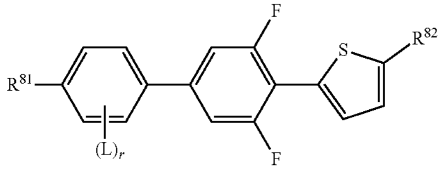

VIII-4a

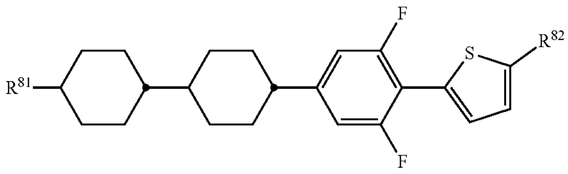

VIII-5a

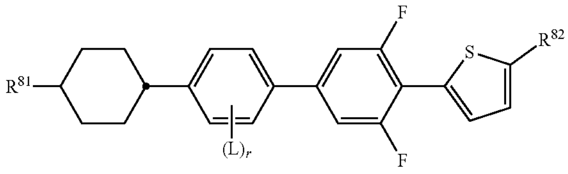

VIII-6a

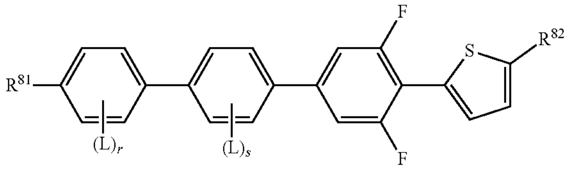

in which $R^{81}$, $R^{82}$, r and s have the meanings defined above.

In a second very preferred embodiment, the compounds of the formulae VIII-1 to VIII-6 are selected from the compounds of the formula VIII-1 b to VIII-6b, in particular of the formula I3-b:

VIII-1b

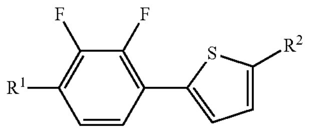

VIII-2b

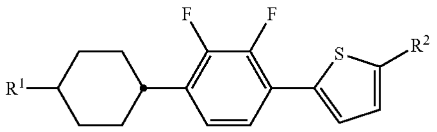

-continued

VIII-3b

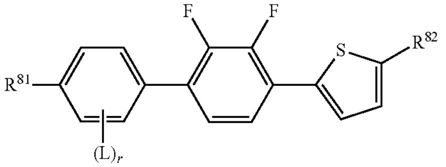

VIII-4b

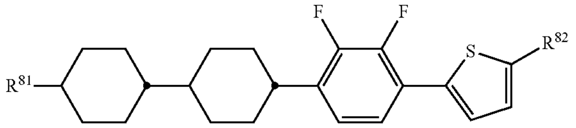

VIII-5b

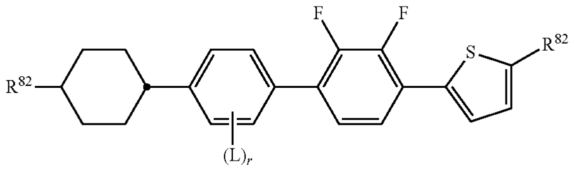

VIII-6b

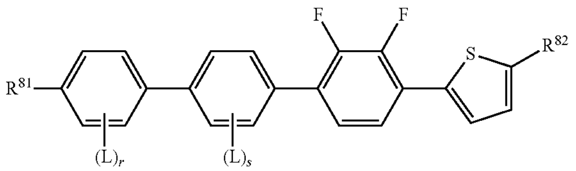

in which $R^{81}$, $R^{82}$, L, r and s have the meanings defined above.

In a third very preferred embodiment, the compounds of the formulae VIII-1 to VIII-6 are selected from the compounds of the formula VIII-1c to VIII-6c, in particular of the formula I3-c:

VIII-1c

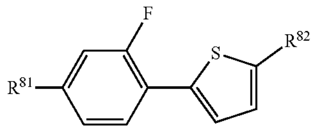

VIII-2c

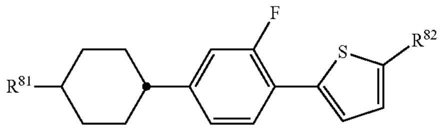

VIII-3c

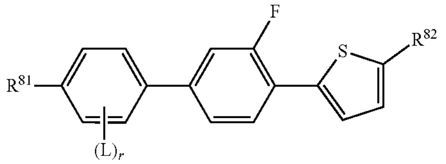

VIII-4c

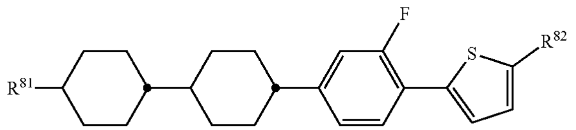

-continued

VIII-5c

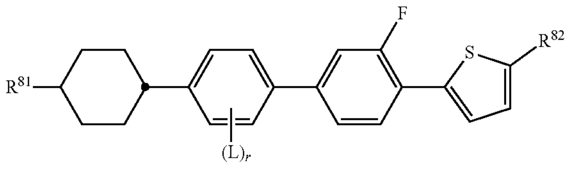

VIII-6c

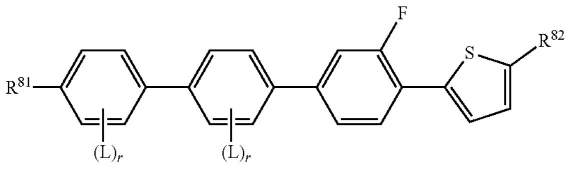

in which $R^{81}$, $R^{82}$, L, r and s have the meanings defined above.

In a fourth very preferred embodiment, the compounds of the formulae VIII-1 to VIII-6 are selected from the compounds of the formula VIII-1d to VIII-6d, in particular of the formula VIII-3d:

VIII-1d

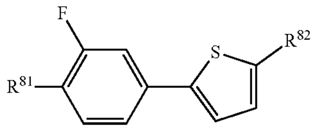

VIII-2d

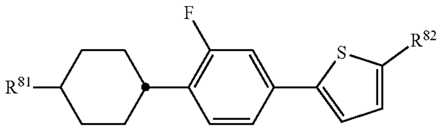

VIII-3d

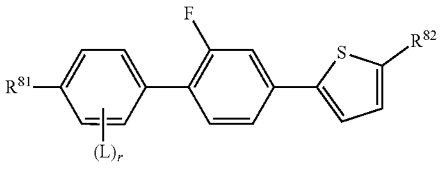

VIII-4d

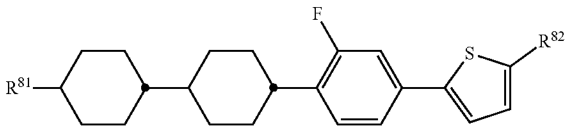

VIII-5d

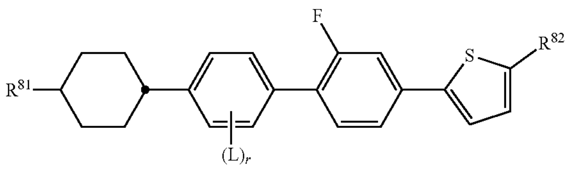

-continued

VIII-6d

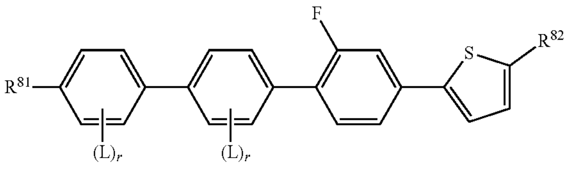

in which $R^{81}$, $R^{82}$, L, r and s have the meanings defined above.

In a particularly preferred embodiment, the medium according to the invention comprises one or more compounds selected from the group of the formulae VIII-1a to VIII-6a and one or more compounds selected from the group of the formulae VIII-1 b to VIII-6b.

Very particularly preferably the medium comprises one or more compounds selected from the group of compounds of the formulae VIII-3a, VIII-3b, VIII-3c and VIII-3d:

VIII-3a

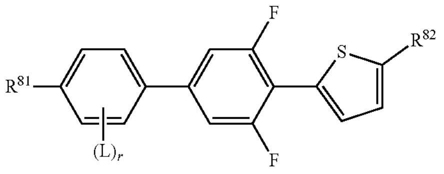

VIII-3b

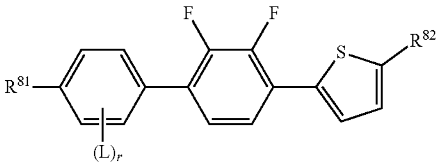

VIII-3c

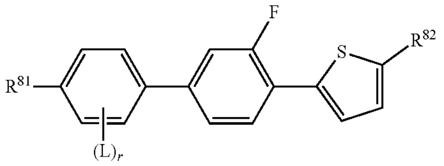

VIII-3d

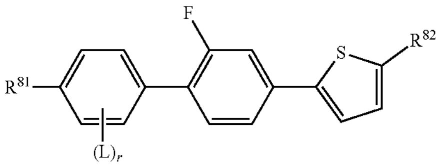

in which $R^{81}$, $R^{82}$, L and r have the meanings defined above and preferably r is 0.

Most preferred compounds of formula I include, in particular, one or more of the following:

VIII-3a-1

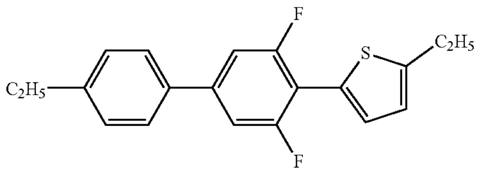

-continued
VIII-3a-2
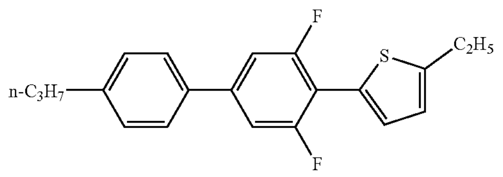
VIII-3a-3
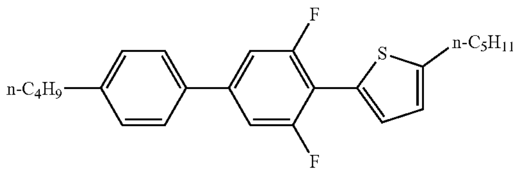
VIII-3a-4
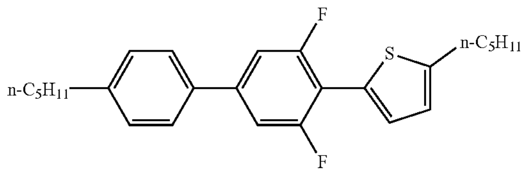
VIII-3a-5
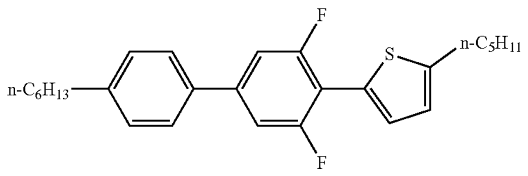
VIII-3a-6
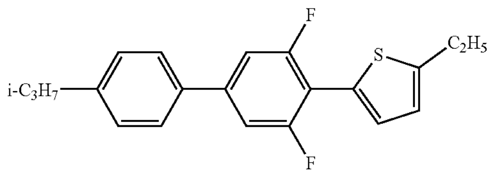
VIII-3b-1
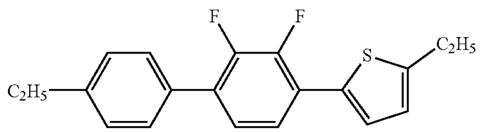
VIII-3b-2
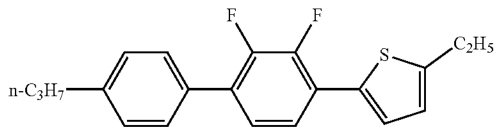
VIII-3b-3
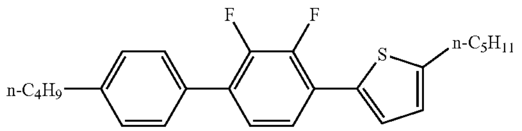
-continued
VIII-3b-4
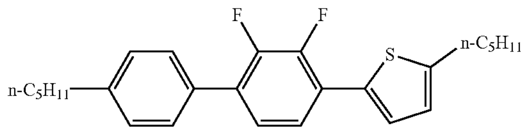
VIII-3b-5
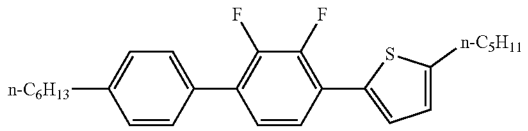
VIII-3b-6
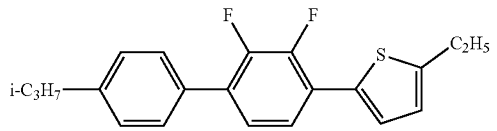
VIII-3c-1
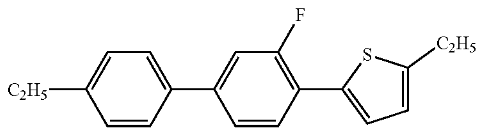
VIII-3c-2
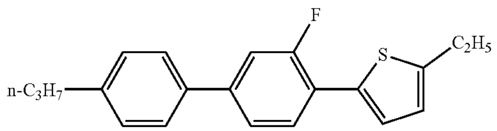
VIII-3c-3
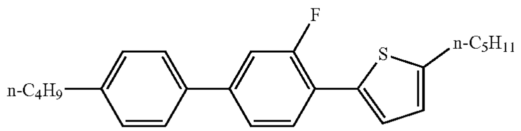
VIII-3c-4
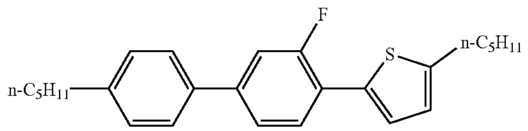
VIII-3c-5
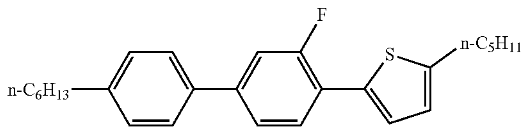
VIII-3c-6
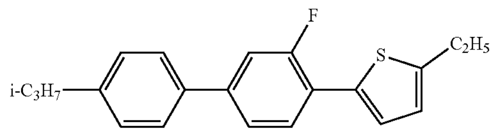
Alternatively, or additionally, the following compounds of formula I can be used:

VIII-3a-7
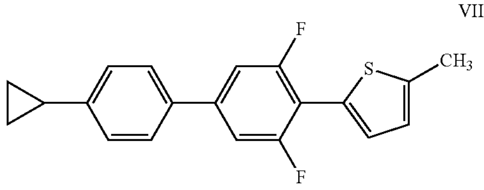
VIII-3a-8
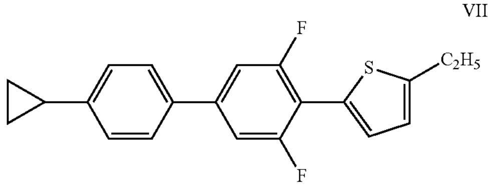
VIII-3a-9
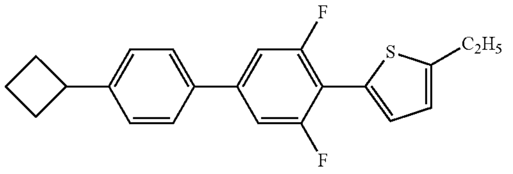
VIII-3a-10
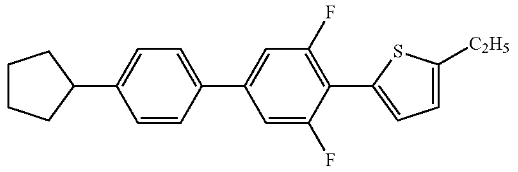
VIII-3a-11
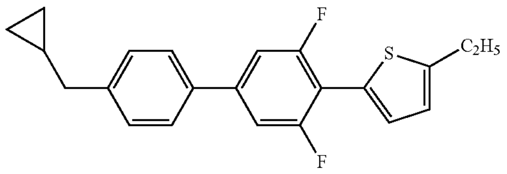
VIII-3a-12
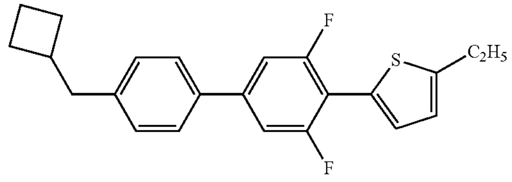
VIII-3a-13
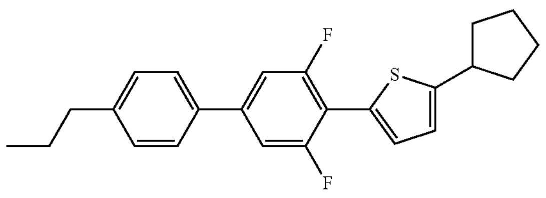
VIII-3a-14
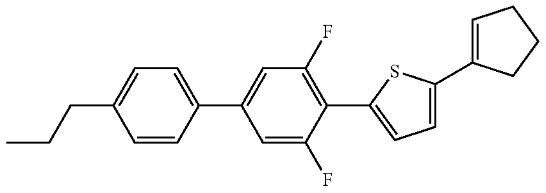
-continued
VIII-3a-15
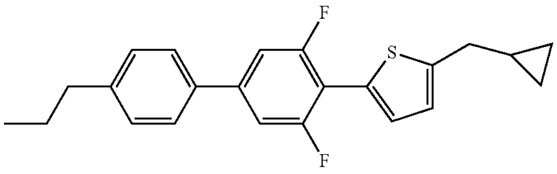
VIII-3b-7
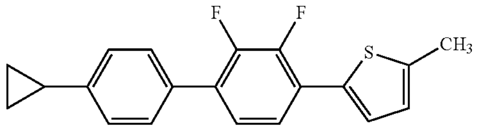
VIII-3b-8
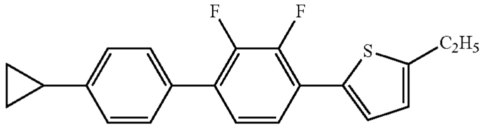
VIII-3b-9
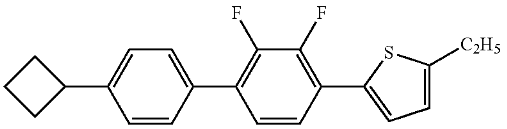
VIII-3b-10
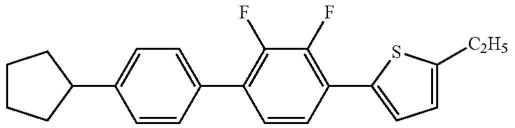
VIII-3b-11
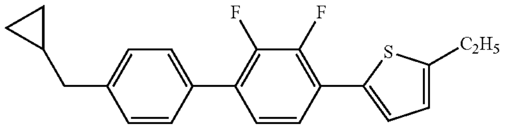
VIII-3b-12
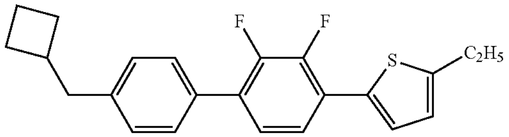
VIII-3b-13
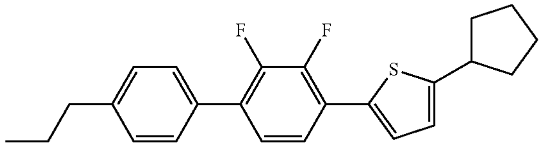
VIII-3b-14
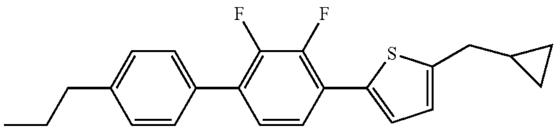

-continued

VIII-3c-7

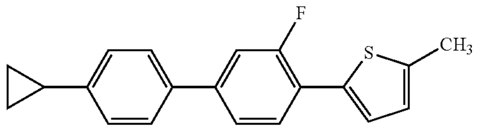

VIII-3c-8

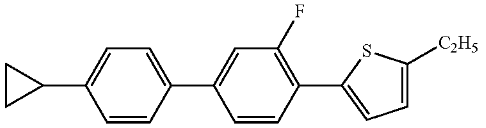

VIII-3c-9

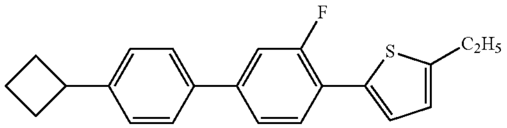

VIII-3c-10

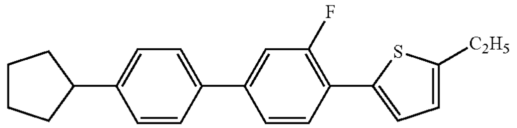

VIII-3c-11

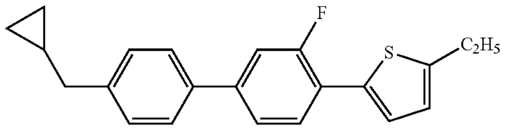

VIII-3c-12

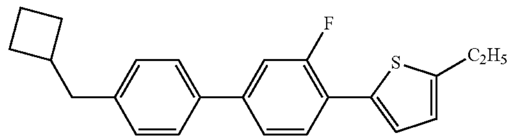

VIII-3c-13

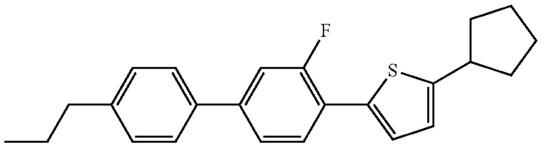

VIII-3c-14

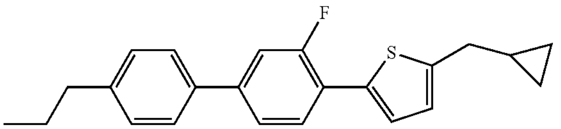

In a preferred embodiment, the medium comprises one or more compounds of the formula IX (IX)

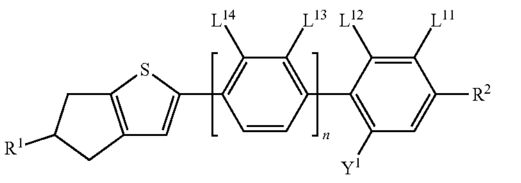

in which $R^1$ and $R^2$, identically or differently, denote H, halogen, straight chain alkyl or alkoxy having 1 to 15 C atoms, straight chain alkenyl or alkenyloxy having 2 to 15 C atoms or branched alkyl, alkoxy, alkenyl or alkenyloxy each having 3 to 15 C atoms, where one or more $CH_2$ groups in these radicals may each be replaced, independently of one another, by

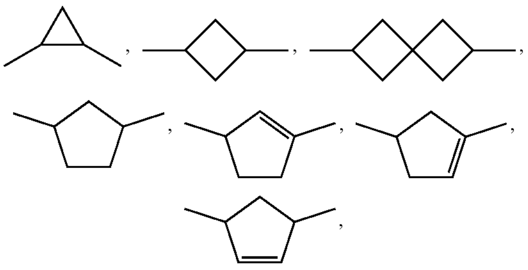

—C≡C—, —$CF_2O$—, —$OCF_2$—, —CH═CH—, by —O—, —CO—O— or —O—CO— in such a way that O atoms are not linked directly to one another, and in which one or more H atoms may be replaced by halogen, $L^{11}$ and $L^{12}$, each, independently of one another, denote F, Cl, $CF_3$ or $CHF_2$, $L^{13}$ and $L^{14}$, each, independently of one another, denote H, F, Cl, $CF_3$ or $CHF_2$, $Y^1$ denotes H, F, Cl, $CF_3$, $CHF_2$ or $CH_3$, preferably H or $CH_3$, and n is 0 or 1.

Preference is given to LC media comprising the compounds of formula IX in which n is 0, Y denotes H or $CH_3$, more preferably H, and $L^{11}$ and $L^{12}$ denote F.

Very preferred compounds of the formula IX are selected from the compounds of the formulae IX-1 to IX-35

IX-1

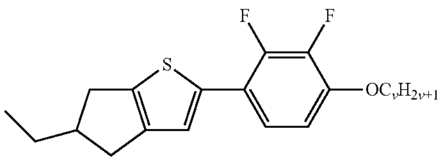

IX-2

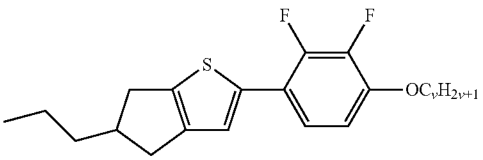

IX-3

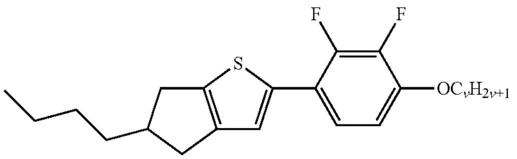

-continued
IX-4
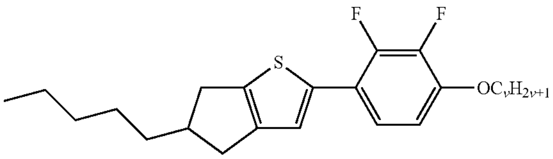
IX-5
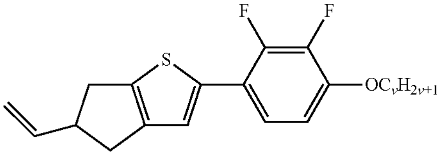
IX-6
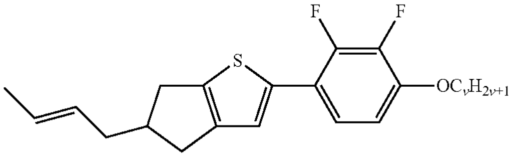
IX-7
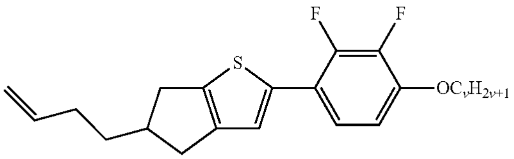
IX-8
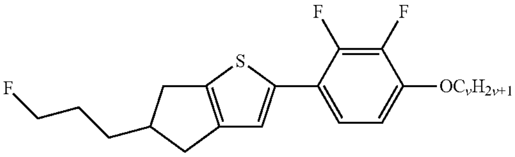
IX-9
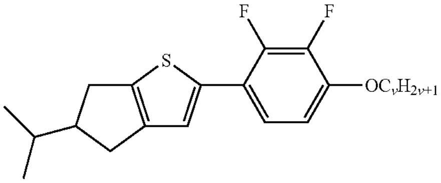
IX-10
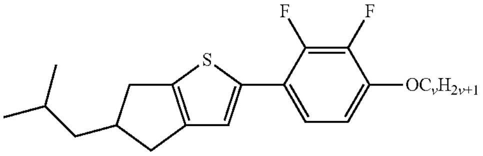
IX-11
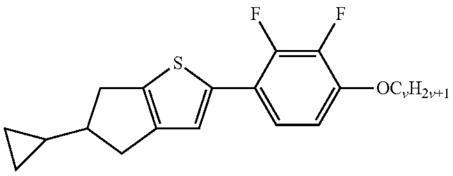
-continued
IX-12
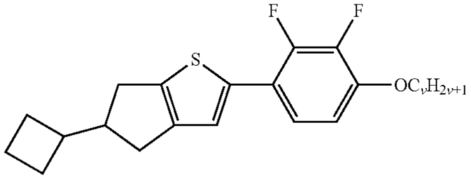
IX-13
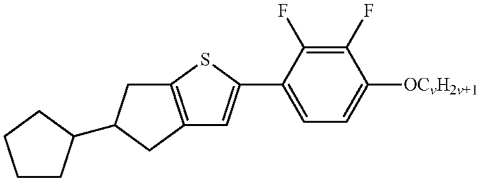
IX-14
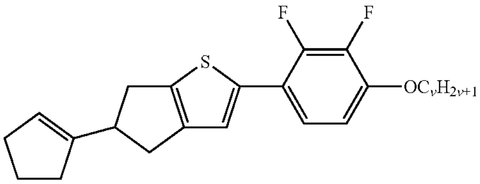
IX-15
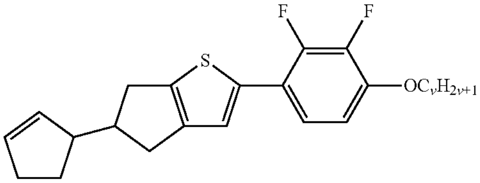
IX-16
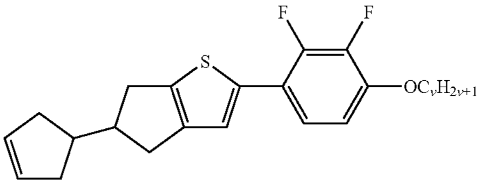
IX-17
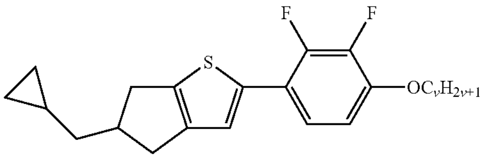
IX-18
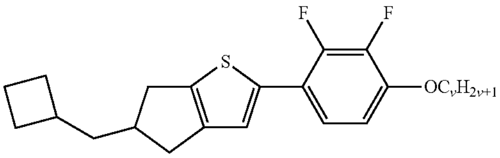
IX-19
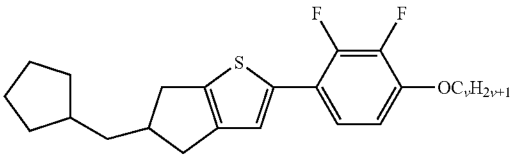

-continued
IX-20
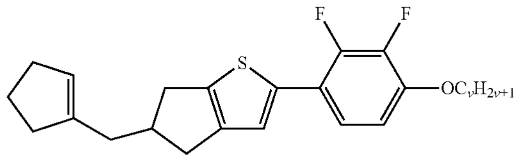
IX-21
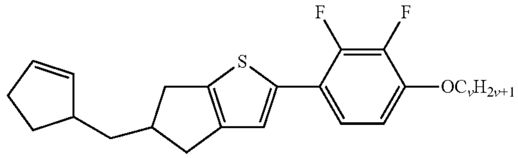
IX-22
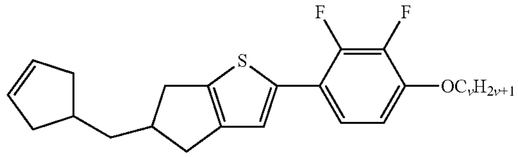
IX-23
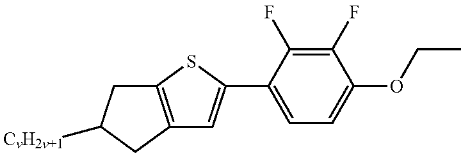
IX-24
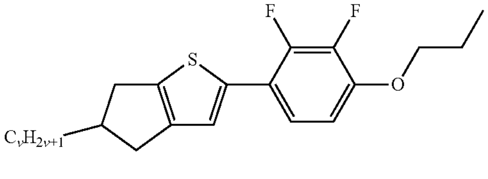
IX-25
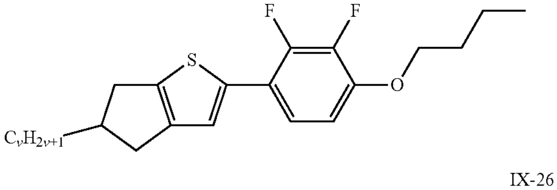
IX-26
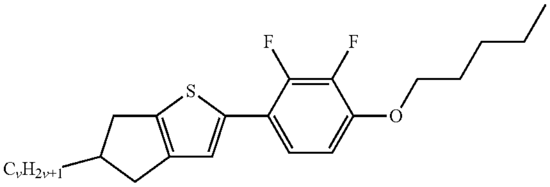
IX-27
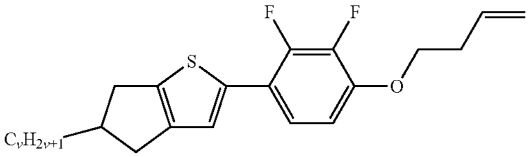
-continued
IX-28
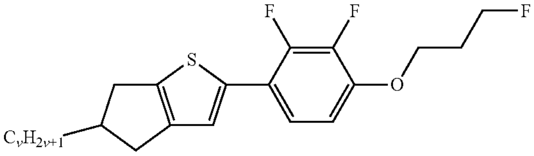
IX-29
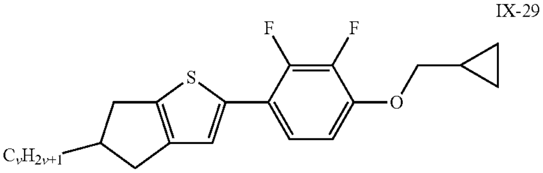
IX-30
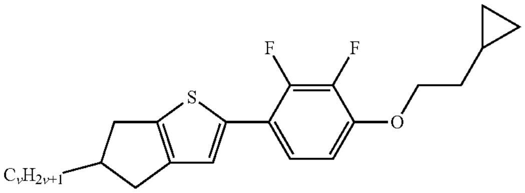
IX-31
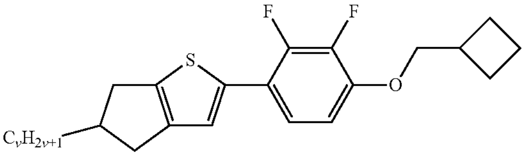
IX-32
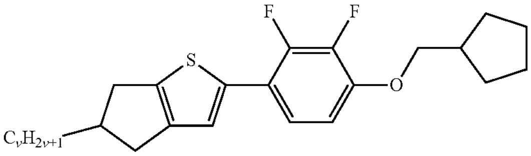
IX-33
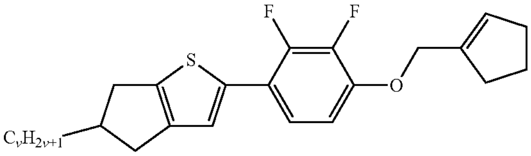
IX-34
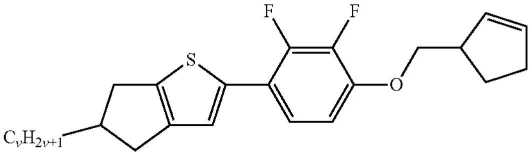
IX-35
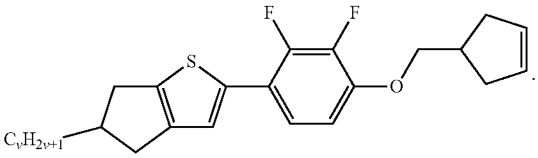
In a preferred embodiment of the present invention the medium comprises one or more compounds of the formula X

X

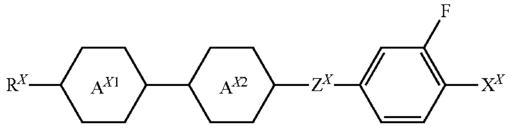

in which

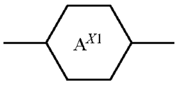 denotes 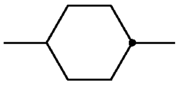,

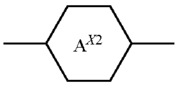 denotes 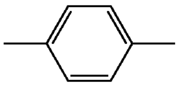,

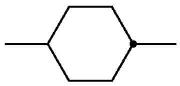, 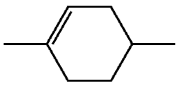,

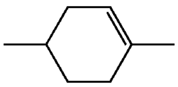, or 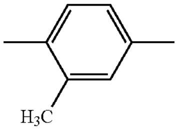, $R^X$ denote a straight chain or branched alkyl or alkoxy radical having 1 to 15 C atoms, where one or more $CH_2$ groups in these radicals may each be replaced, independently of one another, by

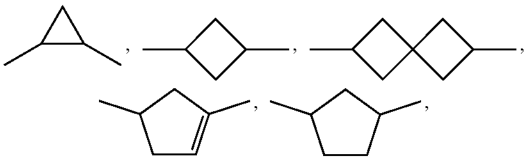

$-C{\equiv}C-$, $-CF_2O-$, $-OCF_2-$, $-CH{=}CH-$, $-O-$, $-CO-O-$ or $-O-CO-$ in such a way that O atoms are not linked directly to one another, and in which, in addition, one or more H atoms may be replaced by halogen, preferably by F, $X^X$ denotes F, Cl, CN, $SF_5$, SCN, NCS, a halogenated alkyl radical or a halogenated alkoxy radical each having 1 to 6 C atoms or a halogenated alkenyl radical or a halogenated alkenyloxy radical each having 2 to 6 C atoms, $Z^X$ denotes $-C_2H_4-$, $-CH_2O-$, $CF_2O$, $-CH{=}CH-$ or a single bond.

In the compounds of formula X, $R^X$ denotes preferably alkyl with 1 to 6 C atoms or alkenyl with 2 to 6 C atoms which are preferably straight-chain.

In the compounds of formula X, $X^X$ is preferably F, C or a mono- or polyfluorinated alkyl or alkoxy radical having 1, 2 or 3 C atoms or a mono- or polyfluorinated alkenyl radical having 2 or 3 C atoms. $X^X$ is more preferably F, C, $CF_3$, $CHF_2$, $OCF_3$, $OCHF_2$, $OCFHCF_3$, $OCFHCHF_2$, $OCFHCHF_2$, $OCF_2CH_3$, $OCF_2CHF_2$, $OCF_2CHF_2$, $OCF_2CF_2CHF_2$, $OCF_2CF_2CHF_2$, $OCFHCF_2CF_3$, $OCFHCF_2CHF_2$, $OCF_2CF_2CF_3$, $OCF_2CF_2CClF_2$, $OCClFCF_2CF_3$, $OCH{=}CF_2$ or $CH{=}CF_2$, very preferably F or $OCF_3$, furthermore $CF_3$, $OCF{=}CF_2$, $OCHF_2$ or $OCH{=}CF_2$, very particularly preferably F, $OCF_3$ or $CF_3$, most preferably F.

Preferred compounds of formula X are selected from the following sub-formulae:

X1

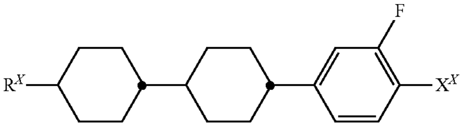

X2

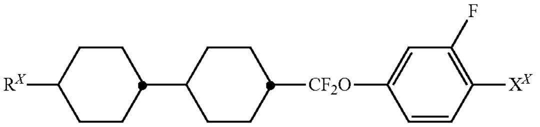

X3

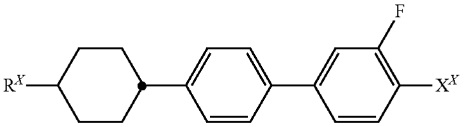

X4

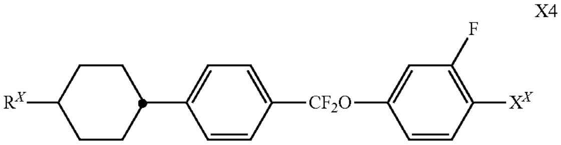

X5

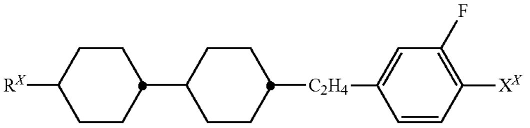

X6

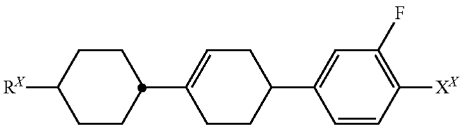

X7

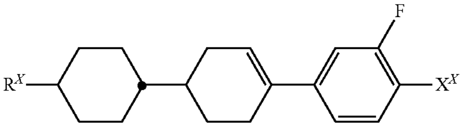

in which $R^X$ has one of the meanings given in formula X and preferably denotes straight-chain alkyl having 1-6 C atoms, very preferably ethyl, propyl, or butyl, or straight-chain alkenyl with 2 to 6 C atoms very preferably vinyl or 1-propenyl, most preferably vinyl, and $X^X$ has one of the meanings given in formula X and preferably denotes F, $CF_3$ or $OCF_3$, very preferably F.

Very preferred compounds of formula X are selected from the following sub-formulae:

X1-1

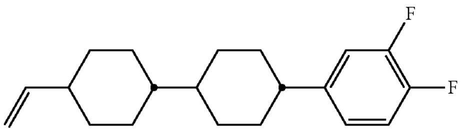

X1-2

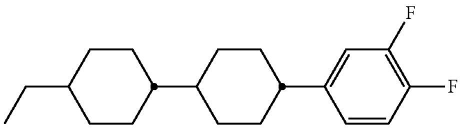

-continued
X1-3
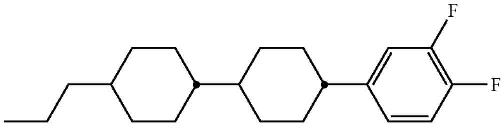
X1-4
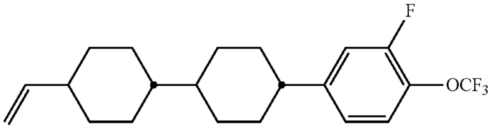
X1-5
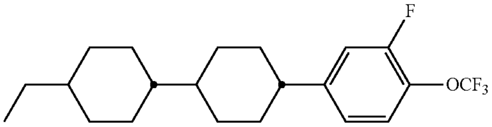
X1-6
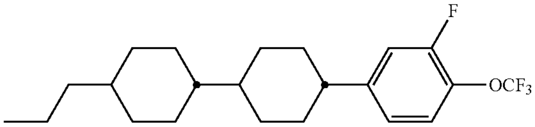
X1-7
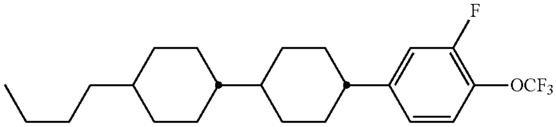
X1-8
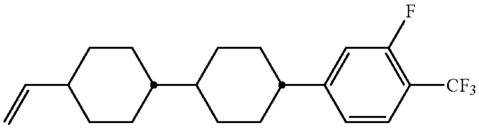
X1-9
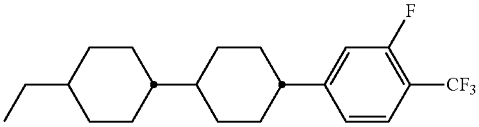
X1-10
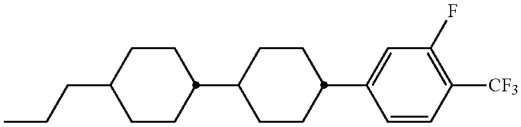
X1-11
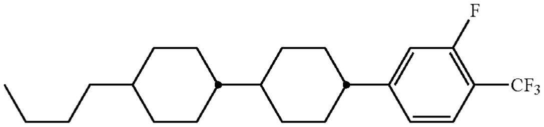
X2-1
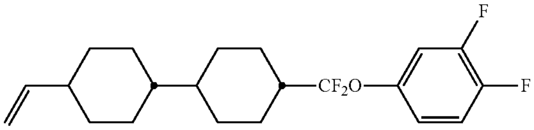
-continued
X2-2
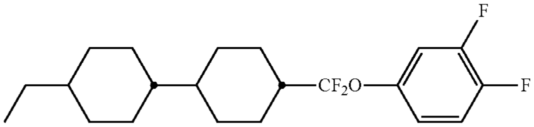
X2-3
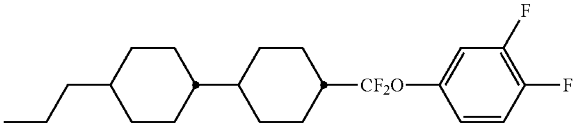
X3-1
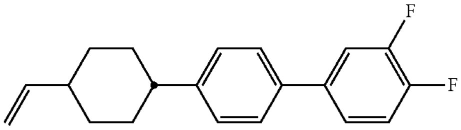
X3-2
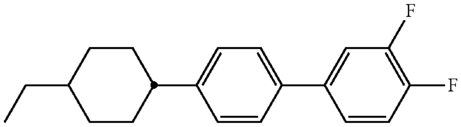
X3-3
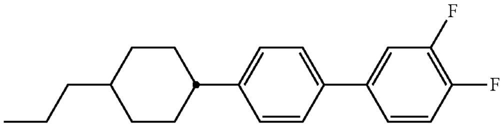
X3-4
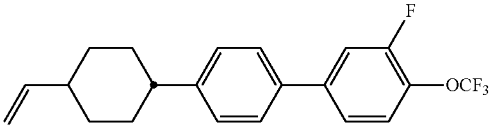
X3-5
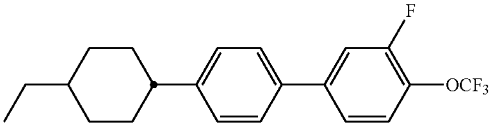
X3-6
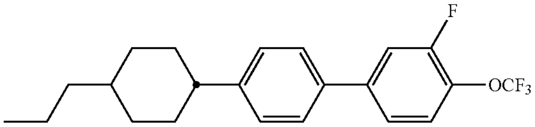
X4-1
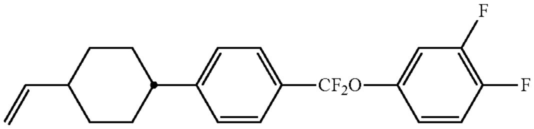
X4-2
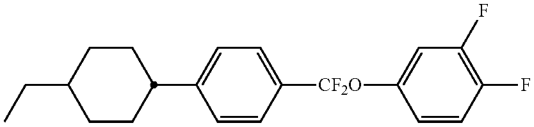

-continued
X4-3
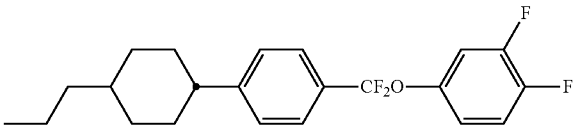
X5-1
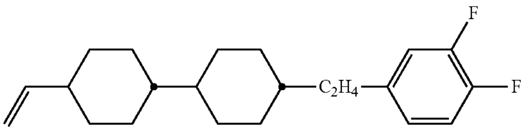
X5-2
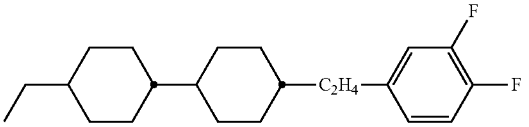
X5-3
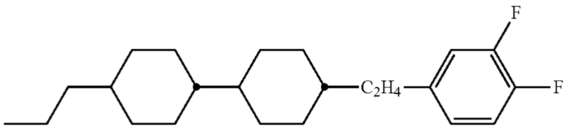
X6-1
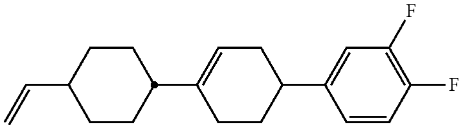
X6-2
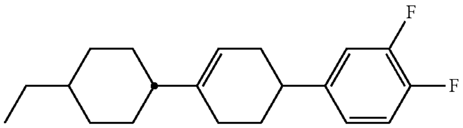
X6-3
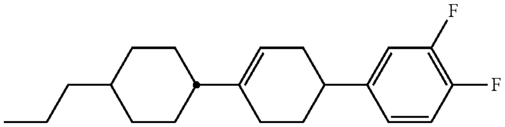
X6-4
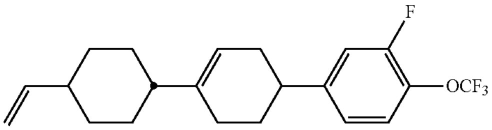
X6-5
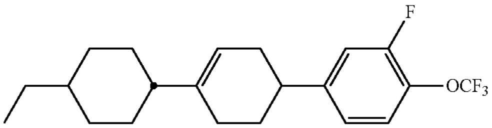
X6-6
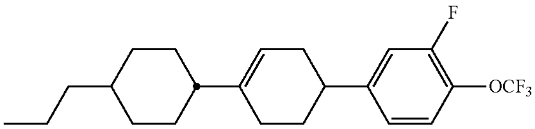
-continued
X7-1
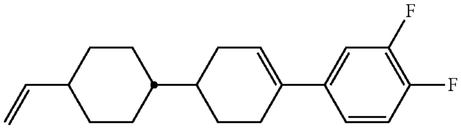
X7-2
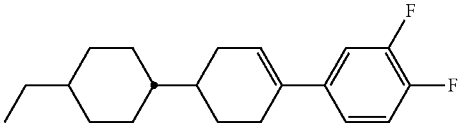
X7-3
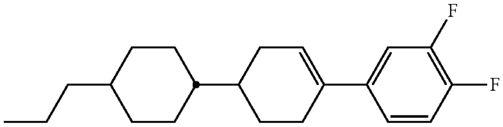
Preferably the LC medium contains one or more compounds selected from the group consisting of the formulae X1-1, X1-3, X2-1 and X2-3.
Further preferred embodiments are listed below:
a) Liquid-crystalline medium comprising at least one compound of the formulae Z-1 to Z-8, preferably of the formulae Z-2, Z-4 and Z-6, very preferably Z-4
Z-1
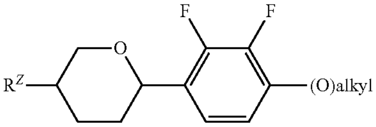
Z-2
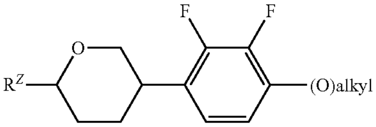
Z-3
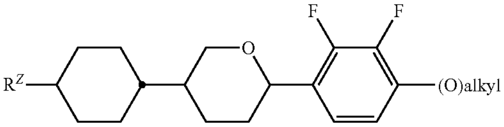
Z-4
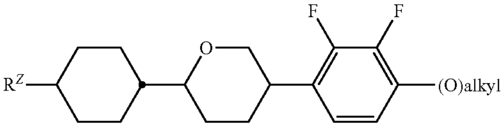
Z-5
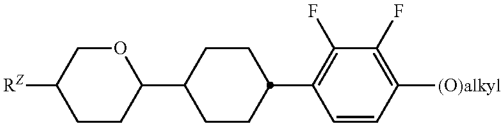
Z-6
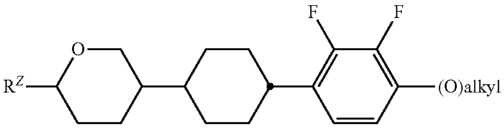

-continued

Z-7

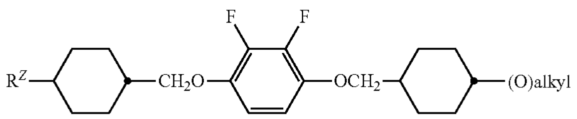

Z-8

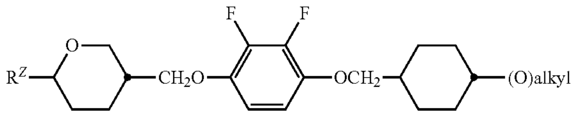

in which $R^z$ has the meaning of $R^{2A}$ indicated above and preferably denotes alkyl having 1 to 7 C atoms or alkenyl having 2 to 7 C atoms, (O) denotes O or a single bond and alkyl denotes alkyl having 1 to 7 C atoms.

b) Preferred liquid-crystalline media according to the invention comprise one or more substances which contain a tetrahydronaphthyl or naphthyl unit, such as, for example, the compounds of the formulae N-1 to N-5,

N-1

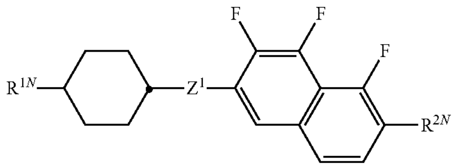

N-2

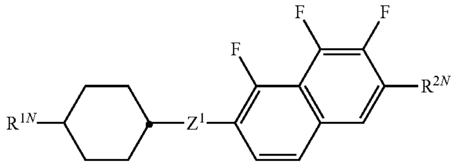

N-3

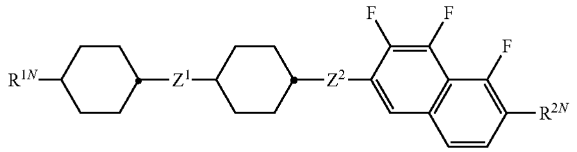

N-4

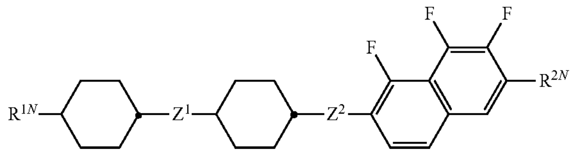

N-5

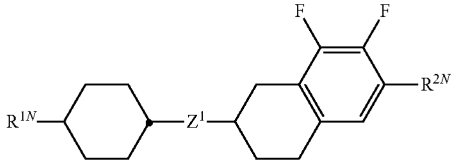

in which $R^{1N}$ and $R^{2N}$ each, independently of one another, have the meanings indicated for $R^{2A}$, preferably denote straight-chain alkyl, straight-chain alkoxy or straight-chain alkenyl, and $Z^1$ and $Z^2$ each, independently of one another, denote $—C_2H_4—$, $—CH{=}CH—$, $—(CH_2)_4—$, $—(CH_2)_3O—$, $—O(CH_2)_3—$, $—CH{=}CHCH_2CH_2—$, $—CH_2CH_2CH{=}CH—$, $—CH_2O—$, $—OCH_2—$, $—COO—$, $—OCO—$, $—C_2F_4—$, $—CF{=}CF—$, $—CF{=}CH—$, $—CH{=}CF—$, $—CF_2O—$, $—OCF_2—$, $—CH_2—$ or a single bond.

c) Preferred mixtures comprise one or more compounds selected from the group of the difluorodibenzochroman compounds of the formula BC, chromans of the formula CR, and fluorinated phenanthrenes of the formulae PH-1 and PH-2,

BC

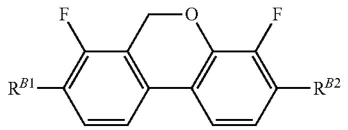

CR

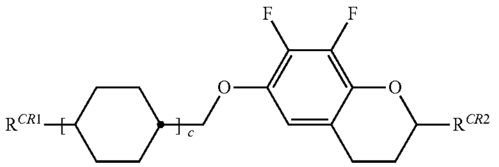

PH-1

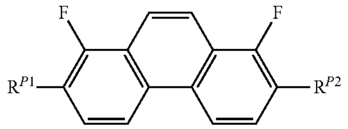

PH-2

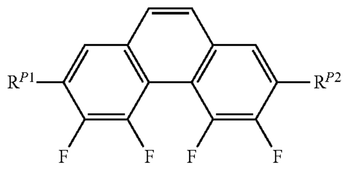

in which $R^{B1}$, $R^{B2}$, $R^{CR1}$, $R^{CR2}$, $R^{P1}$, $R^{P2}$ each, independently of one another, have the meaning of $R^{31}$ of formula III; c is 0, 1 or 2. $R^1$ and $R^2$ preferably, independently of one another, denote alkyl or alkoxy having 1 to 6 C atoms.

Particularly preferred compounds of the formulae BC, CR and PH-1 are the compounds BC-1 to BC-7, CR-1 to CR-5, and BP-1 to BP-7

BC-1

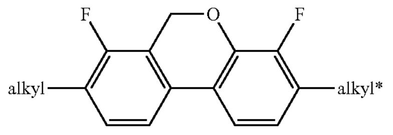

BC-2

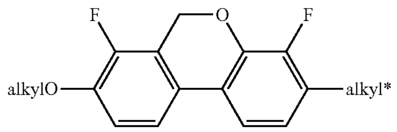

BC-3

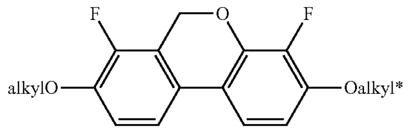

-continued

BC-4

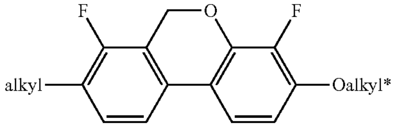

BC-5

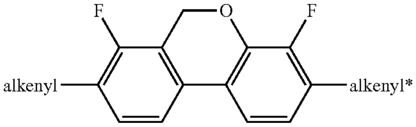

BC-6

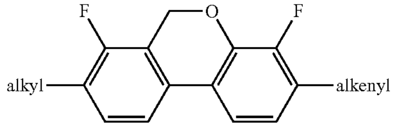

BC-7

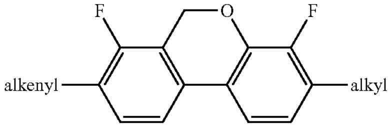

CR-1

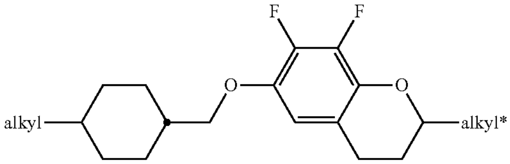

CR-2

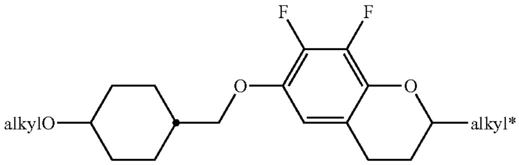

CR-3

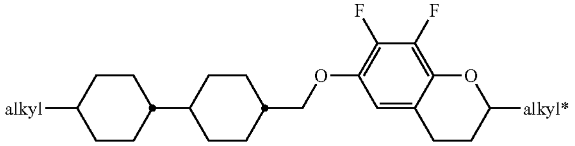

CR-4

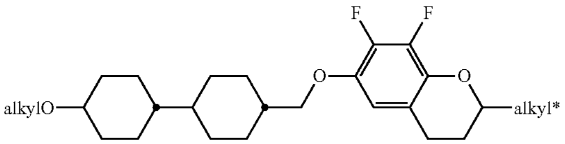

CR-5

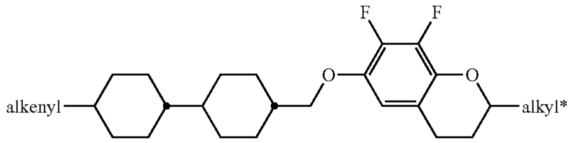

BP-1

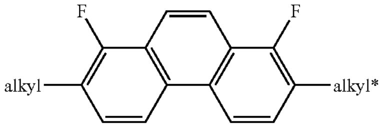

-continued

BP-2

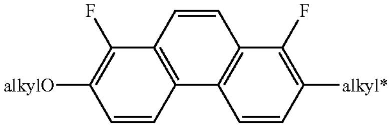

BP-3

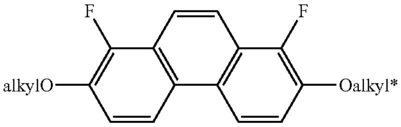

BP-4

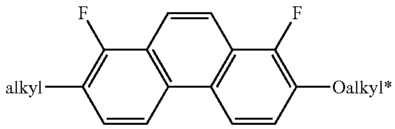

BP-5

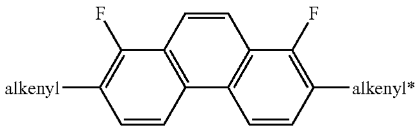

BP-6

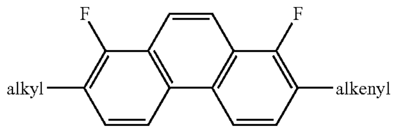

BP-7

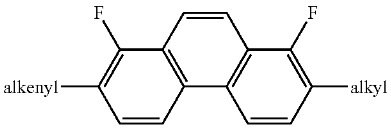

in which alkyl and alkyl* each, independently of one another, denote a straight-chain alkyl radical having 1 to 6 C atoms, and alkenyl and alkenyl* each, independently of one another, denote a straight-chain alkenyl radical having 2 to 6 C atoms.

More preference is given to mixtures comprising one, two or three compounds of the formula BC-2, BC-3, BP-2 and/or BP-3, very preferably BP-2 and/or BP-3, in particular BP-3.

d) Preferred mixtures comprise one or more indane compounds of the formula In,

In

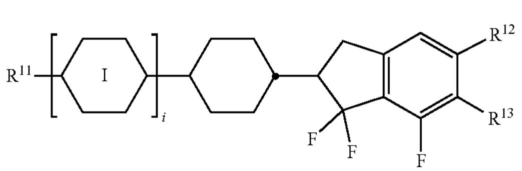

in which $R^{11}$, $R^{12}$, and $R^{13}$ each, independently of one another, denote a straight-chain alkyl, alkoxy, alkoxyalkyl or alkenyl radical having 1 to 6 C atoms, $R^{12}$ and $R^{13}$ alternatively denote halogen, preferably F,

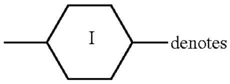 denotes 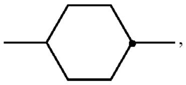
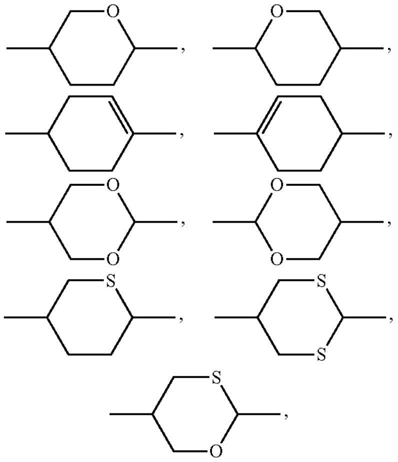
i denotes 0, 1 or 2.
Preferred compounds of the formula In are the compounds of the formulae In-1 to In-16 indicated below:
In-1
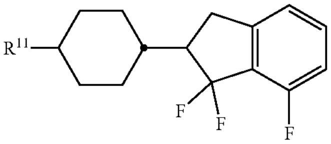
In-2
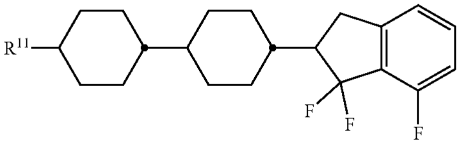
In-3
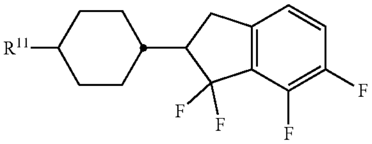
In-4
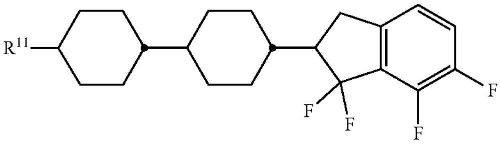
In-5
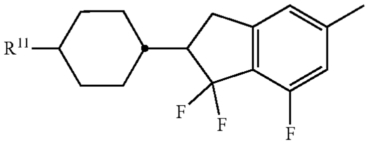
In-6
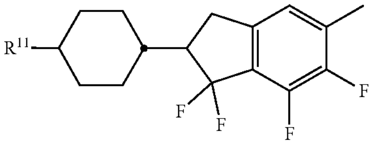
-continued
In-7
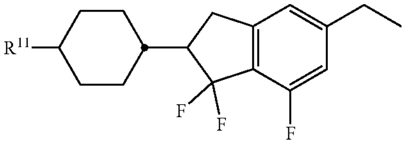
In-8
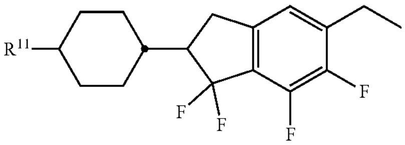
In-9
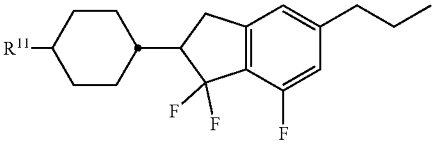
In-10
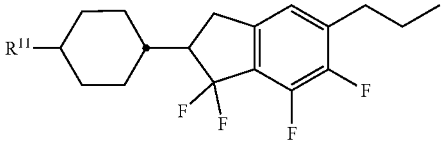
In-11
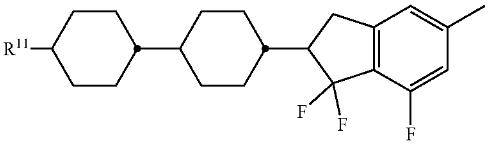
In-12
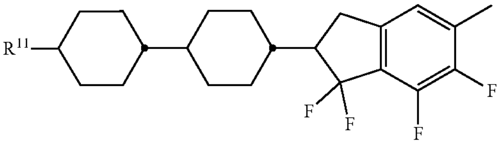
In-13
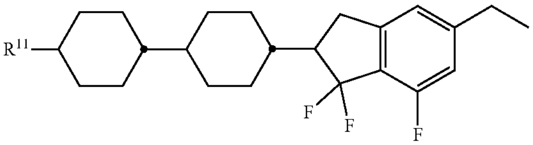
In-14
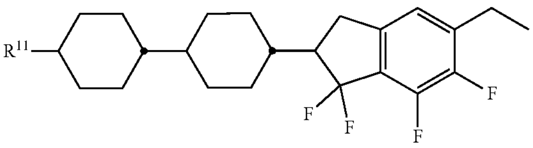
In-15
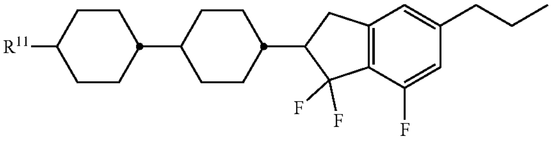

-continued

In-16

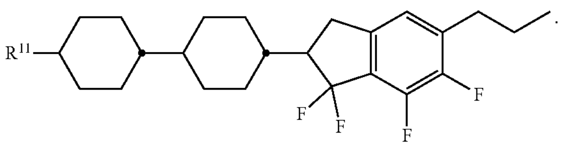

Particular preference is given to the compounds of the formulae In-1, In-2, In-3 and In-4.

e) Preferred mixtures additionally comprise one or more compounds of the formulae L-1 to L-5,

L-1

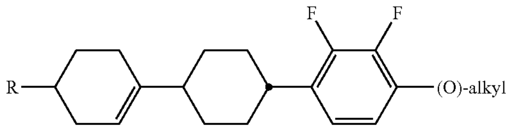

L-2

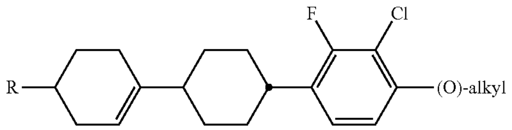

L-3

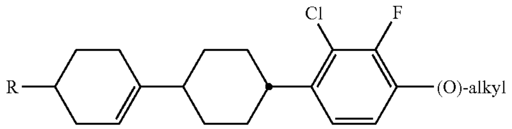

L-4

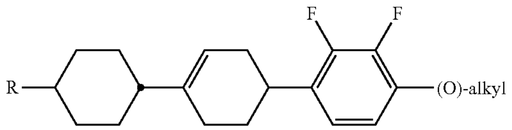

L-5

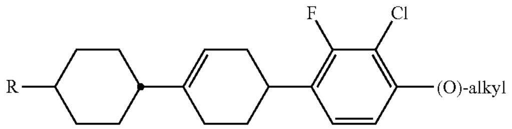

L-6

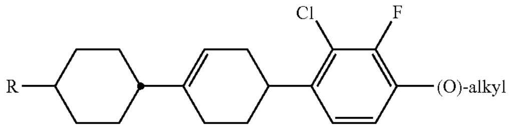

L-7

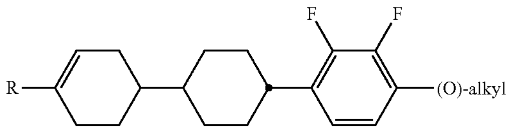

L-8

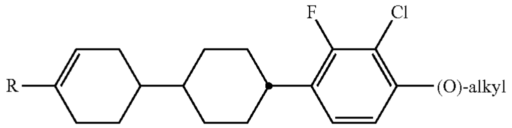

L-9

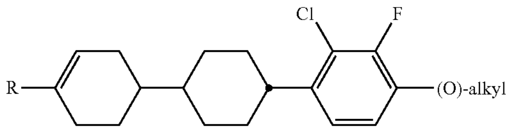

-continued

L-10

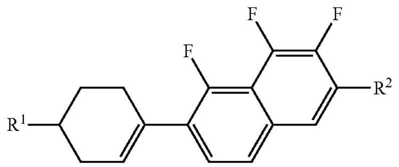

L-11

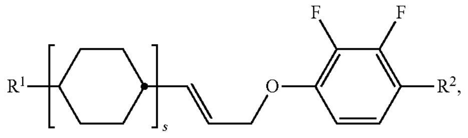

in which

R, $R^1$ and $R^2$ each, independently of one another, have the meanings indicated for $R^{2A}$ in formula IIA above, and alkyl denotes an alkyl radical having 1 to 6 C atoms. The parameter s denotes 1 or 2.

The compounds of the formulae L-1 to L-9 are preferably employed in concentrations of 5 to 15% by weight, in particular 5 to 12% by weight and very particularly preferably 8 to 10% by weight.

f) Preferred mixtures additionally comprise one or more compounds of formula IIA-Y

IIA-Y

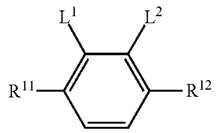

in which $R^{11}$ and $R^{12}$ have one of the meanings given for $R^{2A}$ in formula IIA above, and $L^1$ and $L^2$, identically or differently, denote F or Cl.

Preferred compounds of the formula IIA-Y are selected from the group consisting of the following sub-formulae

IIA-Y1

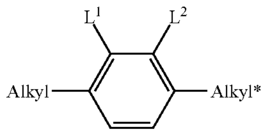

IIA-Y2

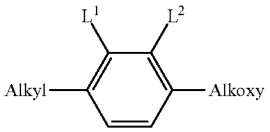

IIA-Y3

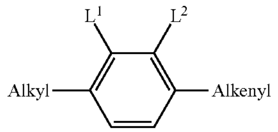

IIA-Y4

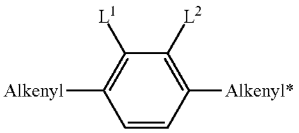

-continued

IIA-Y5

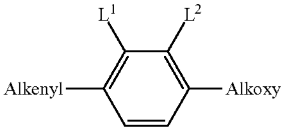

IIA-Y6

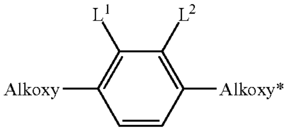

IIA-Y7

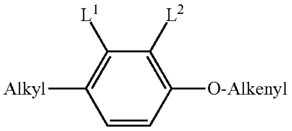

IIA-Y8

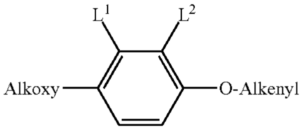

IIA-Y9

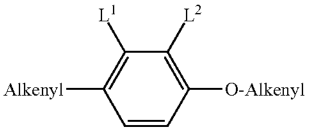

IIA-Y10

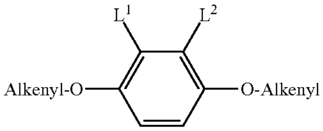

in which, Alkyl and Alkyl* each, independently of one another, denote a straight-chain alkyl radical having 1-6 C atoms, Alkoxy denotes a straight-chain alkoxy radical having 1-6 C atoms, Alkenyl and Alkenyl* each, independently of one another, denote a straight-chain alkenyl radical having 2-6 C atoms, and O denotes an oxygen atom or a single bond. Alkenyl and Alkenyl* preferably denote $CH_2{=}CH—$, $CH_2{=}CHCH_2CH_2—$, $CH_3—CH{=}CH—$, $CH_3—CH_2—CH{=}CH—$, $CH_3—(CH_2)_2—CH{=}CH—$, $CH_3—(CH_2)_3—CH{=}CH—$ or $CH_3—CH{=}CH—(CH_2)_2—$.

Particularly preferred compounds of the formula IIA-Y are selected from the group consisting of following sub-formulae:

IIA-Y6a

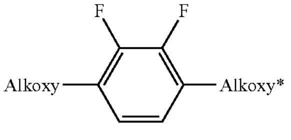

IIA-Y6b

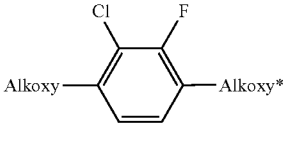

in which Alkoxy and Alkoxy* have the meanings defined above and preferably denote methoxy, ethoxy, n-propyloxy, n-butyloxy or n-pentyloxy.

Preferably, the medium according to the invention comprises a compound selected from the group of compounds of the formulae ST-1 to ST-18, very preferably of the formula ST-3:

ST-1

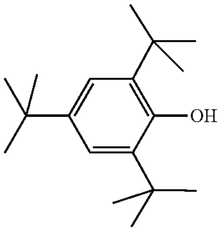

ST-2

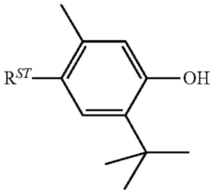

ST-3

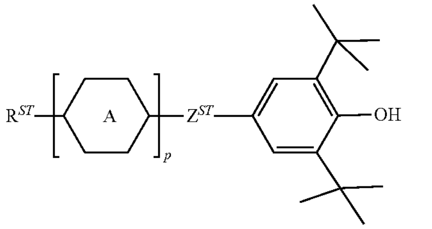

ST-4

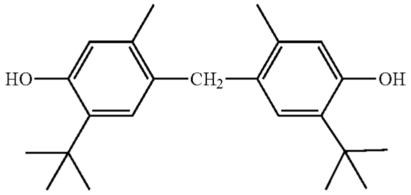

ST-5

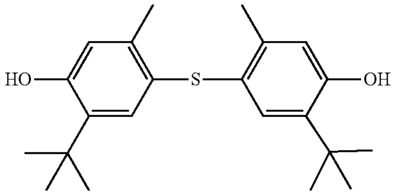

ST-6

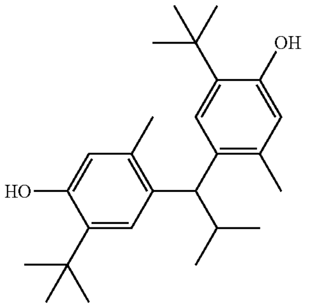

-continued
ST-7
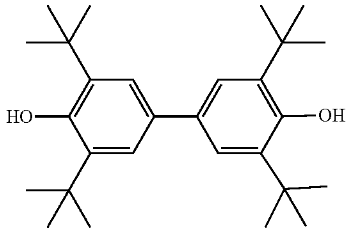
ST-8
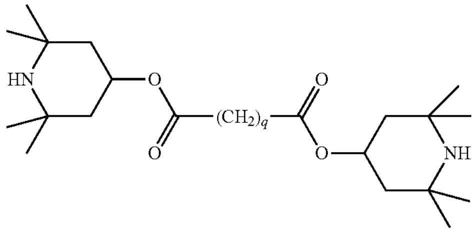
ST-9
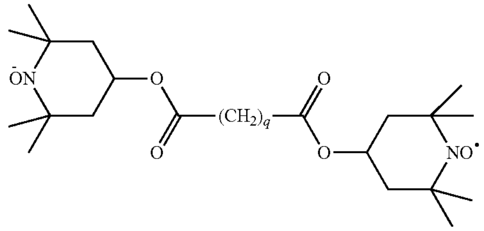
ST-10
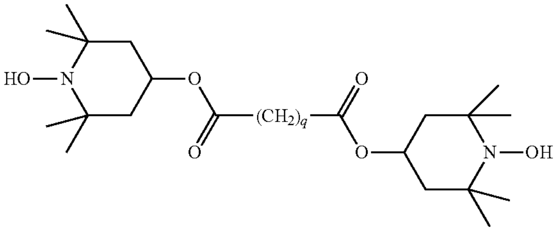
ST-11
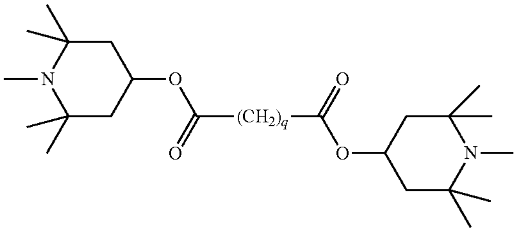
ST-12a
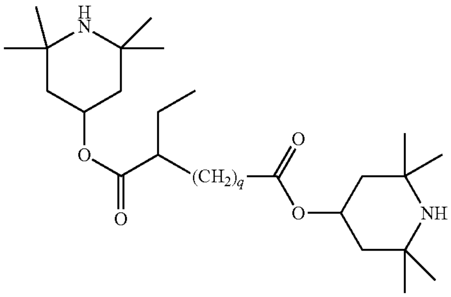
-continued
ST-12b
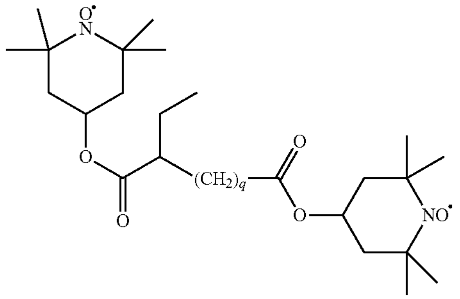
ST-13
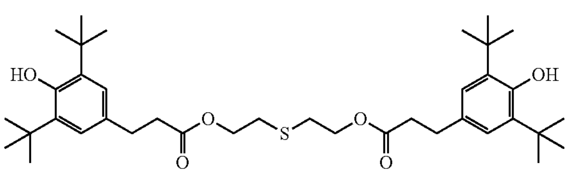
ST-14
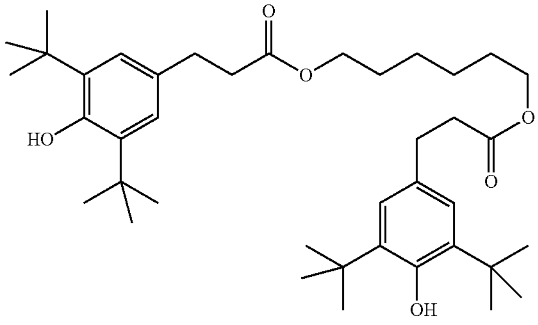
ST-15
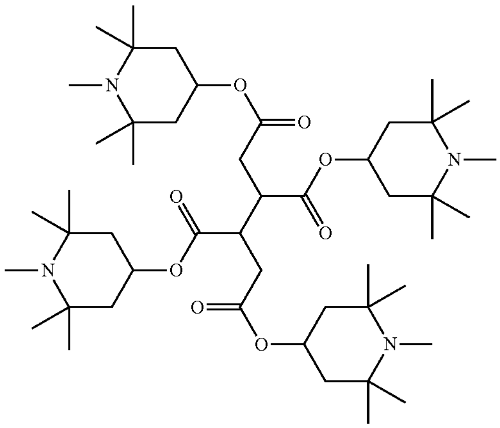
ST-16
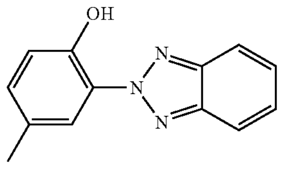

-continued

ST-17

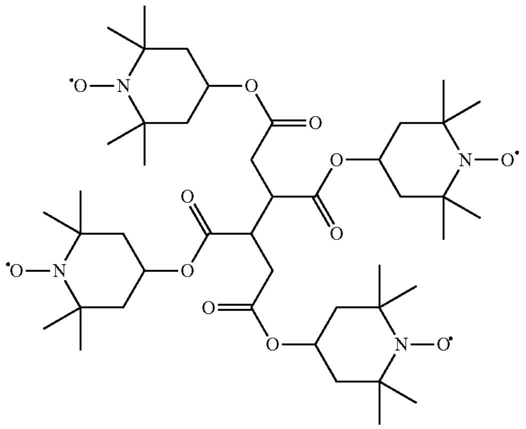

ST-18

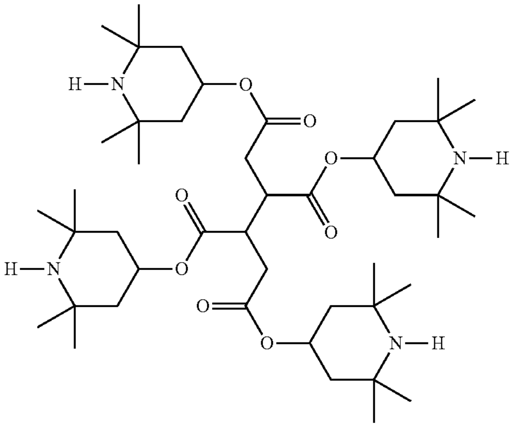

in which $R^{ST}$ denotes H, an alkyl or alkoxy radical having 1 to 15 C atoms, where, in addition, one or more $CH_2$ groups in these radicals may each be replaced, independently of one another by —C≡C—, —$CF_2O$—, —$OCF_2$—, —CH═CH—,

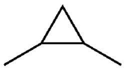, 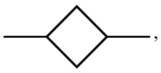, 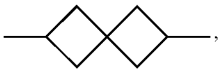,

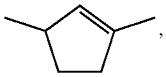, 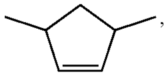, 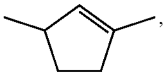,

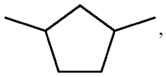,

—O—, —CO—O—, —O—CO— in such a way that O atoms are not linked directly to one another, and in which, in addition, one or more H atoms may be replaced by halogen,

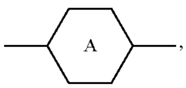, on each occurrence, identically or differently, denotes

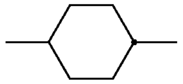 or 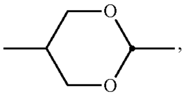, $Z^{ST}$ each, independently of one another, denote —CO—O—, —O—CO—, —$CF_2O$—, —$OCF_2$—, —$CH_2O$—, —$OCH_2$—, —$CH_2$—, —$CH_2CH_2$—, —$(CH_2)_4$—, —CH═CH—, —$CH_2O$—, —$C_2F_4$—, —$CH_2CF_2$—, —$CF_2CH_2$—, —CF═CF—, —CH═CF—, —CF═CH—, —CH═CH—, —C≡C— or a single bond, $L^1$ and $L^2$ each, independently of one another, denote F, Cl, $CH_3$, $CF_3$ or $CHF_2$, p denotes 0, 1 or 2, q denotes 1, 2, 3, 4, 5, 6, 7, 8, 9 or 10.

Of the compounds of the formula ST, special preference is given to the compounds of the formulae

ST-1

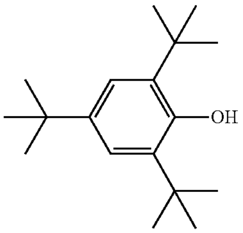

ST-2a

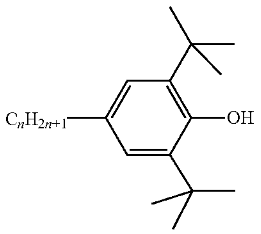

in which n=1, 2, 3, 4, 5, 6 or 7, preferably n=1 or 7

ST-3a

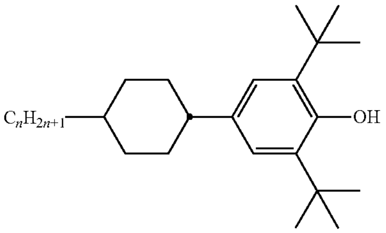

in which n=1, 2, 3, 4, 5, 6 or 7, preferably n=3

ST-3b

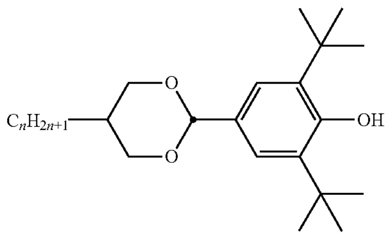

in which n=1, 2, 3, 4, 5, 6 or 7, preferably n=3

ST-3c

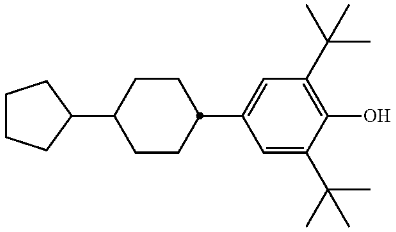

ST-3d

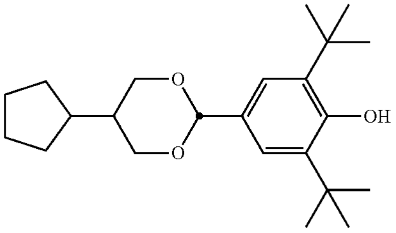

ST-8-1

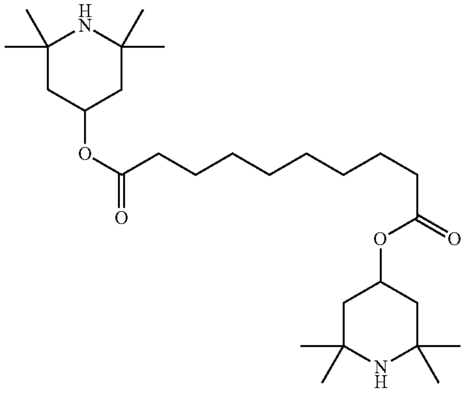

ST-9-1

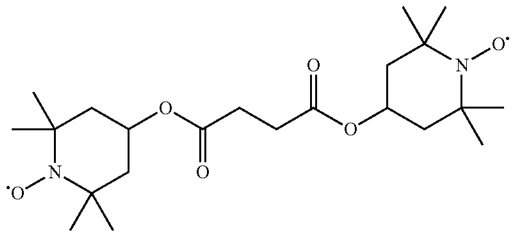

-continued

ST-12

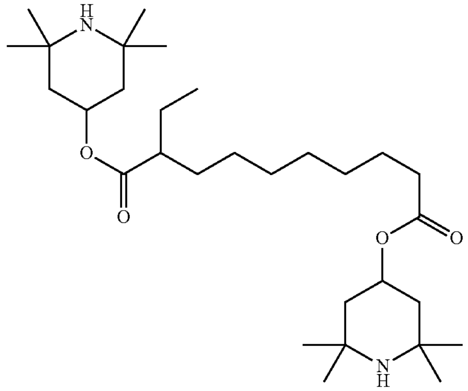

ST-16

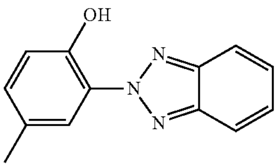

ST-17

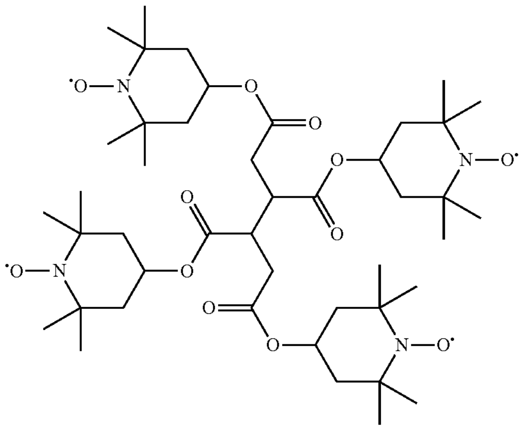

ST-18

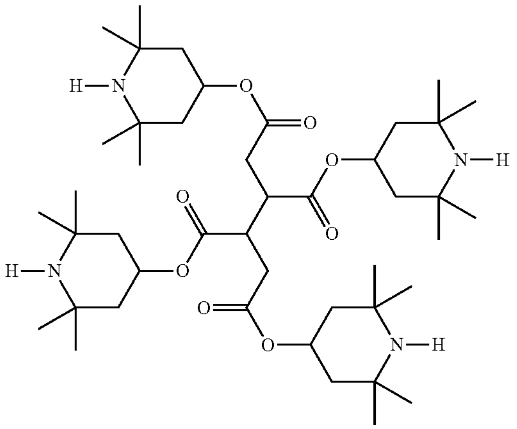

In the compounds of the formulae ST-3a and ST-3b, n preferably denotes 3. In the compounds of the formula ST-2a, n preferably denotes 7.

Very particularly preferred mixtures according to the invention comprise one or more stabilizers from the group of the compounds of the formulae ST-2a-1, ST-3a-1, ST-3b-1, ST-8-1, ST-9-1 and ST-12:

ST-2a-1

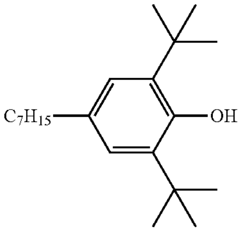

ST-3a-1

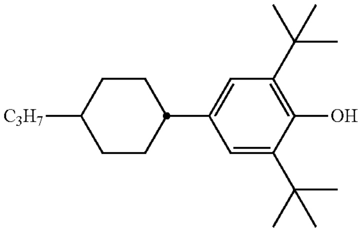

ST-3b-1

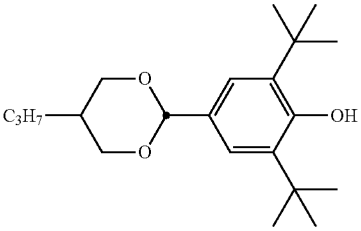

ST-8-1

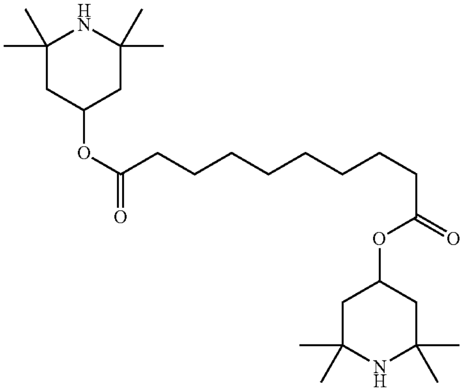

ST-9-1

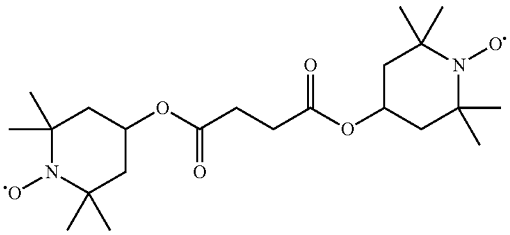

-continued

ST-12

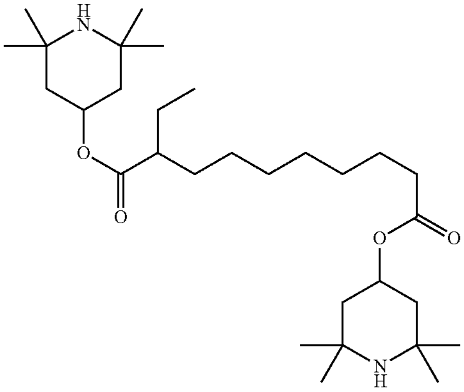

Preferably, the medium comprises one or more compounds of the formula S

S

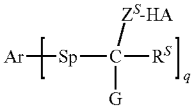

in which

Ar denotes a methylene group or an aromatic hydrocarbon group having 6 to 40 C atoms or a heteroaromatic hydrocarbon group having 4 to 40 C atoms; preferably an aromatic hydrocarbon group having 6 to 40 C atoms;

Sp denotes a spacer group;

$R^S$ denotes H, alkyl having 1 to 12 C atoms or alkenyl having 2 to 12 C atoms;

$Z^S$ denotes —O—, —C(O)O—, $-(CH_2)_z-$ or $-(CH_2)_zO-$, or a single bond;

HA denotes

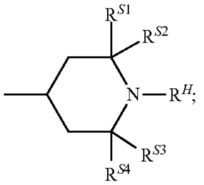

$R^H$ denotes H, $O^\bullet$, $CH_3$, OH or $OR^S$;

$R^{S1}$, $R^{S2}$, $R^{S3}$ and $R^{S4}$, identically or differently, denote alkyl having 1 to 6 C atoms, preferably having 1 to 3 C atoms, very preferably $CH_3$;

G denotes H or $R^S$ or a group $Z^S$-HA;

z is an integer from 1 to 6, and q is 2, 3 or 4, preferably 3 or 4.

In formula S, aryl denotes an aromatic or heteroaromatic hydrocarbon group having 4 to 40 C atoms, comprising one, two, three or four aromatic rings including condensed rings that may be linked directly or via an alkylene linking group having 1 to 12 C atoms, in which one or more H atoms are optionally replaced with alkyl or alkoxy having 1 to 6 C atoms or alkenyl having 2 to 6 C atoms, or with CN, $CF_3$ or halogen, and in which one or more $CH_2$ groups may each, independently of one another, be replaced by —O—, —S—, —NH—, —N($C_1$-$C_4$-alkyl)-, —CO—, —CO—O—, —O—CO—, —O—CO—O—, —CH═CH— or —C≡C— in such a way that O or S atoms are not linked directly to one another.

Preferred aryl groups are benzene, naphthalene, anthracene, biphenyl, m-terphenyl, p-terphenyl, and (phenylalkyl) benzene in which alkyl is straight chain alkyl having 1 to 12 C atoms.

In a preferred embodiment, the medium according to the invention comprises a compound of the formula S in which the parameter q is 3 and G denotes a group $Z^S$-HA.

In another preferred embodiment, the medium according to the invention comprises a compound of the formula S in which the parameter q is 4 and G denotes H or $R^S$.

The compounds of formula S are preferably selected from the compounds of the formulae S-1, S-2 and S-3:

S-1

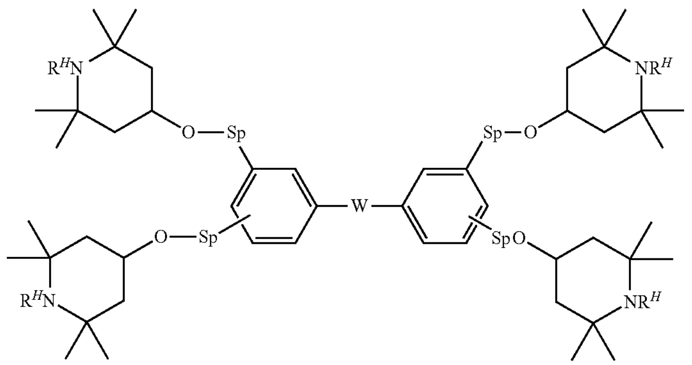

S-2

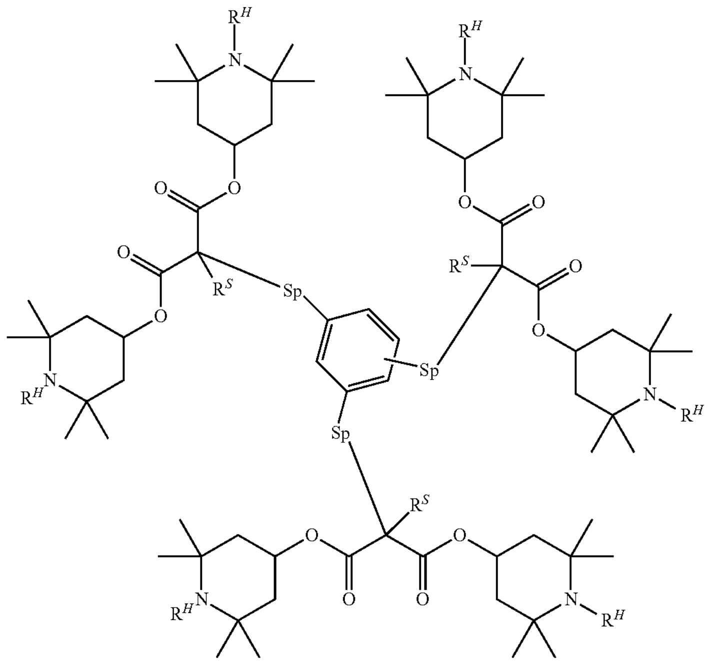

-continued

S-3

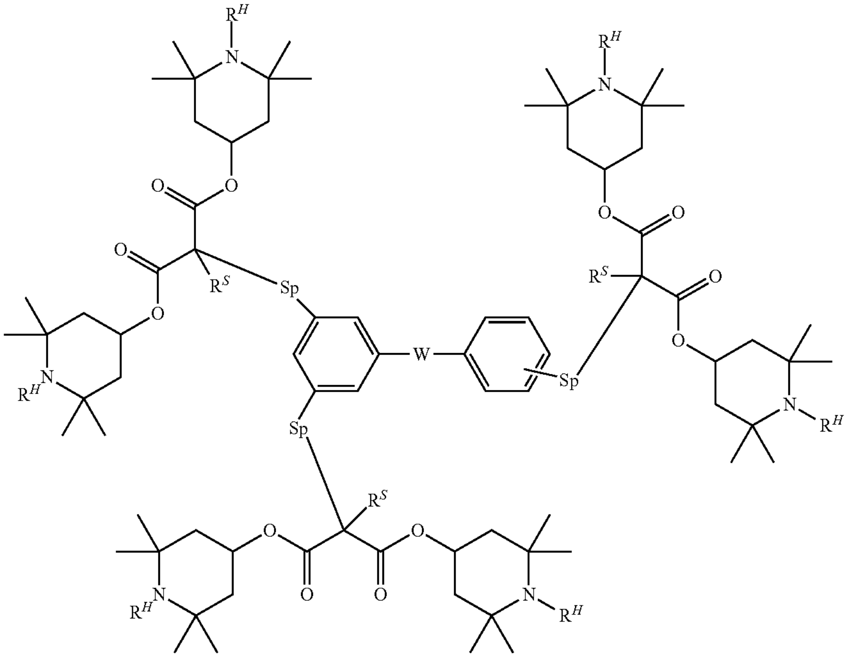

in which R has the meanings given above and preferably denotes H or $O^-$,

Sp on each occurrence, identically or differently, denotes a spacer group, and

W denotes linear or branched, optionally unsaturated alkylene having 1 to 12 C atoms, in which one or more non-adjacent $-CH_2-$ groups may be replaced with $-O-$.

Preferred compounds of formula S-1 are selected from the compounds of the formula S-1-1:

S-1-1

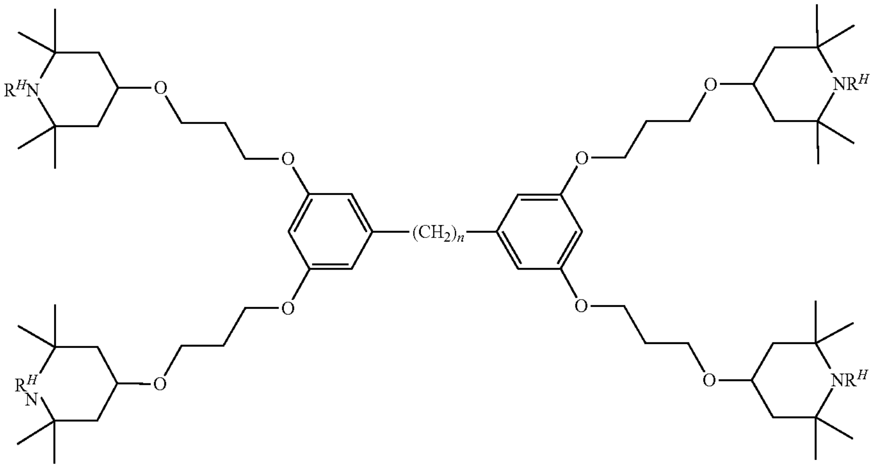

in which $R^H$ has the meanings given above and preferably denotes H or $O^-$, and n is an integer from 0 to 12, preferably 5, 6, 7, 8 or 9, very preferably 7.

Preferred compounds of formula S-2 are selected from the compounds of the formula S-2-1:

S-2-1

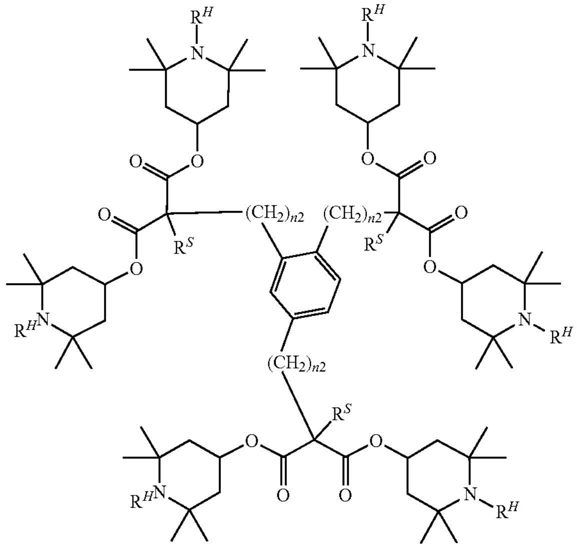

in which $R^H$ has the meanings given above and preferably denotes H or $O^-$, and n2, on each occurrence identically or differently, preferably identically, is an integer from 1 to 12, preferably 2, 3, 4, 5, or 6, very preferably 3, and $R^S$ on each occurrence identically or differently, preferably identically, denotes alkyl having 1 to 6 C atoms, preferably n-butyl.

Preferred compounds of formula S-3 are selected from the compounds of the formula S-3-1:

S-3-1

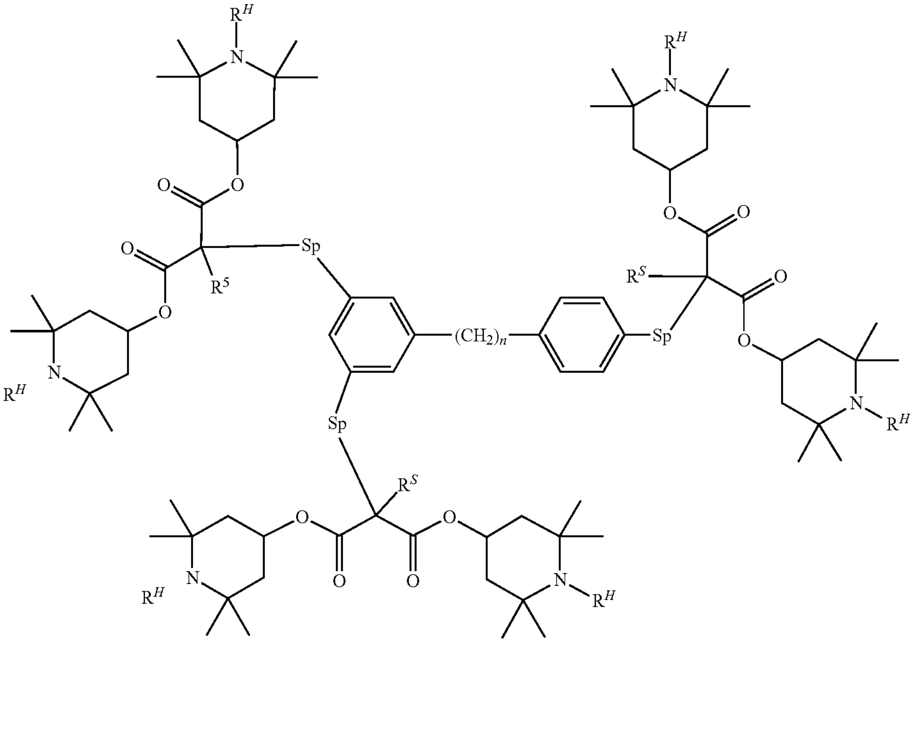

in which $R^H$ has the meanings given above and preferably denotes H or $O^-$, and n is an integer from 0 to 12, preferably 5, 6, 7, 8 or 9, very preferably 7.

The compounds of the formulae S and ST-1 to ST-18 are preferably each present in the liquid-crystal mixtures according to the invention in amounts of 0.005-0.5%, based on the mixture.

If the mixtures according to the invention comprise two or more compounds from the group of the compounds of the formulae S and ST-1 to ST-18, the concentration correspondingly increases to 0.01-1% in the case of two compounds, based on the mixtures.

However, the total proportion of the compounds of the formulae S and ST-1 to ST-18, based on the mixture according to the invention, should not exceed 2%.

The liquid crystal medium according to the invention, herein also referred to as liquid crystal host mixture, is suitable for the use in polymer stabilised displays. To this end, the medium according to the invention optionally comprises one or more polymerisable compounds of formula P $$P\text{-}Sp\text{-}A^1\text{-}(Z^1\text{-}A^2)_z\text{-}R \qquad P$$

in which independently of each other and on each occurrence identically or differently, P denotes a polymerisable group, Sp denotes a spacer group or a single bond, $A^1$, $A^2$ denote an aromatic, heteroaromatic, alicyclic or heterocyclic group, preferably having 4 to 25 ring atoms, which may also contain fused rings, and which is unsubstituted, or mono- or polysubstituted by L, SCHZ$^1$ denotes —O—, —S—, —CO—, —CO—O—, —O—CO—, —O—CO—O—, —$OCH_2$—, —$CH_2O$—, -$_2$-, —$CH_2S$—, —$CF_2O$—, —$OCF_2$—, —$CF_2S$—, —$SCF_2$—, —$(CH_2)_{n1}$—, —$CF_2CH_2$—, —$CH_2CF_2$—, SCH—$(CF_2)_{n1}$—, —CH═CH—, —CF═CF—, —CH═CF—, —CF═CH—, —C≡C—, —CH=CH—CO—O—, SCH—O—CO—CH=CH—, —$CH_2$—$CH_2$—CO—O—, —O—CO—$CH_2$—$CH_2$—, —$CR^0R^{00}$—, or a single bond, $R^0$, $R^0$ denote H or alkyl having 1 to 12 C atoms, R denotes H, L, or P-Sp-, L denotes F, Cl, —CN, P-Sp- or straight chain, branched or cyclic alkyl having 1 to 25 C atoms, wherein one or more non-adjacent $CH_2$-groups are optionally replaced by —O—, —S—, —CO—, —CO—O—, —O—CO—, —O—CO—O— in such a manner that O- and/or S-atoms are not directly connected with each other, and wherein one or more H atoms are each optionally replaced by P-Sp-, F or Cl, z is 0, 1, 2 or 3, and n1 is 1, 2, 3 or 4.

The term "reliability" as used herein means the quality of the performance of the display during time and with different stress loads, such as light load, temperature, humidity, voltage, and comprises display effects such as image sticking (area and line image sticking), mura, yogore etc. which are known to the skilled person in the field of LC displays. As a standard parameter for categorising the reliability usually the voltage holding ration (VHR) value is used, which is a measure for maintaining a constant electrical voltage in a test display. Among other factors, a high VHR is a prerequisite for a high reliability of the LC medium.

Unless indicated otherwise, the term "PSA" is used hereinafter when referring to displays of the polymer sustained alignment type in general, and the term "PS" is used when referring to specific display modes, like PS-VA, PS-TN and the like.

As used herein, the terms "active layer" and "switchable layer" mean a layer in an electrooptical display, for example an LC display, that comprises one or more molecules having structural and optical anisotropy, like for example LC molecules, which change their orientation upon an external stimulus like an electric or magnetic field, resulting in a change of the transmission of the layer for polarized or unpolarized light.

As used herein, the terms "tilt" and "tilt angle" will be understood to mean a tilted alignment of the LC molecules of an LC medium relative to the surfaces of the cell in an LC display (here preferably a PSA display). The tilt angle here denotes the average angle (<90°) between the longitudinal molecular axes of the LC molecules (LC director) and the surface of the plane-parallel outer plates which form the LC cell. A low value for the tilt angle (i.e., a large deviation from the 90° angle) corresponds to a large tilt here. A suitable method for measurement of the tilt angle is given in the examples. Unless indicated otherwise, tilt angle values disclosed above and below relate to this measurement method.

As used herein, the terms "reactive mesogen" and "RM" will be understood to mean a compound containing a mesogenic or liquid crystalline skeleton, and one or more functional groups attached thereto which are suitable for polymerisation and are also referred to as "polymerisable group" or "P".

Unless stated otherwise, the term "polymerisable compound" as used herein will be understood to mean a polymerisable monomeric compound.

As used herein, the term "low-molecular-weight compound" will be understood to mean to a compound that is monomeric and/or is not prepared by a polymerisation reaction, as opposed to a "polymeric compound" or a "polymer".

As used herein, the term "unpolymerisable compound" will be understood to mean a compound that does not contain a functional group that is suitable for polymerisation under the conditions usually applied for the polymerisation of the RMs.

The term "mesogenic group" as used herein is known to the person skilled in the art and described in the literature, and means a group which, due to the anisotropy of its attracting and repelling interactions, essentially contributes to causing a liquid-crystal (LC) phase in low-molecular-weight or polymeric substances. Compounds containing mesogenic groups (mesogenic compounds) do not necessarily have to have an LC phase themselves. It is also possible for mesogenic compounds to exhibit LC phase behaviour only after mixing with other compounds and/or after polymerisation. Typical mesogenic groups are, for example, rigid rod- or disc-shaped units. An overview of the terms and definitions used in connection with mesogenic, or LC compounds is given in *Pure Appl. Chem.* 2001, 73(5), 888 and C. Tschierske, G. Pelzl, S. Diele, *Angew. Chem.* 2004, 116, 6340-6368.

As used herein, the terms "optically active" and "chiral" are synonyms for materials that are able to induce a helical pitch in a nematic host material, also referred to as "chiral dopants".

The term "spacer group", above and below also referred to as "Sp", as used herein is known to the person skilled in the art and is described in the literature, see, for example, *Pure Appl. Chem.* 2001, 73(5), 888 and C. Tschierske, G. Pelzl, S. Diele, *Angew. Chem.* 2004, 116, 6340-6368. As used herein, the terms "spacer group" or "spacer" mean a flexible group, for example an alkylene group, which connects the mesogenic group and the polymerisable group(s) in a polymerisable mesogenic compound.

Likewise, in the compounds of formula I, a spacer group connects a central hydrocarbon group with a photoactive, stabilising hindered amine functional group.

Above and below,

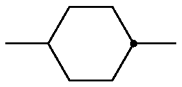

denotes a trans-1,4-cyclohexylene ring.

In a group

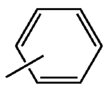

the single bond shown between the two ring atoms can be attached to any free position of the benzene ring.

Above and below "organic group" denotes a carbon or hydrocarbon group.

"Carbon group" denotes a mono- or polyvalent organic group containing at least one carbon atom, where this either contains no further atoms (such as, for example, —C≡C—) or optionally contains one or more further atoms, such as, for example, N, O, S, B, P, Si, Se, As, Te or Ge (for example carbonyl, etc.). The term "hydrocarbon group" denotes a carbon group which additionally contains one or more H atoms and optionally one or more heteroatoms, such as, for example, N, O, S, B, P, Si, Se, As, Te or Ge.

"Halogen" denotes F, Cl, Br or I, preferably F or Cl. —CO—, —C(=O)— and —C(O)— denote a carbonyl group, i.e.,

A carbon or hydrocarbon group can be a saturated or unsaturated group. Unsaturated groups are, for example, aryl, alkenyl or alkynyl groups. A carbon or hydrocarbon radical having more than 3 C atoms can be straight-chain, branched and/or cyclic and may also contain spiro links or condensed rings.

The terms “alkyl”, “aryl”, “heteroaryl”, etc., also encompass polyvalent groups, for example alkylene, arylene, heteroarylene, etc.

The term “aryl” denotes an aromatic carbon group, or a group derived therefrom. The term “heteroaryl” denotes “aryl” as defined above, containing one or more heteroatoms, preferably selected from N, O, S, Se, Te, Si and Ge.

Preferred carbon and hydrocarbon groups are optionally substituted, straight-chain, branched or cyclic, alkyl, alkenyl, alkynyl, alkoxy, alkylcarbonyl, alkoxycarbonyl, alkylcarbonyloxy and alkoxycarbonyloxy having 1 to 40, preferably 1 to 20, very preferably 1 to 12, C atoms, optionally substituted aryl or aryloxy having 5 to 30, preferably 6 to 25, C atoms, or optionally substituted alkylaryl, arylalkyl, alkylaryloxy, arylalkyloxy, arylcarbonyl, aryloxycarbonyl, arylcarbonyloxy and aryloxycarbonyloxy having 5 to 30, preferably 6 to 25, C atoms, wherein one or more C atoms may also be replaced by hetero atoms, preferably selected from N, O, S, Se, Te, Si and Ge.

Further preferred carbon and hydrocarbon groups are $C_1$-$C_{20}$ alkyl, $C_2$-$C_{20}$ alkenyl, $C_2$-$C_{20}$ alkynyl, $C_3$-$C_{20}$ allyl, $C_4$-$C_{20}$ alkyldienyl, $C_4$-$C_{20}$ polyenyl, $C_6$-$C_{20}$ cycloalkyl, $C_4$-$C_{15}$ cycloalkenyl, $C_6$-$C_{30}$ aryl, $C_6$-$C_{30}$ alkylaryl, $C_6$-$C_{30}$ arylalkyl, $C_6$-$C_{30}$ alkylaryloxy, $C_6$-$C_{30}$ aryl-alkyloxy, $C_2$-$C_{30}$ heteroaryl, $C_2$-$C_{30}$ heteroaryloxy.

Particular preference is given to $C_1$-$C_{12}$ alkyl, $C_2$-$C_{12}$ alkenyl, $C_2$-$C_{12}$ alkynyl, $C_6$-$C_{25}$ aryl and $C_2$-$C_{25}$ heteroaryl.

Further preferred carbon and hydrocarbon groups are straight-chain, branched or cyclic alkyl having 1 to 20, preferably 1 to 12, C atoms, which are unsubstituted or mono- or polysubstituted by F, Cl, Br, I or CN and in which one or more non-adjacent $CH_2$ groups may each be replaced, independently of one another, by —C($R^x$)═C($R^x$)—, —C≡-, —N($R^x$)—, —O—, —S—, —CO—, —CO—O—, —O—CO—, —O—CO—O— in such a way that 0 and/or S atoms are not linked directly to one another.

$R^x$ preferably denotes H, F, Cl, CN, a straight-chain, branched or cyclic alkyl chain having 1 to 25 C atoms, in which, in addition, one or more non-adjacent C atoms may be replaced by —O—, —S—, —CO—, —CO—O—, —O—CO—, —O—CO—O— and in which one or more H atoms may be replaced by F or C, or denotes an optionally substituted aryl or aryloxy group with 6 to 30 C atoms, or an optionally substituted heteroaryl or heteroaryloxy group with 2 to 30 C atoms.

Preferred alkyl groups are, for example, methyl, ethyl, n-propyl, isopropyl, n-butyl, isobutyl, s-butyl, t-butyl, 2-methylbutyl, n-pentyl, s-pentyl, cyclopentyl, n-hexyl, cyclohexyl, 2-ethylhexyl, n-heptyl, cycloheptyl, n-octyl, cyclooctyl, n-nonyl, n-decyl, n-undecyl, n-dodecyl, dodecanyl, trifluoromethyl, perfluoro-n-butyl, 2,2,2-trifluoroethyl, perfluorooctyl, perfluorohexyl, etc.

Preferred alkenyl groups are, for example, ethenyl, propenyl, butenyl, pentenyl, cyclopentenyl, hexenyl, cyclohexenyl, heptenyl, cycloheptenyl, octenyl, cyclooctenyl, etc.

Preferred alkynyl groups are, for example, ethynyl, propynyl, butynyl, pentynyl, hexynyl, octynyl, etc.

Preferred alkoxy groups are, for example, methoxy, ethoxy, 2-methoxyethoxy, n-propoxy, i-propoxy, n-butoxy, i-butoxy, s-butoxy, t-butoxy, 2-methylbutoxy, n-pentoxy, n-hexoxy, n-heptoxy, n-octoxy, n-nonoxy, n-decoxy, n-undecoxy, n-dodecoxy, etc.

Preferred amino groups are, for example, dimethylamino, methylamino, methylphenylamino, phenylamino, etc.

Aryl and heteroaryl groups can be monocyclic or polycyclic, i.e., they can contain one ring (such as, for example, phenyl) or two or more rings, which may also be fused (such as, for example, naphthyl) or covalently bonded (such as, for example, biphenyl), or contain a combination of fused and linked rings. Heteroaryl groups contain one or more heteroatoms, preferably selected from O, N, S and Se.

Particular preference is given to mono-, bi- or tricyclic aryl groups having 6 to 25 C atoms and mono-, bi- or tricyclic heteroaryl groups having 5 to 25 ring atoms, which optionally contain fused rings and are optionally substituted. Preference is furthermore given to 5-, 6- or 7-membered aryl and heteroaryl groups, in which, in addition, one or more CH groups may be replaced by N, S or O in such a way that O atoms and/or S atoms are not linked directly to one another.

Preferred aryl groups are, for example, phenyl, biphenyl, terphenyl, [1,1':3',1" ]terphenyl-2'-yl, naphthyl, anthracene, binaphthyl, phenanthrene, 9,10-dihydro-phenanthrene, pyrene, dihydropyrene, chrysene, perylene, tetracene, pentacene, benzopyrene, fluorene, indene, indenofluorene, spirobifluorene, etc.

Preferred heteroaryl groups are, for example, 5-membered rings, such as pyrrole, pyrazole, imidazole, 1,2,3-triazole, 1,2,4-triazole, tetrazole, furan, thiophene, selenophene, oxazole, isoxazole, 1,2-thiazole, 1,3-thiazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 6-membered rings, such as pyridine, pyridazine, pyrimidine, pyrazine, 1,3,5-triazine, 1,2,4-triazine, 1,2,3-triazine, 1,2,4,5-tetrazine, 1,2,3,4-tetrazine, 1,2,3,5-tetrazine, or condensed groups, such as indole, isoindole, indolizine, indazole, benzimidazole, benzotriazole, purine, naphthimidazole, phenanthrimidazole, pyridimidazole, pyrazinimidazole, quinoxalinimidazole, benzoxazole, naphthoxazole, anthroxazole, phenanthroxazole, isoxazole, benzothiazole, benzofuran, isobenzofuran, dibenzofuran, quinoline, isoquinoline, pteridine, benzo-5,6-quinoline, benzo-6,7-quinoline, benzo-7,8-quinoline, benzoisoquinoline, acridine, phenothiazine, phenoxazine, benzopyridazine, benzopyrimidine, quinoxaline, phenazine, naphthyridine, azacarbazole, benzocarboline, phenanthridine, phenanthroline, thieno[2,3b]thiophene, thieno[3,2b] thiophene, dithienothiophene, isobenzothiophene, dibenzothiophene, benzothiophene, benzothiadiazothiophene, or combinations of these groups.

The aryl and heteroaryl groups mentioned above and below may also be substituted by alkyl, alkoxy, thioalkyl, fluorine, fluoroalkyl or further aryl or heteroaryl groups.

The (non-aromatic) alicyclic and heterocyclic groups encompass both saturated rings, i.e., those containing exclusively single bonds, and also partially unsaturated rings, i.e., those which may also contain multiple bonds. Heterocyclic rings contain one or more heteroatoms, preferably selected from Si, O, N, S and Se.

The (non-aromatic) alicyclic and heterocyclic groups can be monocyclic, i.e., contain only one ring (such as, for example, cyclohexane), or polycyclic, i.e., contain a plurality of rings (such as, for example, decahydronaphthalene or bicyclooctane). Particular preference is given to saturated groups. Preference is furthermore given to mono-, bi- or tricyclic groups having 5 to 25 ring atoms, which optionally contain fused rings and are optionally substituted. Preference is furthermore given to 5-, 6-, 7- or 8-membered carbocyclic groups, in which, in addition, one or more C atoms may be replaced by Si and/or one or more CH groups may be replaced by N and/or one or more non-adjacent $CH_2$ groups may be replaced by —O— and/or —S—.

Preferred alicyclic and heterocyclic groups are, for example, 5-membered groups, such as cyclopentane, tetrahydrofuran, tetrahydrothiophen, pyrrolidine, 6-membered groups, such as cyclohexane, silinane, cyclohexene, tetrahydropyran, tetrahydrothiopyran, 1,3-dioxane, 1,3-dithiane, piperidine, 7-membered groups, such as cycloheptane, and fused groups, such as tetrahydronaphthalene, decahydronaphthalene, indane, bicyclo[1.1.1]pentane-1,3-diyl, bicyclo[2.2.2]octane-1,4-diyl, spiro[3.3]heptane-2,6-diyl, octahydro-4,7-methanoindane-2,5-diyl.

Preferred substituents are, for example, solubility-promoting groups, such as alkyl or alkoxy, electron-withdrawing groups, such as fluorine, nitro or nitrile, or substituents for increasing the glass transition temperature (Tg) in the polymer, in particular bulky groups, such as, for example, t-butyl or optionally substituted aryl groups.

NCSOCN Preferred substituents, hereinafter also referred to as "$L^S$", are, for example, F, Cl, Br, I, —CN, —$NO_2$, —NCO, -, -, —SCN, —C(═O)N($R^x$)$_2$, —C(═O)$Y^1$, NCSOCN—C(═O)$R^x$, —N($R^x$)$_2$, straight-chain or branched alkyl, alkoxy, alkylcarbonyl, alkoxycarbonyl, alkylcarbonyloxy or alkoxycarbonyloxy each having 1 to 25 C atoms, in which one or more H atoms may optionally be replaced by F or C, optionally substituted silyl having 1 to 20 Si atoms, or optionally substituted aryl having 6 to 25, preferably 6 to 15, C atoms, wherein $R^x$ denotes H, F, C, CN, or straight chain, branched or cyclic alkyl having 1 to 25 C atoms, wherein one or more non-adjacent $CH_2$-groups are optionally replaced by —O—, —S—, —CO—, —CO—O—, —O—CO—, —O—CO—O— in such a manner that O- and/or S-atoms are not directly connected with each other, and wherein one or more H atoms are each optionally replaced by F, Cl, P— or P-Sp-, and $Y^1$ denotes halogen.

"Substituted silyl or aryl" preferably means substituted by halogen, —CN, $R^0$, —$OR^0$, —CO—$R^0$, —CO—O—$R^0$, —O—CO—$R^0$ or —O—CO—O—$R^0$, wherein $R^0$ denotes H or alkyl with 1 to 20 C atoms.

Particularly preferred substituents L are, for example, F, C, CN, $NO_2$, $CH_3$, $C_2H_5$, $OCH_3$, $OC_2H_5$, $COCH_3$, $COC_2H_5$, $COOCH_3$, $COOC_2H_5$, $CF_3$, $OCF_3$, $OCHF_2$, $OC_2F_5$, furthermore phenyl.

$A^1$ and $A^2$ very preferably denote

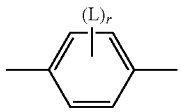

In which L has one of the meanings indicated above and r denotes 0, 1, 2, 3 or 4, in particular

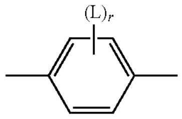

denotes

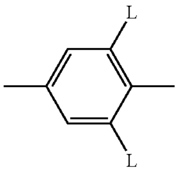

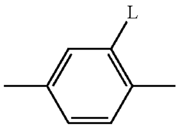

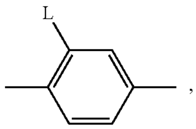

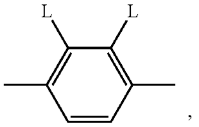

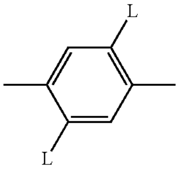

or

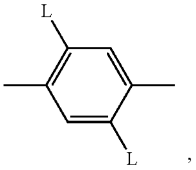

The polymerisable group P is a group which is suitable for a polymerisation reaction, such as, for example, free-radical or ionic chain polymerisation, polyaddition or polycondensation, or for a polymer-analogous reaction, for example addition or condensation onto a main polymer chain. Particular preference is given to groups for chain polymerisation, in particular those containing a C═C double bond or —C≡C— triple bond, and groups which are suitable for polymerisation with ring opening, such as, for example, oxetane or epoxide groups.

Preferred groups P are selected from the group consisting of $CH_2$═$CW^1$—CO—O—, $CH_2$═$CW^1$—CO—,

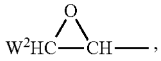

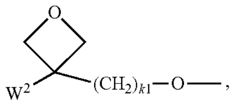

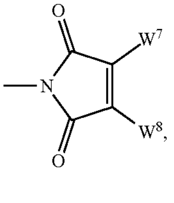

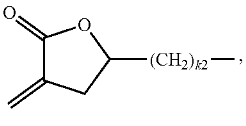

$CH_2$═$CW^2$—(O)$_{k3}$—, $CW^1$═CH—CO—(O)$_{k3}$—, $CW^1$═CH—CO—NH—, $CH_2$═$CW^1$—CO—NH—, $CH_3$—CH═CH—O—, ($CH_2$═CH)$_2$CH—OCO—, ($CH_2$═CH—$CH_2$)$_2$CH—OCO—, ($CH_2$═CH)$_2$CH—O—, ($CH_2$═CH—$CH_2$)$_2$N—, ($CH_2$═CH—$CH_2$)$_2$N—CO—, HO—$CW^2W^3$—, HS—$CW^2W^3$—, $HW^2N$—, HO—$CW^2W^3$—NH—, $CH_2$═$CW^1$—CO—NH—, $CH_2$═CH—(COO)$_{k1}$-Phe-(O)$_{k2}$—, $CH_2$═CH—(CO)$_{k1}$-Phe-(O)$_{k2}$—, Phe-CH═CH—, HOOC—, OCN— and $W^4W^5W^6$Si—, in which $W^1$ denotes H, F, Cl, CN, $CF_3$, phenyl or alkyl having 1 to 5 C atoms, in particular H, F, Cl or $CH_3$, $W^2$ and $W^3$ each, independently of one another, denote H or alkyl having 1 to 5 C atoms, in particular H, methyl, ethyl or n-propyl, $W^4$, $W^5$ and $W^6$ each, independently of one another, denote Cl, oxaalkyl or oxacarbonylalkyl having 1 to 5 C atoms, $W^7$ and $W^a$ each, independently of one another, denote H, Cl or alkyl having 1 to 5 C atoms, Phe denotes 1,4-phenylene, which is optionally substituted by one or more radicals L as defined above which are other than P-Sp-, $k_1$, $k_2$ and $k_3$ each, independently of one another, denote 0 or 1, $k_3$ preferably denotes 1, and $k_4$ denotes an integer from 1 to 10.

Very preferred groups P are selected from the group consisting of $CH_2{=}CW^1{-}CO{-}O{-}$, $CH_2{=}CW^1{-}CO{-}$,

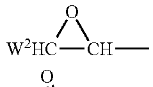,
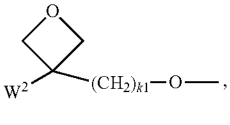,
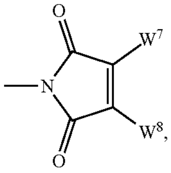,
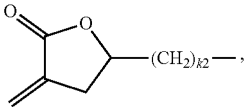, $CH_2{=}CW^2{-}O{-}$, $CH_2{=}CW^2{-}$, $CW^1{=}CH{-}CO{-}(O)_{k3}{-}$, $CW^1{=}CH{-}CO{-}NH{-}$, $CH_2{=}CW^1{-}CO{-}NH{-}$, $(CH_2{=}CH)_2CH{-}OCO{-}$, $(CH_2{=}CH{-}CH_2)_2CH{-}OCO{-}$, $(CH_2{=}CH)_2CH{-}O{-}$, $(CH_2{=}CH{-}CH_2)_2N{-}$, $(CH_2{=}CH{-}CH_2)_2N{-}CO{-}$, $CH_2{=}CW^1{-}CO{-}NH{-}$, $CH_2{=}CH{-}(COO)_{k1}$-Phe-$(O)_{k2}{-}$, $CH_2{=}CH{-}(CO)_{k1}$-Phe-$(O)_{k2}{-}$, Phe-$CH{=}CH{-}$ and $W^4W^5W^6Si{-}$, in which $W^1$ denotes H, F, Cl, CN, $CF_3$, phenyl or alkyl having 1 to 5 C atoms, in particular H, F, Cl or $CH_3$, $W^2$ and $W^3$ each, independently of one another, denote H or alkyl having 1 to 5 C atoms, in particular H, methyl, ethyl or n-propyl, $W^4$, $W^5$ and $W^6$ each, independently of one another, denote Cl, oxaalkyl or oxacarbonylalkyl having 1 to 5 C atoms, $W^7$ and $W^a$ each, independently of one another, denote H, Cl or alkyl having 1 to 5 C atoms, Phe denotes 1,4-phenylene, $k_1$, $k_2$ and $k_3$ each, independently of one another, denote 0 or 1, $k_3$ preferably denotes 1, and $k_4$ denotes an integer from 1 to 10.

Very particularly preferred groups P are selected from the group consisting of $CH_2{=}CW^1{-}CO{-}O{-}$, in particular $CH_2{=}CH{-}CO{-}O{-}$, $CH_2{=}C(CH_3){-}CO{-}O{-}$ and $CH_2{=}CF{-}CO{-}O{-}$, furthermore $CH_2{=}CH{-}O{-}$, $(CH_2{=}CH)_2CH{-}O{-}CO{-}$, $(CH_2{=}CH)_2CH{-}O{-}$,

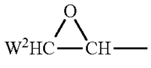 and 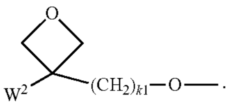.

Further preferred polymerisable groups P are selected from the group consisting of vinyloxy, acrylate, methacrylate, fluoroacrylate, chloroacrylate, oxetane and epoxide, most preferably from acrylate and methacrylate.

If the spacer group Sp is different from a single bond, it is preferably of the formula Sp"-X", so that the respective radical P-Sp- conforms to the formula R-Sp"—X"—, wherein Sp" denotes linear or branched alkylene having 1 to 20, preferably 1 to 12, C atoms, which is optionally mono- or polysubstituted by F, Cl, Br, I or CN and in which, in addition, one or more non-adjacent $CH_2$ groups may each be replaced, independently of one another, by —O—, —S—, —NH—, —$N(R^0)$—, —$Si(R^0R^{00})$—, —CO—, —CO—O—, —O—CO—, —O—CO—O—, —S—CO—, —CO—S—, —$N(R^{00})$—CO—O—, —O—CO—$N(R^0)$—, —$N(R^0)$—CO—$N(R^{00})$—, —CH=CH— or —C≡C— in such a way that 0 and/or S atoms are not linked directly to one another, X" denotes —O—, —S—, —CO—, —CO—O—, —O—CO—, —O—CO—O—, —CO—$N(R^0)$—, —$N(R^0)$—CO—, —$N(R^0)$—CO—$N(R^{00})$—, —$OCH_2$—, —$CH_2O$—, —$SCH_2$—, —$CH_2S$—, —$CF_2O$—, —$OCF_2$—, —$CF_2S$—, —$SCF_2$—, —$CF_2CH_2$—, —$CH_2CF_2$—, —$CF_2CF_2$—, —CH=N—, —N=CH—, —N=N—, —CH=$CR^0$—, —$CY^2$=$CY^3$—, —C≡C—, —CH=CH—CO—O—, —O—CO—CH=CH— or a single bond, $R^0$ and $R^{00}$, each, independently of one another, denote H or alkyl having 1 to 20 C atoms, and $Y^2$ and $Y^3$ each, independently of one another, denote H, F, C or CN.

COOCOOX" is preferably —O—, —S—, —CO—, -, —OCO—, —O—, —CO—$NR^0$—COOCOO—$NR^0$—CO—, —$NR^0$—CO—$NR^{00}$— or a single bond.

Typical spacer groups Sp and —Sp"—X"— are, for example, —$(CH_2)_{p1}$—$(CH_2)_{p1}$—O—, —$(CH_2)_{p1}$—O—CO—, —$(CH_2)_{p1}$—CO—O—, —$(CH_2)_{p1}$—O—CO—O—, —$(CH_2CH_2O)_{q1}$—$CH_2CH_2$—, —$CH_2CH_2$—S—$CH_2CH_2$—, —$CH_2CH_2$—NH—$CH_2CH_2$— or —$(SiR^0R^{00}$—$O)_{p1}$— in which p1 is an integer from 1 to 12, q1 is an integer from 1 to 3, and $R^0$ and $R^{00}$ have the meanings indicated above.

Particularly preferred groups Sp and —Sp"—X"— are —$(CH_2)_{p1}$—, —$(CH_2)_{p1}$—O—, —$(CH_2)_{p1}$—O—CO—, —$(CH_2)_{p1}$—CO—O—, —$(CH_2)_{p1}$—O—CO—O—, in which p1 and q1 have the meanings indicated above.

Particularly preferred groups Sp" are, in each case straight-chain, ethylene, propylene, butylene, pentylene, hexylene, heptylene, octylene, nonylene, decylene, undecylene, dodecylene, octadecylene, ethyleneoxyethylene, methyleneoxybutylene, ethylenethioethylene, ethylene-N-methyliminoethylene, 1-methylalkylene, ethenylene, propenylene and butenylene.

In a preferred embodiment of the invention the compounds of formula P and its sub-formulae contain a spacer group Sp that is substituted by one or more polymerisable groups P, so that the group Sp-P corresponds to $Sp(P)_s$, with s being ≥2 (branched polymerisable groups).

Preferred compounds of formula P according to this preferred embodiment are those wherein s is 2, i.e., compounds which contain a group $Sp(P)_2$. Very preferred compounds of formula P according to this preferred embodiment contain a group selected from the following formulae:

—X-alkyl-CHPP S1

—X-alkyl-CH($(CH_2)_{aa}$P)($(CH_2)_{bb}$P) S2

—X—N($(CH_2)_{aa}$P)($(CH_2)_{bb}$P) S3

—X-alkyl-CHP—$CH_2$—$CH_2$P S4

—X-alkyl-C($CH_2$P)($CH_2$P)—$C_{aa}H_{2aa+1}$ S5

—X-alkyl-CHP—$CH_2$P S6

—X-alkyl-CPP—$C_{aa}H_{2aa+1}$ S7

—X-alkyl-CHPCHP—$C_{aa}H_{2aa+1}$ S8 in which P is as defined in formula P, alkyl denotes a single bond or straight-chain or branched alkylene having 1 to 12 C atoms which is unsubstituted or mono- or polysubstituted by F, Cl or CN and in which one or more non-adjacent $CH_2$ groups may each, independently of one another, be replaced by —C($R^0$)═C($R^0$)—, —C≡C—, —N($R^0$)—, —O—, —S—, —CO—, —CO—O—, —O—CO—, —O—CO—O— in such a way that 0 and/or S atoms are not linked directly to one another, where $R^0$ has the meaning indicated above, aa and bb each, independently of one another, denote 0, 1, 2, 3, 4, 5 or 6, X has one of the meanings indicated for X", and is preferably O, CO, $SO_2$, O—CO—, CO—O or a single bond.

Preferred spacer groups $Sp(P)_2$ are selected from formulae S1, S2 and S3.

Very preferred spacer groups $Sp(P)_2$ are selected from the following sub-formulae:

—CHPP S1a

—O—CHPP S1b

—$CH_2$—CHPP S1c

—$OCH_2$—CHPP S1d

—CH($CH_2$—P)($CH_2$—P) S2a

—OCH($CH_2$—P)($CH_2$—P) S2b

—$CH_2$—CH($CH_2$—P)($CH_2$—P) S2c

—$OCH_2$—CH($CH_2$—P)($CH_2$—P) S2d

—CO—NH($(CH_2)_2$P)($(CH_2)_2$P) S3a

In the compounds of formula P and its sub-formulae as described above and below, P is preferably selected from the group consisting of vinyloxy, acrylate, methacrylate, fluoroacrylate, chloroacrylate, oxetane and epoxide, most preferably from acrylate and methacrylate.

Further preferred are compounds of formula P and its sub-formulae as described above and below, wherein all polymerisable groups P that are present in the compound have the same meaning, and very preferably denote acrylate or methacrylate, most preferably methacrylate.

In the compounds of formula P and its sub-formulae as described above and below, R preferably denotes P-Sp-.

Further preferred are compounds of formula P and its sub-formulae as described above and below, wherein Sp denotes a single bond or —$(CH_2)_{p1}$—, —O—$(CH_2)_{p1}$—, —O—CO—$(CH_2)_{p1}$, or —CO—O—$(CH_2)_{p1}$, wherein p1 is 2, 3, 4, 5 or 6, and, if Sp is —O—$(CH_2)_{p1}$—, —O—CO—$(CH_2)_{p1}$ or —CO—O—$(CH_2)_{p1}$ the O-atom or CO-group, respectively, is linked to the benzene ring.

Further preferred are compounds of formula P and its sub-formulae as described above and below, wherein at least one group Sp is a single bond.

Further preferred are compounds of formula P and its sub-formulae as described above and below, wherein at least one group Sp is different from a single bond, and is preferably selected from —$(CH_2)_{p1}$—, —O—$(CH_2)_{p1}$—, —O—CO—$(CH_2)_{p1}$, or —CO—O—$(CH_2)_{p1}$, wherein p1 is 2, 3, 4, 5 or 6, and, if Sp is —O—$(CH_2)_{p1}$—, —O—CO—$(CH_2)_{p1}$ or —CO—O—$(CH_2)_{p1}$ the O-atom or CO-group, respectively, is linked to the benzene ring.

Very preferred groups -$A^1$-(Z-$A^2$)$_z$- in formula P are selected from the following formulae

A1

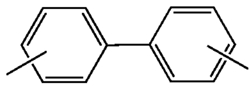

A2

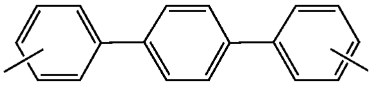

A3

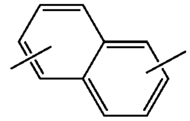

A4

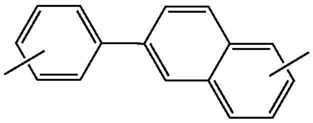

A5

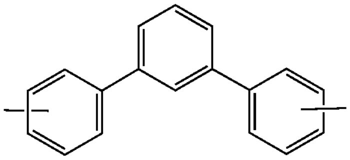

A6

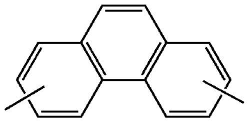

wherein at least one benzene ring is substituted by at last one group L and the benzene rings are optionally further substituted by one or more groups L or P-Sp-.

Preferred compounds of formula P and their sub-formulae are selected from the following preferred embodiments, including any combination thereof:

All groups P in the compound have the same meaning,

-$A^1$-(Z-$A^2$)$^z$- is selected from formulae A1, A2 and A5, the compounds contain exactly two polymerizable groups (represented by the groups P), the compounds contain exactly three polymerizable groups (represented by the groups P), P is selected from the group consisting of acrylate, methacrylate and oxetane, very preferably acrylate or methacrylate, P is methacrylate, all groups Sp are a single bond, at least one of the groups Sp is a single bond and at least one of the groups Sp is different from a single bond, Sp, when being different from a single bond, is —$(CH_2)_{p2}$—, —$(CH_2)_{p2}$—O—, —$(CH_2)_{p2}$—CO—O—, —$(CH_2)_{p2}$—O—CO—, wherein p2 is 2, 3, 4, 5 or 6, and the O-atom or the CO-group, respectively, is connected to the benzene ring, Sp is a single bond or denotes —$(CH_2)_{p2}$—, —$(CH_2)_{p2}$—O—, —$(CH_2)_{p2}$—CO—O—, —$(CH_2)_{p2}$—O—CO—, wherein p2 is 2, 3, 4, 5 or 6, and the O-atom or the CO-group, respectively, is connected to the benzene ring, R denotes P-Sp-, R does not denote or contain a polymerizable group, R does not denote or contain a polymerizable group and denotes straight chain, branched or cyclic alkyl having 1 to 25 C atoms, wherein one or more non-adjacent $CH_2$-groups are optionally replaced by —O—, —S—, —CO—, —CO—O—, —O—CO—, —O—CO—O— in such a manner that O- and/or S-atoms are not directly connected with each other, and wherein one or more H atoms are each optionally replaced by F, Cl or $L^a$, L or L' denote F, Cl or CN, L is F.

Suitable and preferred compounds of formula P are selected from the following formulae:

P1

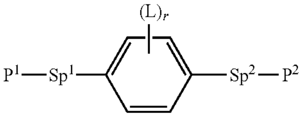

P2

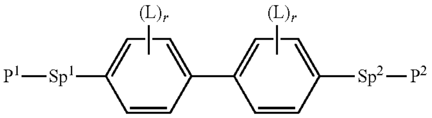

P3

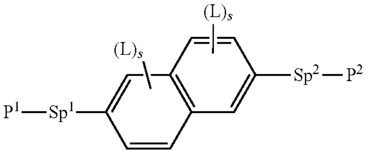

P4

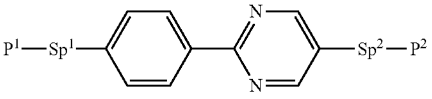

P5

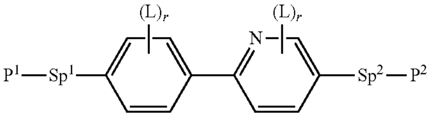

P6

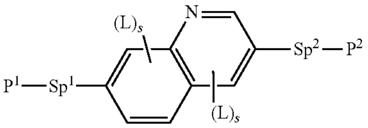

P7

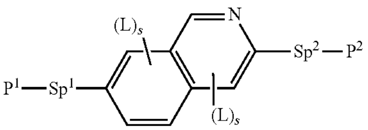

P8

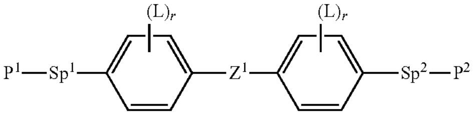

P9

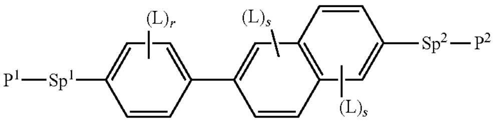

-continued

P10

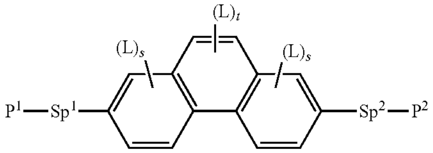

P11

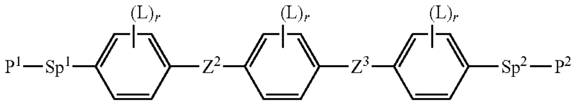

P12

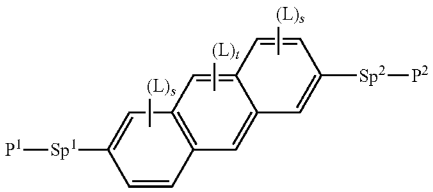

P13

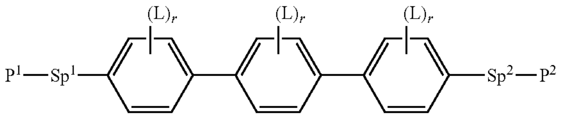

P14

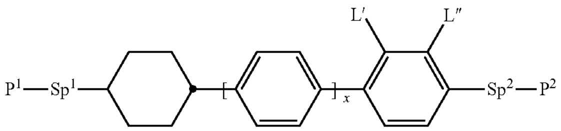

P15

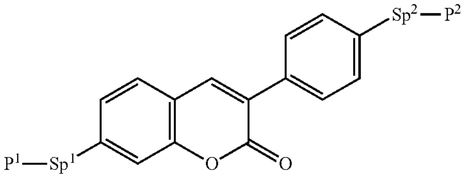

P16

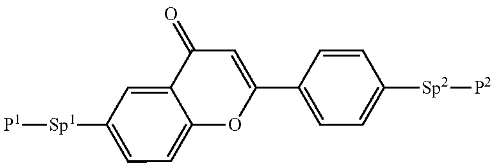

P17

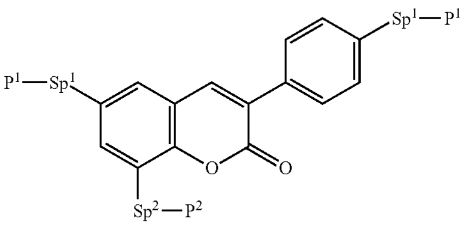

-continued
P18
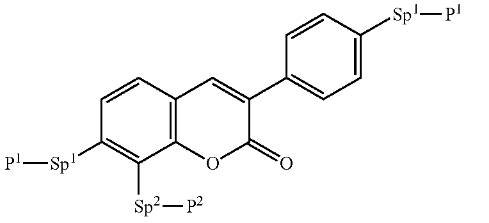
P19
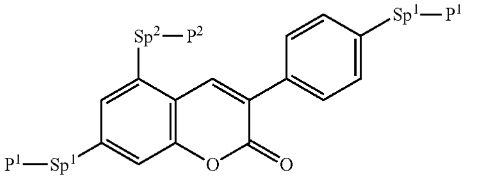
P20
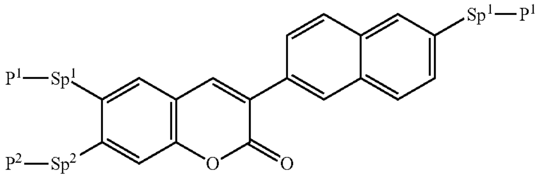
P21
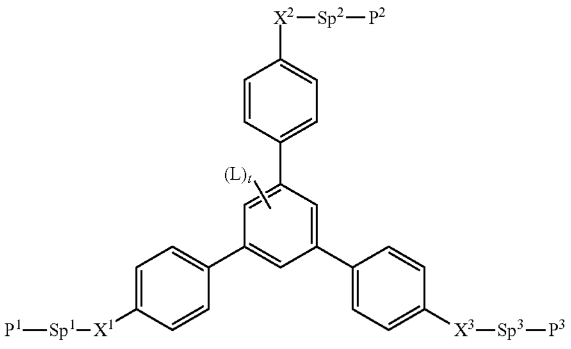
P22
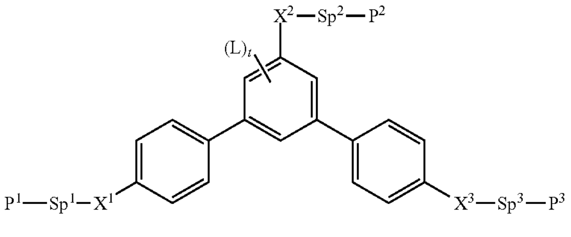
P23
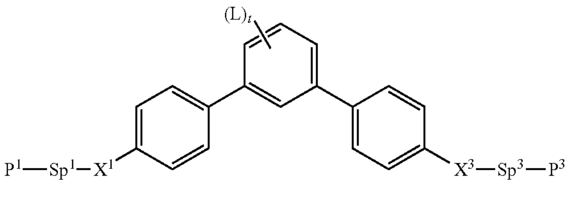
-continued
P24
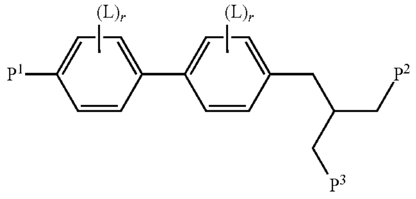
P25
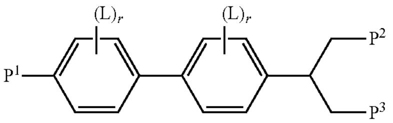
P26
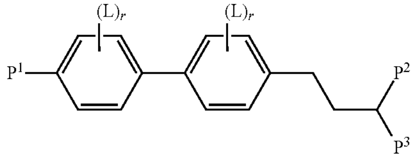
P27
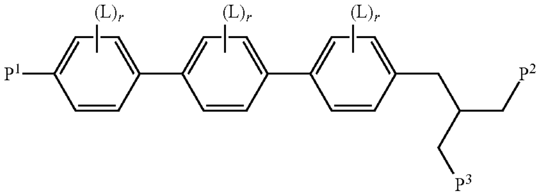
P28
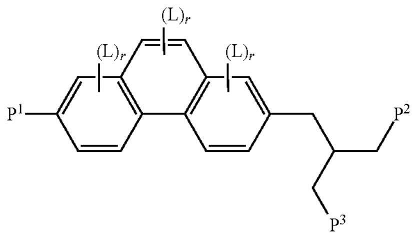
P29
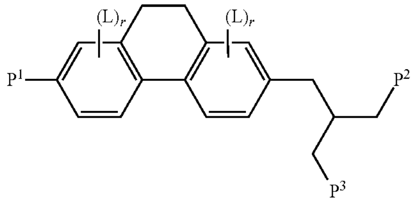
P30
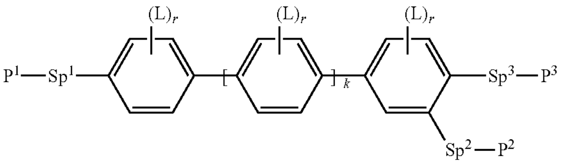
P31
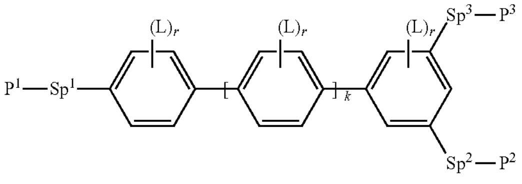

-continued

P32

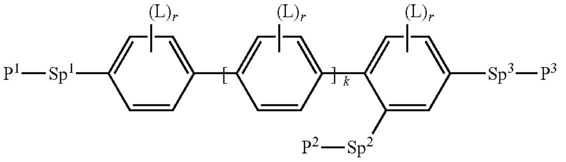

in which the individual radicals have the following meanings:

$P^1$, $P^2$ and $P^3$ each, independently of one another, denote an acrylate or methacrylate group, $Sp^1$, $Sp^2$ and $Sp^3$ each, independently of one another, denote a single bond or a spacer group having one of the meanings indicated above and below for Sp, and particularly preferably denote $—(CH_2)_{p1}—$, $—(CH_2)_{p1}—O—$, $—(CH_2)_{p1}—CO—O—$, $—(CH_2)_{p1}—O—CO—$ or $—(CH_2)_{p1}—O—CO—O—$, in which p1 is an integer from 1 to 12, where, in addition, one or more of the radicals $P^1—Sp^1$-, $P^2—Sp^2$- and $P^3—Sp^3$- may denote $R^{aa}$, with the proviso that at least one of the radicals $P^1—Sp^1$-, $P^2—Sp^2$- and $P^3—Sp^3$- present is different from $R^{aa}$, $R^{aa}$ denotes H, F, Cl, CN or straight-chain or branched alkyl having 1 to 25 C atoms, in which, in addition, one or more non-adjacent $CH_2$ groups may each be replaced, independently of one another, by $—C(R^0)=C(R^{00})—$, $—C≡C—$, $—N(R^0)—$, —O—, —S—, —CO—, —CO—O—, —O—CO—, —O—CO—O— in such a way that 0 and/or S atoms are not linked directly to one another, and in which, in addition, one or more H atoms may be replaced by F, Cl, CN or $P^1—Sp^1$-, particularly preferably straight-chain or branched, optionally mono- or polyfluorinated alkyl, alkoxy, alkenyl, alkynyl, alkylcarbonyl, alkoxycarbonyl, alkylcarbonyloxy or alkoxycarbonyloxy having 1 to 12 C atoms (where the alkenyl and alkynyl radicals have at least two C atoms and the branched radicals have at least three C atoms), $R^0$, $R^{00}$ each, independently of one another and identically or differently on each occurrence, denote H or alkyl having 1 to 12 C atoms, $R^y$ and $R^z$ each, independently of one another, denote H, F, $CH_3$ or $CF_3$, $X^1$, $X^2$ and $X^3$ each, independently of one another, denote —CO—O—, —O—CO— or a single bond, $Z^1$ denotes —O—, —CO—, $—C(R^yR^z)—$ or $—CF_2CF_2—$, $Z^2$ and $Z^3$ each, independently of one another, denote —CO—O—, —O—CO—, $—CH_2O—$, $—OCH_2—$, $—CF_2O—$, $—OCF_2—$ or $—(CH_2)_n—$, where n is 2, 3 or 4, L on each occurrence, identically or differently, denotes F, Cl, CN or straight-chain or branched, optionally mono- or polyfluorinated alkyl, alkoxy, alkenyl, alkynyl, alkylcarbonyl, alkoxycarbonyl, alkylcarbonyloxy or alkoxycarbonyloxy having 1 to 12 C atoms, preferably F, L' and L" each, independently of one another, denote H, F or Cl, k denotes 0 or 1, r denotes 0, 1, 2, 3 or 4, s denotes 0, 1, 2 or 3, t denotes 0, 1 or 2, x denotes 0 or 1.

Especially preferred are compounds of the formulae P2, P13, P17, P22, P23, P24, P30, P31 and P32.

Further preferred are trireaktive compounds P15 to P30, in particular P17, P18, P19, P22, P23, P24, P25, P26, P30, P31 and P32.

In the compounds of formulae P1 to P32 the group

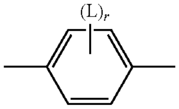

is preferably

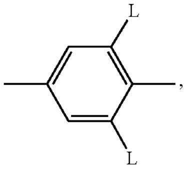

,

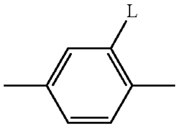

,

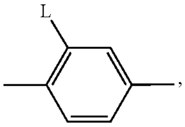

,

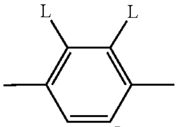

,

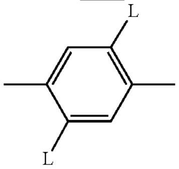

or

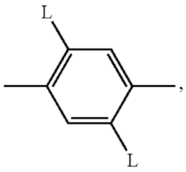

, wherein L on each occurrence, identically or differently, has one of the meanings given above or below, and is preferably F, Cl, CN, $NO_2$, $CH_3$, $C_2H_5$, $C(CH_3)_3$, $CH(CH_3)_2$, $CH_2CH(CH_3)C_2H_5$, $OCH_3$, $OC_2H_5$, $COCH_3$, $COC_2H_5$, $COOCH_3$, $COOC_2H_5$, $CF_3$, $OCF_3$, $OCHF_2$, $OC_2F_5$ or P-Sp-, very preferably F, Cl, CN, $CH_3$, $C_2H_5$, $OCH_3$, $COCH_3$, $OCF_3$ or P-Sp-, more preferably F, Cl, $CH_3$, $OCH_3$, $COCH_3$ oder $OCF_3$, especially F or $CH_3$.

Very particularly preferred compounds of the formula P are selected from Table E below.

For the production of PSA displays, the polymerisable compounds contained in the LC medium are polymerised or crosslinked (if one compound contains two or more polymerisable groups) by in-situ polymerisation in the LC medium between the substrates of the LC display, optionally while a voltage is applied to the electrodes.

The structure of the PSA displays according to the invention corresponds to the usual geometry for PSA displays, as described in the prior art cited at the outset. Geometries without protrusions are preferred, in particular those in which, in addition, the electrode on the colour filter side is unstructured and only the electrode on the TFT side has slots. Particularly suitable and preferred electrode structures for PS-VA displays are described, for example, in US 2006/0066793 A1.

A preferred PSA type LC display of the present invention comprises:

a first substrate including a pixel electrode defining pixel areas, the pixel electrode being connected to a switching element disposed in each pixel area and optionally including a micro-slit pattern, and optionally a first alignment layer disposed on the pixel electrode, a second substrate including a common electrode layer, which may be disposed on the entire portion of the second substrate facing the first substrate, and optionally a second alignment layer, an LC layer disposed between the first and second substrates and including an LC medium comprising a polymerisable component comprising one or more compounds of formula R and a liquid crystal host including as described above and below, wherein the polymerisable component may also be polymerised.

The first and/or second alignment layer controls the alignment direction of the LC molecules of the LC layer. For example, in PS-VA displays the alignment layer is selected such that it imparts to the LC molecules homeotropic (or vertical) alignment (i.e., perpendicular to the surface) or tilted alignment. Such an alignment layer may for example comprise a polyimide, which may also be rubbed, or may be prepared by a photoalignment method.

The LC layer with the LC medium can be deposited between the substrates of the display by methods that are conventionally used by display manufacturers, for example the so-called one-drop-filling (ODF) method. The polymerisable component of the LC medium is then polymerised for example by UV photopolymerisation. The polymerisation can be carried out in one step or in two or more steps.

The PSA display may comprise further elements, like a colour filter, a black matrix, a passivation layer, optical retardation layers, transistor elements for addressing the individual pixels, etc., all of which are well known to the person skilled in the art and can be employed without inventive skill.

The electrode structure can be designed by the skilled person depending on the individual display type. For example, for PS-VA displays a multi-domain orientation of the LC molecules can be induced by providing electrodes having slits and/or bumps or protrusions in order to create two, four or more different tilt alignment directions.

Upon polymerisation the polymerisable compounds form a crosslinked polymer, which causes a certain pretilt of the LC molecules in the LC medium. Without wishing to be bound to a specific theory, it is believed that at least a part of the crosslinked polymer, which is formed by the polymerisable compounds, will phase-separate or precipitate from the LC medium and form a polymer layer on the substrates or electrodes, or the alignment layer provided thereon. Microscopic measurement data (like SEM and AFM) have confirmed that at least a part of the formed polymer accumulates at the LC/substrate interface.

The polymerisation can be carried out in one step. It is also possible firstly to carry out the polymerisation, optionally while applying a voltage, in a first step in order to produce a pretilt angle, and subsequently, in a second polymerisation step without an applied voltage, to polymerise or crosslink the compounds which have not reacted in the first step ("end curing").

Suitable and preferred polymerisation methods are, for example, thermal or photopolymerisation, preferably photopolymerisation, in particular UV induced photopolymerisation, which can be achieved by exposure of the polymerisable compounds to UV radiation.

Optionally one or more polymerisation initiators are added to the LC medium. Suitable conditions for the polymerisation and suitable types and amounts of initiators are known to the person skilled in the art and are described in the literature. Suitable for free-radical polymerisation are, for example, the commercially available photo initiators Irgacure651®, Irgacure184®, Irgacure907®, Irgacure369® or Darocure1173® (Ciba AG). If a polymerisation initiator is employed, its proportion is preferably 0.001 to 5% by weight, particularly preferably 0.001 to 1% by weight.

The polymerisable compounds according to the invention are also suitable for polymerisation without an initiator, which is accompanied by considerable advantages, such, for example, lower material costs and in particular less contamination of the LC medium by possible residual amounts of the initiator or degradation products thereof. The polymerisation can thus also be carried out without the addition of an initiator. In a preferred embodiment, the LC medium thus does not contain a polymerisation initiator.

The LC medium may also comprise one or more stabilisers in order to prevent undesired spontaneous polymerisation of the RMs, for example during storage or transport. Suitable types and amounts of stabilisers are known to the person skilled in the art and are described in the literature. Particularly suitable are, for example, the commercially available stabilisers from the Irganox® series (Ciba AG), such as, for example, Irganox®1076. If stabilisers are employed, their proportion, based on the total amount of RMs or the polymerisable component (component P), is preferably 10-500,000 ppm, particularly preferably 50-50,000 ppm.

The polymerisable compounds of formula P in particular show good UV absorption in, and are therefore especially suitable for, a process of preparing a PSA display including one or more of the following features:

the polymerisable medium is exposed to UV light in the display in a 2-step process, including a first UV exposure step ("UV-1 step") to generate the tilt angle, and a second UV exposure step ("UV-2 step") to finish polymerization, the polymerisable medium is exposed to UV light in the display generated by an energy-saving UV lamp (also known as "green UV lamps"). These lamps are characterized by a relative low intensity (1/100-1/10 of a conventional UV1 lamp) in their absorption spectra from 300-380 nm, and are preferably used in the UV2 step, but are optionally also used in the UV1 step when avoiding high intensity is necessary for the process.

the polymerisable medium is exposed to UV light in the display generated by a UV lamp with a radiation spectrum that is shifted to longer wavelengths, preferably 340 nm or more, to avoid short UV light exposure in the PS-VA process.

Both using lower intensity and a UV shift to longer wavelengths protect the organic layer against damage that may be caused by the UV light.

A preferred embodiment of the present invention relates to a process for preparing a PSA display as described above and below, comprising one or more of the following features:

- the polymerisable LC medium is exposed to UV light in a 2-step process, including a first UV exposure step ("UV-1 step") to generate the tilt angle, and a second UV exposure step ("UV-2 step") to finish polymerization,
- the polymerisable LC medium is exposed to UV light generated by a UV lamp having an intensity of from 0.5 $mW/cm^2$ to 10 $mW/cm^2$ in the wavelength range from 300-380 nm, preferably used in the UV2 step, and optionally also in the UV1 step,
- the polymerisable LC medium is exposed to UV light having a wavelength of 340 nm or more, and preferably 400 nm or less.

This preferred process can be carried out for example by using the desired UV lamps or by using a band pass filter and/or a cut-off filter, which are substantially transmissive for UV light with the respective desired wavelength(s) and are substantially blocking light with the respective undesired wavelengths. For example, when irradiation with UV light of wavelengths X of 300-400 nm is desired, UV exposure can be carried out using a wide band pass filter being substantially transmissive for wavelengths 300 nm<λ<400 nm.

When irradiation with UV light of wavelength λ of more than 340 nm is desired, UV exposure can be carried out using a cut-off filter being substantially transmissive for wavelengths λ>340 nm.

"Substantially transmissive" means that the filter transmits a substantial part, preferably at least 50% of the intensity, of incident light of the desired wavelength(s). "Substantially blocking" means that the filter does not transmit a substantial part, preferably at least 50% of the intensity, of incident light of the undesired wavelengths. "Desired (undesired) wavelength" e.g., in case of a band pass filter means the wavelengths inside (outside) the given range of X, and in case of a cut-off filter means the wavelengths above (below) the given value of X.

This preferred process enables the manufacture of displays by using longer UV wavelengths, thereby reducing or even avoiding the hazardous and damaging effects of short UV light components.

UV radiation energy is in general from 6 to 100 J, depending on the production process conditions.

Preferably the LC medium according to the present invention essentially consist of a polymerisable component P) comprising or one or more polymerisable compounds of formula P, and an LC host mixture, and an optically active component comprising one or more chiral dopants, as described above and below. However, the LC medium may additionally comprise one or more further components or additives, preferably selected from the list including but not limited to co-monomers, polymerisation initiators, inhibitors, stabilizers, surfactants, wetting agents, lubricating agents, dispersing agents, hydrophobing agents, adhesive agents, flow improvers, defoaming agents, deaerators, diluents, reactive diluents, auxiliaries, colourants, dyes, pigments and nanoparticles.

Particular preference is given to LC media comprising one, two or three polymerisable compounds of formula P.

Preferably the proportion of compounds of formula P in the LC medium is from >0 to <5%, very preferably from >0 to <1%, most preferably from 0.01 to 0.5%.

In a preferred embodiment, the medium according to the invention preferably comprises one or more compounds of formula S in a total concentration in the range of from 10 ppm to 2000 ppm, more preferably from 100 ppm to 1000 ppm, still more preferably from 150 ppm to 500 ppm, very preferably from 200 ppm to 400 ppm and in particular from 250 to 300 ppm.

In another preferred embodiment, the medium according to the invention preferably comprises one or more compounds of formula S in a total concentration in the range of from 1000 ppm to 5000 ppm, more preferably from more than 1000 ppm to 5000 ppm, still more preferably from 1200 ppm to 4500 ppm, very preferably from 2000 ppm to 4000 ppm and in particular from 2500 to 3500 ppm.

The medium according to the invention preferably has negative dielectric anisotropy.

The liquid crystal mixture according to the invention is nematic, preferably at a temperature of −20° C. or less, preferably at −30° C. or less, very preferably at −40° C. or less.

It is advantageous for the liquid-crystalline medium according to the invention to preferably have a nematic phase from ≤−20° C. to ≥90° C., particularly preferably from ≤−30° C. to ≥100° C., very particularly preferably from ≤−40° C. to ≥108° C.

The expression "have a nematic phase" herein means on the one hand that no smectic phase and no crystallisation are observed at low temperatures at the corresponding temperature and on the other hand that clearing (phase transition to the isotropic phase) still does not occur on heating from the nematic phase. The investigation at low temperatures is carried out in a flow viscometer at the corresponding temperature and checked by storage in test cells having a layer thickness corresponding to the electro-optical use for at least 100 hours. If the storage stability at a temperature of −20° C. in a corresponding test cell is 1000 h or more, the medium is referred to as stable at this temperature. At temperatures of −30° C. and −40° C., the corresponding times are 500 h and 250 h respectively. At high temperatures, the clearing point is measured by conventional methods in capillaries.

In a first preferred embodiment, the medium according to the invention has a clearing temperature of 90° C. or more, preferably of 100° C. or more, more preferably of 105° C. or more and in particular of 108° C. or more.

In a preferred embodiment, the liquid-crystal mixture according to the invention has a dielectric anisotropy Δε of −2.0 to −6.0, preferably of −2.2 to −5.0, in particular −2.4 to −4.3.

The rotational viscosity $\gamma_1$ at 20° C. is preferably in the range of from 100 to 250 mPas, more preferably from 120 to 230 mPa s.

The medium according to the invention comprises the compound of the formula I in a concentration in the range of from 0.1% to 10%, preferably from 0.5% to 8%, more preferably from 1% to 7%, and very preferably from 1.5% to 6%.

Preferred embodiments, taken alone or in combination with one another are the following.

The medium preferably comprises:

- one or more compounds of formula IIA, preferably IIA-10, more preferably one or more compounds CCY-n-Om, in particular CCY-4-02, CCY-3-02, CCY-3-03, CCY-3-01 and/or CCY-5-02, preferably in a total concentration in the range of from 3% to 25%, more preferably from 6% to 20%, particularly preferably from 8% to 15%;

one or more compounds of formula IID, preferably selected from the compounds of the formulae IID-4 and IID-10, preferably in a total concentration in the range of from 2% to 40%, more preferably, from 15% to 35%, particularly preferably from 20% to 30%, and/or one or more compounds of formula IID-4, preferably CLY-n-Om, in particular CLY-2-04, CLY-3-02 and/or CLY-3-03, preferably in a total concentration in the range of from 3% to 38%, more preferably, from 8% to 25%, particularly preferably from 10% to 20%;

and/or one or more compounds of formula IID-10, preferably CLOY-n-Om, in particular CLOY-3-02, preferably in a total concentration in the range of from 2% to 35%, more preferably, from 4% to 30%, particularly preferably from 6% to 26%;

and/or less than 5% of one or more compounds of the formula IIB, more preferably less than 3%, very preferably less than 1%;

and/or less than 5% of one or more compounds of the formula IIC, more preferably less than 3%, very preferably less than 1%;

and/or one or more compounds of the formula III, preferably of the formula III-2 and/or III-3, more preferably of the formula III-2-6 and/or III-3, in particular one or more compounds B(S)-nO-Om and/or COB(S)-n-Om, very particularly B(S)-20-04, B(S)-20-05, B(S)-20-06, and/or COB(S)-2-04, preferably in a total concentration in the range of from 1% to 20%, more preferably from 2% to 17% and very preferably from 4% to 15%;

and/or one or more compounds of the formula III and/or PH-1, preferably of the formula III-2 and/or BP-3, more preferably of the formula III-2-6, in particular selected from B(S)-20-04, B(S)-20-05 and B(S)-20-06, preferably in a total concentration in the range of from 1% to 12%, more preferably from 2% to 11% and very preferably from 3% to 10%;

and/or one or more compounds of the formula III, preferably of the formula III-2 and III-3, more preferably of the formula III-2-6 and III-3, in particular one or more compounds B(S)-nO-Om and COB(S)-n-Om, very particularly B(S)-20-04, B(S)-20-05, B(S)-20-06, and COB(S)-2-04, preferably in a total concentration in the range of from 4% to 20%, more preferably from 6% to 14% and very preferably from 8% to 12%;

and/or one or more compounds of formula IV, preferably in a total concentration in the range of from 25% to 70%, more preferably from 30% to 60%, particularly preferably from 35% to 55%;

and/or one or more compounds of the formula VI-1, preferably IV-1-6, preferably in a total concentration in the range of from 1% to 20%, more preferably from 2% to 18% and very preferably from 3% to 15%;

and/or the compound(s) of the formula CC-3-V1 and/or CC-4-V1, in a total concentration in the range of from 5 to 35%, more preferably from 10% to 28%, particularly preferably from 12% to 26%, and/or one or more compounds of the formula IV-3-1, preferably CC-3-V and/or CC-4-V, preferably in a total concentration in the range of from 1% to 25%, more preferably from 2% to 22% and very preferably from 3% to 20%;

and/or one or more compounds of the formula IVa, more preferably of the formula IVa-2, in particular CP-3-02, in a total concentration in the range of from 0.5% to 8%, more preferably from 1% to 6%, very preferably from 2% to 5%;

and/or one or more compounds of the formula V, more preferably selected from the compounds of the formulae V-2-1 and V-2-2, in particular CCP-n-m and/or CCP-Vn-m and/or CPP-n-m, very particularly selected from the group consisting of CCP-3-1, CCP—V-1, CCP-V2-1 and CPP-3-2, preferably in a total concentration in the range of from 1% to 20%, more preferably from 2% to 17%, very preferably from 3% to 14%;

and/or one or more compounds selected from the compounds of the formulae V-1-1 and V-1-6, in particular CCC-n-m and/or CCC-n-V, very particularly CCC-3-V and/or CCC—V—V, preferably in a total concentration in the range of from 1% to 20%, more preferably from 2% to 17%, very preferably from 3% to 14%;

and/or one or more compounds of the formula CL, more preferably of the formula CL-3, very preferably selected form the compounds CLP-V-m, CLP—V-Om, CLP-n-m, and CLP-n-Om, in which n and m independently are 1, 2, 3, 4 or 5, preferably in a total concentration in the range of from 1% to 12%, more preferably from 2% to 10% and very preferably from 3% to 7%, and/or one or more compounds of the formula COYOIC-n-m and/or one or more compounds of the formula CCOY-n-Om and/or 0.1% to 3% of the compound PPGU-3-F.

The liquid-crystal media according to the invention have high values for the voltage holding ratio in liquid-crystal cells.

In general, liquid-crystal media having a low addressing voltage or threshold voltage exhibit a lower voltage holding ratio than those having a higher addressing voltage or threshold voltage and vice versa.

As used herein, the term “dielectrically positive compounds” denotes compounds having a $\Delta\varepsilon>1.5$, the term “dielectrically neutral compounds” denotes those having $-1.5\leq\Delta\varepsilon\leq1.5$ and the term “dielectrically negative compounds” denotes those having $\Delta\varepsilon<-1.5$. The dielectric anisotropy of the compounds is determined here by dissolving 10% of the compounds in a liquid-crystalline host and determining the capacitance of the resultant mixture in at least one test cell in each case having a layer thickness of 20 μm with homeotropic and with homogeneous surface alignment at 1 kHz. The measurement voltage is typically 0.5 V to 1.0 V but is always lower than the capacitive threshold of the respective liquid-crystal mixture investigated.

All temperature values indicated for the present invention are in ° C.

The mixtures according to the invention are suitable for all VA-TFT applications, such as, for example, VAN, MVA, (S)-PVA, ASV, PSA (polymer sustained VA) and PS-VA (polymer stabilized VA). They are furthermore suitable for IPS (in-plane switching) and FFS (fringe field switching) applications having negative Δε, in particular UB-FFS.

It goes without saying for the person skilled in the art that the VA, IPS or FFS mixture according to the invention may also comprise compounds in which, for example, H, N, O, Cl and F have been replaced by the corresponding isotopes.

The compounds according to the present invention can be synthesized by or in analogy to known methods described in the literature (for example in the standard works such as Houben-Weyl, Methoden der Organischen Chemie [Methods of Organic Chemistry], Georg-Thieme-Verlag, Stuttgart), under reaction conditions which are known and suitable for said reactions. Use may also be made here of variants which are known per se but are not mentioned here. In particular, they can be prepared as described in or in analogy to the following reaction schemes. Further methods for preparing the inventive compounds can be taken from the examples.

Other mesogenic compounds which are not explicitly mentioned above can optionally and advantageously also be used in the media in accordance with the present invention. Such compounds are known to the person skilled in the art.

For the present invention and in the following examples, the structures of the liquid-crystal compounds are indicated by means of acronyms, with the transformation into chemical formulae taking place in accordance with Tables A to C below. All radicals $C_mH_{2m+1}$, $C_nH_{2n+1}$, and $C_lH_{2l+1}$ or $C_mH_{2m-1}$, $C_nH_{2n-1}$ and $CH_{2l-1}$ are straight-chain alkyl radicals or alkylene radicals, in each case having n, m and l C atoms respectively. Preferably n, m and l are independently of each other 1, 2, 3, 4, 5, 6, or 7. Table A shows the codes for the ring elements of the nuclei of the compound, Table B lists the bridging units, and Table C lists the meanings of the symbols for the left- and right-hand end groups of the molecules. The acronyms are composed of the codes for the ring elements with optional linking groups, followed by a first hyphen and the codes for the left-hand end group, and a second hyphen and the codes for the right-hand end group. Table D shows illustrative structures of compounds together with their respective abbreviations.

TABLE A

| Ring elements | |
|---|---|
| C | 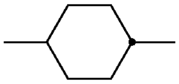 |
| D | 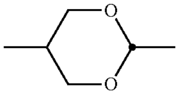 |
| DI | 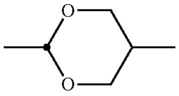 |
| A | 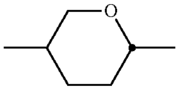 |
| AI | 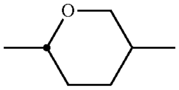 |

TABLE A-continued

| Ring elements | |
|---|---|
| P | 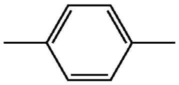 |
| G | 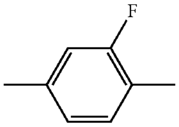 |
| GI | 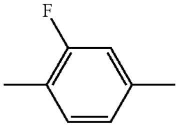 |
| U | 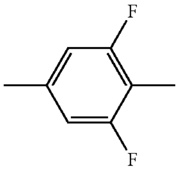 |
| UI | 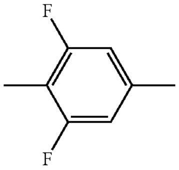 |
| U(1) | 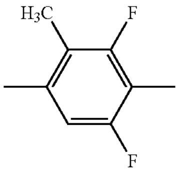 |
| U(1)I | 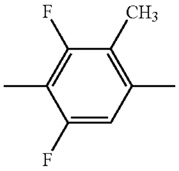 |
| Y | 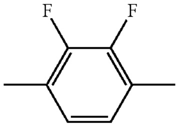 |
| P(F, Cl)Y | 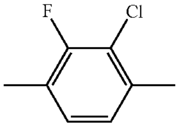 |
| P(Cl, F)Y | 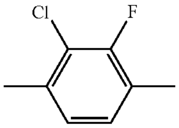 |

TABLE A-continued
| Ring elements | |
|---|---|
| np | 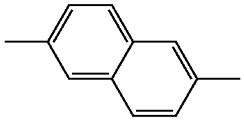 |
| n3f | 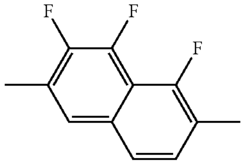 |
| nN3fl | 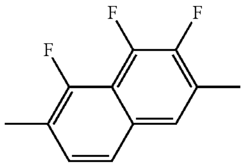 |
| th | 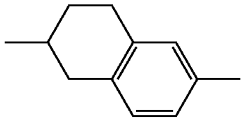 |
| thl | 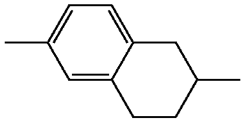 |
| tH2f | 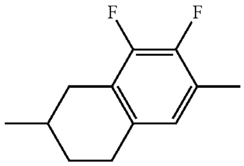 |
| tH2fl | 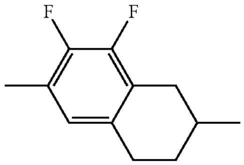 |
| o2f | 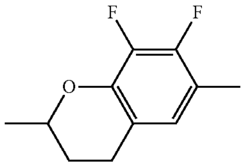 |
| o2fl | 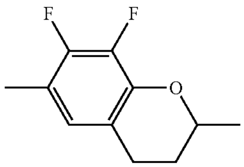 |
| dh | 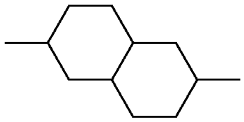 |
TABLE A-continued
| Ring elements | |
|---|---|
| O | 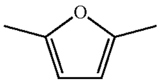 |
| S | 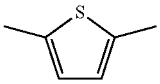 |
| cpS | 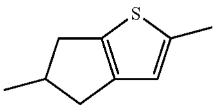 |
| K | 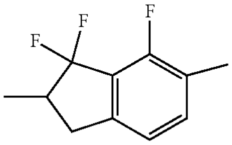 |
| Kl | 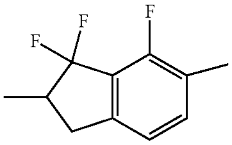 |
| L | 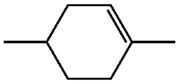 |
| Ll | 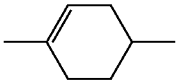 |
| F | 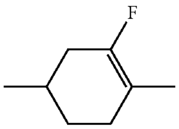 |
| Fl | 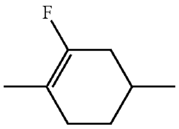 |
| B | 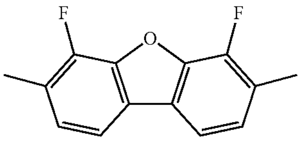 |
| B(S) | 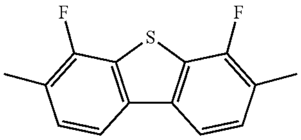 |

TABLE A-continued

| Ring elements | |
|---|---|
| Bh | 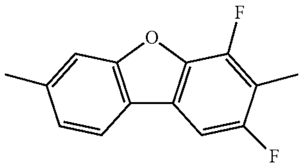 |
| Bh(S) | 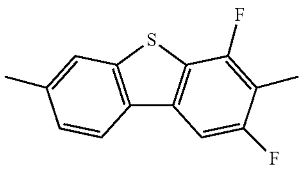 |
| Bf | 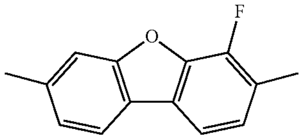 |
| Bf(S) | 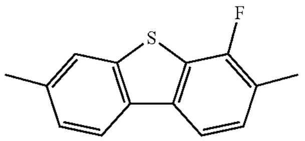 |
| Bfi | 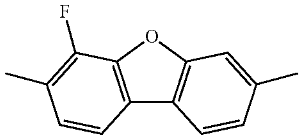 |

TABLE A-continued

| Ring elements | |
|---|---|
| Bfi(S) | 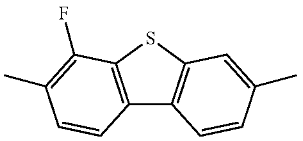 |
| B(P) | 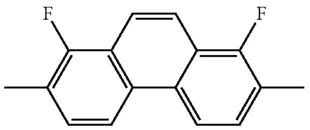 |
| B(A) | 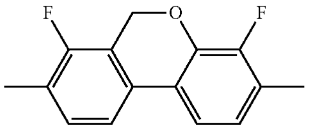 |

TABLE B

| Bridging units | | | |
|---|---|---|---|
| E | —$CH_2$—$CH_2$— | | |
| V | —CH═CH— | | |
| T | —CC— | | |
| W | —$CF_2$—$CF_2$— | | |
| B | —CF═CF— | | |
| Z | —CO—O— | ZI | —O—CO— |
| X | —CF═CH— | XI | —CH═CF— |
| O | —$CH_2$—O— | OI | —O—$CH_2$— |
| Q | —$CF_2$—O— | QI | —O—$CF_2$— |

TABLE C

| End groups | | | |
|---|---|---|---|
| On the left individually or in combination | | On the right individually or in combination | |
| -n- | $CnH_{2n+1}$— | -n | —$CnH_{2n+1}$ |
| -no- | $CnH_{2n+1}$—O— | -On | —O—$CnH_{2n+1}$ |
| —V— | $CH_2$=CH— | —V | —CH=$CH_2$ |
| -nV- | $CnH_{2n+1}$—CH=CH— | -nV | —$CnH_{2n}$—CH=$CH_2$ |
| -Vn- | $CH_2$=CH—$CnH_{2n}$— | -Vn | —CH=CH—$CH_{2n+1}$ |
| -nVm- | $CnH_{2n+1}$—CH=CH—$CmH_{2m}$— | -nVm | —$CnH_{2n}$—CH=CH—$CmH_{2m+1}$ |
| —N— | N≡C— | —N | —C≡N |
| —S— | S=C=N— | —S | —N=C=S |
| —F— | F— | —F | —F |
| -CL- | Cl— | -CL | —Cl |
| -M- | $CFH_2$— | -M | —$CFH_2$ |
| -D- | $CF_2H$— | -D | —$CF_2H$ |
| -T- | $CF_3$— | -T | —$CF_3$ |
| -MO- | $CFH_2O$ — | -OM | —$OCFH_2$ |
| -DO- | $CF_2HO$ — | -OD | —$OCF_2H$ |
| -TO- | $CF_3O$ — | -OT | —$OCF_3$ |
| -A- | H—C≡C— | -A | —C≡C—H |
| -nA- | $C_nH_{2n+1}$—C≡C— | -An | —C≡C—$C_{nH2n+1}$ |
| -NA- | N≡C—C≡C— | -AN | —C≡C—C≡N |
| -(cn)- | 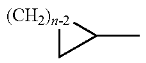 | -(cn) | 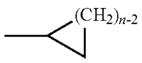 |
| -(cn)m- | 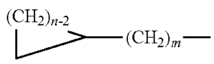 | -m(cn) | 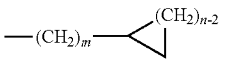 |

TABLE C-continued

| End groups | | | |
|---|---|---|---|
| -(c5-1en)m- | 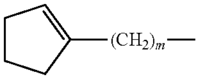 | -m(c5-1en) | 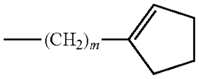 |
| -(c5-2en)m- | 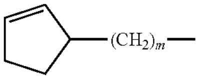 | -m(c5-2en) | 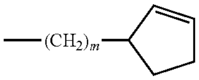 |
| -(c5-3en)m- | 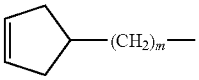 | -m(c5-3en) | 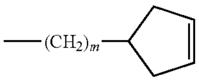 |

| On the left only in combination | | On the right only in combination | |
|---|---|---|---|
| - . . . n . . . - | $—C_nH_{2n}—$ | - . . . n . . . | $—C_nH_{2n}—$ |
| - . . . M . . . - | —CFH— | - . . . M . . . | —CFH— |
| - . . . D . . . - | $—CF_2—$ | - . . . D . . . | $—CF_2—$ |
| - . . . V . . . - | —CH=CH— | - . . . V . . . | —CH=CH— |
| - . . . Z . . . - | —CO—O— | - . . . Z . . . | —CO—O— |
| - . . . Zl . . . - | —O—CO— | - . . . Zl . . . | —O—CO— |
| - . . . K . . . - | —CO— | - . . . K . . . | —CO— |
| - . . . W . . . - | —CF=CF— | - . . . W . . . | —CF=CF— |

in which n and m are each integers, and the three dots " . . . " are placeholders for other abbreviations from this table.

Apart from the compounds of formula I, IIA, IIB, IIC and/or IID, IVa, IVb and V, the mixtures according to the invention optionally comprise one or more compounds of the compounds mentioned below.

The following abbreviations are used:

(n, m, k and l are, independently of one another, each an integer, preferably 1 to 9 preferably 1 to 7, k and l possibly may be also 0 and preferably are 0 to 4, more preferably 0 or 2 and most preferably 2, n preferably is 1, 2, 3, 4 or 5, in the combination "-nO—" it preferably is 1, 2, 3 or 4, preferably 2 or 4, m preferably is 1, 2, 3, 4 or 5, in the combination "—Om" it preferably is 1, 2, 3 or 4, more preferably 2 or 4. The combination "-IVm" preferably is "2V1".)

TABLE D

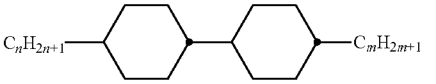

CC-n-m

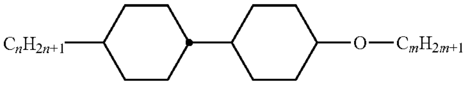

CC-n-Om

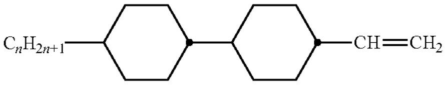

CC-n-V

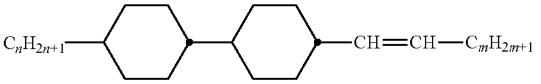

CC-n-Vm

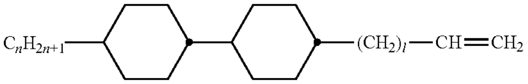

CC-n-IV

TABLE D-continued
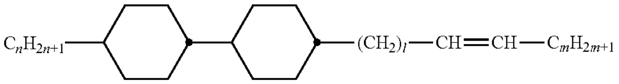
CC-n-IVm
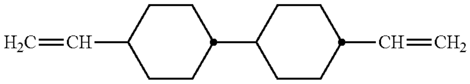
CC-V-V
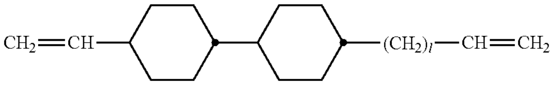
CC-V-IV
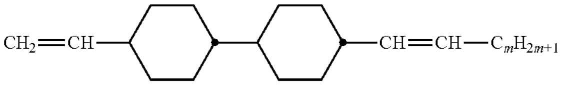
CC-V-Vm
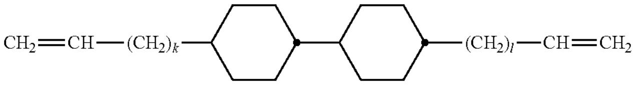
CC-Vk-IV
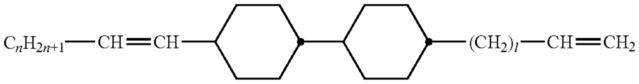
CC-nV-IV
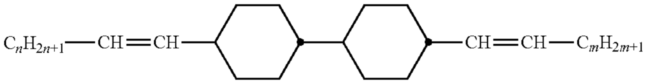
CC-nV-Vm
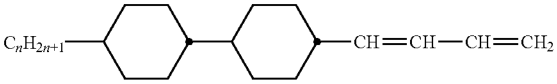
CC-n-VV
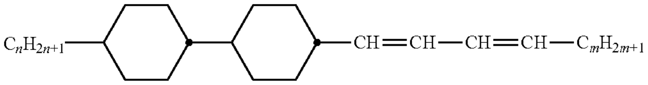
CC-n-VVm
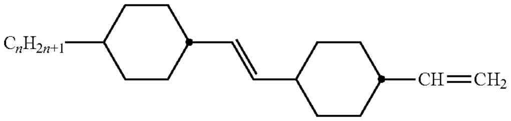
CVC-n-V
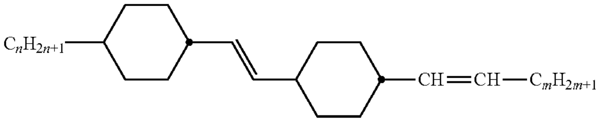
CVC-n-Vm TABLE D-continued
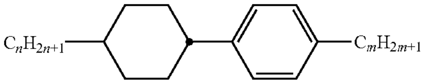
CP-n-m
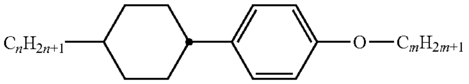
CP-n-Om
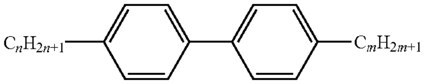
PP-n-m
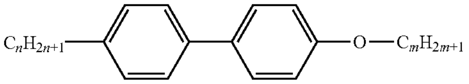
PP-n-Om
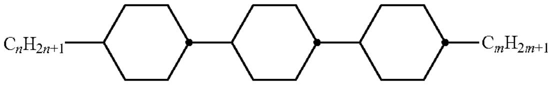
CCC-n-m
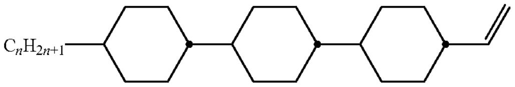
CCC-n-V
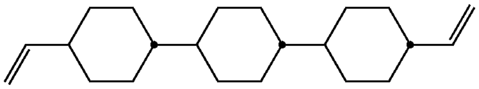
CCC-V-V
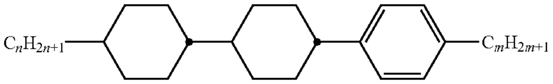
CCP-n-m
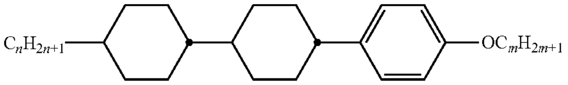
CCP-n-Om
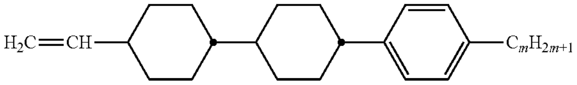
CCP-V-m
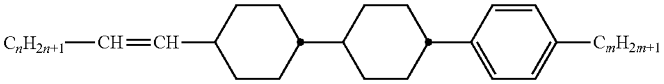
CCP-nV-m TABLE D-continued
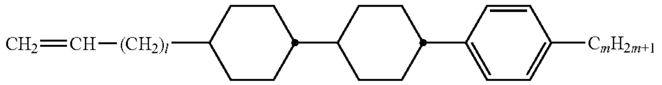
CCP-VI-m
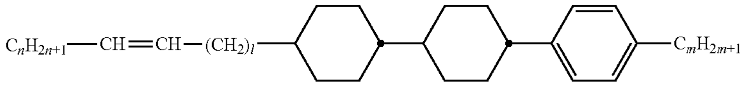
CCP-nVI-m
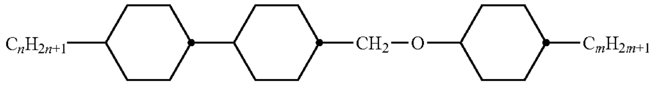
CCOC-n-m
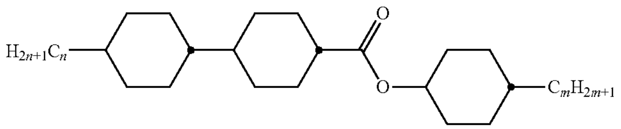
CCZC-n-m
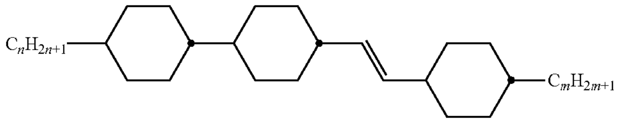
CCVC-n-m
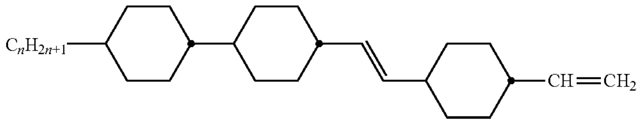
CCVC-n-V
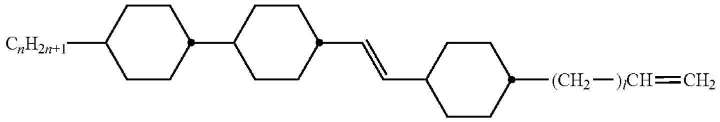
CCVC-n-IV
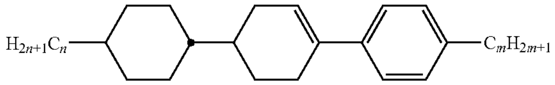
CLP-n-m
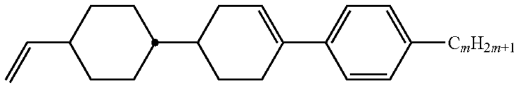
CLP-V-n
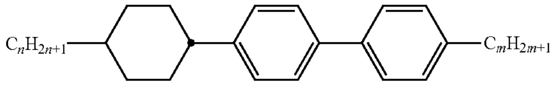
CPP-n-m TABLE D-continued
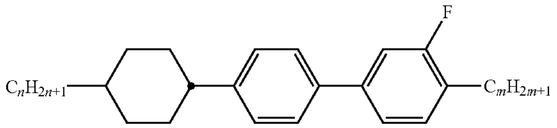
CPG-n-m
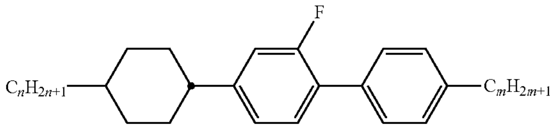
CGP-n-m
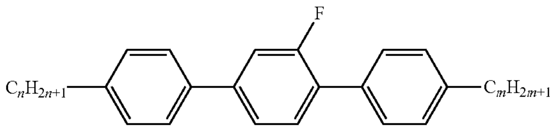
PGP-n-m
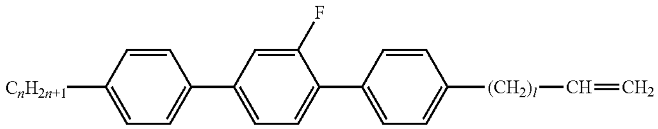
PGP-n-IV
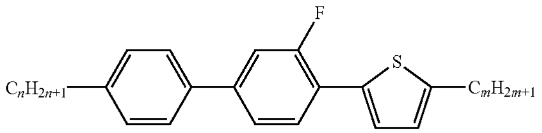
PGS-n-m
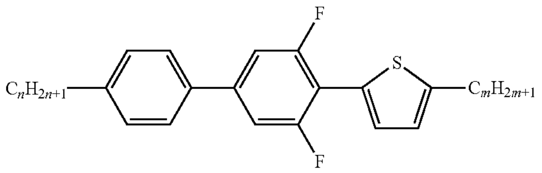
PUS-n-m
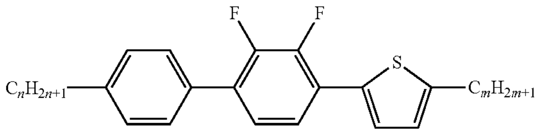
PYS-n-m
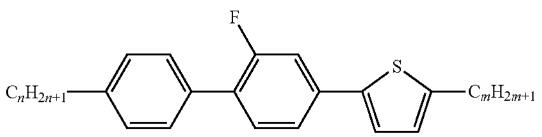
SGP-m-n TABLE D-continued
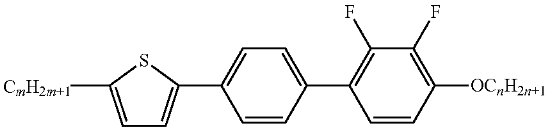
SPY-m-On
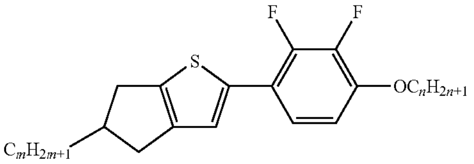
cpSY-m-On
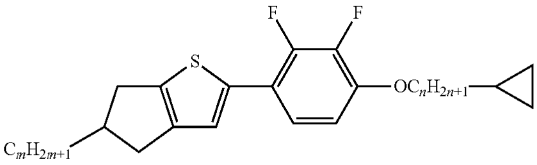
cpSY-m-On(c3)
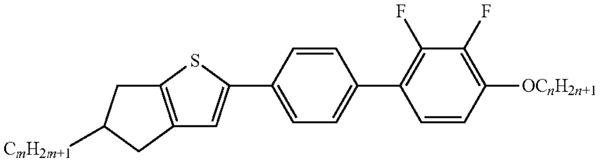
cpSPY-m-On
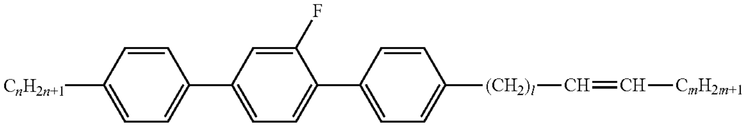
PGP-n-IVm
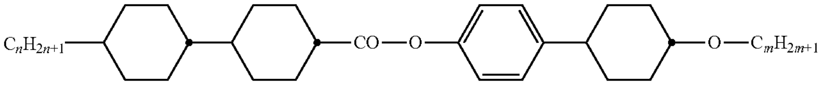
CCZPC-n-m
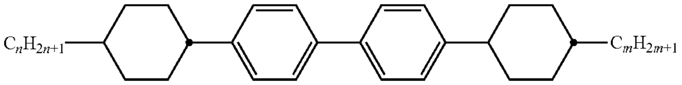
CPPC-n-m
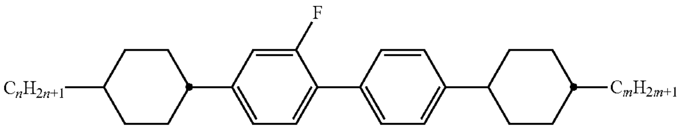
CGPC-n-m TABLE D-continued
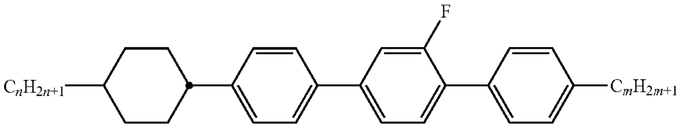
CPGP-n-m
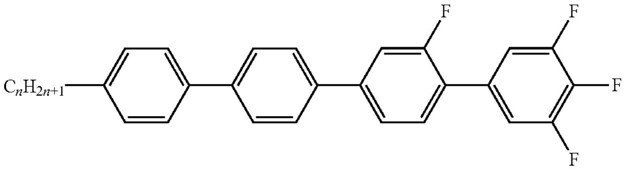
PPGU-n-F
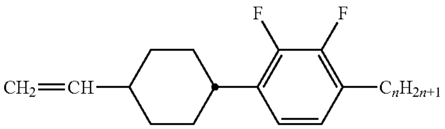
CY-V-n
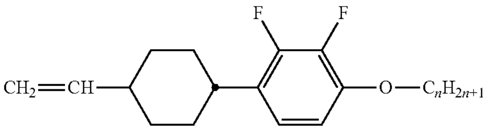
CY-V-On
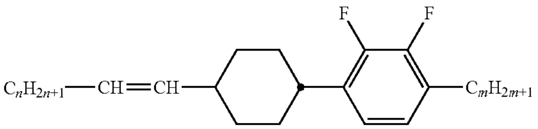
CY-nV-m
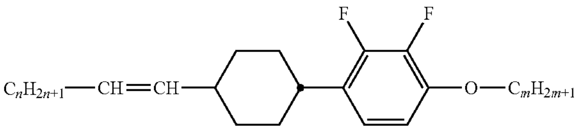
CY-nV-Om
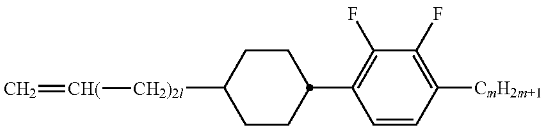
CY-VI-m
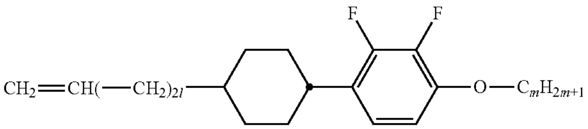
CY-VI-Om TABLE D-continued
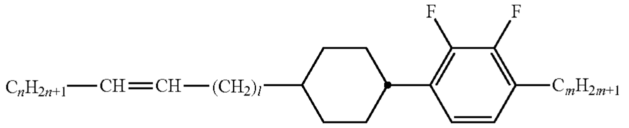
CY-nVI-m
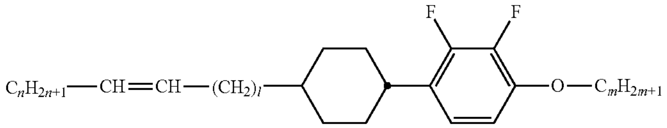
CY-nVI-Om
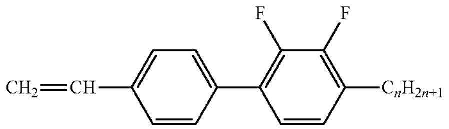
PY-V-n
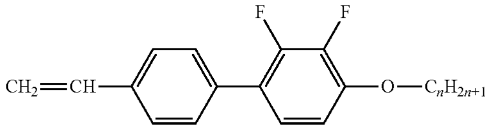
PY-V-On
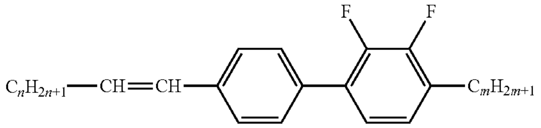
PY-nV-m
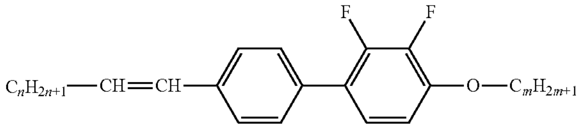
PY-nV-Om
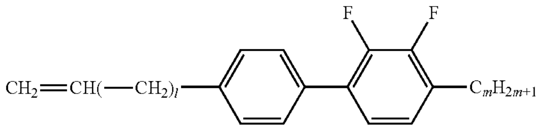
PY-VI-m
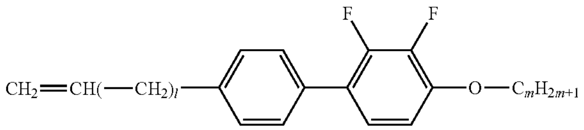
PY-VI-Om
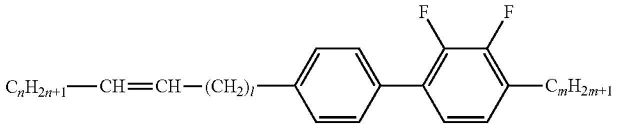
PY-nVI-m TABLE D-continued
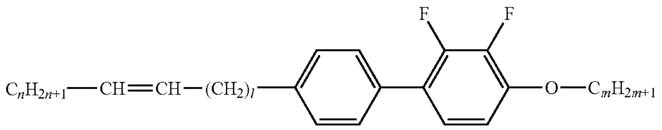
PY-nVI-Om
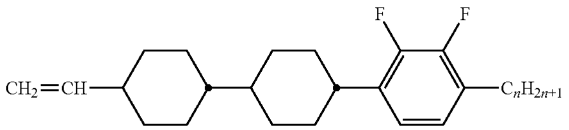
CCY-V-n
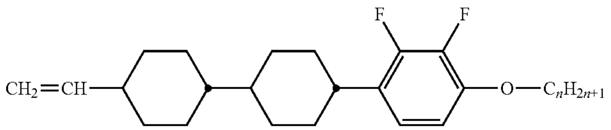
CCY-V-On
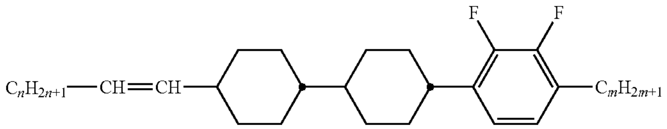
CCY-nV-m
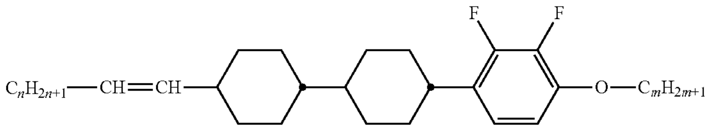
CCY-nV-Om
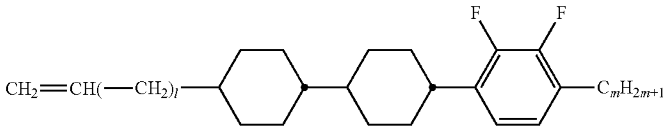
CCY-VI-m
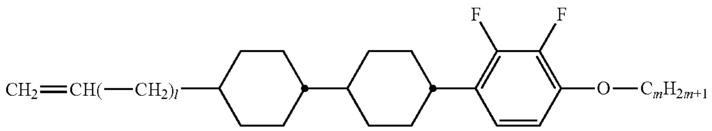
CCY-VI-Om
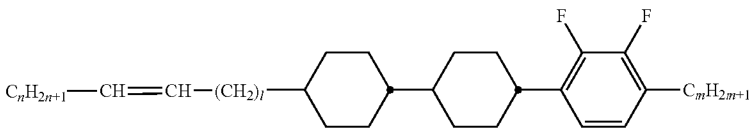
CCY-nVI-m
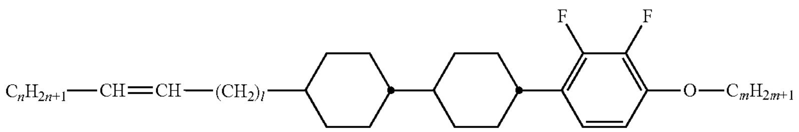
CCY-nVI-Om TABLE D-continued
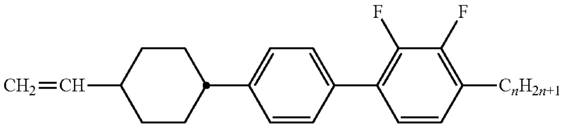
CPY-V-n
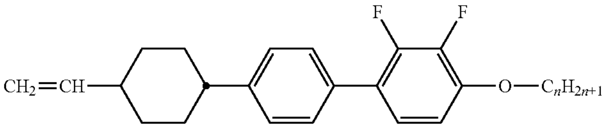
CPY-V-On
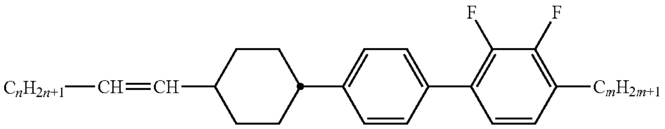
CPY-nV-m
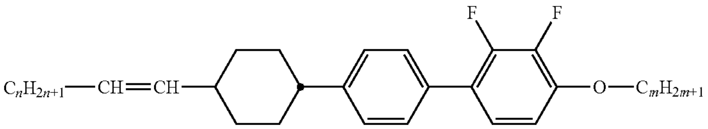
CPY-nV-Om
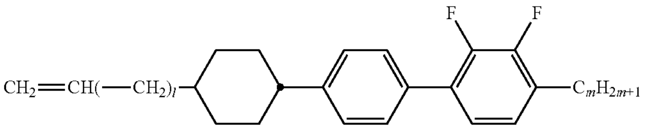
CPY-VI-m
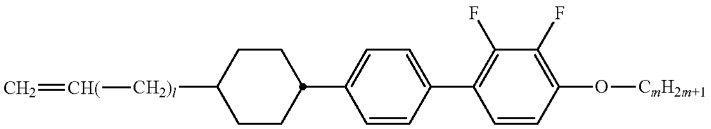
CPY-VI-Om
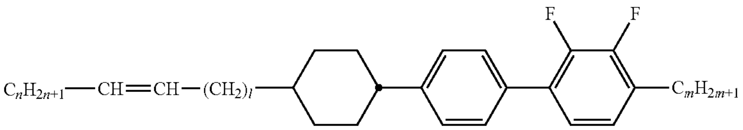
CPY-nVI-k
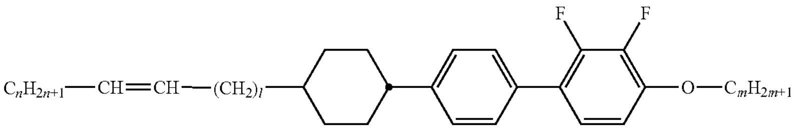
CPY-nVI-Om
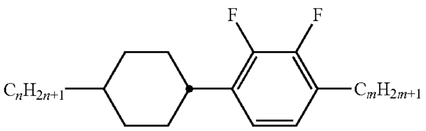
CY-n-m TABLE D-continued
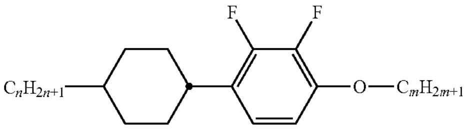
CY-n-Om
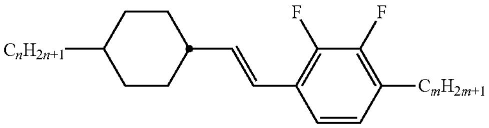
CVY-n-m
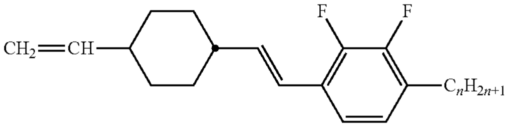
CVY-V-n
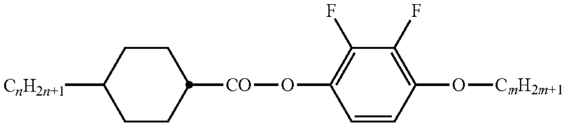
CZY-n-Om
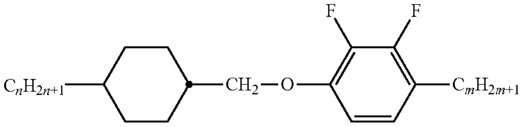
COY-n-m
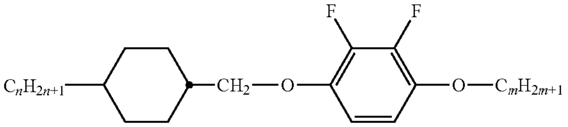
COY-n-Om
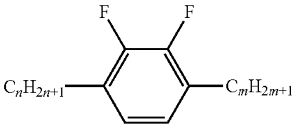
Y-n-m
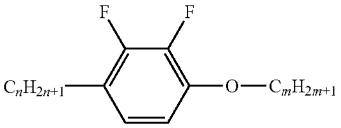
Y-n-Om TABLE D-continued
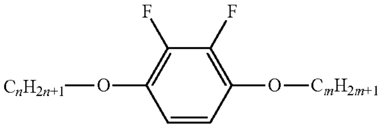
Y-nO-Om
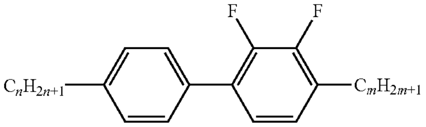
PY-n-m
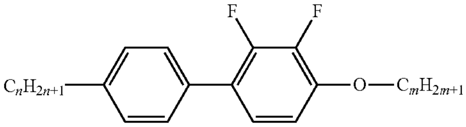
PY-n-Om
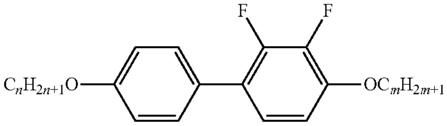
PY-nO-Om
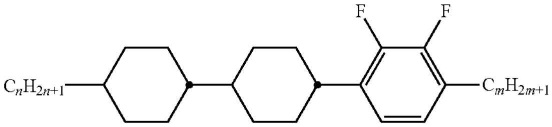
CCY-n-m
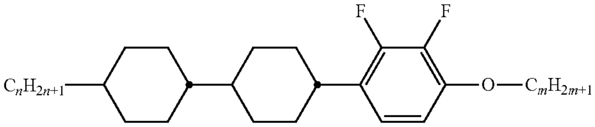
CCY-n-Om
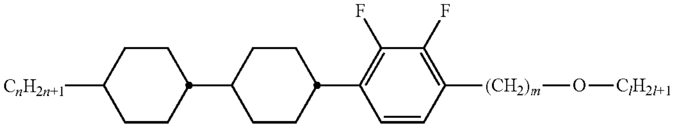
CCY-n-mOl
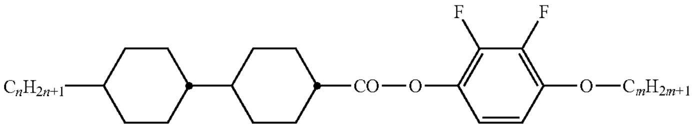
CCZY-n-Om TABLE D-continued
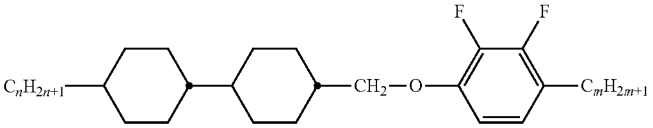
CCOY-n-m
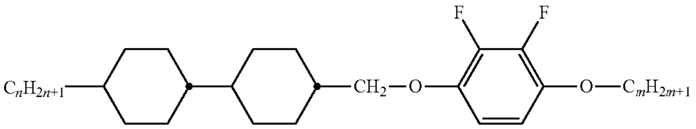
CCOY-n-Om
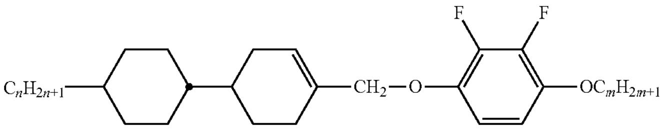
CLOY-n-Om
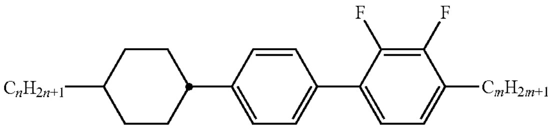
CPY-n-m
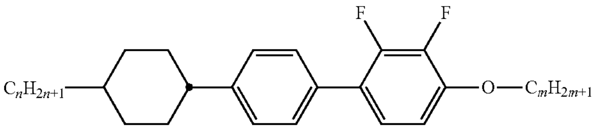
CPY-n-Om
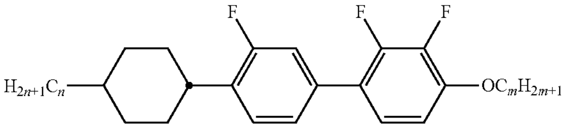
CGIY-n-Om
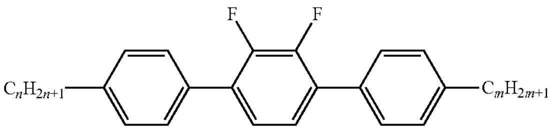
PYP-n-m
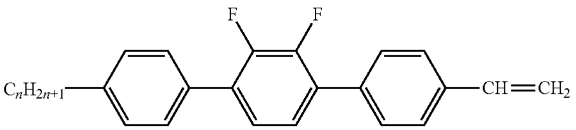
PYP-n-V
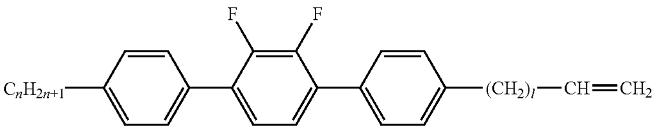
PYP-n-IV TABLE D-continued
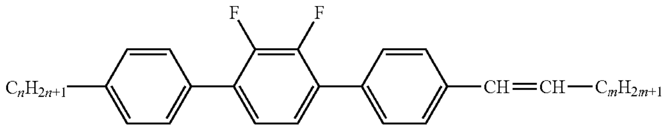
PYP-n-Vm
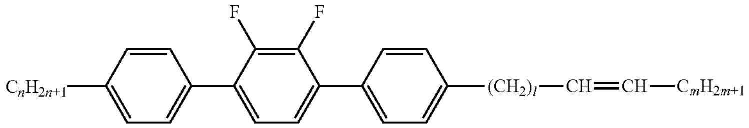
PYP-n-IVm
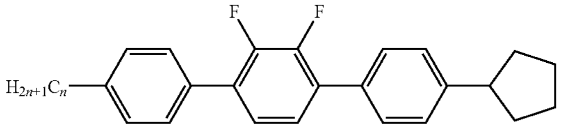
PYP-n-(c5)
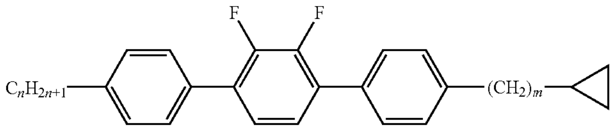
PYP-n-m(c3)
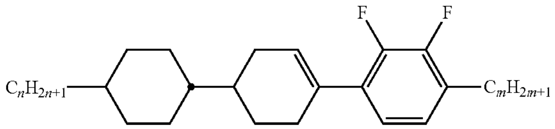
CLY-n-m
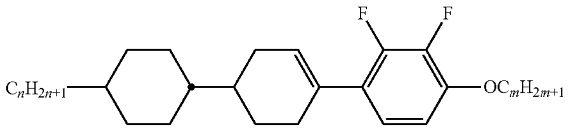
CLY-n-Om
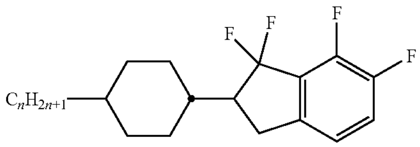
CK-n-F
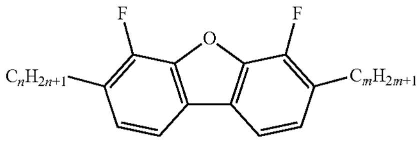
B-n-m TABLE D-continued
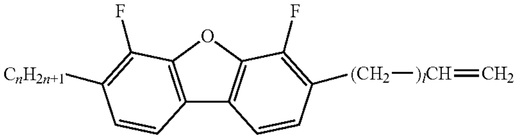
B-n-IV
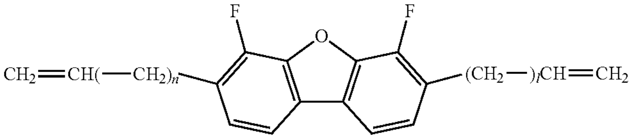
B-Vn-IV
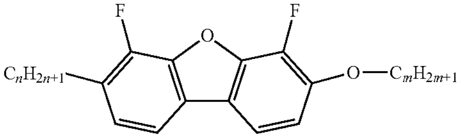
B-n-Om
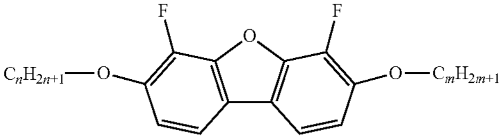
B-nO-Om
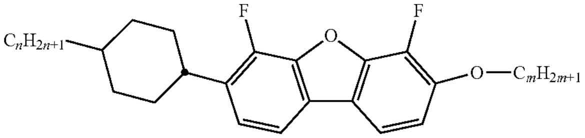
CB-n-Om
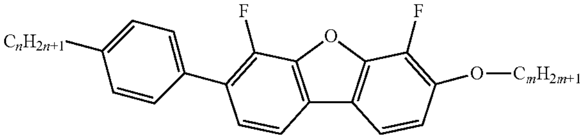
PB-n-Om
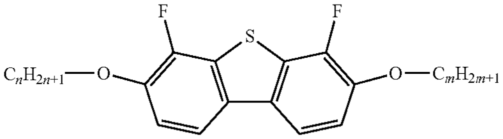
B(S)-nO-Om
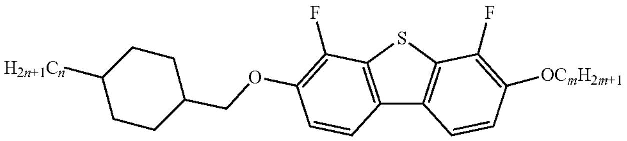
COB(S)-n-Om TABLE D-continued
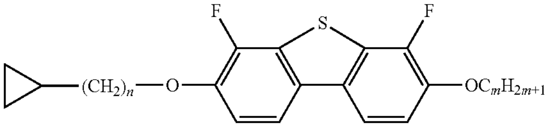
B(S)-(c3)nO-Om
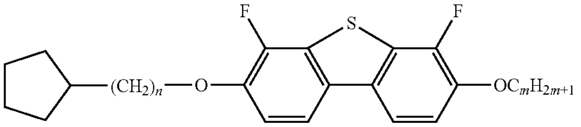
B(S)-(c5)nO-Om
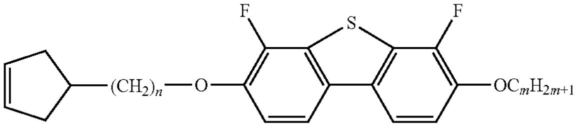
B(S)-(c5-3en)nO-Om
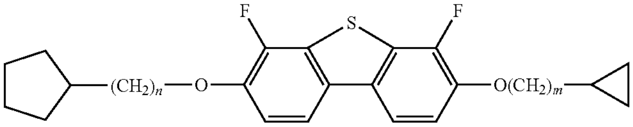
B(S)-(c5)nO-Om(c3)
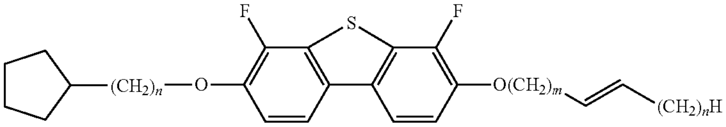
B(S)-(c5)IO-OmVn
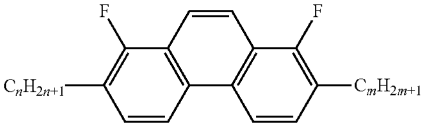
B(P)-n-m
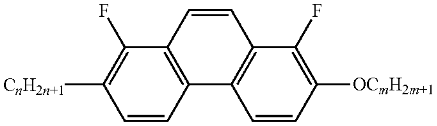
B(P)-n-Om
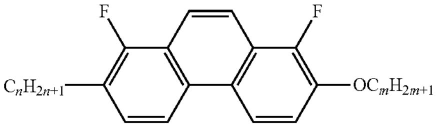
B(P)-n-Om
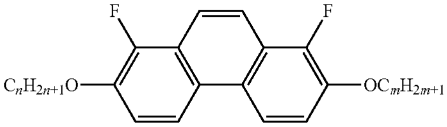
B(P)-nO-Om TABLE D-continued
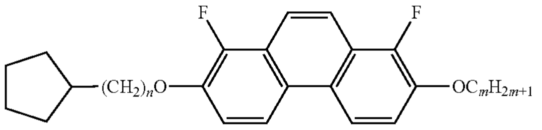
B(P)-(c5)nO-Om
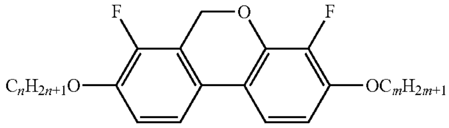
B(A)-nO-Om
TABLE E
Table E shows illustrative reactive mesogenic compounds which can be used in the LC media in accordance with the present invention.
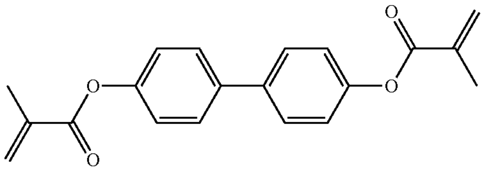 [SMILES: C=C(C)C(=O)Oc1ccc(-c2ccc(OC(=O)C(=C)C)cc2)cc1]
RM-1
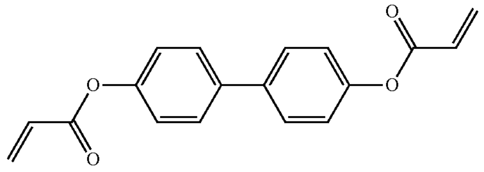 [SMILES: C=CC(=O)Oc1ccc(-c2ccc(OC(=O)C=C)cc2)cc1]
RM-2
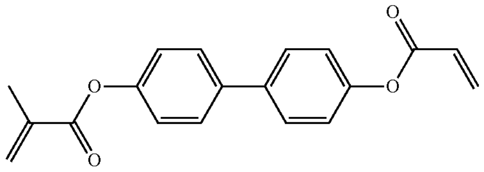 [SMILES: C=CC(=O)Oc1ccc(-c2ccc(OC(=O)C(=C)C)cc2)cc1]
RM-3
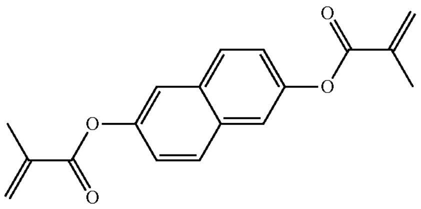 [SMILES: C=C(C)C(=O)Oc1ccc2cc(OC(=O)C(=C)C)ccc2c1]
RM-4
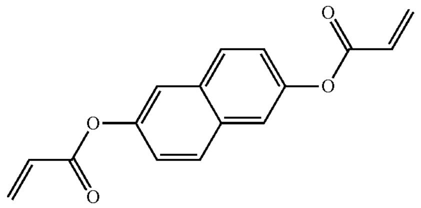 [SMILES: C=CC(=O)Oc1ccc2cc(OC(=O)C=C)ccc2c1]
RM-5

TABLE E-continued
Table E shows illustrative reactive mesogenic compounds which can be used in the LC media in accordance with the present invention.
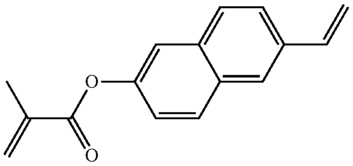 [SMILES: C=Cc1ccc2cc(OC(=O)C(=C)C)ccc2c1]
RM-6
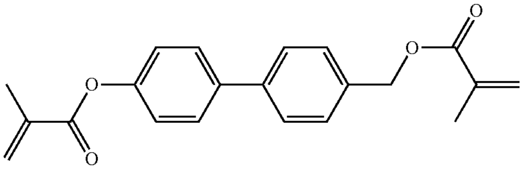 [SMILES: C=C(C)C(=O)OCc1ccc(-c2ccc(OC(=O)C(=C)C)cc2)cc1]
RM-7
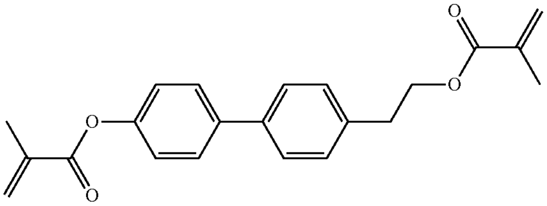 [SMILES: C=C(C)C(=O)OCCc1ccc(-c2ccc(OC(=O)C(=C)C)cc2)cc1]
RM-8
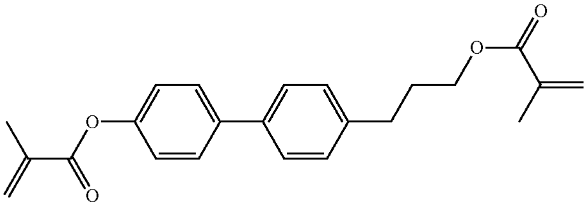 [SMILES: C=C(C)C(=O)OCCCc1ccc(-c2ccc(OC(=O)C(=C)C)cc2)cc1]
RM-9
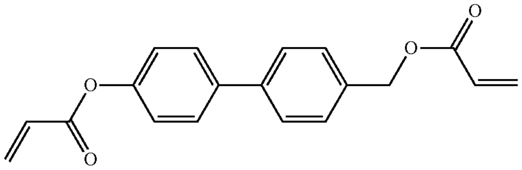 [SMILES: C=CC(=O)OCc1ccc(-c2ccc(OC(=O)C=C)cc2)cc1]
RM-10
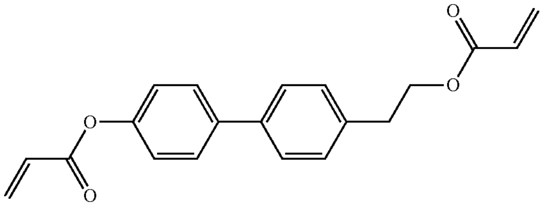 [SMILES: C=CC(=O)OCCc1ccc(-c2ccc(OC(=O)C=C)cc2)cc1]
RM-11
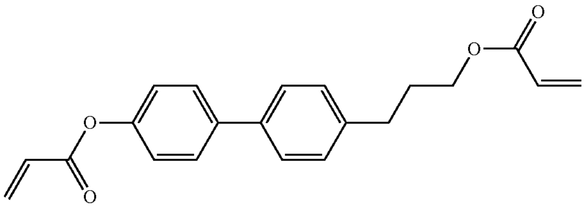 [SMILES: C=CC(=O)OCCCc1ccc(-c2ccc(OC(=O)C=C)cc2)cc1]
RM-12
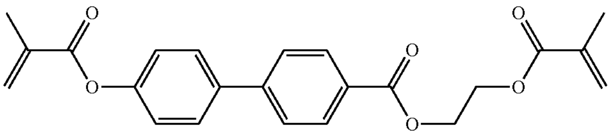 [SMILES: C=C(C)C(=O)OCCOC(=O)c1ccc(-c2ccc(OC(=O)C(=C)C)cc2)cc1]
RM-13

TABLE E-continued
Table E shows illustrative reactive mesogenic compounds which can be used in the LC media in accordance with the present invention.
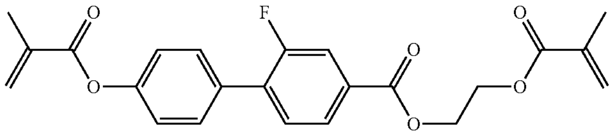 [SMILES: C=C(C)C(=O)OCCOC(=O)c1ccc(-c2ccc(OC(=O)C(=C)C)cc2)c(F)c1]
RM-14
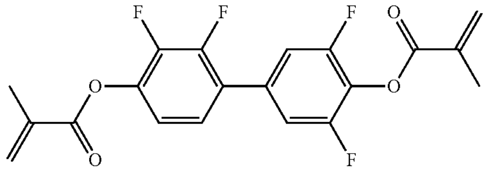
RM-15
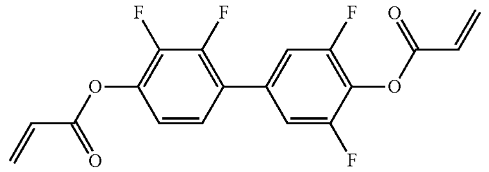 [SMILES: C=CC(=O)Oc1ccc(-c2cc(F)c(OC(=O)C=C)c(F)c2)c(F)c1F]
RM-16
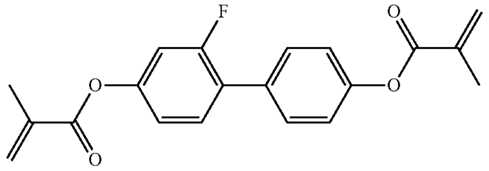 [SMILES: C=C(C)C(=O)Oc1ccc(-c2ccc(OC(=O)C(=C)C)cc2F)cc1]
RM-17
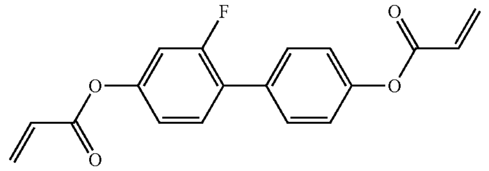 [SMILES: C=CC(=O)Oc1ccc(-c2ccc(OC(=O)C=C)cc2F)cc1]
RM-18
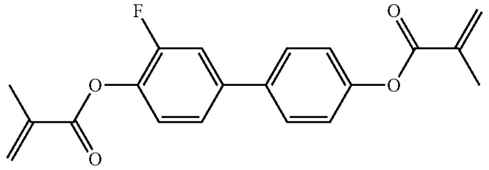
RM-19
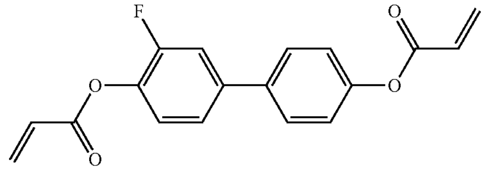
RM-20
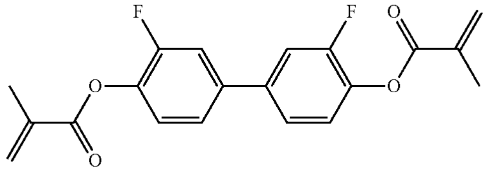
RM-21
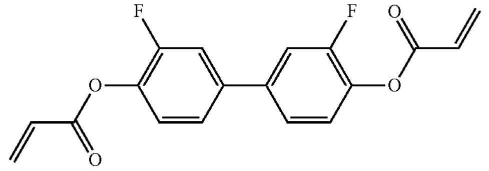
RM-22

TABLE E-continued
Table E shows illustrative reactive mesogenic compounds which can be used in the LC media in accordance with the present invention.
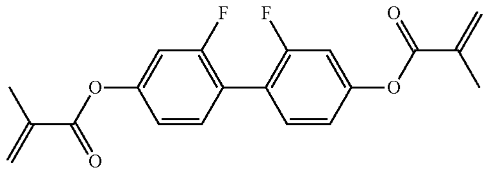 [SMILES: C=C(C)C(=O)Oc1ccc(-c2ccc(OC(=O)C(=C)C)cc2F)c(F)c1]
RM-23
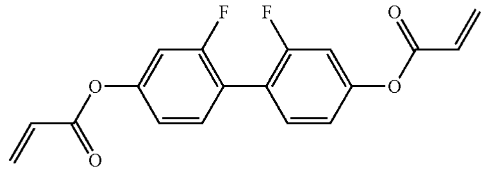
RM-24
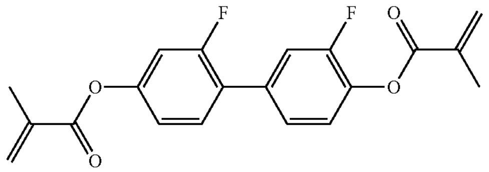 [SMILES: C=C(C)C(=O)Oc1ccc(-c2ccc(OC(=O)C(=C)C)c(F)c2)c(F)c1]
RM-25
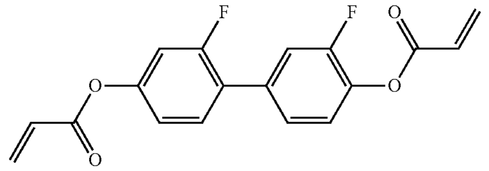 [SMILES: C=CC(=O)Oc1ccc(-c2ccc(OC(=O)C=C)c(F)c2)c(F)c1]
RM-26
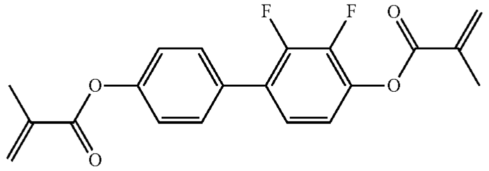 [SMILES: C=C(C)C(=O)Oc1ccc(-c2ccc(OC(=O)C(=C)C)c(F)c2F)cc1]
RM-27
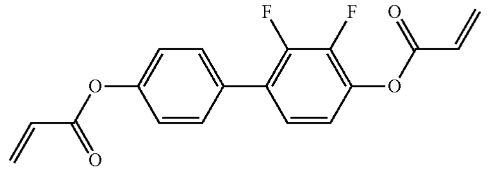 [SMILES: C=CC(=O)Oc1ccc(-c2ccc(OC(=O)C=C)c(F)c2F)cc1]
RM-28
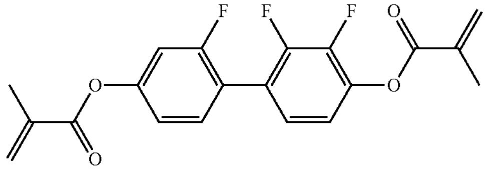
RM-29
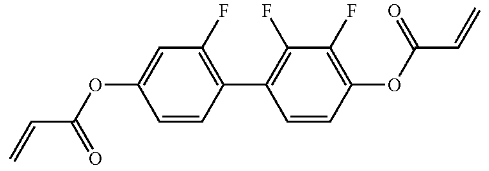 [SMILES: C=CC(=O)Oc1ccc(-c2ccc(OC(=O)C=C)c(F)c2F)c(F)c1]
RM-30

TABLE E-continued
| Table E shows illustrative reactive mesogenic compounds which can be used in the LC media in accordance with the present invention. | |
|---|---|
| 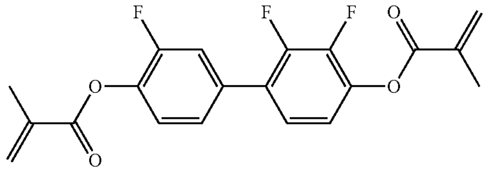 | RM-31 |
| 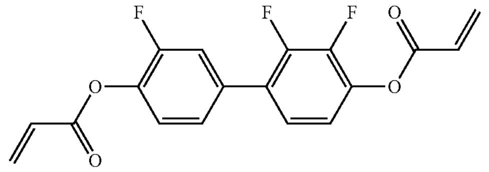 [SMILES: C=CC(=O)Oc1ccc(-c2ccc(OC(=O)C=C)c(F)c2F)cc1F] | RM-32 |
| 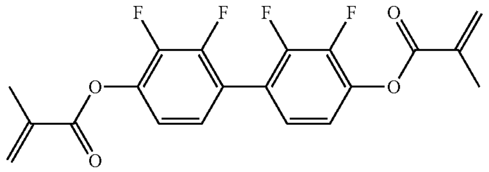 [SMILES: C=C(C)C(=O)Oc1ccc(-c2ccc(OC(=O)C(=C)C)c(F)c2F)c(F)c1F] | RM-33 |
| 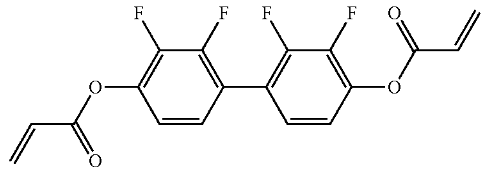 [SMILES: C=CC(=O)Oc1ccc(-c2ccc(OC(=O)C=C)c(F)c2F)c(F)c1F] | RM-34 |
| 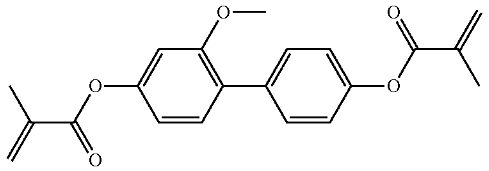 [SMILES: C=C(C)C(=O)Oc1ccc(-c2ccc(OC(=O)C(=C)C)cc2OC)cc1] | RM-35 |
| 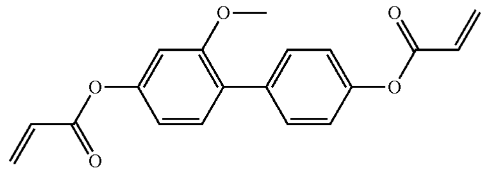 | RM-36 |
| 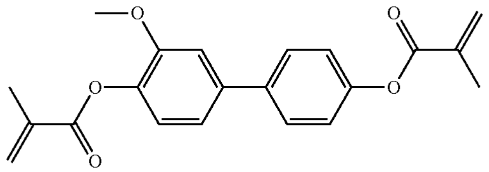 | RM-37 |
| 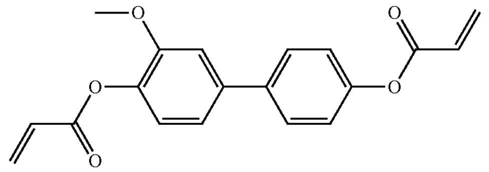 [SMILES: C=CC(=O)Oc1ccc(-c2ccc(OC(=O)C=C)c(OC)c2)cc1] | RM-38 |

TABLE E-continued
Table E shows illustrative reactive mesogenic compounds which can be used in the LC media in accordance with the present invention.
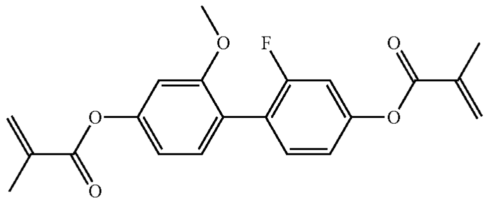 [SMILES: C=C(C)C(=O)Oc1ccc(-c2ccc(OC(=O)C(=C)C)cc2OC)c(F)c1]
RM-39
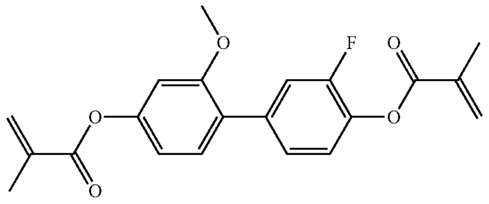 [SMILES: C=C(C)C(=O)Oc1ccc(-c2ccc(OC(=O)C(=C)C)c(F)c2)c(OC)c1]
RM-40
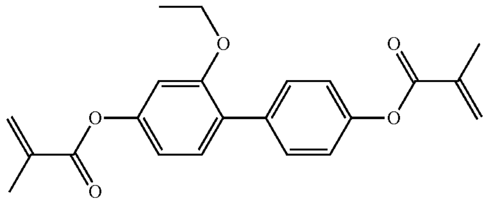 [SMILES: C=C(C)C(=O)Oc1ccc(-c2ccc(OC(=O)C(=C)C)cc2OCC)cc1]
RM-41
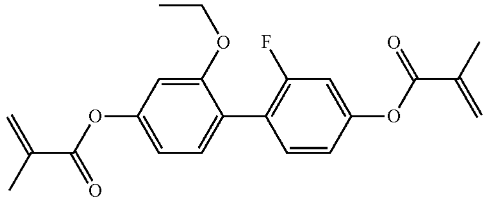 [SMILES: C=C(C)C(=O)Oc1ccc(-c2ccc(OC(=O)C(=C)C)cc2OCC)c(F)c1]
RM-42
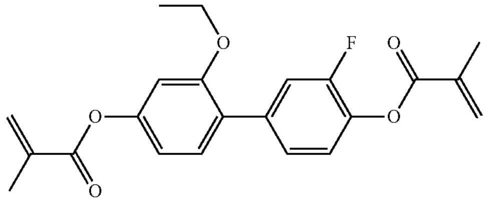 [SMILES: C=C(C)C(=O)Oc1ccc(-c2ccc(OC(=O)C(=C)C)c(F)c2)c(OCC)c1]
RM-43
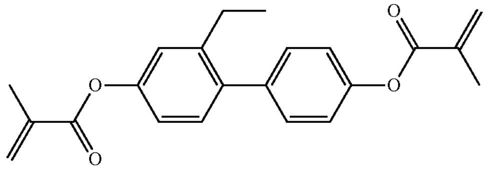
RM-44
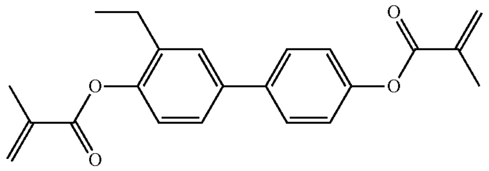 [SMILES: C=C(C)C(=O)Oc1ccc(-c2ccc(OC(=O)C(=C)C)c(CC)c2)cc1]
RM-45

TABLE E-continued
Table E shows illustrative reactive mesogenic compounds which can be used in the LC media in accordance with the present invention.
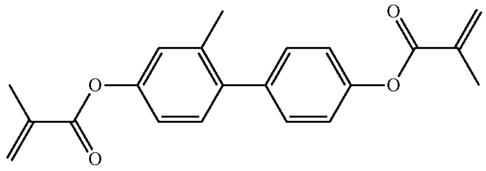
RM-46
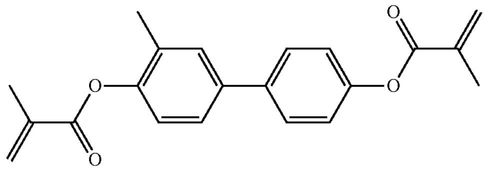
RM-47
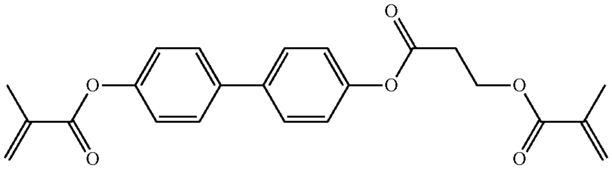
RM-48
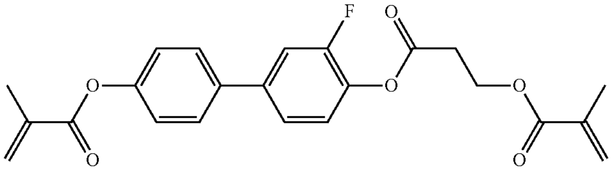 [SMILES: C=C(C)C(=O)OCCC(=O)Oc1ccc(-c2ccc(OC(=O)C(=C)C)cc2)cc1F]
RM-49
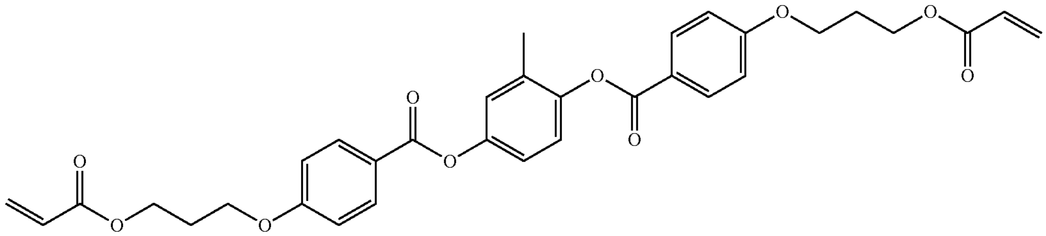 [SMILES: C=CC(=O)OCCCOc1ccc(C(=O)Oc2ccc(OC(=O)c3ccc(OCCCOC(=O)C=C)cc3)c(C)c2)cc1]
RM-50
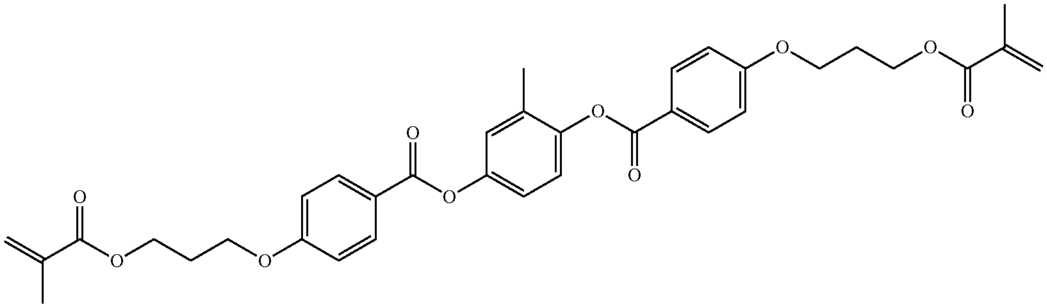 [SMILES: C=C(C)C(=O)OCCCOc1ccc(C(=O)Oc2ccc(OC(=O)c3ccc(OCCCOC(=O)C(=C)C)cc3)c(C)c2)cc1]
RM-51
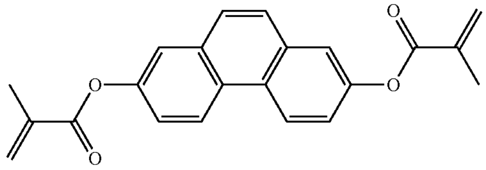 [SMILES: C=C(C)C(=O)Oc1ccc2c(ccc3cc(OC(=O)C(=C)C)ccc32)c1]
RM-52

TABLE E-continued
Table E shows illustrative reactive mesogenic compounds which can be used in the LC media in accordance with the present invention.
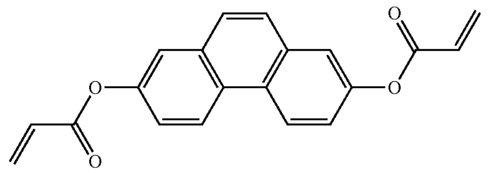 [SMILES: C=CC(=O)Oc1ccc2c(ccc3cc(OC(=O)C=C)ccc32)c1]
RM-53
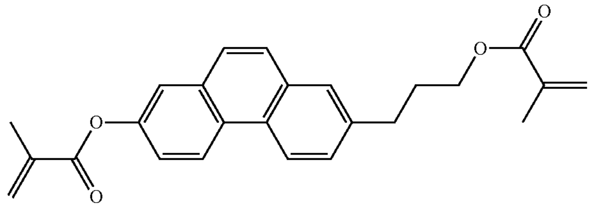 [SMILES: C=C(C)C(=O)OCCCc1ccc2c(ccc3cc(OC(=O)C(=C)C)ccc32)c1]
RM-54
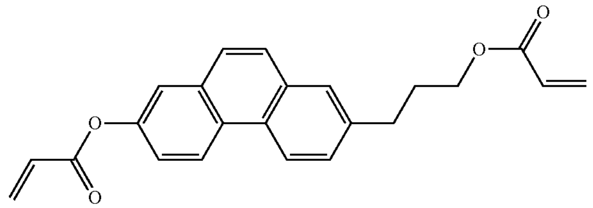 [SMILES: C=CC(=O)OCCCc1ccc2c(ccc3cc(OC(=O)C=C)ccc32)c1]
RM-55
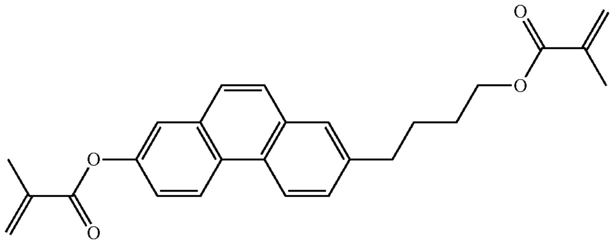 [SMILES: C=C(C)C(=O)OCCCCc1ccc2c(ccc3cc(OC(=O)C(=C)C)ccc32)c1]
RM-56
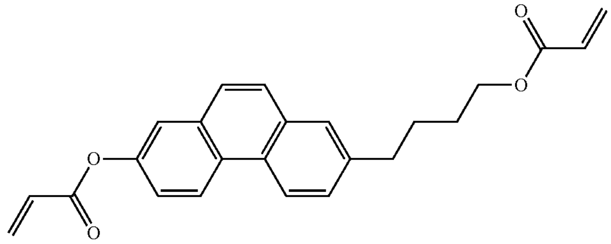 [SMILES: C=CC(=O)OCCCCc1ccc2c(ccc3cc(OC(=O)C=C)ccc32)c1]
RM-57
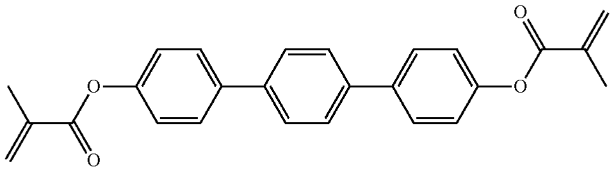 [SMILES: C=C(C)C(=O)Oc1ccc(-c2ccc(-c3ccc(OC(=O)C(=C)C)cc3)cc2)cc1]
RM-58
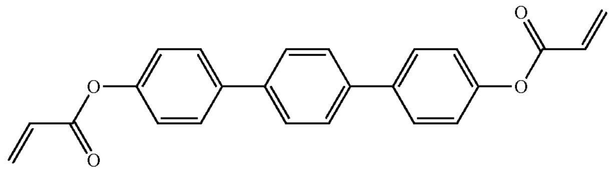 [SMILES: C=CC(=O)Oc1ccc(-c2ccc(-c3ccc(OC(=O)C=C)cc3)cc2)cc1]
RM-59

TABLE E-continued
Table E shows illustrative reactive mesogenic compounds which can be used in the LC media in accordance with the present invention.
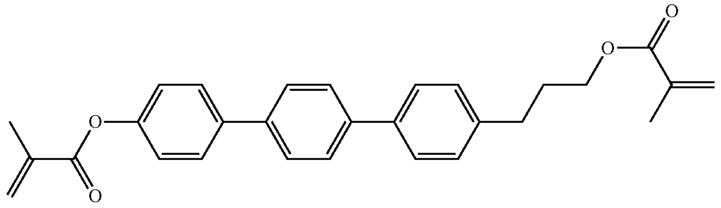 [SMILES: C=C(C)C(=O)OCCCc1ccc(-c2ccc(-c3ccc(OC(=O)C(=C)C)cc3)cc2)cc1]
RM-60
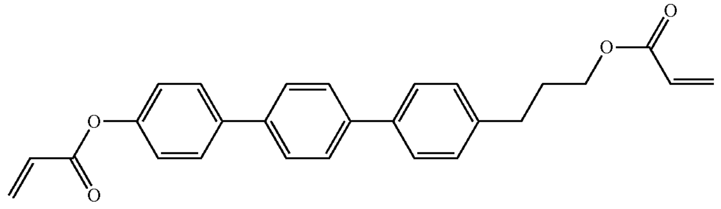 [SMILES: C=CC(=O)OCCCc1ccc(-c2ccc(-c3ccc(OC(=O)C=C)cc3)cc2)cc1]
RM-61
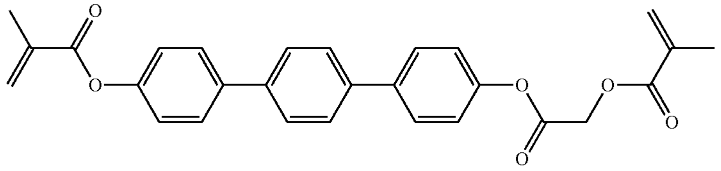 [SMILES: C=C(C)C(=O)OCC(=O)Oc1ccc(-c2ccc(-c3ccc(OC(=O)C(=C)C)cc3)cc2)cc1]
RM-62
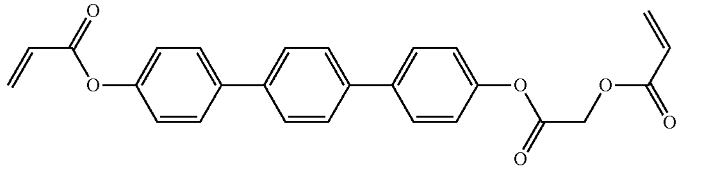
RM-63
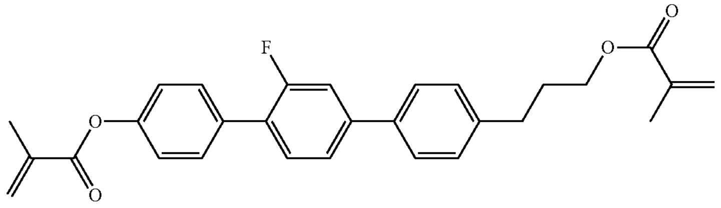 [SMILES: C=C(C)C(=O)OCCCc1ccc(-c2ccc(-c3ccc(OC(=O)C(=C)C)cc3)c(F)c2)cc1]
RM-64
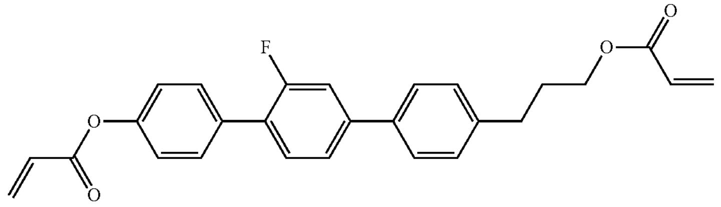 [SMILES: C=CC(=O)OCCCc1ccc(-c2ccc(-c3ccc(OC(=O)C=C)cc3)c(F)c2)cc1]
RM-65
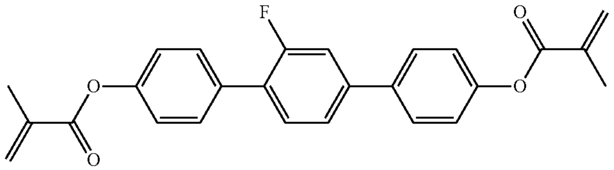 [SMILES: C=C(C)C(=O)Oc1ccc(-c2ccc(-c3ccc(OC(=O)C(=C)C)cc3)c(F)c2)cc1]
RM-66
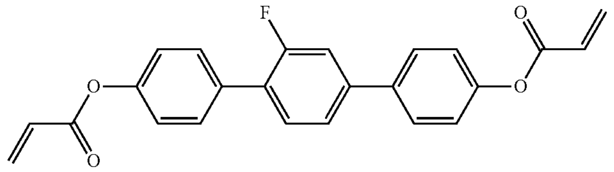 [SMILES: C=CC(=O)Oc1ccc(-c2ccc(-c3ccc(OC(=O)C=C)cc3)c(F)c2)cc1]
RM-67

TABLE E-continued
| Table E shows illustrative reactive mesogenic compounds which can be used in the LC media in accordance with the present invention. |
|---|
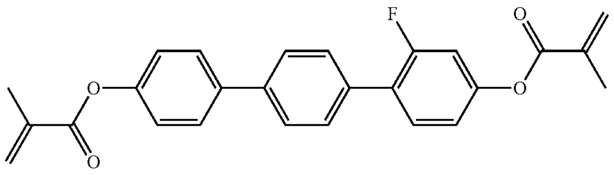 [SMILES: C=C(C)C(=O)Oc1ccc(-c2ccc(-c3ccc(OC(=O)C(=C)C)cc3F)cc2)cc1]
RM-68
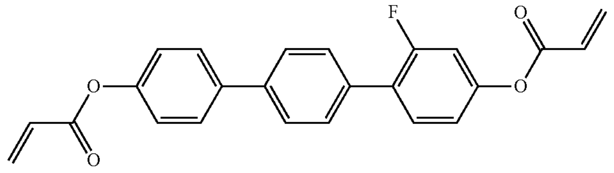 [SMILES: C=CC(=O)Oc1ccc(-c2ccc(-c3ccc(OC(=O)C=C)cc3F)cc2)cc1]
RM-69
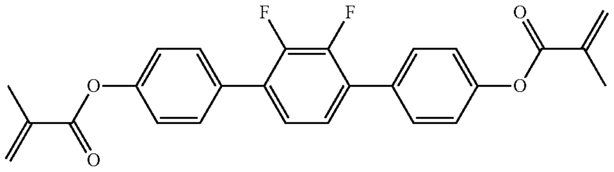 [SMILES: C=C(C)C(=O)Oc1ccc(-c2ccc(-c3ccc(OC(=O)C(=C)C)cc3)c(F)c2F)cc1]
RM-70
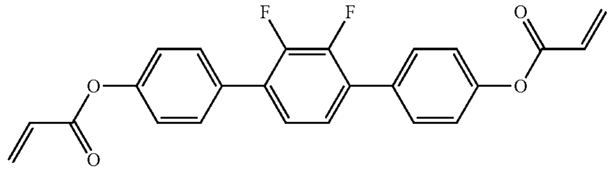 [SMILES: C=CC(=O)Oc1ccc(-c2ccc(-c3ccc(OC(=O)C=C)cc3)c(F)c2F)cc1]
RM-71
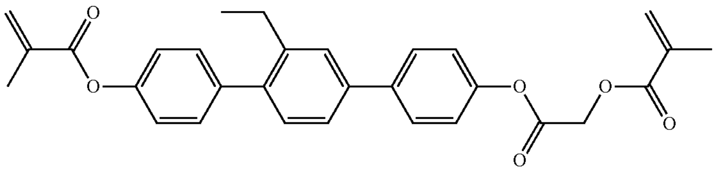 [SMILES: C=C(C)C(=O)OCC(=O)Oc1ccc(-c2ccc(-c3ccc(OC(=O)C(=C)C)cc3)c(CC)c2)cc1]
RM-72
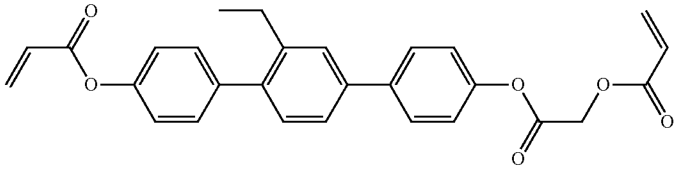 [SMILES: C=CC(=O)OCC(=O)Oc1ccc(-c2ccc(-c3ccc(OC(=O)C=C)cc3)c(CC)c2)cc1]
RM-73
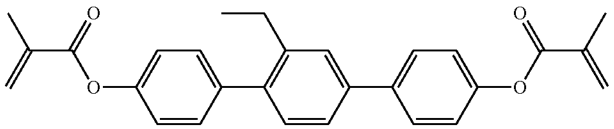 [SMILES: C=C(C)C(=O)Oc1ccc(-c2ccc(-c3ccc(OC(=O)C(=C)C)cc3)c(CC)c2)cc1]
RM-74
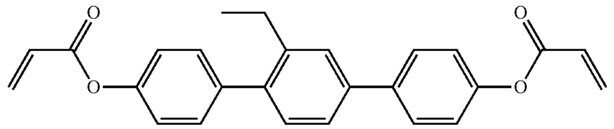 [SMILES: C=CC(=O)Oc1ccc(-c2ccc(-c3ccc(OC(=O)C=C)cc3)c(CC)c2)cc1]
RM-75
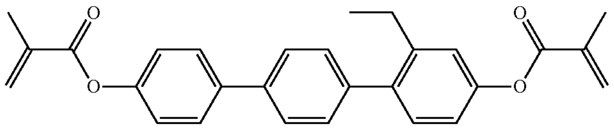 [SMILES: C=C(C)C(=O)Oc1ccc(-c2ccc(-c3ccc(OC(=O)C(=C)C)cc3CC)cc2)cc1]
RM-76

TABLE E-continued
Table E shows illustrative reactive mesogenic compounds which can be used in the LC media in accordance with the present invention.
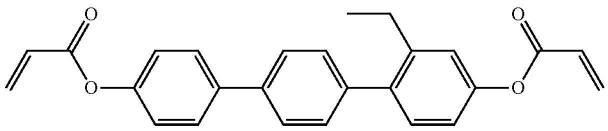 [SMILES: C=CC(=O)Oc1ccc(-c2ccc(-c3ccc(OC(=O)C=C)cc3CC)cc2)cc1]
RM-77
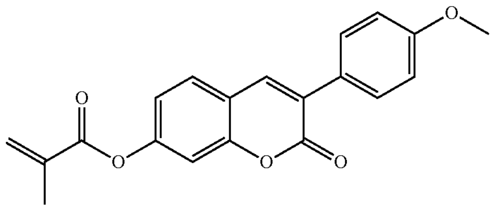 [SMILES: C=C(C)C(=O)Oc1ccc2cc(-c3ccc(OC)cc3)c(=O)oc2c1]
RM-78
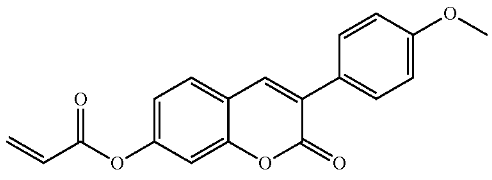 [SMILES: C=CC(=O)Oc1ccc2cc(-c3ccc(OC)cc3)c(=O)oc2c1]
RM-79
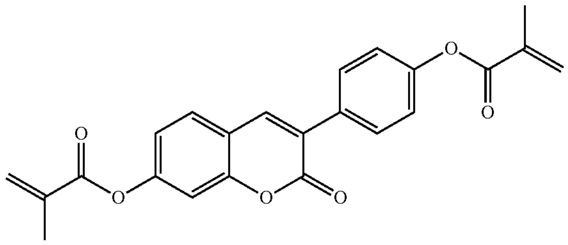 [SMILES: C=C(C)C(=O)Oc1ccc(-c2cc3ccc(OC(=O)C(=C)C)cc3oc2=O)cc1]
RM-80
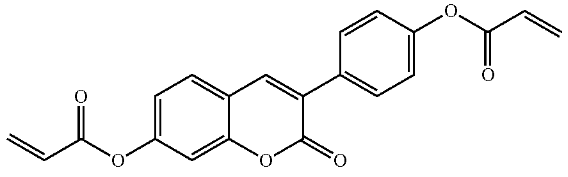 [SMILES: C=CC(=O)Oc1ccc(-c2cc3ccc(OC(=O)C=C)cc3oc2=O)cc1]
RM-81
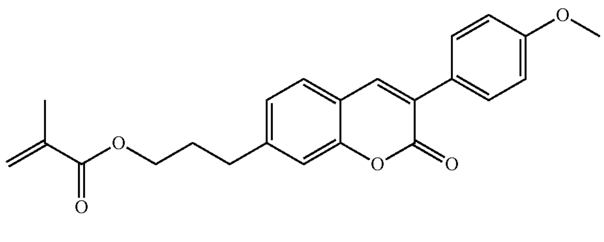 [SMILES: C=C(C)C(=O)OCCCc1ccc2cc(-c3ccc(OC)cc3)c(=O)oc2c1]
RM-82
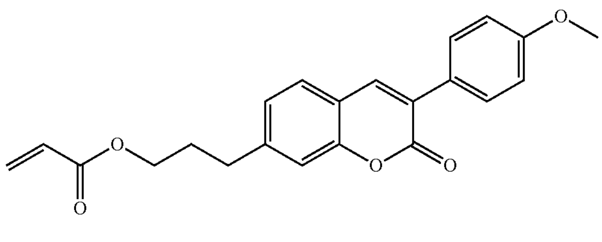 [SMILES: C=CC(=O)OCCCc1ccc2cc(-c3ccc(OC)cc3)c(=O)oc2c1]
RM-83

TABLE E-continued
| Table E shows illustrative reactive mesogenic compounds which can be used in the LC media in accordance with the present invention. | |
|---|---|
| 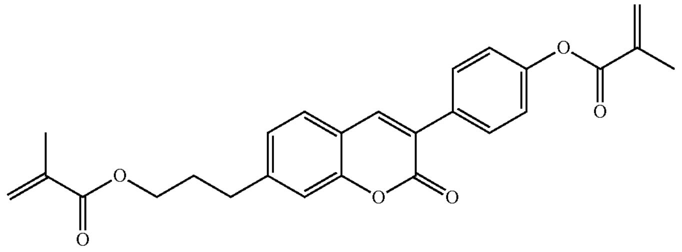 [SMILES: C=C(C)C(=O)OCCCc1ccc2cc(-c3ccc(OC(=O)C(=C)C)cc3)c(=O)oc2c1] | RM-84 |
| 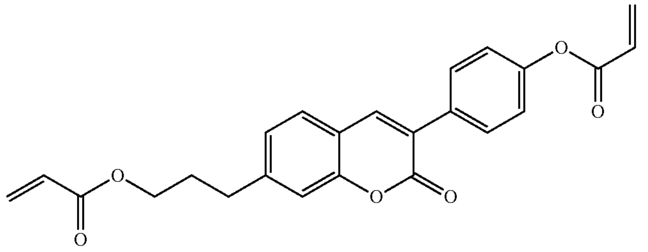 [SMILES: C=CC(=O)OCCCc1ccc2cc(-c3ccc(OC(=O)C=C)cc3)c(=O)oc2c1] | RM-85 |
| 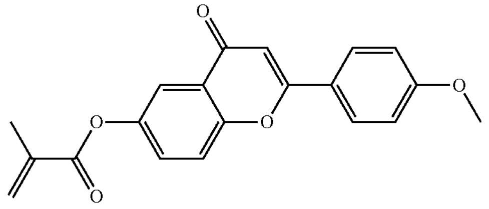 [SMILES: C=C(C)C(=O)Oc1ccc2oc(-c3ccc(OC)cc3)cc(=O)c2c1] | RM-86 |
| 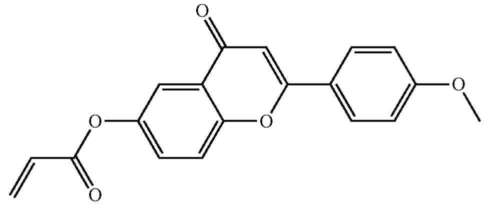 [SMILES: C=CC(=O)Oc1ccc2oc(-c3ccc(OC)cc3)cc(=O)c2c1] | RM-87 |
| 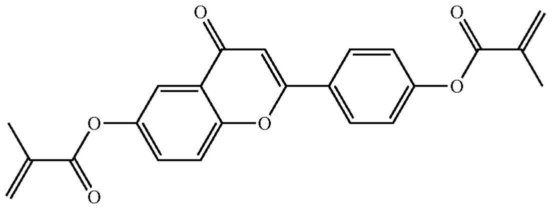 [SMILES: C=C(C)C(=O)Oc1ccc(-c2cc(=O)c3cc(OC(=O)C(=C)C)ccc3o2)cc1] | RM-88 |
| 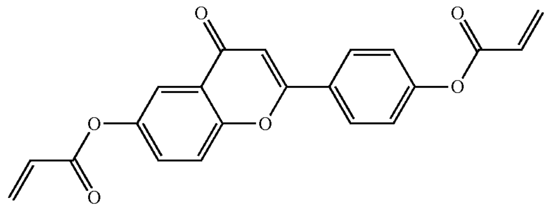 [SMILES: C=CC(=O)Oc1ccc(-c2cc(=O)c3cc(OC(=O)C=C)ccc3o2)cc1] | RM-89 |

TABLE E-continued
| Table E shows illustrative reactive mesogenic compounds which can be used in the LC media in accordance with the present invention. |
|---|
RM-90
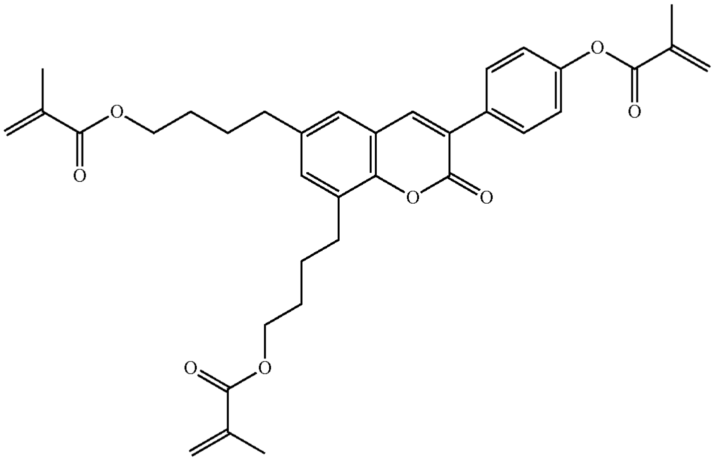 [SMILES: C=C(C)C(=O)OCCCCc1cc(CCCCOC(=O)C(=C)C)c2oc(=O)c(-c3ccc(OC(=O)C(=C)C)cc3)cc2c1]
RM-91
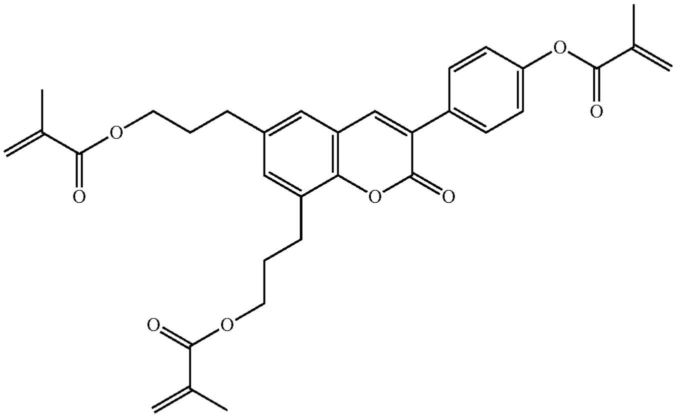 [SMILES: C=C(C)C(=O)OCCCc1cc(CCCOC(=O)C(=C)C)c2oc(=O)c(-c3ccc(OC(=O)C(=C)C)cc3)cc2c1]
RM-92
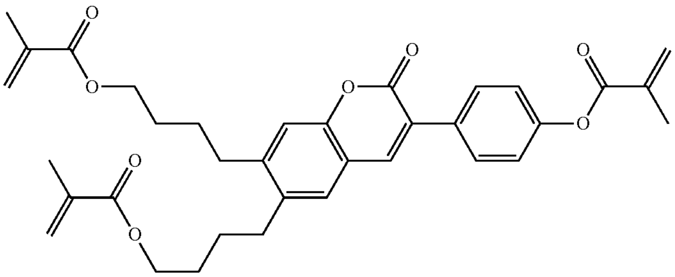 [SMILES: C=C(C)C(=O)OCCCCc1cc2cc(-c3ccc(OC(=O)C(=C)C)cc3)c(=O)oc2cc1CCCCOC(=O)C(=C)C]
RM-93
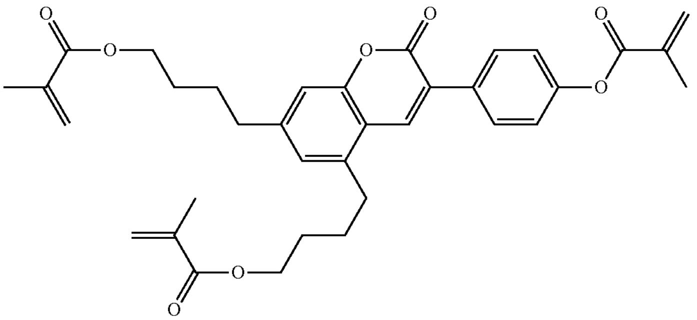 [SMILES: C=C(C)C(=O)OCCCCc1cc(CCCCOC(=O)C(=C)C)c2cc(-c3ccc(OC(=O)C(=C)C)cc3)c(=O)oc2c1]

TABLE E-continued
| Table E shows illustrative reactive mesogenic compounds which can be used in the LC media in accordance with the present invention. | |
|---|---|
| 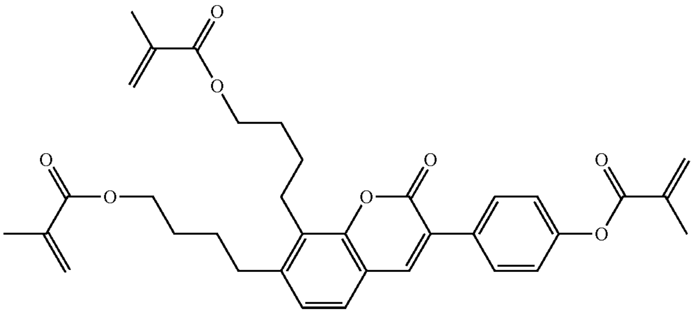 [SMILES: C=C(C)C(=O)OCCCCc1ccc2cc(-c3ccc(OC(=O)C(=C)C)cc3)c(=O)oc2c1CCCCOC(=O)C(=C)C] | RM-94 |
| 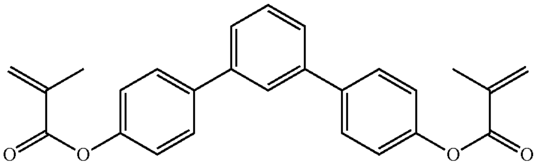 [SMILES: C=C(C)C(=O)Oc1ccc(-c2cccc(-c3ccc(OC(=O)C(=C)C)cc3)c2)cc1] | RM-95 |
| 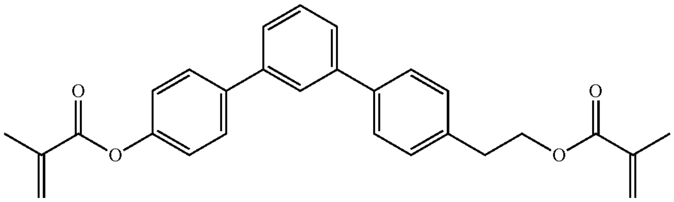 [SMILES: C=C(C)C(=O)OCCc1ccc(-c2cccc(-c3ccc(OC(=O)C(=C)C)cc3)c2)cc1] | RM-96 |
| 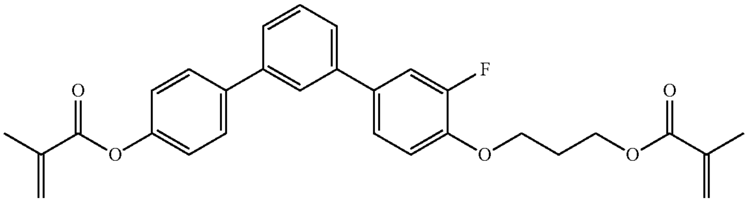 [SMILES: C=C(C)C(=O)OCCCOc1ccc(-c2cccc(-c3ccc(OC(=O)C(=C)C)cc3)c2)cc1F] | RM-97 |
| 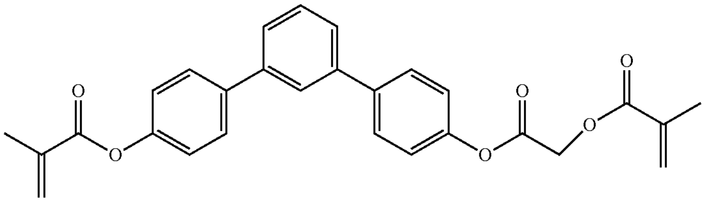 [SMILES: C=C(C)C(=O)OCC(=O)Oc1ccc(-c2cccc(-c3ccc(OC(=O)C(=C)C)cc3)c2)cc1] | RM-98 |
| 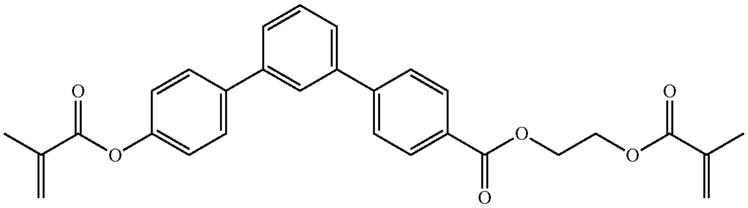 [SMILES: C=C(C)C(=O)OCCOC(=O)c1ccc(-c2cccc(-c3ccc(OC(=O)C(=C)C)cc3)c2)cc1] | RM-99 |

TABLE E-continued
Table E shows illustrative reactive mesogenic compounds which can be used in the LC media in accordance with the present invention.
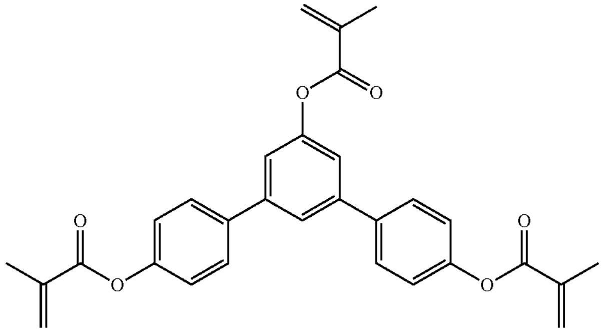 [SMILES: C=C(C)C(=O)Oc1ccc(-c2cc(OC(=O)C(=C)C)cc(-c3ccc(OC(=O)C(=C)C)cc3)c2)cc1]
RM-100
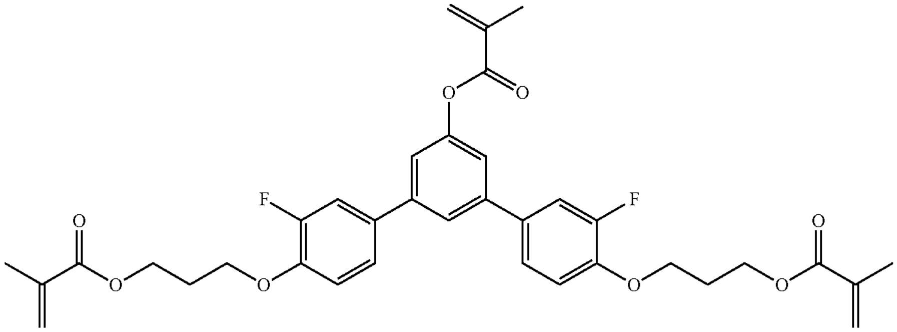 [SMILES: C=C(C)C(=O)OCCCOc1ccc(-c2cc(OC(=O)C(=C)C)cc(-c3ccc(OCCCOC(=O)C(=C)C)c(F)c3)c2)cc1F]
RM-101
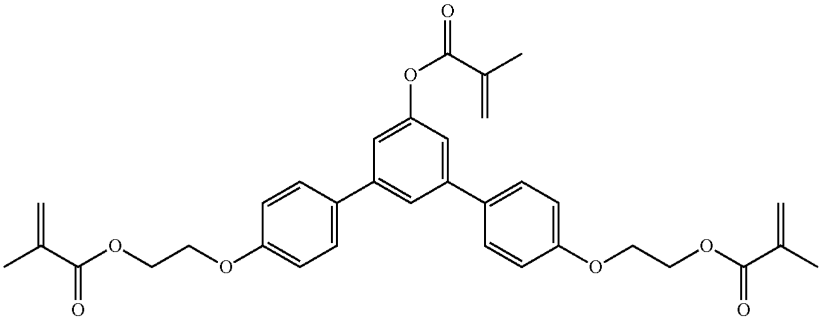 [SMILES: C=C(C)C(=O)OCCOc1ccc(-c2cc(OC(=O)C(=C)C)cc(-c3ccc(OCCOC(=O)C(=C)C)cc3)c2)cc1]
RM-102
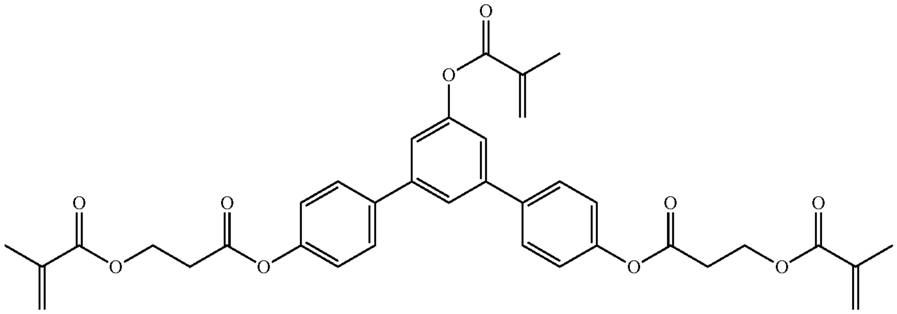 [SMILES: C=C(C)C(=O)OCCC(=O)Oc1ccc(-c2cc(OC(=O)C(=C)C)cc(-c3ccc(OC(=O)CCOC(=O)C(=C)C)cc3)c2)cc1]
RM-103

TABLE E-continued
| Table E shows illustrative reactive mesogenic compounds which can be used in the LC media in accordance with the present invention. |
| --- |
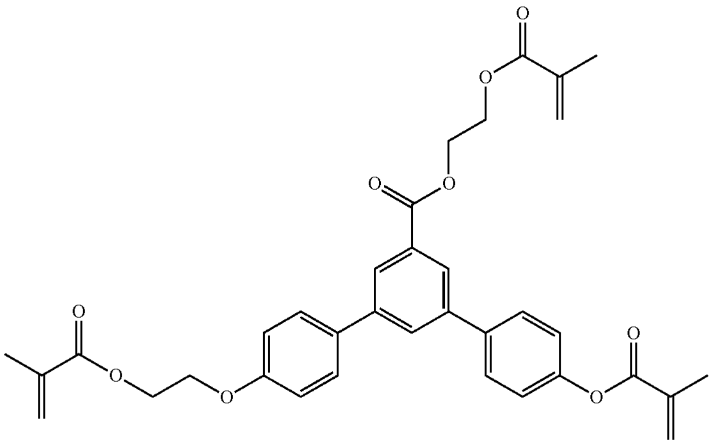 [SMILES: C=C(C)C(=O)OCCOC(=O)c1cc(-c2ccc(OCCOC(=O)C(=C)C)cc2)cc(-c2ccc(OC(=O)C(=C)C)cc2)c1]
RM-104
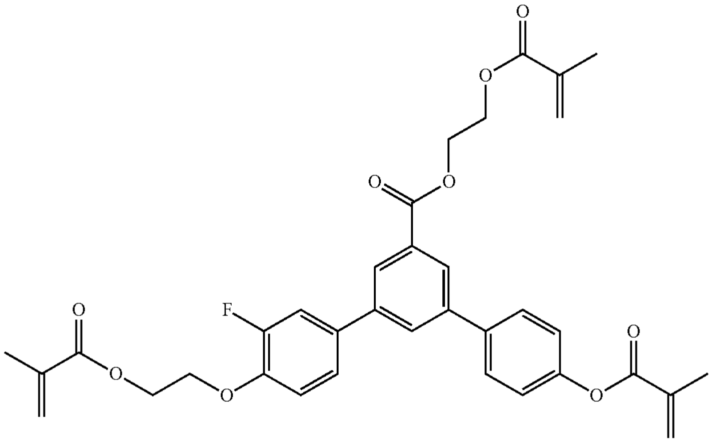 [SMILES: C=C(C)C(=O)OCCOC(=O)c1cc(-c2ccc(OC(=O)C(=C)C)cc2)cc(-c2ccc(OCCOC(=O)C(=C)C)c(F)c2)c1]
RM-105
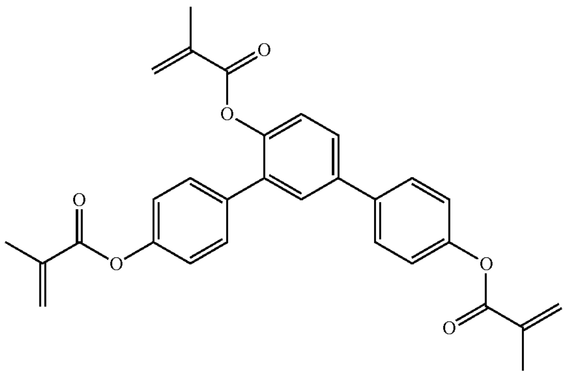 [SMILES: C=C(C)C(=O)Oc1ccc(-c2ccc(OC(=O)C(=C)C)c(-c3ccc(OC(=O)C(=C)C)cc3)c2)cc1]
RM-106

TABLE E-continued
Table E shows illustrative reactive mesogenic compounds which can be used in the LC media in accordance with the present invention.
RM-107
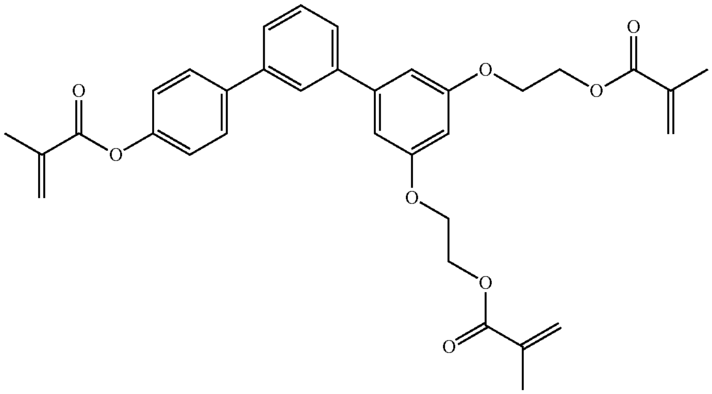 [SMILES: C=C(C)C(=O)OCCOc1cc(OCCOC(=O)C(=C)C)cc(-c2cccc(-c3ccc(OC(=O)C(=C)C)cc3)c2)c1]
RM-108
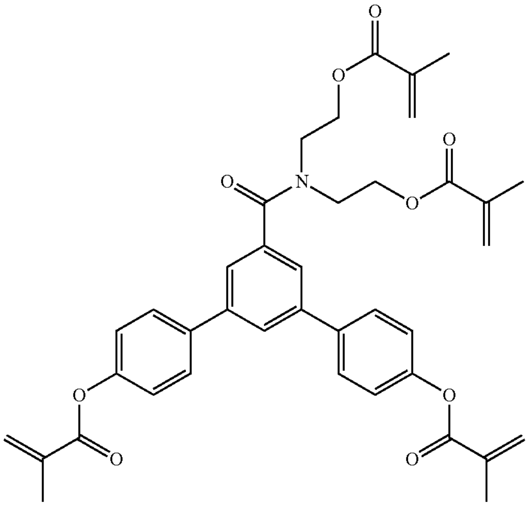 [SMILES: C=C(C)C(=O)OCCN(CCOC(=O)C(=C)C)C(=O)c1cc(-c2ccc(OC(=O)C(=C)C)cc2)cc(-c2ccc(OC(=O)C(=C)C)cc2)c1]
RM-109
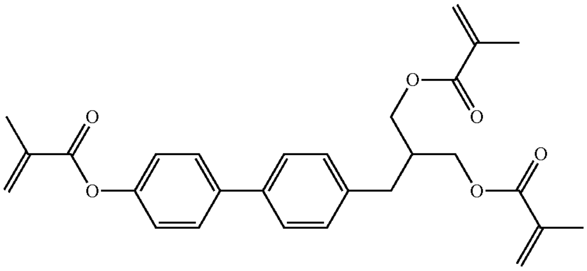 [SMILES: C=C(C)C(=O)OCC(COC(=O)C(=C)C)Cc1ccc(-c2ccc(OC(=O)C(=C)C)cc2)cc1]
RM-110
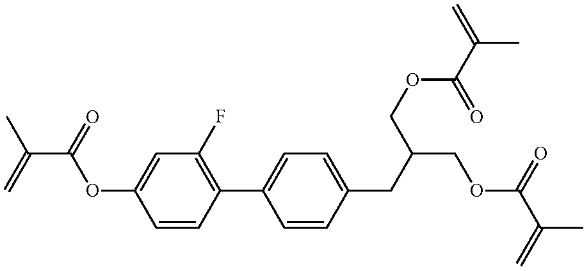 [SMILES: C=C(C)C(=O)OCC(COC(=O)C(=C)C)Cc1ccc(-c2ccc(OC(=O)C(=C)C)cc2F)cc1]

TABLE E-continued
Table E shows illustrative reactive mesogenic compounds which can be used in the LC media in accordance with the present invention.
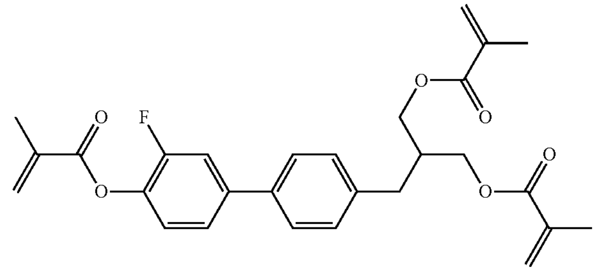 [SMILES: C=C(C)C(=O)OCC(COC(=O)C(=C)C)Cc1ccc(-c2ccc(OC(=O)C(=C)C)c(F)c2)cc1]
RM-111
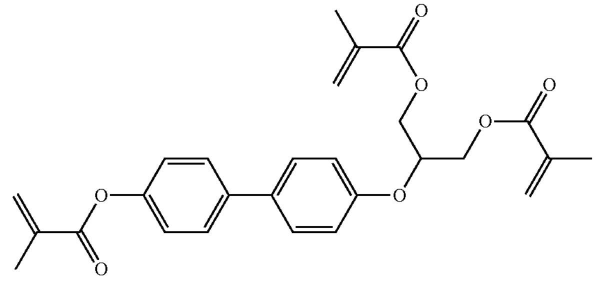 [SMILES: C=C(C)C(=O)OCC(COC(=O)C(=C)C)Oc1ccc(-c2ccc(OC(=O)C(=C)C)cc2)cc1]
RM-112
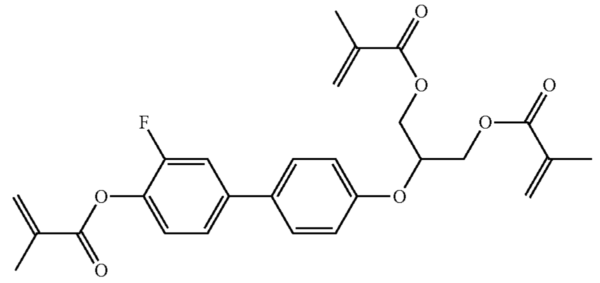
RM-113
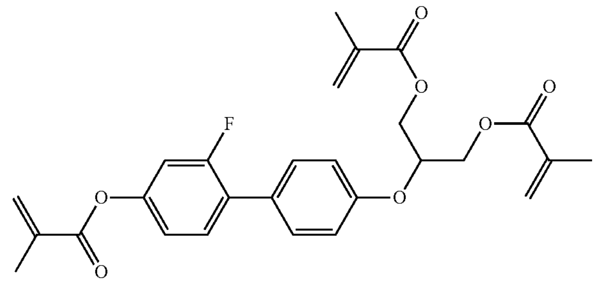 [SMILES: C=C(C)C(=O)OCC(COC(=O)C(=C)C)Oc1ccc(-c2ccc(OC(=O)C(=C)C)cc2F)cc1]
RM-114
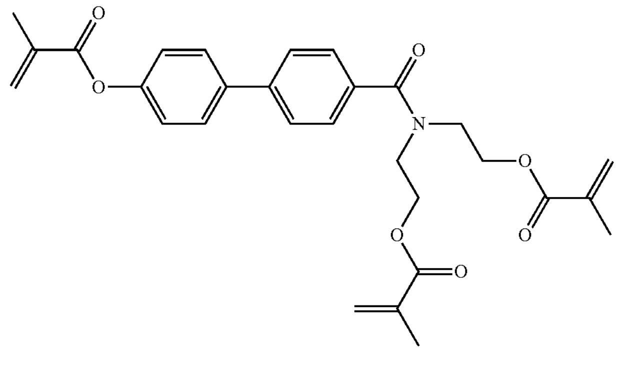 [SMILES: C=C(C)C(=O)OCCN(CCOC(=O)C(=C)C)C(=O)c1ccc(-c2ccc(OC(=O)C(=C)C)cc2)cc1]
RM-115

TABLE E-continued
Table E shows illustrative reactive mesogenic compounds which can be used in the LC media in accordance with the present invention.
RM-116
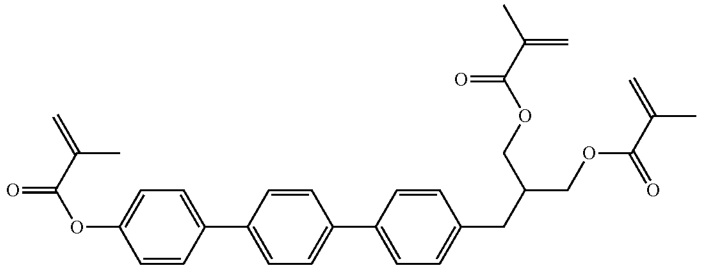 [SMILES: C=C(C)C(=O)OCC(COC(=O)C(=C)C)Cc1ccc(-c2ccc(-c3ccc(OC(=O)C(=C)C)cc3)cc2)cc1]
RM-117
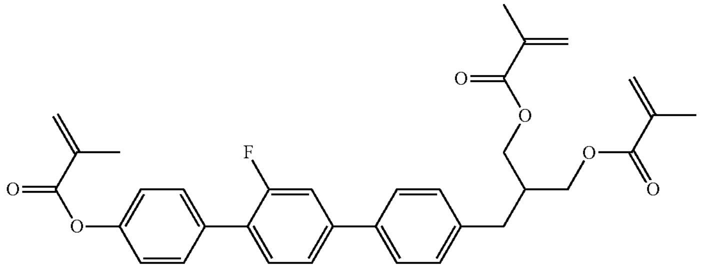 [SMILES: C=C(C)C(=O)OCC(COC(=O)C(=C)C)Cc1ccc(-c2ccc(-c3ccc(OC(=O)C(=C)C)cc3)c(F)c2)cc1]
RM-118
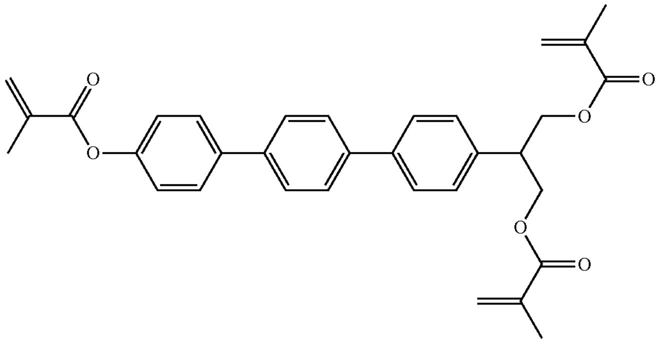 [SMILES: C=C(C)C(=O)OCC(COC(=O)C(=C)C)c1ccc(-c2ccc(-c3ccc(OC(=O)C(=C)C)cc3)cc2)cc1]
RM-119
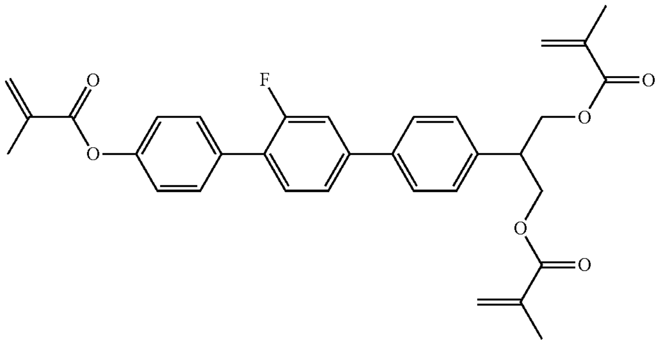 [SMILES: C=C(C)C(=O)OCC(COC(=O)C(=C)C)c1ccc(-c2ccc(-c3ccc(OC(=O)C(=C)C)cc3)c(F)c2)cc1]
RM-120
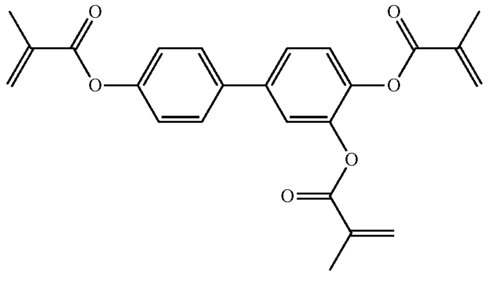 [SMILES: C=C(C)C(=O)Oc1ccc(-c2ccc(OC(=O)C(=C)C)c(OC(=O)C(=C)C)c2)cc1]

TABLE E-continued
Table E shows illustrative reactive mesogenic compounds which can be used in the LC media in accordance with the present invention.
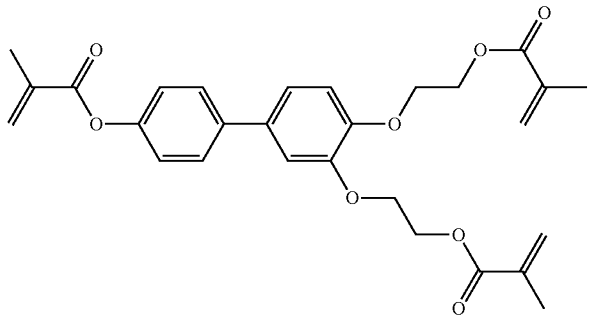 [SMILES: C=C(C)C(=O)OCCOc1ccc(-c2ccc(OC(=O)C(=C)C)cc2)cc1OCCOC(=O)C(=C)C]
RM-121
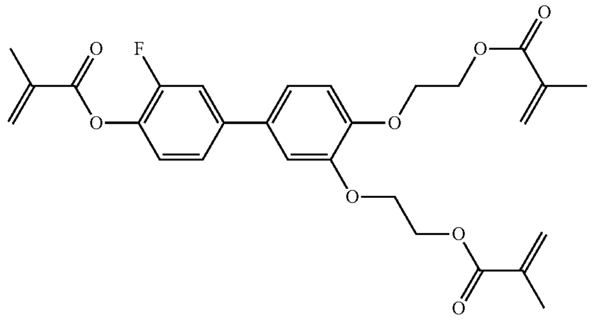 [SMILES: C=C(C)C(=O)OCCOc1ccc(-c2ccc(OC(=O)C(=C)C)c(F)c2)cc1OCCOC(=O)C(=C)C]
RM-122
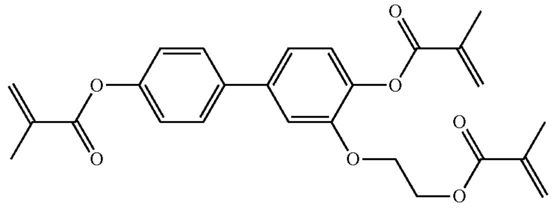 [SMILES: C=C(C)C(=O)OCCOc1cc(-c2ccc(OC(=O)C(=C)C)cc2)ccc1OC(=O)C(=C)C]
RM-123
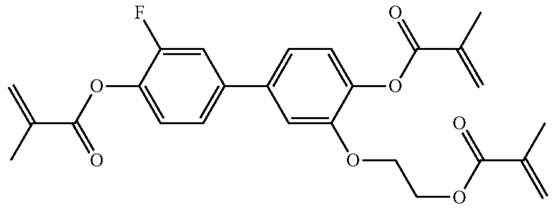
RM-124
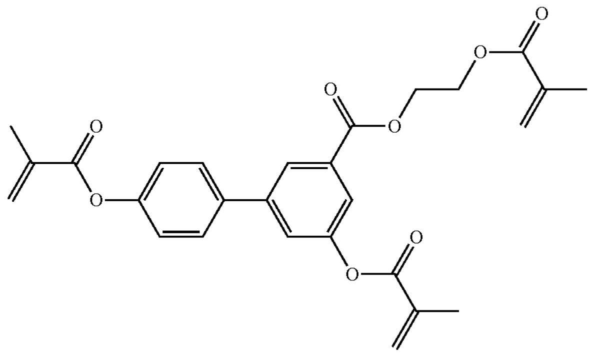 [SMILES: C=C(C)C(=O)OCCOC(=O)c1cc(OC(=O)C(=C)C)cc(-c2ccc(OC(=O)C(=C)C)cc2)c1]
RM-125

TABLE E-continued
Table E shows illustrative reactive mesogenic compounds which can be used in the LC media in accordance with the present invention.
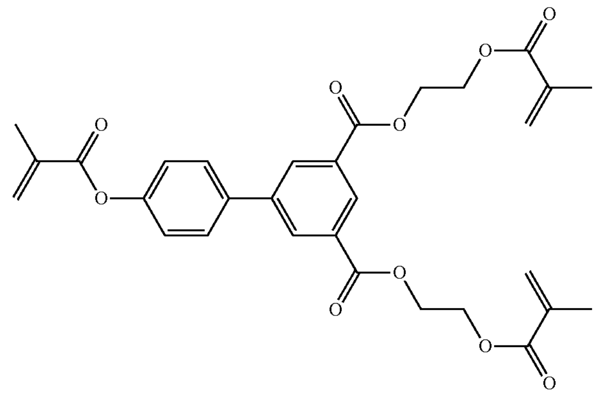 [SMILES: C=C(C)C(=O)OCCOC(=O)c1cc(C(=O)OCCOC(=O)C(=C)C)cc(-c2ccc(OC(=O)C(=C)C)cc2)c1]
RM-126
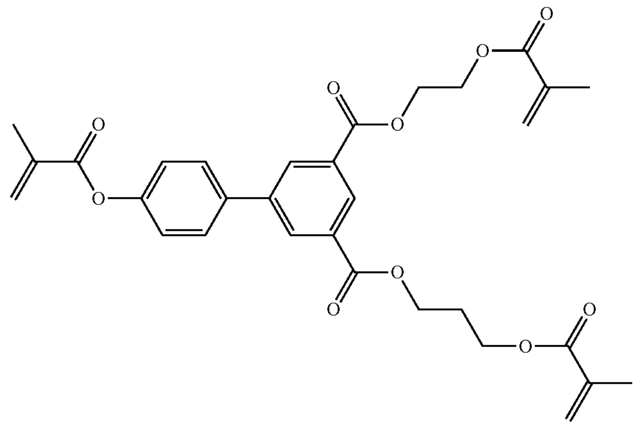 [SMILES: C=C(C)C(=O)OCCCOC(=O)c1cc(C(=O)OCCOC(=O)C(=C)C)cc(-c2ccc(OC(=O)C(=C)C)cc2)c1]
RM-127
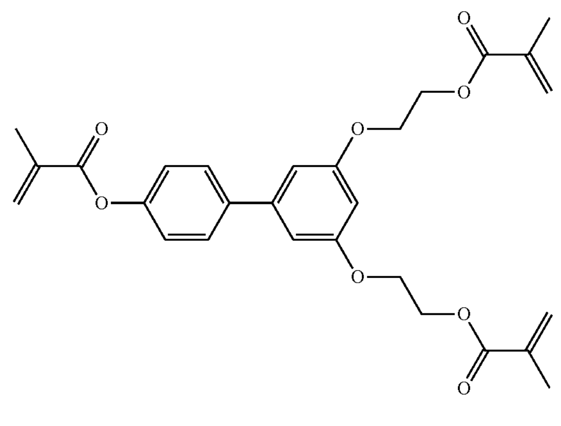 [SMILES: C=C(C)C(=O)OCCOc1cc(OCCOC(=O)C(=C)C)cc(-c2ccc(OC(=O)C(=C)C)cc2)c1]
RM-128

TABLE E-continued
Table E shows illustrative reactive mesogenic compounds which can be used in the LC media in accordance with the present invention.
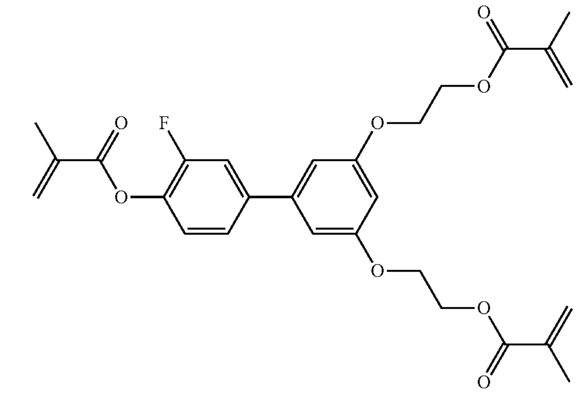 [SMILES: C=C(C)C(=O)OCCOc1cc(OCCOC(=O)C(=C)C)cc(-c2ccc(OC(=O)C(=C)C)c(F)c2)c1]
RM-129
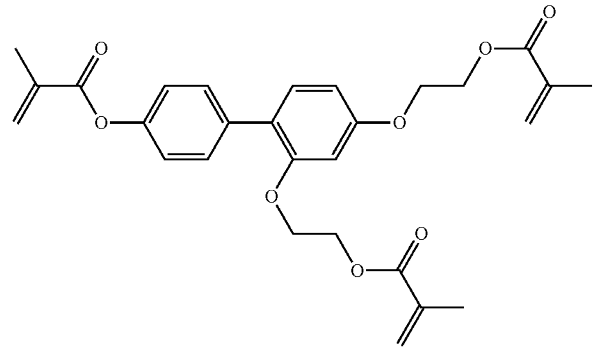 [SMILES: C=C(C)C(=O)OCCOc1ccc(-c2ccc(OC(=O)C(=C)C)cc2)c(OCCOC(=O)C(=C)C)c1]
RM-130
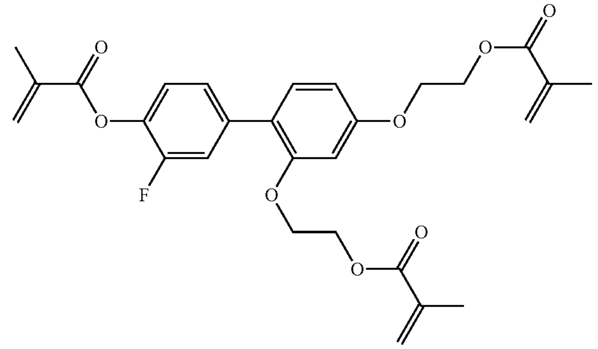 [SMILES: C=C(C)C(=O)OCCOc1ccc(-c2ccc(OC(=O)C(=C)C)c(F)c2)c(OCCOC(=O)C(=C)C)c1]
RM-131
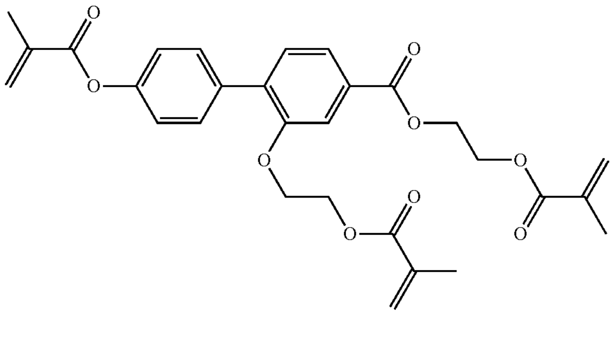 [SMILES: C=C(C)C(=O)OCCOC(=O)c1ccc(-c2ccc(OC(=O)C(=C)C)cc2)c(OCCOC(=O)C(=C)C)c1]
RM-132

TABLE E-continued
Table E shows illustrative reactive mesogenic compounds which can be used in the LC media in accordance with the present invention.
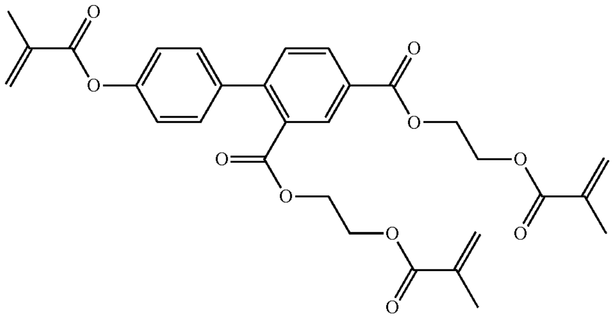 [SMILES: C=C(C)C(=O)OCCOC(=O)c1ccc(-c2ccc(OC(=O)C(=C)C)cc2)c(C(=O)OCCOC(=O)C(=C)C)c1]
RM-133
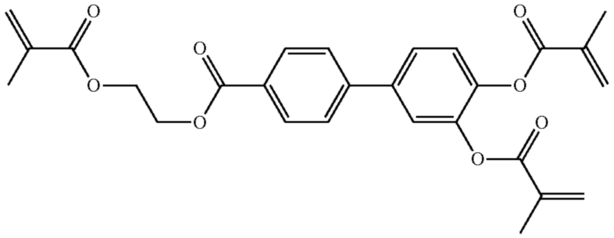 [SMILES: C=C(C)C(=O)OCCOC(=O)c1ccc(-c2ccc(OC(=O)C(=C)C)c(OC(=O)C(=C)C)c2)cc1]
RM-134
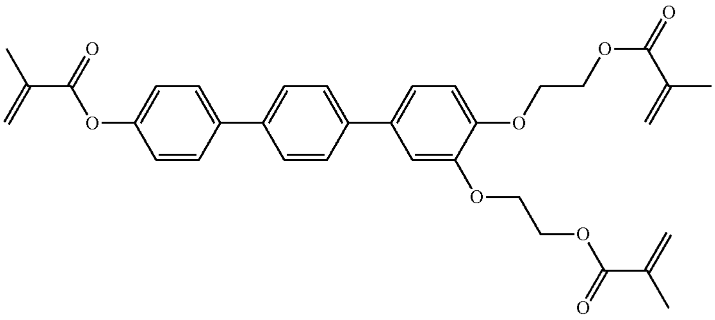 [SMILES: C=C(C)C(=O)OCCOc1ccc(-c2ccc(-c3ccc(OC(=O)C(=C)C)cc3)cc2)cc1OCCOC(=O)C(=C)C]
RM-135
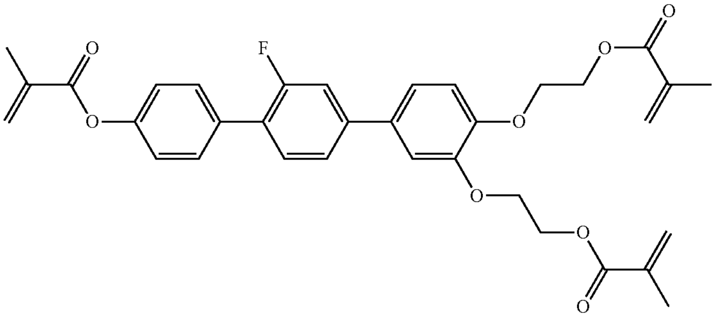 [SMILES: C=C(C)C(=O)OCCOc1ccc(-c2ccc(-c3ccc(OC(=O)C(=C)C)cc3)c(F)c2)cc1OCCOC(=O)C(=C)C]
RM-136

TABLE E-continued
| Table E shows illustrative reactive mesogenic compounds which can be used in the LC media in accordance with the present invention. | |
|---|---|
| 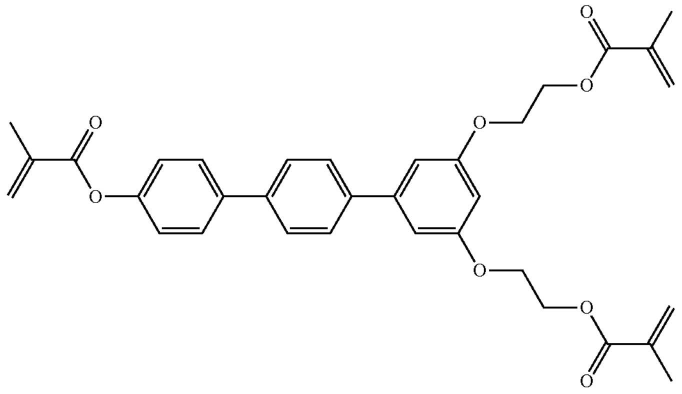 [SMILES: C=C(C)C(=O)OCCOc1cc(OCCOC(=O)C(=C)C)cc(-c2ccc(-c3ccc(OC(=O)C(=C)C)cc3)cc2)c1] | RM-137 |
| 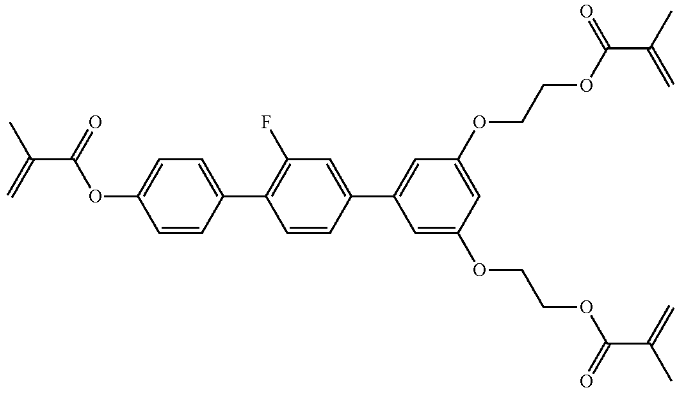 [SMILES: C=C(C)C(=O)OCCOc1cc(OCCOC(=O)C(=C)C)cc(-c2ccc(-c3ccc(OC(=O)C(=C)C)cc3)c(F)c2)c1] | RM-138 |
| 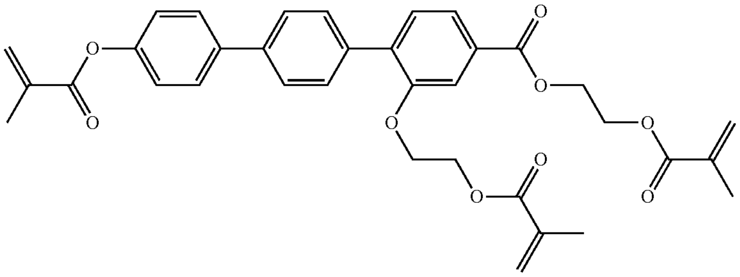 [SMILES: C=C(C)C(=O)OCCOC(=O)c1ccc(-c2ccc(-c3ccc(OC(=O)C(=C)C)cc3)cc2)c(OCCOC(=O)C(=C)C)c1] | RM-139 |
| 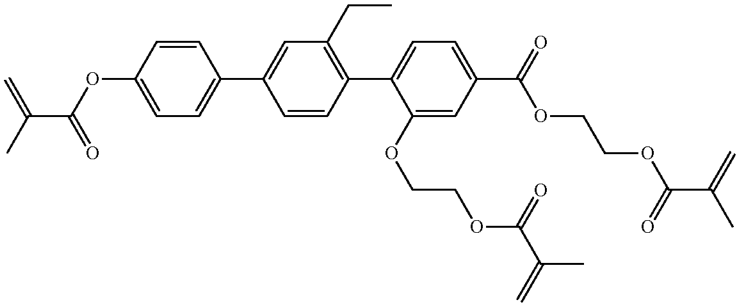 [SMILES: C=C(C)C(=O)OCCOC(=O)c1ccc(-c2ccc(-c3ccc(OC(=O)C(=C)C)cc3)cc2CC)c(OCCOC(=O)C(=C)C)c1] | RM-140 |

TABLE E-continued
Table E shows illustrative reactive mesogenic compounds which can be used in the LC media in accordance with the present invention.
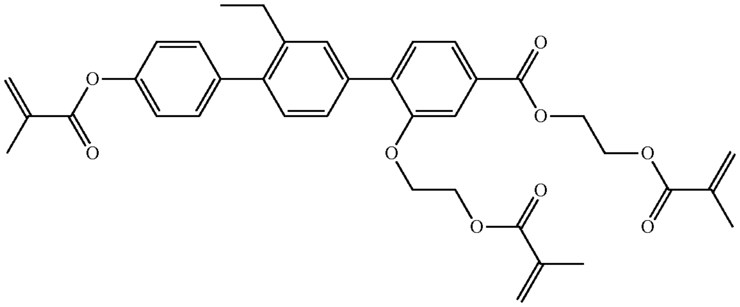 [SMILES: C=C(C)C(=O)OCCOC(=O)c1ccc(-c2ccc(-c3ccc(OC(=O)C(=C)C)cc3)c(CC)c2)c(OCCOC(=O)C(=C)C)c1]
RM-141
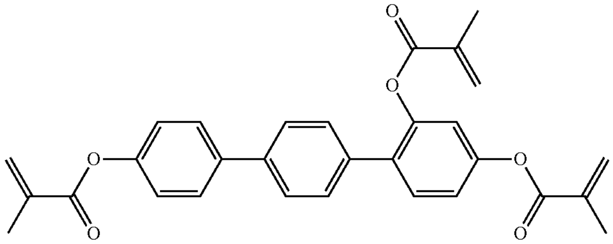 [SMILES: C=C(C)C(=O)Oc1ccc(-c2ccc(-c3ccc(OC(=O)C(=C)C)cc3OC(=O)C(=C)C)cc2)cc1]
RM-142
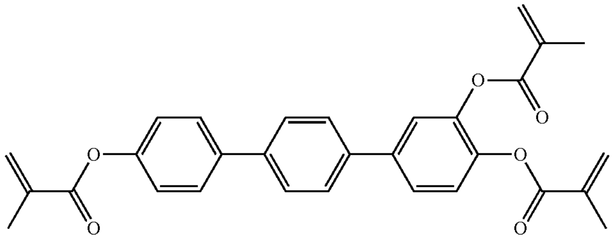 [SMILES: C=C(C)C(=O)Oc1ccc(-c2ccc(-c3ccc(OC(=O)C(=C)C)c(OC(=O)C(=C)C)c3)cc2)cc1]
RM-143
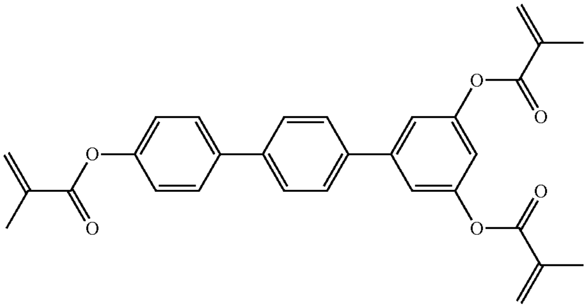 [SMILES: C=C(C)C(=O)Oc1ccc(-c2ccc(-c3cc(OC(=O)C(=C)C)cc(OC(=O)C(=C)C)c3)cc2)cc1]
RM-144
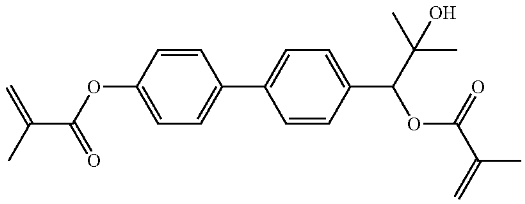 [SMILES: C=C(C)C(=O)Oc1ccc(-c2ccc(C(OC(=O)C(=C)C)C(C)(C)O)cc2)cc1]
RM-145
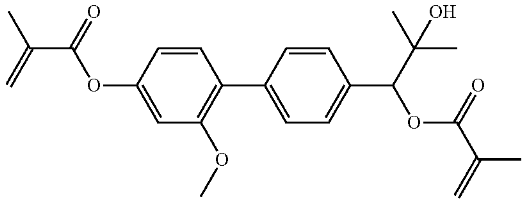 [SMILES: C=C(C)C(=O)Oc1ccc(-c2ccc(C(OC(=O)C(=C)C)C(C)(C)O)cc2)c(OC)c1]
RM-146

TABLE E-continued
Table E shows illustrative reactive mesogenic compounds which can be used in the LC media in accordance with the present invention.
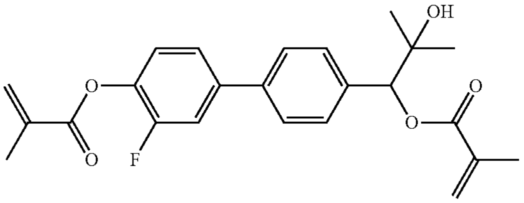 [SMILES: C=C(C)C(=O)Oc1ccc(-c2ccc(C(OC(=O)C(=C)C)C(C)(C)O)cc2)cc1F]
RM-147
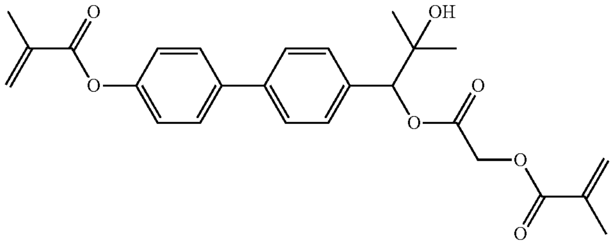 [SMILES: C=C(C)C(=O)OCC(=O)OC(c1ccc(-c2ccc(OC(=O)C(=C)C)cc2)cc1)C(C)(C)O]
RM-148
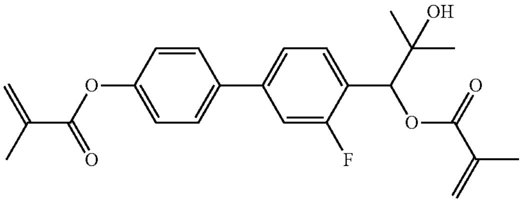 [SMILES: C=C(C)C(=O)Oc1ccc(-c2ccc(C(OC(=O)C(=C)C)C(C)(C)O)c(F)c2)cc1]
RM-149
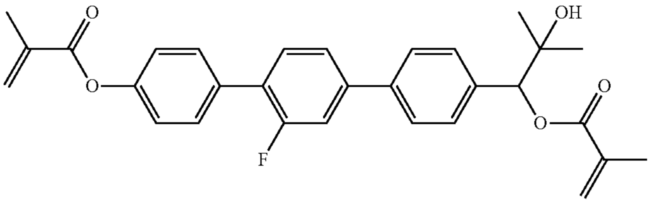 [SMILES: C=C(C)C(=O)Oc1ccc(-c2ccc(-c3ccc(C(OC(=O)C(=C)C)C(C)(C)O)cc3)cc2F)cc1]
RM-150
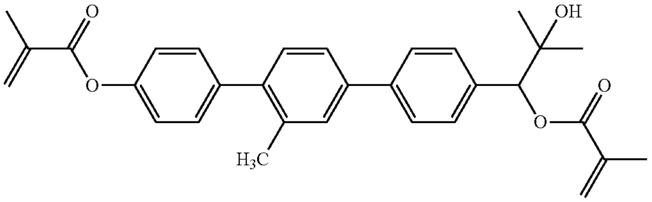 [SMILES: C=C(C)C(=O)Oc1ccc(-c2ccc(-c3ccc(C(OC(=O)C(=C)C)C(C)(C)O)cc3)cc2C)cc1]
RM-151
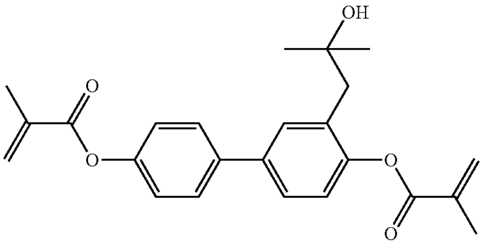 [SMILES: C=C(C)C(=O)Oc1ccc(-c2ccc(OC(=O)C(=C)C)c(CC(C)(C)O)c2)cc1]
RM-152
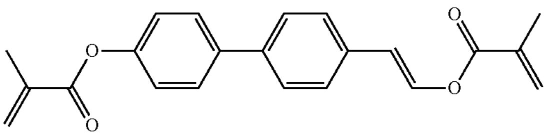 [SMILES: C=C(C)C(=O)O/C=C/c1ccc(-c2ccc(OC(=O)C(=C)C)cc2)cc1]
RM-153

TABLE E-continued
Table E shows illustrative reactive mesogenic compounds which can be used in the LC media in accordance with the present invention.
RM-154
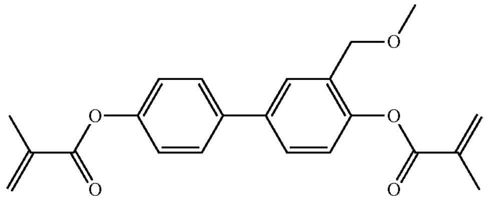 [SMILES: C=C(C)C(=O)Oc1ccc(-c2ccc(OC(=O)C(=C)C)c(COC)c2)cc1]
RM-155
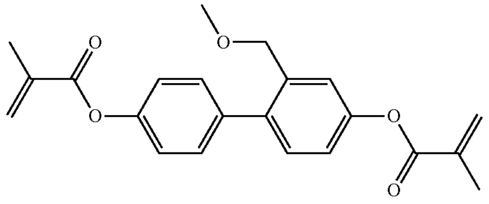 [SMILES: C=C(C)C(=O)Oc1ccc(-c2ccc(OC(=O)C(=C)C)cc2COC)cc1]
RM-156
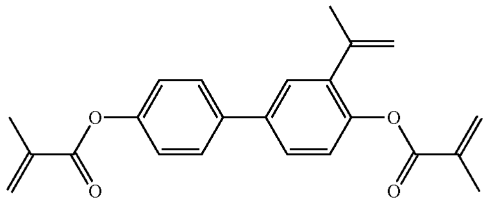 [SMILES: C=C(C)C(=O)Oc1ccc(-c2ccc(OC(=O)C(=C)C)c(C(=C)C)c2)cc1]
RM-157
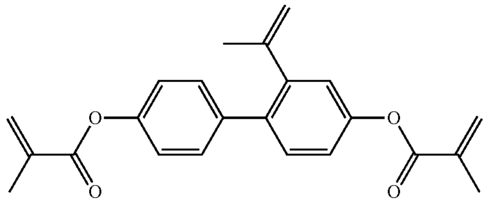 [SMILES: C=C(C)C(=O)Oc1ccc(-c2ccc(OC(=O)C(=C)C)cc2C(=C)C)cc1]
RM-158
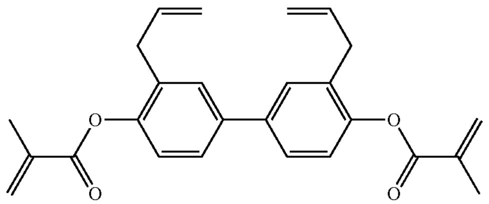 [SMILES: C=CCc1cc(-c2ccc(OC(=O)C(=C)C)c(CC=C)c2)ccc1OC(=O)C(=C)C]
RM-159
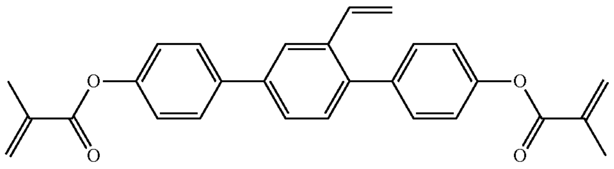 [SMILES: C=Cc1cc(-c2ccc(OC(=O)C(=C)C)cc2)ccc1-c1ccc(OC(=O)C(=C)C)cc1]
RM-160
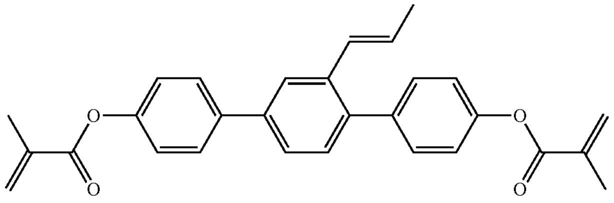 [SMILES: C=C(C)C(=O)Oc1ccc(-c2ccc(-c3ccc(OC(=O)C(=C)C)cc3)c(/C=C/C)c2)cc1]

TABLE E-continued
Table E shows illustrative reactive mesogenic compounds which can be used in the LC media in accordance with the present invention.
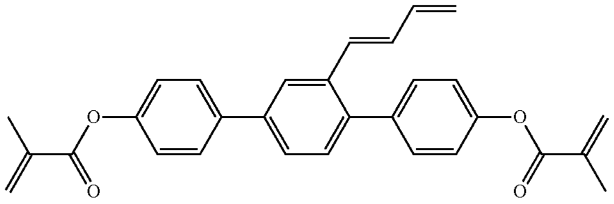 [SMILES: C=C/C=C/c1cc(-c2ccc(OC(=O)C(=C)C)cc2)ccc1-c1ccc(OC(=O)C(=C)C)cc1]
RM-161
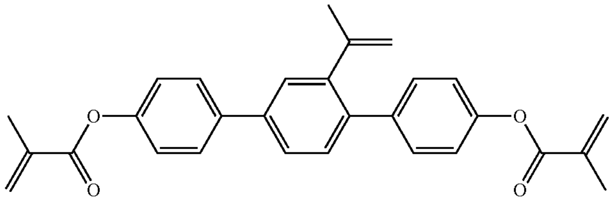 [SMILES: C=C(C)C(=O)Oc1ccc(-c2ccc(-c3ccc(OC(=O)C(=C)C)cc3)c(C(=C)C)c2)cc1]
RM-162
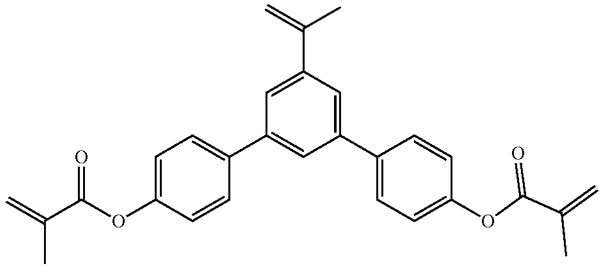 [SMILES: C=C(C)C(=O)Oc1ccc(-c2cc(C(=C)C)cc(-c3ccc(OC(=O)C(=C)C)cc3)c2)cc1]
RM-163
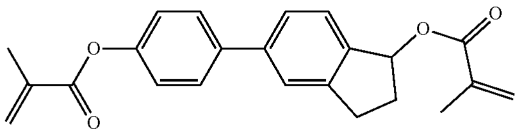 [SMILES: C=C(C)C(=O)Oc1ccc(-c2ccc3c(c2)CCC3OC(=O)C(=C)C)cc1]
RM-164
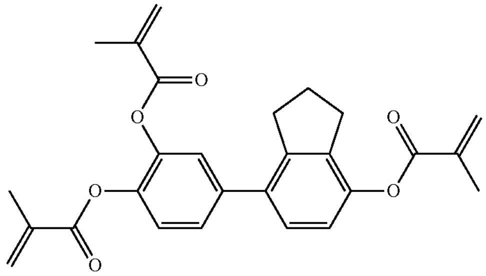 [SMILES: C=C(C)C(=O)Oc1ccc(-c2ccc(OC(=O)C(=C)C)c3c2CCC3)cc1OC(=O)C(=C)C]
RM-165
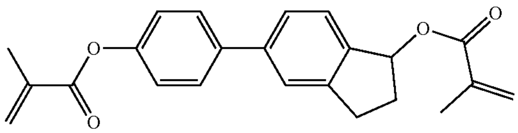 [SMILES: C=C(C)C(=O)Oc1ccc(-c2ccc3c(c2)CCC3OC(=O)C(=C)C)cc1]
RM-166
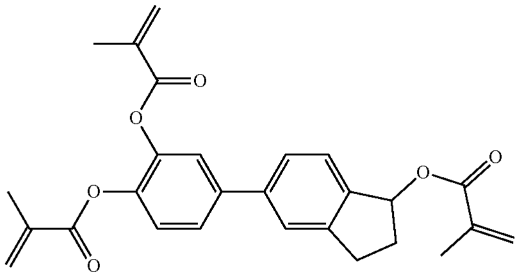 [SMILES: C=C(C)C(=O)Oc1ccc(-c2ccc3c(c2)CCC3OC(=O)C(=C)C)cc1OC(=O)C(=C)C]
RM-167

TABLE E-continued
| Table E shows illustrative reactive mesogenic compounds which can be used in the LC media in accordance with the present invention. | |
|---|---|
| 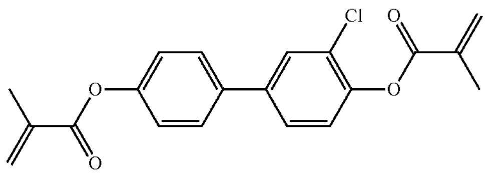 [SMILES: C=C(C)C(=O)Oc1ccc(-c2ccc(OC(=O)C(=C)C)c(Cl)c2)cc1] | RM-168 |
| 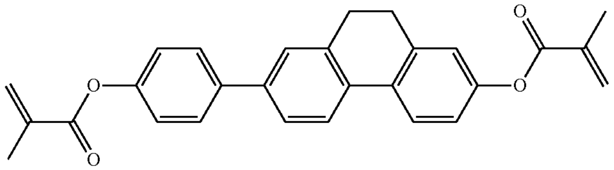 | RM-169 |
| 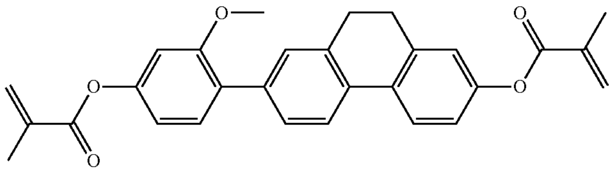 [SMILES: C=C(C)C(=O)Oc1ccc2c(c1)CCc1cc(-c3ccc(OC(=O)C(=C)C)cc3OC)ccc1-2] | RM-170 |
| 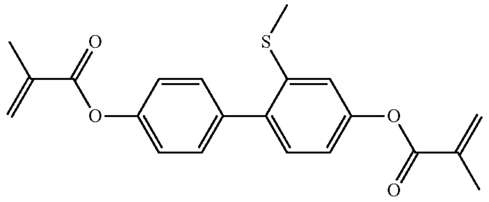 [SMILES: C=C(C)C(=O)Oc1ccc(-c2ccc(OC(=O)C(=C)C)cc2SC)cc1] | RM-171 |
| 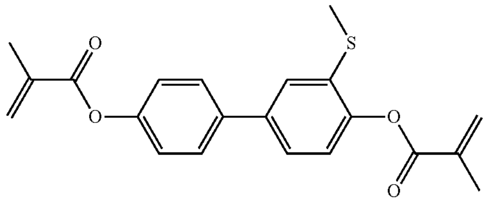 [SMILES: C=C(C)C(=O)Oc1ccc(-c2ccc(OC(=O)C(=C)C)c(SC)c2)cc1] | RM-172 |
| 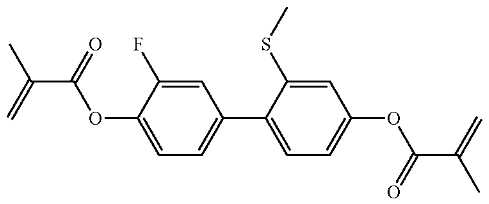 [SMILES: C=C(C)C(=O)Oc1ccc(-c2ccc(OC(=O)C(=C)C)c(F)c2)c(SC)c1] | RM-173 |
| 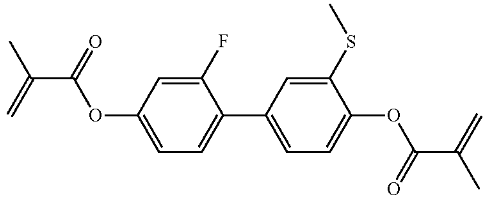 | RM-174 |

TABLE E-continued
Table E shows illustrative reactive mesogenic compounds which can be used in the LC media in accordance with the present invention.
RM-175
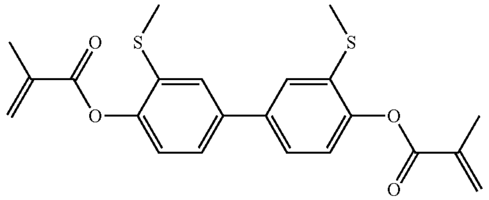 [SMILES: C=C(C)C(=O)Oc1ccc(-c2ccc(OC(=O)C(=C)C)c(SC)c2)cc1SC]
RM-176
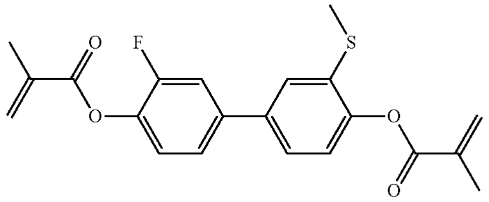 [SMILES: C=C(C)C(=O)Oc1ccc(-c2ccc(OC(=O)C(=C)C)c(SC)c2)cc1F]
RM-177
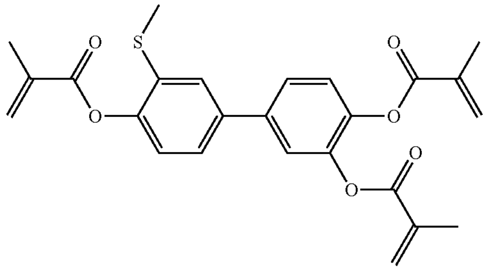 [SMILES: C=C(C)C(=O)Oc1ccc(-c2ccc(OC(=O)C(=C)C)c(SC)c2)cc1OC(=O)C(=C)C]
RM-178
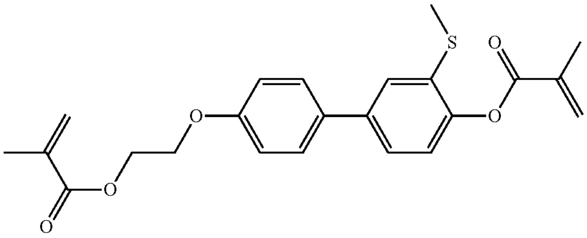 [SMILES: C=C(C)C(=O)OCCOc1ccc(-c2ccc(OC(=O)C(=C)C)c(SC)c2)cc1]
RM-179
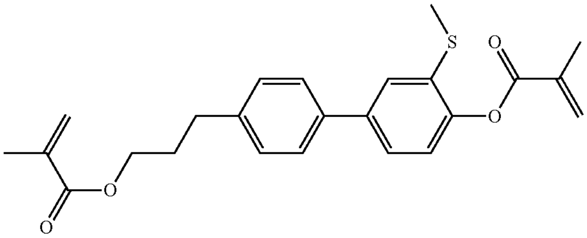 [SMILES: C=C(C)C(=O)OCCCc1ccc(-c2ccc(OC(=O)C(=C)C)c(SC)c2)cc1]
RM-180
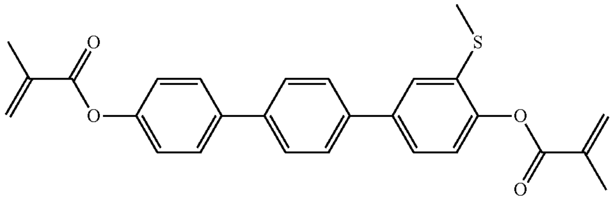

TABLE E-continued

Table E shows illustrative reactive mesogenic compounds which can be used in the LC media in accordance with the present invention.

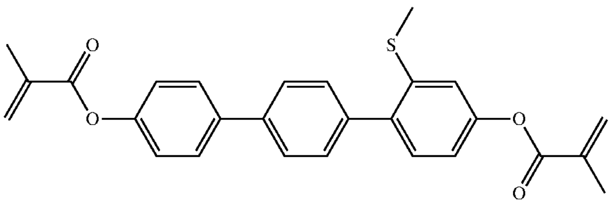 [SMILES: C=C(C)C(=O)Oc1ccc(-c2ccc(-c3ccc(OC(=O)C(=C)C)cc3SC)cc2)cc1]
RM-181

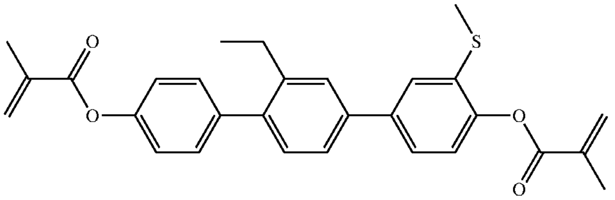 [SMILES: C=C(C)C(=O)Oc1ccc(-c2ccc(-c3ccc(OC(=O)C(=C)C)c(SC)c3)cc2CC)cc1]
RM-182

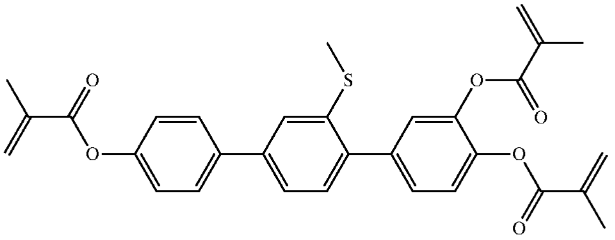 [SMILES: C=C(C)C(=O)Oc1ccc(-c2ccc(-c3ccc(OC(=O)C(=C)C)c(OC(=O)C(=C)C)c3)c(SC)c2)cc1]
RM-183

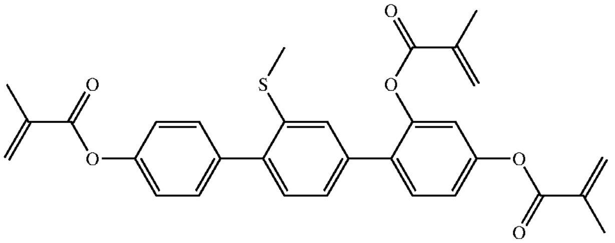 [SMILES: C=C(C)C(=O)Oc1ccc(-c2ccc(-c3ccc(OC(=O)C(=C)C)cc3OC(=O)C(=C)C)cc2SC)cc1]
RM-184

In a preferred embodiment, the mixtures according to the invention comprise one or more polymerizable compounds, preferably selected from the polymerizable compounds of the formulae RM-1 to RM-182. Of these, compounds RM-1, RM-4, RM-8, RM-17, RM-19, RM-35, RM-37, RM-39, RM-40, RM-41, RM-48, RM-52, RM-54, RM-57, RM-58, RM-64, RM-74, RM-76, RM-88, RM-91, RM-102, RM-103, RM-109, RM-116, RM-117, RM-120, RM-121, RM-122, RM-139, RM-140, RM-142, RM-143, RM-145, RM-146, RM-147, RM-149, RM-156 to RM-163, RM-169, RM-170 and RM-171 to RM-184 are particularly preferred.

EXAMPLES

The present invention is illustrated in detail by the following non-restrictive working examples.

The following abbreviations and symbols are used:

$V_0$ threshold voltage, capacitive [V] at 20° C., $n_e$ extraordinary refractive index at 20° C. and 589 nm, $n_o$ ordinary refractive index at 20° C. and 589 nm, Δn optical anisotropy at 20° C. and 589 nm, $\varepsilon_\perp$ dielectric permittivity perpendicular to the director at 20° C. and 1 kHz, $\varepsilon_\parallel$ dielectric permittivity parallel to the director at 20° C. and 1 kHz, Δε dielectric anisotropy at 20° C. and 1 kHz, cl.p., T(N,I) clearing point [° C.], $\gamma_1$ rotational viscosity at 20° C. [mPa·s], $K_1$ elastic constant, "splay" deformation at 20° C. [pN], $K_2$ elastic constant, "twist" deformation at 20° C. [pN], $K_3$ elastic constant, "bend" deformation at 20° C. [pN], $K_{av}$ denotes the average elastic constant defined as $$K_{av}=\frac{1}{3}(1.5K_1+K_3)$$

at 20° C. [pN].

Unless explicitly noted otherwise, all concentrations in the present application are quoted in percent by weight and relate to the corresponding mixture as a whole, comprising all solid or liquid-crystalline components, without solvents.

Unless explicitly noted otherwise, all temperature values indicated in the present application, such as, for example, for the melting point T(C,N), the transition from the smectic (S) to the nematic (N) phase T(S,N) and the clearing point T(N,I), are quoted in degrees Celsius (° C.). M.p. denotes melting point, cl.p.=clearing point. Furthermore, C=crystalline state, N=nematic phase, S=smectic phase and I=isotropic phase. The data between these symbols represent the transition temperatures.

All physical properties are and have been determined in accordance with "Merck Liquid Crystals, Physical Properties of Liquid Crystals", Status November 1997, Merck KGaA, Germany, and apply for a temperature of 20° C., and Δn is determined at 589 nm and Δε at 1 kHz, unless explicitly indicated otherwise in each case.

The term "threshold voltage" for the present invention relates to the capacitive threshold ($V_0$), also known as the Freedericks threshold, unless explicitly indicated otherwise. In the examples, the optical threshold may also, as generally usual, be quoted for 10% relative contrast ($V_{10}$).

Unless stated otherwise, the process of polymerising the polymerisable compounds in the PSA displays as described above and below is carried out at a temperature where the LC medium exhibits a liquid crystal phase, preferably a nematic phase, and most preferably is carried out at room temperature.

Unless stated otherwise, methods of preparing test cells and measuring their electrooptical and other properties are carried out by the methods as described hereinafter or in analogy thereto.

The display used for measurement of the capacitive threshold voltage consists of two plane-parallel glass outer plates with a distance of 25 μm, each of which has on the inside an electrode layer and an unrubbed polyimide alignment layer on top, which effect homeotropic alignment of the liquid-crystal molecules.

The display or test cell used for measurement of the tilt angles consists of two plane-parallel glass outer plates at a separation of 4 μm, each of which has on the inside an electrode layer and a polyimide alignment layer on top, where the two polyimide layers are rubbed antiparallel to one another and effect a homeotropic edge alignment of the liquid-crystal molecules.

The polymerisable compounds are polymerised in the display or test cell by irradiation with UV light of defined intensity for a prespecified time, with a voltage simultaneously being applied to the display (usually 10 V to 30 V alternating current, 1 kHz). In the examples, unless indicated otherwise, a fluorescent lamp and an intensity of 0 to 20 mW/cm$^2$ is used for polymerisation. The intensity is measured using a standard meter (Ushio Accumulate UV meter with central wavelength of 313 nm).

The transmission measurements are performed in test cells with fishbone electrode layout (from Merck Ltd., Japan; 1 pixel fishbone electrode (ITO, 10×10 mm, 47.7° angle of fishbone with 3 μm line/3 μm space), 3.2 μm cell gap, AF-glass, tilt angle 1°).

The storage stability in the bulk ($LTS_{bulk}$) of the media according to the invention at a given temperature T is determined by visual inspection. 2 g of the media of interest are filled into a closed glass vessel (bottle) of appropriate size placed in a refrigerator at a predetermined temperature. The bottles are checked at defined time intervals for the occurrence of smectic phases or crystallisation. For every material and at each temperature two bottles are stored. If crystallisation or the appearance of a smectic phase is observed in at least one of the two correspondent bottles the test is terminated and the time of the last inspection before the one at which the occurrence of a higher ordered phase is observed is recorded as the respective storage stability.

Compound Example 1: 1-(4-ethylcyclohexyl)-4-[4-(4-propylcyclohexyl)cyclohex-1-en-1-yl]benzene

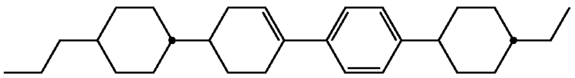

1-(4-ethylcyclohexyl)-4-[4-(4-propylcyclohexyl)cyclohex-1-en-1-yl]benzene is prepared by addition of [4-(4-ethylcyclohexyl)phenyl]magnesiumbromide to 4'-propyl-[1,1'-bi(cyclohexane)]-4-one to give the intermediate 4-[4-(4-ethylcyclohexyl)phenyl]-4'-propyl-[1,1'-bi(cyclohexane)]-4-ol, followed by elimination of water.

Phase sequence: K 239 N 290 I

Δε=0.5

Δn=0.1352

Compound Example 2: 1-(4-ethylcyclohexyl)-2-fluoro-4-[4-(4-propylcyclohexyl)cyclohex-1-en-1-yl]benzene

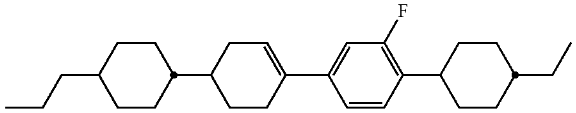

In an analogy to Compound Example 1, 1-(4-etylcyclohexyl)-2-fluoro-4-[4-(4-propylcyclohexyl)cyclohex-1-en-1-yl]benzene is obtained as colorless crystals.

Phase sequence: K 68 SmB 163 SmA 188 N 272.0 I.

Δε=2.3

Δn=0.1348

Mixture Examples

The Comparative Example C1 and the Mixture Examples M1 to M15 and P1 to P10 have the compositions and properties given in the following tables. The quantities in the tables are given in percent by weight.

Comparative Mixture Example C1

| | | | |
|---|---|---|---|
| B(S)-2O-O4 | 4.0 | cl. p. [° C.]: | 118.5 |
| B(S)-2O-O5 | 3.0 | Δn [589 nm, 20° C.]: | 0.1030 |
| B(S)-2O-O6 | 4.0 | Δε [1 kHz, 20° C.]: | −3.6 |
| CC-3-V1 | 10.0 | $\gamma_1$ [mPa s, 20° C.]: | 209 |
| CC-4-V1 | 15.0 | $K_1$ [pN, 20° C.]: | 28.8 |
| CC-3-5 | 10.5 | $K_3$ [pN, 20° C.]: | 28.4 |
| CCP-3-1 | 8.0 | LTS bulk [h, −20° C.]: | 216 |
| CCP-3-3 | 2.5 | | |
| CCP-V2-1 | 10.0 | | |
| CCY-3-O2 | 5.0 | | |
| CLOY-3-O2 | 15.0 | | |
| CLY-3-O2 | 7.0 | | |
| CLY-5-O2 | 5.0 | | |
| CPY-3-O2 | 1.0 | | |
| Σ | 100 | | |

Mixture Example M1

| | | | |
|---|---|---|---|
| B(S)-2O-O4 | 4.0 | cl. p. [° C.]: | 123.0 |
| B(S)-2O-O5 | 3.0 | Δn [589 nm, 20° C.]: | 0.1019 |
| B(S)-2O-O6 | 4.0 | Δε [1 kHz, 20° C.]: | −3.7 |
| CC-3-V | 5.5 | $\gamma_1$ [mPa s, 20° C.]: | 202 |
| CC-3-V1 | 9.5 | $K_1$ [pN, 20° C.]: | 29.8 |
| CC-4-V1 | 8.0 | $K_3$ [pN, 20° C.]: | 29.7 |
| CC-3-O3 | 3.0 | | |
| CC-3-5 | 12.5 | | |
| CCP-3-1 | 8.0 | | |
| CCP-V2-1 | 3.0 | | |
| CCY-3-O2 | 11.0 | | |
| CLOY-3-O2 | 6.25 | | |
| CLPC-3-2 | 3.0 | | |
| CLY-3-O2 | 9.25 | | |
| CLY-4-O2 | 5.0 | | |
| CLY-5-O2 | 5.0 | | |
| Σ | 100 | | |

In the following table, key parameters of the mixtures C1 and M1 are summarized.

| | Δε | Δn | $K_{av}$ [pN] | $\gamma_1$ [mPas] | $\gamma_1/K_1$ [mPas/pN] |
|---|---|---|---|---|---|
| C1 | −3.6 | 0.1030 | 23.9 | 209 | 7.3 |
| M1 | −3.7 | 0.1019 | 24.8 | 202 | 6.8 |

It is surprisingly found that by use of the compound of formula I in Mixture Example 1, despite the higher clearing temperature a favorably lower rotational viscosity ($\gamma_1$) and at the same time a very low ratio $\gamma_1/K_1$ can be achieved, which improves the response time of a display.

Mixture Example M2

| | | | |
|---|---|---|---|
| B(S)-2O-O5 | 5.0 | cl. p. [° C.]: | 108.5 |
| CC-3-V | 19.25 | Δn [589 nm, 20° C.]: | 0.0909 |
| CC-3-V1 | 14.0 | Δε[1 kHz, 20° C.]: | −2.4 |
| CC-4-V1 | 12.0 | $\gamma_1$ [mPa s, 20° C.]: | 134 |
| CC-3-O3 | 3.25 | $K_1$ [pN, 20° C.]: | 22.2 |
| CC-3-5 | 5.0 | $K_3$ [pN, 20° C.]: | 21.9 |
| CCP-3-1 | 5.25 | | |
| CCY-3-O2 | 9.0 | | |
| CLOY-3-O2 | 6.25 | | |
| CLPC-3-2 | 5.0 | | |
| CLY-3-O2 | 9.0 | | |
| COB(S)-2-O4 | 6.0 | | |
| CP-3-O2 | 1.0 | | |
| Σ | 100.0 | | |

Mixture Example M3

| | | | |
|---|---|---|---|
| B(S)-2O-O4 | 1.0 | cl. p. [° C.]: | 116.5 |
| CC-3-V | 14.75 | Δn [589 nm, 20° C.]: | 0.0893 |
| CC-3-V1 | 12.5 | Δε [1 kHz, 20° C.]: | −3.1 |
| CC-3-5 | 12.0 | $\gamma_1$ [mPa s, 20° C.]: | 224 |
| CCP-3-1 | 10.5 | $K_1$ [pN, 20° C.]: | 24.7 |
| CCY-3-O2 | 11.0 | $K_3$ [pN, 20° C.]: | 28.2 |
| CLOY-3-O2 | 23.25 | LTS bulk [h, −20° C.]: | 1000 |
| CLPC-3-2 | 5.0 | | |
| CLY-3-O2 | 10.0 | | |
| Σ | 100.0 | | |

Mixture Example M4

| | | | |
|---|---|---|---|
| B(S)-2O-O4 | 1.0 | cl. p. [° C.]: | 116.5 |
| CC-3-V | 4.0 | Δn [589 nm, 20° C.]: | 0.0892 |
| CC-3-V1 | 12.0 | Δε [1 kHz, 20° C.]: | −3.2 |
| CC-4-V1 | 10.0 | $\gamma_1$ [mPa s, 20° C.]: | 235 |
| CC-3-O3 | 2.5 | $K_1$ [pN, 20° C.]: | 26.1 |
| CC-3-5 | 12.0 | $K_3$ [pN, 20° C.]: | 28.4 |
| CCP-3-1 | 10.5 | LTS bulk [h, −20° C.]: | 288 |
| CCY-3-O2 | 11.0 | | |
| CLOY-3-O2 | 23.5 | | |
| CLPC-3-2 | 2.5 | | |
| CLY-3-O2 | 11.0 | | |
| Σ | 100.0 | | |

Mixture Example M5

| | | | |
|---|---|---|---|
| B(S)-2O-O4 | 4.0 | cl. p. [° C.]: | 123.0 |
| B(S)-2O-O5 | 3.0 | Δn [589 nm, 20° C.]: | 0.1015 |
| B(S)-2O-O6 | 4.0 | Δε [1 kHz, 20° C.]: | −3.7 |
| CC-3-V | 5.5 | | |
| CC-3-V1 | 9.5 | | |
| CC-4-V1 | 8.0 | | |
| CC-3-O3 | 3.0 | | |
| CC-3-5 | 12.5 | | |
| CCP-3-1 | 8.0 | | |
| CCP-V2-1 | 3.0 | | |
| CCY-3-O2 | 11.0 | | |
| CLOY-3-O2 | 6.25 | | |
| CLPC-4-3 | 3.0 | | |
| CLY-3-O2 | 9.25 | | |
| CLY-4-O2 | 5.0 | | |
| CLY-5-O2 | 5.0 | | |
| Σ | 100.0 | | |

Mixture Example M6

| | | | |
|---|---|---|---|
| B(S)-2O-O4 | 4.0 | cl. p. [° C.]: | 122.5 |
| B(S)-2O-O5 | 3.0 | Δn [589 nm, 20° C.]: | 0.1021 |
| B(S)-2O-O6 | 4.0 | Δε [1 kHz, 20° C.]: | −3.7 |
| CC-3-V | 5.5 | | |
| CC-3-V1 | 9.5 | | |
| CC-4-V1 | 8.0 | | |
| CC-3-O3 | 3.0 | | |
| CC-3-5 | 12.5 | | |
| CCP-3-1 | 8.0 | | |
| CCP-V2-1 | 3.0 | | |
| CCY-3-O2 | 11.0 | | |
| CLOY-3-O2 | 6.25 | | |
| CLPC-V-1 | 3.0 | | |
| CLY-3-O2 | 9.25 | | |
| CLY-4-O2 | 5.0 | | |
| CLY-5-O2 | 5.0 | | |
| Σ | 100.0 | | |

Mixture Example M7

| | | | |
|---|---|---|---|
| B(S)-2O-O4 | 4.0 | cl. p. [° C.]: | 124 |
| B(S)-2O-O5 | 3.0 | Δn [589 nm, 20° C.]: | 0.1021 |
| B(S)-2O-O6 | 4.0 | Δε [1 kHz, 20° C.]: | −3.7 |
| CC-3-V | 5.5 | | |
| CC-3-V1 | 9.5 | | |
| CC-4-V1 | 8.0 | | |
| CC-3-O3 | 3.0 | | |
| CC-3-5 | 12.5 | | |
| CCP-3-1 | 8.0 | | |
| CCP-V2-1 | 3.0 | | |
| CCY-3-O2 | 11.0 | | |
| CLOY-3-O2 | 6.25 | | |
| CLPC-3-O1 | 3.0 | | |
| CLY-3-O2 | 9.25 | | |
| CLY-4-O2 | 5.0 | | |
| CLY-5-O2 | 5.0 | | |
| Σ | 100.0 | | |

Mixture Example M8

| | | | |
|---|---|---|---|
| B(S)-2O-O4 | 4.0 | cl. p. [° C.]: | 122.5 |
| B(S)-2O-O5 | 3.0 | Δn [589 nm, 20° C.]: | 0.1010 |
| B(S)-2O-O6 | 4.0 | Δε [1 kHz, 20° C.]: | −4.0 |
| CC-3-V | 5.5 | | |
| CC-3-V1 | 9.5 | | |
| CC-4-V1 | 8.0 | | |
| CC-3-O3 | 3.0 | | |
| CC-3-5 | 12.5 | | |
| CCP-3-1 | 8.0 | | |
| CCP-V2-1 | 3.0 | | |
| CCOY-3-O2 | 11.0 | | |
| CLOY-3-O2 | 6.25 | | |
| CLPC-3-2 | 3.0 | | |
| CLY-3-O2 | 9.25 | | |
| CLY-4-O2 | 5.0 | | |
| CLY-5-O2 | 5.0 | | |
| Σ | 100.0 | | |

Mixture Example M9

| | | | |
|---|---|---|---|
| B(S)-2O-O4 | 4.0 | cl. p. [° C.]: | 123.5 |
| B(S)-2O-O5 | 3.0 | Δn [589 nm, 20° C.]: | 0.1010 |
| B(S)-2O-O6 | 4.0 | Δε [1 kHz, 20° C.]: | −3.6 |
| CC-3-V | 5.5 | | |
| CC-3-V1 | 9.5 | | |
| CC-4-V1 | 8.0 | | |
| CC-3-O3 | 3.0 | | |
| CC-3-5 | 12.5 | | |
| CCP-3-1 | 8.0 | | |
| CCP-V2-1 | 3.0 | | |
| CCEY-3-O2 | 11.0 | | |
| CLOY-3-O2 | 6.25 | | |
| CLPC-3-2 | 3.0 | | |
| CLY-3-O2 | 9.25 | | |
| CLY-4-O2 | 5.0 | | |
| CLY-5-O2 | 5.0 | | |
| Σ | 100.0 | | |

Mixture Example M10

| | | | |
|---|---|---|---|
| B(P)-2O-O3 | 4.0 | cl. p. [° C.]: | 125 |
| B(P)-2O-O4 | 3.0 | Δn [589 nm, 20° C.]: | 0.1036 |
| B(S)-2O-O6 | 4.0 | Δε [1 kHz, 20° C.]: | −3.3 |
| CC-3-V | 5.5 | | |
| CC-3-V1 | 9.5 | | |
| CC-4-V1 | 8.0 | | |
| CC-3-O3 | 3.0 | | |
| CC-3-5 | 12.5 | | |
| CCP-3-1 | 8.0 | | |
| CCP-V2-1 | 3.0 | | |
| CCY-3-O2 | 11.0 | | |
| CLOY-3-O2 | 6.25 | | |
| CLPC-3-2 | 3.0 | | |
| CLY-3-O2 | 9.25 | | |
| CLY-4-O2 | 5.0 | | |
| CLY-5-O2 | 5.0 | | |
| Σ | 100.0 | | |

Mixture Example M11

| | | | |
|---|---|---|---|
| B(S)-2O-O4 | 4.0 | cl. p. [° C.]: | 123.0 |
| B(S)-2O-O5 | 3.0 | Δn [589 nm, 20° C.]: | 0.1014 |
| B(S)-(c5-3en) 1O-O4 | 4.0 | Δε [1 kHz, 20° C.]: | −3.7 |
| CC-3-V | 5.5 | $\gamma_1$ [mPa s, 20° C.]: | 208 |
| CC-3-V1 | 9.5 | | |
| CC-4-V1 | 8.0 | | |
| CC-3-O3 | 3.0 | | |
| CC-3-5 | 12.5 | | |
| CCP-3-1 | 8.0 | | |
| CCP-V2-1 | 3.0 | | |
| CCY-3-O2 | 11.0 | | |
| CLOY-3-O2 | 6.25 | | |
| CLPC-3-2 | 3.0 | | |
| CLY-3-O2 | 9.25 | | |
| CLY-4-O2 | 5.0 | | |
| CLY-5-O2 | 5.0 | | |
| Σ | 100.0 | | |

Mixture Example M12

| | | | |
|---|---|---|---|
| B(S)-2O-O4 | 4.0 | cl. p. [° C.]: | 123.0 |
| B(S)-2O-O5 | 3.0 | Δn [589 nm, 20° C.]: | 0.1019 |
| B(S)-(c5)1O-O2 | 4.0 | Δε [1 kHz, 20° C.]: | −3.7 |
| CC-3-V | 5.5 | $\gamma_1$ [mPa s, 20° C.]: | 209 |
| CC-3-V1 | 9.5 | | |
| CC-4-V1 | 8.0 | | |
| CC-3-O3 | 3.0 | | |
| CC-3-5 | 12.5 | | |
| CCP-3-1 | 8.0 | | |
| CCP-V2-1 | 3.0 | | |
| CCY-3-O2 | 11.0 | | |
| CLOY-3-O2 | 6.25 | | |
| CLPC-3-2 | 3.0 | | |
| CLY-3-O2 | 9.25 | | |
| CLY-4-O2 | 5.0 | | |
| CLY-5-O2 | 5.0 | | |
| Σ | 100.0 | | |

Mixture Example M13

| | | | |
|---|---|---|---|
| B(S)-2O-O4 | 4.0 | cl. p. [° C.]: | 124.0 |
| B(S)-2O-O6 | 4.0 | Δn [589 nm, 20° C.]: | 0.1009 |
| CC-3-V | 6.5 | Δε [1 kHz, 20° C.]: | −3.7 |
| CC-3-V1 | 9.5 | $\gamma_1$ [mPa s, 20° C.]: | 194 |
| CC-4-V1 | 8.0 | $K_1$ [pN, 20° C.]: | 27.5 |
| CC-3-O3 | 3.0 | $K_3$ [pN, 20° C.]: | 28.5 |
| CC-3-5 | 12.5 | | |
| CCP-3-1 | 8.0 | | |
| CCP-V2-1 | 3.0 | | |
| CCY-3-O2 | 11.0 | | |
| CLOY-3-O2 | 6.25 | | |
| CLPC-3-2 | 3.0 | | |
| CGIY-3-O2 | 2.0 | | |
| CLY-3-O2 | 9.25 | | |
| CLY-4-O2 | 5.0 | | |
| CLY-5-O2 | 5.0 | | |
| Σ | 100.0 | | |

Mixture Example M14

| | | | |
|---|---|---|---|
| B(S)-2O-O4 | 4.0 | cl. p. [° C.]: | 122.0 |
| B(S)-2O-O6 | 4.0 | Δn [589 nm, 20° C.]: | 0.1008 |
| CC-3-V | 5.5 | Δε [1 kHz, 20° C.]: | −3.8 |
| CC-3-V1 | 9.5 | $\gamma_1$ [mPa s, 20° C.]: | 192 |
| CC-4-V1 | 8.0 | $K_1$ [pN, 20° C.]: | 27.0 |
| CC-3-O3 | 3.0 | $K_3$ [pN, 20° C.]: | 28.0 |
| CC-3-5 | 12.5 | | |
| CCP-3-1 | 9.0 | | |
| CCP-V2-1 | 3.0 | | |
| CCY-3-O2 | 11.0 | | |
| CLOY-3-O2 | 6.25 | | |
| CLPC-3-2 | 3.0 | | |
| PY-2O-O2 | 3.0 | | |
| CLY-3-O2 | 8.25 | | |
| CLY-4-O2 | 5.0 | | |
| CLY-5-O2 | 5.0 | | |
| Σ | 100.0 | | |

Mixture Example M15

| | | | |
|---|---|---|---|
| B(S)-2O-O5 | 5.0 | cl. p. [° C.]: | 108 |
| CC-3-V | 19.25 | Δn [589 nm, 20° C.]: | 0.0903 |
| CC-3-V1 | 14.0 | Δε [1 kHz, 20° C.]: | −2.4 |
| CC-4-V1 | 12.0 | | |
| CC-3-O3 | 3.25 | | |
| CC-3-5 | 5.0 | | |
| CCP-3-1 | 5.25 | | |
| CCY-3-O2 | 8.0 | | |
| CLOY-3-O2 | 4.25 | | |
| COYOIC-3-3 | 3.0 | | |
| CLPC-3-2 | 5.0 | | |
| CLY-3-O2 | 9.0 | | |
| COB(S)-2-O4 | 6.0 | | |
| CP-3-O2 | 1.0 | | |
| Σ | 100.0 | | |

Mixture Example M15

-continued

| | | | |
|---|---|---|---|
| B(S)-(c5)1O-O4 | 5.0 | cl. p. [° C.]: | 103 |
| PY-3-O2 | 13.5 | Δn [589 nm, 20° C.]: | 0.1133 |
| PY-2O-O2 | 4.5 | Δε [1 kHz, 20° C.]: | −4.8 |
| LY-(c5)-O2 | 0.5 | | |
| COY-3-O2 | 4.0 | | |
| CCOY-3-O2 | 14.0 | | |
| CCY-3-O2 | 14.5 | | |
| CC-3-V | 23.0 | | |
| CC-3-V1 | 6.0 | | |
| CPP-1V-2 | 10.0 | | |
| CLPC-3-2 | 5.0 | | |
| Σ | 100.0 | | |

Polymerisable Mixtures

The polymerisable mixtures P1 to P9 are prepared from the nematic mixtures given in Table 1 by adding a reactive mesogen (RM) selected from the group of compounds of the formulae RM-1, RM-17, RM-35, RM-64 and RM-171, in the amount given in Table 1 (% RM).

RM-1

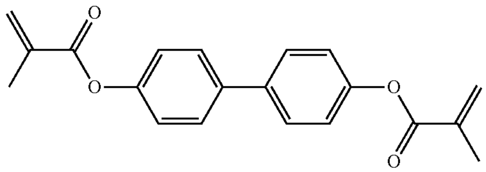

RM-17

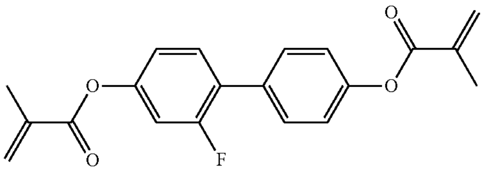

RM-35

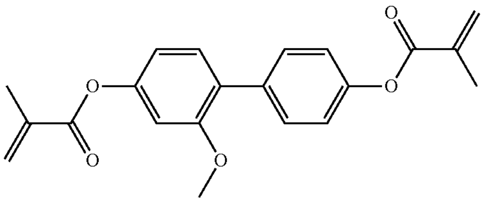

RM-64

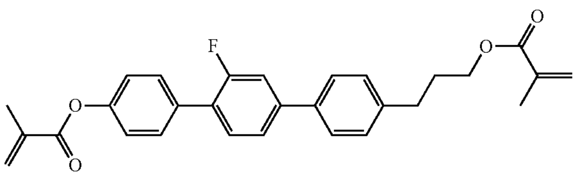

RM-145

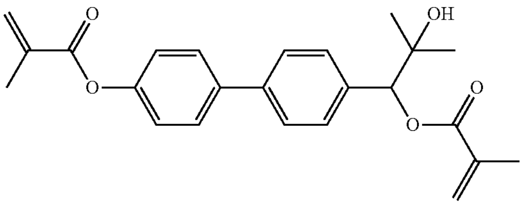

-continued

RM-163

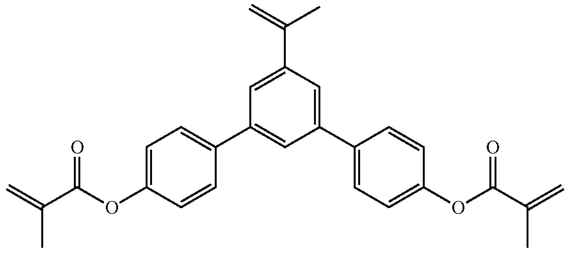

RM-171

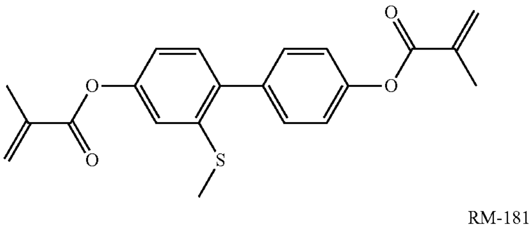

RM-181

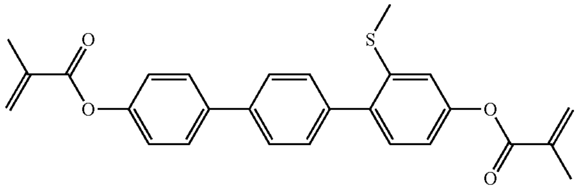

TABLE 1

| Polymerisable Mixtures | | | |
|---|---|---|---|
| Mixture | LC Host | RM | % RM |
| P1 | M1 | RM-1 | 0.3 |
| P2 | M2 | RM-17 | 0.3 |
| P3 | M3 | RM-35 | 0.3 |
| P4 | M4 | RM-64 | 0.3 |
| P5 | M5 | RM1 | 0.25 |
| P6 | M6 | RM-17 | 0.25 |
| P7 | M7 | RM-35 | 0.25 |
| P8 | M8 | RM-64 | 0.25 |
| P9 | M9 | RM-171 | 0.35 |
| P10 | M1 | RM-181 | 0.35 |

Mixture Example P11

The polymerisable mixture P11 consists of 99.434% of Mixture Example M1, 0.300% of RM-1, 0.200% of RM-145, 0.050% of RM-163, 0.001% of Irganox®1076 and 0.015% of the compound ST-3a-1.

ST-3a-1

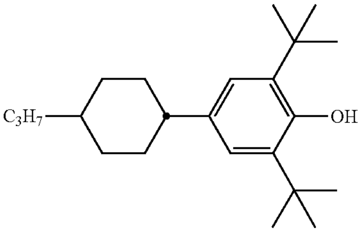

-continued

IRGANOX®-1076

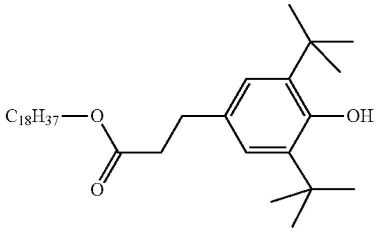

The invention claimed is:

1. A liquid crystal medium comprising one or more compounds of the formula I

I

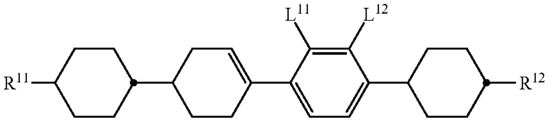

in which $R^{11}$ and $R^{12}$ identically or differently, denote H, straight chain alkyl or alkoxy having 1 to 15 C atoms, straight chain alkenyl or alkenyloxy having 2 to 15 C atoms or branched alkyl, alkoxy, alkenyl, alkenyloxy each having 3 to 15 C atoms, where one or more $CH_2$ groups in these radicals may each be replaced, independently of one another, by

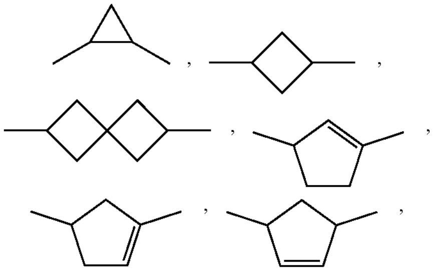

-CH═CH—, —C≡C—, —$CF_2O$—, —$OCF_2$—, —O—, —CO—O— or —O—CO— in such a way that O atoms are not linked directly to one another, and in which one or more H atoms may be replaced by halogen, one of $L^{11}$ and $L^{12}$ denotes H, and the other one of $L^{11}$ and $L^{12}$ denotes H, F, Cl, $CF_3$ or $CHF_2$.

2. The liquid crystal medium according to claim 1, wherein the medium further comprises one or more compounds selected from the group of compounds of the formulae IIA, IIB, IIC and IID

IIA

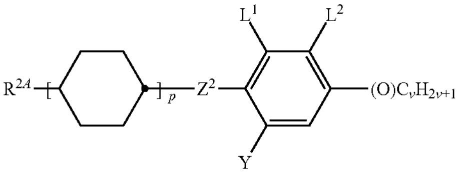

-continued

IIB

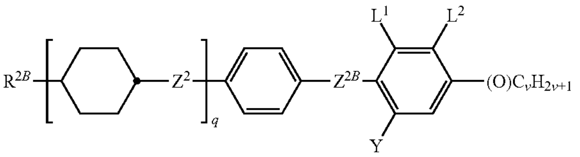

IIC

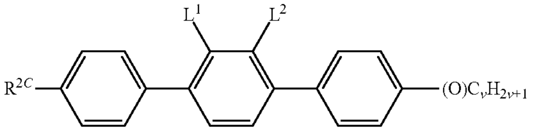

IID

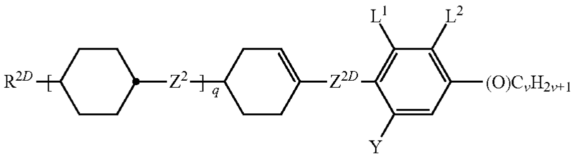

in which $R^{2A}$, $R^{2B}$, $R^{2C}$ and $R^{2D}$, identically or differently, denote H, straight chain alkyl or alkoxy having 1 to 15 C atoms, straight chain alkenyl or alkenyloxy having 2 to 15 C atoms or branched alkyl, alkoxy, alkenyl, alkenyloxy each having 3 to 15 C atoms, where one or more $CH_2$ groups in these radicals may each be replaced, independently of one another, by

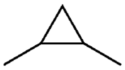,
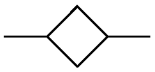,
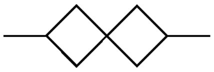,
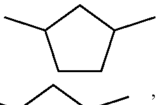,
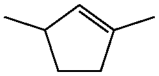,
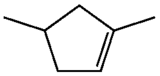,
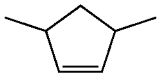, —CH═CH—, —C≡C—, —$CF_2O$—, —$OCF_2$—, —O—, —CO—O— or —O—CO— in such a way that O atoms are not linked directly to one another, and in which one or more H atoms may be replaced by halogen, $L^1$ and $L^2$, each, independently of one another, denote F, Cl, $CF_3$ or $CHF_2$, Y denotes H, F, Cl, $CF_3$, $CHF_2$ or $CH_3$, $Z^2$, $Z^{2B}$ and $Z^{2D}$ each, independently of one another, denote a single bond, —$CH_2CH_2$—, —CH═CH—, —$CF_2O$—, —$OCF_2$—, —$CH_2O$—, —$OCH_2$—, —COO—, —OCO—, —$C_2F_4$—, —CF═CF— or —CH═$CHCH_2O$—, (O) denotes O or a single bond, p denotes 0, 1 or 2, q denotes 0 or 1, and v denotes an integer from 1 to 6.

3. The liquid crystal medium according to claim 2, wherein the medium comprises one, two or more compounds of the formula IID.

4. The liquid crystal medium according to claim 1, wherein the medium further comprises one or more compounds of the formula III

III

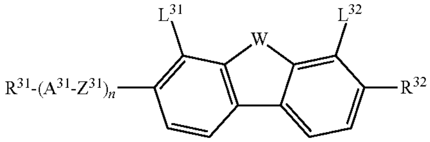

in which $R^{31}$ and $R^{32}$ independently of one another, denote H, an alkyl or alkoxy radical having 1 to 15 C atoms, where one or more $CH_2$ groups in these radicals may each be replaced, independently of one another, by

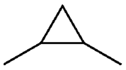,
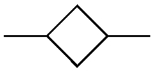,
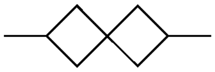,
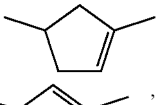,
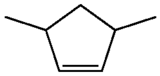,
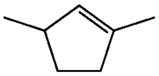,
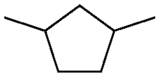, -CH═CH—, —C≡C—, —$CF_2O$—, —$OCF_2$—, —O—, —CO—O— or —O—CO— in such a way that O atoms are not linked directly to one another, and in which one or more H atoms may be replaced by halogen, $A^{31}$ on each occurrence, independently of one another, denotes a) a 1,4-cyclohexylene or 1,4-cyclohexenylene radical, in which one or two non-adjacent $CH_2$ groups may be replaced by —O— or —S—, b) a 1,4-phenylene radical, in which one or two CH groups may be replaced by N, or c) a radical from the group spiro[3.3]heptane-2,6-diyl, 1,4-bicyclo[2.2.2]-octylene, naphthalene-2,6-diyl, decahydronaphthalene-2,6-diyl, 1,2,3,4-tetrahydronaphthalene-2,6-diyl, phenanthrene-2,7-diyl and fluorene-2,7-diyl, where the radicals a), b) and c) may be mono- or polysubstituted by halogen atoms, $Z^{31}$ on each occurrence independently of one another denotes —CO—O—, —O—CO—, —$CF_2O$—, —$OCF_2$—, —$CH_2O$—, —$OCH_2$—, —$CH_2$—, —$CH_2CH_2$—, —$(CH_2)_4$—, —CH═CH—$CH_2O$—, —$C_2F_4$—, —$CH_2CF_2$—, —$CF_2CH_2$—, —CF═CF—, —CH═CF—, —CF═CH—, —CH═CH—, —C≡C— or a single bond, $L^{31}$ and $L^{32}$ each, independently of one another, denote F, Cl, $CF_3$ or $CHF_2$, W denotes O or S, and n denotes 0, 1 or 2.

5. The liquid crystal medium according to claim 1, wherein the medium further comprises one or more compounds selected from the group of compounds of the formulae BC, CR, PH-1, and PH-2

BC

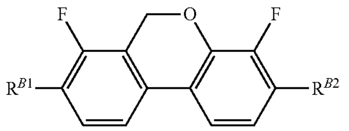

CR

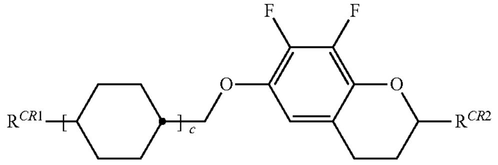

PH-1

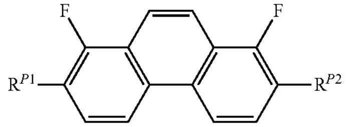

PH-2

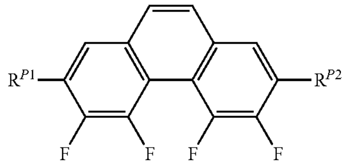

in which $R^{B1}$, $R^{B2}$, $R^{CR1}$, $R^{CR2}$, $R^{P1}$, and $R^{P2}$ each, independently of one another, denote H, an alkyl or alkoxy radical having 1 to 15 C atoms, where one or more $CH_2$ groups in these radicals may each be replaced, independently of one another, by

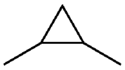 , 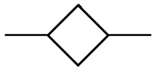 ,

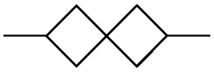 , 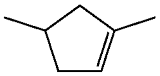 ,

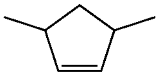 , 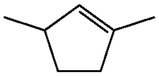 ,

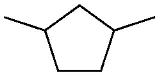 ,

—CH═CH—, —C≡C—, —$CF_2O$—, —$OCF_2$—, —O—, —CO—O— or —O—CO— in such a way that O atoms are not linked directly to one another, and in which one or more H atoms may be replaced by halogen, and c is 0, 1 or 2.

6. The liquid crystal medium according to claim 1, wherein the medium further comprises one or more compounds of the formula IV

IV

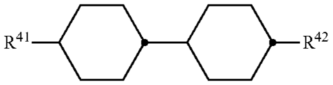

in which $R^{41}$ denotes alkyl having 1 to 7 C atoms or alkenyl having 2 to 7 C atoms, $R^{42}$ denotes alkyl having 1 to 7 C atoms or alkoxy having 1 to 6 C atoms, or alkenyl having 2 to 7 C atoms.

7. The liquid crystal medium according to claim 1, wherein the medium further comprises one or more compounds of the formula V

V

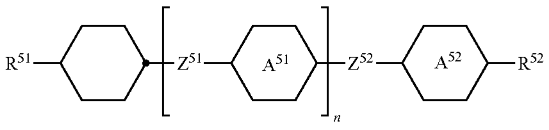

in which $R^{51}$, $R^{52}$, identically or differently, denote alkyl having 1 to 7 C atoms, alkoxy having 1 to 7 C atoms, or alkoxyalkyl, alkenyl or alkenyloxy each having 2 to 7 C atoms,

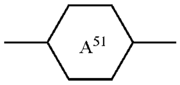 and 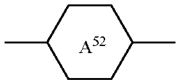 , identically or differently, denote,

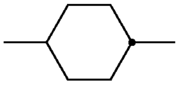 , 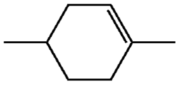 ,

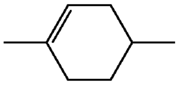 , 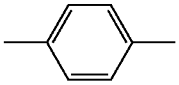 ,

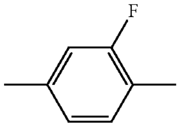 , or 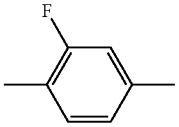 , $Z^{51}$ and $Z^{52}$, identically or differently, denote —$CH_2$—$CH_2$—, —$CH_2$—O—, —CH═CH—, —C≡C—, —COO— or a single bond, and n is 1 or 2, wherein the compound of the formula I is excluded.

8. The liquid crystal medium according to claim 1, wherein the medium further comprises a polymerisable compound.

9. The liquid crystal medium according to claim 1, having a clearing temperature of 100° C. or more.

10. A process of preparing a liquid crystal medium according to claim 1, comprising the steps of mixing one or more compounds of formula I with one or more compounds selected from the group of the formulae IIA, IIB, IIC and IID

IIA

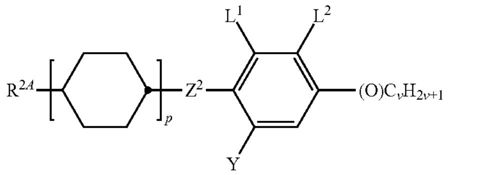

IIB

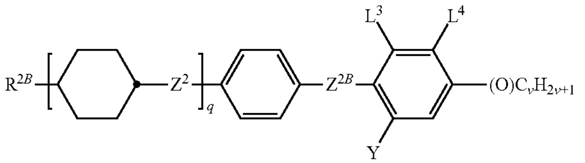

IIC

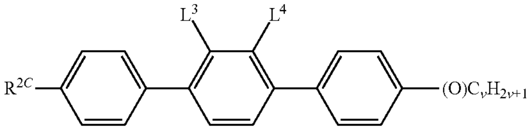

IID

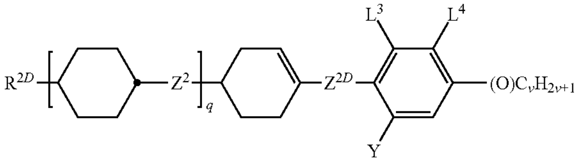

in which $R^{2A}$, $R^{2B}$, $R^{2C}$ and $R^{2D}$, identically or differently, denote H, straight chain alkyl or alkoxy having 1 to 15 C atoms, straight chain alkenyl or alkenyloxy having 2 to 15 C atoms or branched alkyl, alkoxy, alkenyl, alkenyloxy each having 3 to 15 C atoms, where one or more $CH_2$ groups in these radicals may each be replaced, independently of one another, by

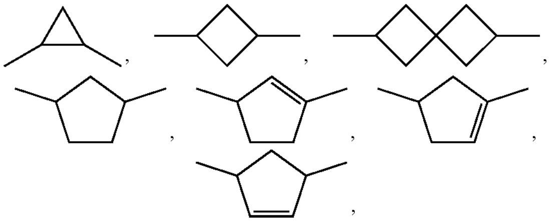

—CH═CH—, —C≡C—, —$CF_2O$—, —$OCF_2$—, —O—, —CO—O— or —O—CO— in such a way that O atoms are not linked directly to one another, and in which one or more H atoms may be replaced by halogen, $L^1$ and $L^2$, each, independently of one another, denote F, Cl, $CF_3$ or $CHF_2$, Y denotes H, F, Cl, $CF_3$, $CHF_2$ or $CH_3$, $Z^2$, $Z^{2B}$ and $Z^{2D}$ each, independently of one another, denote a single bond, —$CH_2CH_2$—, —CH═CH—, —$CF_2O$—, —$OCF_2$—, —$CH_2O$—, —$OCH_2$—, —COO—, —OCO—, —$C_2F_4$—, —CF═CF— or —CH═$CHCH_2O$—, (O) denotes O or a single bond, p denotes 0, 1 or 2, q denotes 0 or 1, and v denotes an integer from 1 to 6, and optionally with a polymerisable compound or further liquid crystal compounds or additives.

11. A liquid crystal display comprising the liquid crystal medium according to claim 1.

12. The liquid crystal display of claim 11, wherein the display is a VA, IPS, FFS, PS-VA, PS—IPS or PS-FFS type display.

13. A compound of the formula I

I

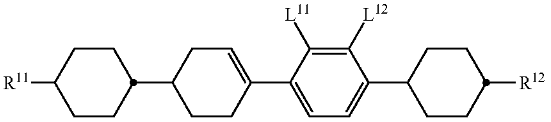

in which $R^{11}$ and $R^{12}$ identically or differently, denote H, straight chain alkyl or alkoxy having 1 to 15 C atoms, straight chain alkenyl or alkenyloxy having 2 to 15 C atoms or branched alkyl, alkoxy, alkenyl, alkenyloxy each having 3 to 15 C atoms, where one or more $CH_2$ groups in these radicals may each be replaced, independently of one another, by

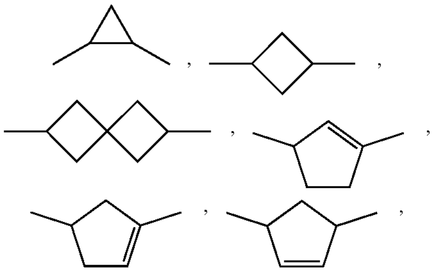

—CH═CH—, —C≡C—, —$CF_2O$—, —$OCF_2$—, —O—, —CO—O— or —O—CO— in such a way that O atoms are not linked directly to one another, and in which one or more H atoms may be replaced by halogen, one of $L^{11}$ and $L^{12}$ denotes H, and the other one of $L^{11}$ and $L^{12}$ denotes F, Cl, $CF_3$ or $CHF_2$.

14. A process for the production of the compound of the formula I of claim 13, comprising at least a step of elimination of water from the compound of the formula (3)

(3)

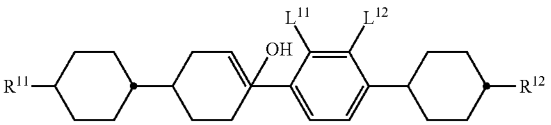

in which $R^{11}$ and $R^{12}$ identically or differently, denote H, straight chain alkyl or alkoxy having 1 to 15 C atoms, straight chain alkenyl or alkenyloxy having 2 to 15 C atoms or branched alkyl, alkoxy, alkenyl, alkenyloxy each having 3 to 15 C atoms, where one or more $CH_2$ groups in these radicals may each be replaced, independently of one another, by

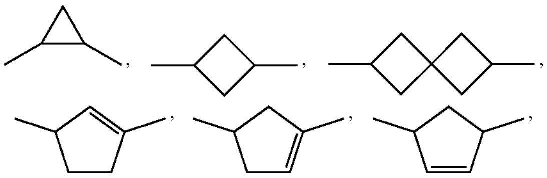

$-CH{=}CH-$, $-C{\equiv}C-$, $-CF_2O-$, $-OCF_2-$, $-O-$, $-CO-O-$ or $-O-CO-$ in such a way that O atoms are not linked directly to one another, and in which one or more H atoms may be replaced by halogen, and one of $L^{11}$ and $L^{12}$ denotes H, and the other one of $L^{11}$ and $L^{12}$ denotes F, Cl, $CF_3$ or $CHF_2$.

15. A compound of formula (3)

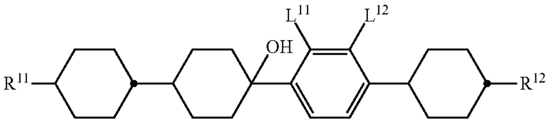

(3)

in which $R^{11}$ and $R^{12}$ identically or differently, denote H, straight chain alkyl or alkoxy having 1 to 15 C atoms, straight chain alkenyl or alkenyloxy having 2 to 15 C atoms or branched alkyl, alkoxy, alkenyl, alkenyloxy each having 3 to 15 C atoms, where one or more $CH_2$ groups in these radicals may each be replaced, independently of one another, by

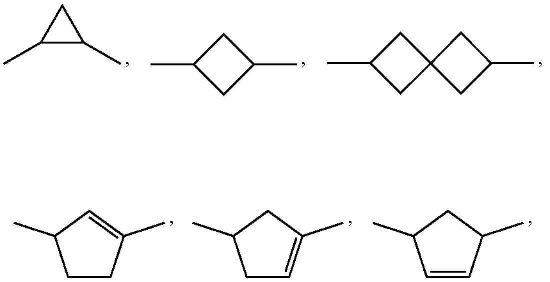

$-CH{=}CH-$, $-C{\equiv}C-$, $-CF_2O-$, $-OCF_2-$, $-O-$, $-CO-O-$ or $-O-CO-$ in such a way that O atoms are not linked directly to one another, and in which one or more H atoms may be replaced by halogen, and one of $L^{11}$ and $L^{12}$ denotes H, and the other one of $L^{11}$ and $L^{12}$ denotes F, Cl, $CF_3$ or $CHF_2$.

* * * * *